(12) United States Patent
Kobler et al.

(10) Patent No.: US 7,645,868 B2
(45) Date of Patent: Jan. 12, 2010

(54) FAMILIES OF NON-CROSS-HYBRIDIZING POLYNUCLEOTIDES FOR USE AS TAGS AND TAG COMPLEMENTS, MANUFACTURE AND USE THEREOF

(75) Inventors: Daniel Kobler, Toronto (CA); Daniel Fieldhouse, Bolton (CA)

(73) Assignee: Luminex Molecular Diagnostics, Inc., Toronto (CA)

( * ) Notice: Subject to any disclaimer, the term of this patent is extended or adjusted under 35 U.S.C. 154(b) by 564 days.

(21) Appl. No.: 10/470,073

(22) PCT Filed: Jan. 25, 2002

(86) PCT No.: PCT/CA02/00089

§ 371 (c)(1),
(2), (4) Date: Jan. 13, 2004

(87) PCT Pub. No.: WO02/059355

PCT Pub. Date: Aug. 1, 2002

(65) Prior Publication Data

US 2005/0191625 A1 Sep. 1, 2005

Related U.S. Application Data

(60) Provisional application No. 60/263,710, filed on Jan. 25, 2001, provisional application No. 60/303,799, filed on Jul. 10, 2001.

(51) Int. Cl.
C07H 21/02 (2006.01)
C07H 21/04 (2006.01)
(52) U.S. Cl. ...................... 536/24.2; 536/23.1
(58) Field of Classification Search ................ None
See application file for complete search history.

(56) References Cited

U.S. PATENT DOCUMENTS

| | | | |
|---|---|---|---|
| 4,851,331 A | 7/1989 | Vary et al. | |
| 4,942,124 A | 7/1990 | Church | |
| 5,002,867 A | 3/1991 | Macevicz | |
| 5,149,625 A | 9/1992 | Church et al. | |
| 5,391,480 A | 2/1995 | Davis et al. | |
| 5,604,097 A | 2/1997 | Brenner et al. | |
| 5,635,400 A * | 6/1997 | Brenner | 435/320.1 |
| 5,654,413 A | 8/1997 | Brenner | |
| 5,830,539 A * | 11/1998 | Yan et al. | 427/551 |
| 5,846,719 A | 12/1998 | Brenner et al. | |
| 5,951,176 A | 9/1999 | Ueda | |
| 5,981,176 A | 11/1999 | Wallace | |
| 6,013,445 A | 1/2000 | Albrecht et al. | |
| 6,040,138 A * | 3/2000 | Lockhart et al. | 435/6 |
| 6,103,463 A | 8/2000 | Chetverin et al. | |
| 6,150,095 A | 11/2000 | Southern et al. | |
| 6,150,516 A | 11/2000 | Brenner et al. | |
| 6,205,444 B1 | 3/2001 | Floratos et al. | |
| 6,287,778 B1 | 9/2001 | Huang et al. | |
| 6,322,971 B1 | 11/2001 | Chetverin et al. | |
| 6,458,530 B1 * | 10/2002 | Morris et al. | 435/6 |
| 6,472,157 B1 * | 10/2002 | Di Rienzo et al. | 435/6 |
| 7,157,564 B1 | 1/2007 | Mittmann et al. | |
| 2002/0177141 A1 | 11/2002 | Chee et al. | |
| 2005/0089851 A1 | 4/2005 | Pancoska et al. | |

FOREIGN PATENT DOCUMENTS

| | | |
|---|---|---|
| EP | 0698792 A | 2/1996 |
| EP | 799897 A | 10/1997 |
| WO | WO 93/17126 | 9/1993 |
| WO | WO 97/31256 | 8/1997 |
| WO | WO 0058516 A | 10/2000 |
| WO | WO 01/59151 A2 | 8/2001 |
| WO | WO 02053728 A | 7/2002 |
| WO | WO-02/059354 A3 | 8/2002 |
| WO | WO-02/059355 A3 | 8/2002 |

OTHER PUBLICATIONS

Michael et al. Randomly ordered addressable high-density optical sensor arrays. Analytical Chemistry. 1998, vol. 70, pp. 1242-1248.*
Definition of "stringency." http://cancerweb.ncl.ac.uk. Dec. 16, 1997. Accessed online on Jan. 21, 2008.*
Byrd et al. The limitations of MALDI-TOF Mass Spectrometry in the analysis of wide polydisperse polymers. Analytical Chemistry, 2000, vol. 72, pp. 4568-4576.*
Maskos et al. A study of oligonucleotide reassociation using large arrays of olionucleotides synthesised on a glass support. Nucleic Acids Research. 1993, vol. 21, pp. 4663-4669.*
Southern et al. Parallel synthesis and analysis of large numbers of related chemical compounds: application to oligonucleotides. Journal of Biotechnology. vol. 35, 1994, pp. 217-227.*
Menkoth et al. Hybridization of Nucleic Acids immobilized on Solid Supports. Analytical Biochemistry, vol. 138, 1984, pp. 267-284.*
Sonina et al. Theor. Appl. Genet. (1989), vol. 78, pp. 589-593.*
Breslauer et al., "Predicting DNA duplex stability from the base sequence", Proc. Natl. Acad. Sci. USA, Jun. 1986, vol. 83, pp. 3746-5750.
Caruthers et al., "Chemical Synthesis of Deoxyoligonucleotides by the Phosphoramidite Method", Methods in Enzymology, 1987, vol. 154, pp. 287-313.
Church et al., "Muliplex DNA Sequencing", Science, vol. 240, Apr. 8, 1988, pp. 185-188.
Kwoh et al., "Transcription-based amplification system and detection of amplified human immunodeficiency virus type 1 with a bead-based sandwich hybridization format", Proc. Natl. Acad. Sci. USA, Feb. 1989, vol. 86, pp. 1173-1177.
Rychlik et al., "A computer program for choosing optimal oligonucleotides for filter hybridization, sequencing and in vitro amplification of DNA", Nucleic Acids Research, 1989, vol. 17, No. 21, pp. 8543-8551.

(Continued)

Primary Examiner—Marjorie Moran
Assistant Examiner—Russell S Negin
(74) Attorney, Agent, or Firm—Goodwin Procter LLP

(57) ABSTRACT

A family of minimally cross-hybridizing nucleotide sequences, methods of use, etc. A specific family of 1168 24mers is described.

28 Claims, 4 Drawing Sheets

OTHER PUBLICATIONS

Fodor et al., "Light-Directed, Spatially Addressable Parallel Chemical synthesis", Science, Feb. 15, 1991, vol. 251, pp. 767-773.

Needels et al., "Generation and screeining of an oligonucleotide-encoded synthetic peptide library", Proc. Natl. Acad. Sci. USA, Nov. 1993, vol. 90, pp. 10700-10704.

Mueller et al., Current Protocols in Molecular Biology, 1993, vol. 15, p. 5.

Alper, J., "Drug Discovery on the Assembly Line", Science, Jun. 3, 1994, vol. 264, pp. 1399-1401.

Nikiforov et al., "Genetic Bit Analysis: a solid phase method for typing single nucleotide polymorphisms", Nucleic Acids Research, 1994, vol. 22, No. 20, pp. 4167-4175.

Southern et al., "Arrays of complementay oligonucleotides for analyzing the hybridization behaviour of nucleic acids", Nucleic Acids Research, 1994, vol. 22, No. 8, pp. 1368-1373.

Hensel et al., "Simultaneous Identification of Bacterial Virulence Genes by Negative Selection", Science, Jul. 21, 1995, vol. 269, pp. 400-403.

Lyttle et al., "Mutagenesis Using Trinucleotide β-Cyanoethyl Phosphoramidites", BioTechniques, 1995, vol. 19, No. 2, pp. 274-280.

Matson et al., "Biopolymer Synthesis on Polypropylene Supports: Oligonucleotide Arrays", Analytical Biochemistry, 1995, vol. 224, pp. 110-116.

Shoemaker et al., "Quantitative phenotypic analysis of yeast deletion mutants using a highly parallel molecular bar-coding strategy", Nature Genetics, Dec. 1996, vol. 14, pp. 450-456.

Hermanson et al., Bioconjugate Techniques; Academic Press, 1996, pp. 640-671.

Head et al., "Nested genetic bit analysis (N-GBA) for mutation detection in the p53 tumor suppressor gene", Nucleic Acids Research, 1997, vol. 25, No. 24, pp. 5065-5071.

Weiler et al., "Hybridisation based DNA screening on peptide nucleic acid (PNA) oligomer arrays", Nucleic Acids Research, 1997, vol. 25, No. 14, pp. 2792-2799.

Proudnikov et al., "Immobilization of DNA in Polyacrylamide Gel for the Manufacture of DNA and DNA-Oligonucleotide Microchips", Analytical Biochemistry, 1998, vol. 259, pp. 34-41.

Robertson et al., "An Introduction to PCR Primer Design and Optimization of Amplification Reactions", Methods in Molecular Biology, 1998, vol. 98, pp. 121-154.

Peyret et al., "Nearest-Neighbor Thermodynamics and NMR of DNA Sequences with Internal A•A, C•C, G•G, and T•T Mismatches", Biochemistry, 1999, vol. 38, pp. 3468-3477.

Southern et al., "Molecular interactions on microarrays", Nature Genetics Supplement, Jan. 1999, vol. 231, pp. 5-9.

Lipshutz et al., "High density synthetic oligonucleotide arrays", Nature Genetics Supplement, Jan. 1999, vol. 21, pp. 20-24.

Niemeyer et al., "DNA-directed immobilization: Efficient, reversible, and site-selective surface binding of proteins by means of covalent DNA-streptavidin conjugates", Analytical Biochemistry, Mar. 1999, vol. 268, No. 1, pp. 54-63.

Hacia et al., "Design of modified oligodeoxyribonucleotide probes to detect telomere repeat sequences in FISH assays", Nucleic Acids Research, 1999, vol. 27, No. 20, pp. 4034-4039.

Nguyen et al., "Smoothing of the thermal stability of DNA duplexes by using modified nucleosides and caotropic agents", Nucleic Acids Research, 1999, vol. 27, No. 6, pp. 1492-1498.

Iannone et al., "Multiplexed Single Nucleotide Polymorphism Genotyping by Oligonucleotide Ligation and Flow Cytometry", 2000, vol. 39, pp. 131-140.

Kane et al., "Assessment of the sensitivity and specificity of oligonucleotide (50mer) microarrays", Nucleic Acids Research, 2000, vol. 28, pp. 4552-4557.

Zammatteo et al., "Comparison between Different Strategies of Covalent Attachment of DNA to Glass Surfaces to Build DNA Microarrays", Analytical Biochemistry, 2000, vol. 280, pp. 143-150.

Brenner S and Lerner RA. "Encoded Combinatorial Chemistry." *Proc Natl Acad Sci U S A*. Jun. 15, 1992;89(12):5381-5383.

Brenner S et al. "In vitro cloning of complex mixtures of DNA on microbeads: physical separation of differentially expressed cDNAs." *Proc Natl Acad Sci U S A*. Feb. 15, 2000;97(4):1665-1670.

Brenner S et al. "Gene expression analysis by massively parallel signature sequencing (MPSS) on microbead arrays." *Nat Biotechnol*, Jun. 2000;18(6):630-634. Erratum in: Nat Biotechnol Oct. 2000;18(10):1021.

Chetverin AB and Kramer FR "Oligonucleotide arrays: new concepts and possibilities." *Biotechnology (N Y)*. Nov. 1994; 12(11): 1093-1099.

Frutos AG et al. "Demonstration of a word design strategy for DNA computing on surfaces." *Nucleic Acids Res*. Dec. 1, 1997; 25(23):4748-4757.

Matthews JA and Kricka LJ "Analytical strategies for the use of DNA probes."*Anal Biochem*. Feb. 15, 1988;169(1):1-25.

Morgan K and Kalsheker N "Simple and efficient cDNA capture utilising a short gene-specific probe attached to magnetic beads." *Biochem Soc Trans*. Nov. 1994; 22(4):453S.

Ohlmeyer MH et al. "Complex synthetic chemical libraries indexed with molecular tags." *Proc Natl Acad Sci USA*. Dec. 1, 1993; 90(23):10922-10926.

Sasaki YF et al. "Construction of a normalized cDNA library by introduction of a semi-solid mRNA-cDNA hybridization system." *Nucleic Acids Res*. Mar. 25, 1994;22(6):987-992.

Ben-Dor A et al. "Universal DNA tag systems: a combinatorial design scheme." *J Comput Biol*. 2000; 7(3-4):503-519.

Kececioglu JD and Myers EW "Combinatorial algorithms for DNA sequence assembly" *Algorithmica* 13:½, 7-51, 1995 (enclosed as p. 1-45).

* cited by examiner

FAMILIES OF NON-CROSS-HYBRIDIZING POLYNUCLEOTIDES FOR USE AS TAGS AND TAG COMPLEMENTS, MANUFACTURE AND USE THEREOF

CROSS-REFERENCE TO RELATED APPLICATION

This application is the 35 U.S.C. 371 National Stage of International Application No. PCT/CA02/00089, filed Jan. 25, 2002, and claims the benefit of U.S. Provisional Application No. 60/263,710, filed Jan. 25, 2001, and U.S. Provisional Application No. 60/303,799, filed Jul. 10, 2001.

This application claims priority from U.S. Provisional Patent Application Nos. 60/263,710 and 60/303,799, filed Jan. 25, 2001 and Jul. 10, 2001. Both of these documents are incorporated herein by reference.

FIELD OF THE INVENTION

This invention relates to families of oligonucleotide tags for use, for example, in sorting molecules. Members of a given family of tags can be distinguished one from the other by specific hybridization to their tag complements.

BACKGROUND OF THE INVENTION

Specific hybridization of oligonucleotides and their analogs is a fundamental process that is employed in a wide variety of research, medical, and industrial applications, including the identification of disease-related polynucleotides in diagnostic assays, screening for clones of novel target polynucleotides, identification of specific polynucleotides in blots of mixtures of polynucleotides, therapeutic blocking of inappropriately expressed genes and DNA sequencing. Sequence specific hybridization is critical in the development of high throughput multiplexed nucleic acid assays. As formats for these assays expand to encompass larger amounts of sequence information acquired through projects such as the Human Genome project, the challenge of sequence specific hybridization with high fidelity is becoming increasingly difficult to achieve.

In large part, the success of hybridization using oligonucleotides depends on minimizing the number of false positives and false negatives. Such problems have made the simultaneous use of multiple hybridization probes in a single experiment i.e. multiplexing, particularly in the analysis of multiple gene sequences on a gene microarray, very difficult. For example, in certain binding assays, a number of nucleic acid molecules are bound to a chip with the desire that a given "target" sequence will bind selectively to its complement attached to the chip. Approaches have been developed that involve the use of oligonucleotide tags attached to a solid support that can be used to specifically hybridize to the tag complements that are coupled to probe sequences. Chetverin et al. (WO 93/17126) uses sectioned, binary oligonucleotide arrays to sort and survey nucleic acids. These arrays have a constant nucleotide sequence attached to an adjacent variable nucleotide sequence, both bound to a solid support by a covalent linking moiety. These binary arrays have advantages compared with ordinary arrays in that they can be used to sort strands according to their terminal sequences so that each strand binds to a fixed location on an array. The design of the terminal sequences in this approach comprises the use of constant and variable sequences. U.S. Pat. Nos. 6,103,463 and 6,322,971 issued to Chetverin et al. on Aug. 15, 2000 and Nov. 27, 2001, respectively.

This concept of using molecular tags to sort a mixture of molecules is analogous to molecular tags developed for bacterial and yeast genetics (Hensel et al., Science; 269, 400-403: 1995 and Schoemaker et al., Nature Genetics; 14, 450-456: 1996). Here, a method termed "signature tagged" mutagenesis in which each mutant is tagged with a different DNA sequence is used to recover mutant genes from a complex mixture of approximately 10,000 bacterial colonies. In the tagging approach of Barany et al. (WO 9731256), known as the "zip chip", a family of nucleic acid molecules, the "zipcode addresses", each different from each other, are set out on a grid. Target molecules are attached to oligonucleotide sequences complementary to the "zipcode addresses," referred to as "zipcodes," which are used to specifically hybridize to the address locations on the grid. While the selection of these families of polynucleotide sequences used as addresses is critical for correct performance of the assay, the performance has not been described.

Working in a highly parallel hybridization environment requiring specific hybridization imposes very rigorous selection criteria for the design of families of oligonucleotides that are to be used. The success of these approaches is dependent on the specific hybridization of a probe and its complement. Problems arise as the family of nucleic acid molecules cross-hybridize or hybridize incorrectly to the target sequences. While it is common to obtain incorrect hybridization resulting in false positives or an inability to form hybrids resulting in false negatives, the frequency of such results must be minimized. In order to achieve this goal certain thermodynamic properties of forming nucleic acid hybrids must be considered. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbour interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., Current Protocols in Mol. Biol.; 15, 5:1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur forming duplexes with measurable mismatch stability (Santalucia et al., Biochemistry; 38: 3468-77, 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore, design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

The development of such families of tags has been attempted over the years with varying degrees of success. There are a number of different approaches for selecting sequences for use in multiplexed hybridization assays. The selection of sequences that can be used as zipcodes or tags in an addressable array has been described in the patent literature in an approach taken by Brenner and co-workers. U.S. Pat. No. 5,654,413 describes a population of oligonucleotide tags (and corresponding tag complements) in which each oligonucleotide tag includes a plurality of subunits, each subunit consisting of an oligonucleotide having a length of from three to six nucleotides and each subunit being selected from a minimally cross hybridizing set, wherein a subunit of the set would have at least two mismatches with any other sequence of the set. Table II of the Brenner patent specification describes exemplary groups of 4mer subunits that are minimally cross hybridizing according to the aforementioned criteria. In the approach taken by Brenner, constructing non cross-hybridizing oligonucleotides, relies on the use of subunits that form a duplex having at least two mismatches with the complement of any other subunit of the same set. The ordering of subunits in the construction of oligonucleotide tags is not specifically defined.

Parameters used in the design of tags based on subunits are discussed in Barany et al. (WO 9731256). For example, in the design of polynucleotide sequences that are for example 24 nucleotides in length (24mer) derived from a set of four possible tetramers in which each 24mer "address" differs from its nearest 24mer neighbour by 3 tetramers. They discuss further that, if each tetramer differs from each other by at least two nucleotides, then each 24mer will differ from the next by at least six nucleotides. This is determined without consideration for insertions or deletions when forming the alignment between any two sequences of the set. In this way a unique "zip code" sequence is generated. The zip code is ligated to a label in a target dependent manner, resulting in a unique "zip code" which is then allowed to hybridize to its address on the chip. To minimize cross-hybridization of a "zip code" to other "addresses", the hybridization reaction is carried out at temperatures of 75-80° C. Due to the high temperature conditions for hybridization, 24mers that have partial homology hybridize to a lesser extent than sequences with perfect complementarity and represent 'dead zones'. This approach of implementing stringent hybridization conditions for example, involving high temperature hybridization, is also practiced by Brenner et. al.

The current state of technology for designing non-cross hybridizing tags based on subunits does not provide sufficient guidance to construct a family of relatively large numbers of sequences with practical value in assays that require stringent non-cross hybridizing behavior.

A multiplex sequencing method has been described in U.S. Pat. No. 4,942,124, which issued to Church on Jul. 17, 1990. The method requires at least two vectors which differ from each other at a tag sequence. It is stated that a tag sequence in one vector will not hybridize under stringent hybridization conditions to a tag sequence (i.e., complementary probes do not cross-hybridize) in another vector. Exemplary stringent hybridization conditions are given as 42° C. in 500-1000 mM sodium phosphate buffer. A set of 42 20-mer tag sequences, all of which lack G residues, is given in FIG. 3 of the specification. Details of how the sequences were obtained are not provided, although Church states that initially 92 were chosen on the basis of their having sufficient sequence diversity to insure uniqueness.

So while it is possible for a person knowledgeable in the field to design a small number of non-cross hybridizing tags, it is difficult to design a larger number such tags. A copending application of the owner of this patent application describes such a set of 210 non-cross hybridizing tags that have a practical value. A method described in international patent application No. PCT/CA 01/00141 published under WO 01/59151 on Aug. 16, 2001. Little guidance is provided, however, for the provision of a larger set, say 1000 or so, of non-cross hybridizing tags. Since having sets of approximately 1000 non-cross hybridizing tags, or more, would be of considerable practical value, it would be useful to develop such a set.

Thus, while it is desirable with such arrays to have, at once, a large number of address molecules, the address molecules should each be highly selective for its own complement sequence: While such an array provides the advantage that the family of molecules making up the grid is entirely of design, and does not rely on sequences as they occur in nature, the provision of a family of molecules, which is sufficiently large and where each individual member is sufficiently selective for its complement over all the other zipcode molecules (i.e., where there is sufficiently low cross-hybridization, or crosstalk) continues to elude researchers.

SUMMARY OF INVENTION

A family of 1168 sequences was obtained using a computer algorithm to have desirable hybridization properties for use in nucleic acid detection assays. The sequence set of 1168 oligonucleotides was partially characterized in hybridization assays, demonstrating the ability of family members to correctly hybridize to their complementary sequences with minimal cross hybridization. These are the sequences having SEQ ID NOs: 1 to 1168 of Table I.

Variant families of sequences (seen as tags or tag complements) of a family of sequences taken from Table I are also part of the invention. For the purposes of discussion, a family or set of oligonucleotides will often be described as a family of tag complements, but it will be understood that such a set could just easily be a family of tags.

A family of complements is obtained from a set of oligonucleotides based on a family of oligonucleotides such as those of Table I. To simplify discussion, providing a family of complements based on the oligonucleotides of Table I will be described.

Firstly, the groups of sequences based on the oligonucleotides of Table I can be represented as shown in Table IA.

TABLE IA

Numeric sequences corresponding to nucleotide base patterns of a set of oligonucleotides

| Numeric Pattern | Sequence Identifier |
|---|---|
| 1 1 1 2 2 3 2 3 1 1 1 3 1 2 2 3 2 2 2 3 2 3 2 1 | 1 |
| 3 2 2 1 3 1 3 2 2 1 1 2 2 3 2 1 2 2 2 3 1 2 3 1 | 2 |
| 1 2 3 2 2 1 1 1 3 2 1 1 3 2 3 2 2 3 1 1 1 2 3 2 | 3 |

TABLE IA-continued

Numeric sequences corresponding to nucleotide base patterns of a set of oligonucleotides

| Numeric Pattern | Sequence Identifier |
|---|---|
| 2 3 1 2 3 2 2 1 3 1 1 3 2 1 2 1 2 2 3 2 3 1 1 2 | 4 |
| 2 2 2 3 2 3 2 1 3 1 1 2 1 2 3 2 3 2 2 3 2 2 1 1 | 5 |
| 1 2 1 1 3 2 3 2 1 1 3 2 3 1 1 1 2 1 1 3 1 1 3 1 | 6 |
| 1 1 3 1 3 2 1 2 2 2 3 2 2 3 2 3 1 3 2 2 1 1 1 2 | 7 |
| 3 2 3 2 2 2 1 2 3 2 2 1 2 1 2 3 2 3 1 1 3 2 2 2 | 8 |
| 1 1 1 3 1 3 1 1 2 1 3 1 1 2 1 2 3 2 3 2 1 1 3 2 | 9 |
| 2 1 2 3 1 1 1 3 1 3 2 3 1 3 1 2 1 1 2 3 2 2 2 1 | 10 |
| 1 2 3 1 3 1 1 1 2 1 2 3 2 2 1 3 1 1 2 3 2 3 1 2 | 11 |
| 2 2 1 3 2 2 3 2 2 3 1 2 3 2 2 2 1 3 2 1 3 2 2 2 | 12 |
| 3 2 1 1 1 3 1 3 2 1 2 1 1 3 2 2 2 3 1 2 3 1 2 1 | 13 |
| 1 1 1 3 2 1 1 3 1 1 2 3 1 2 3 2 1 1 2 1 1 3 2 3 | 14 |
| 3 2 1 3 1 1 1 2 1 3 2 2 2 1 2 2 3 1 2 3 1 2 2 3 | 15 |
| 2 3 2 1 1 3 2 3 1 1 1 2 1 3 2 3 1 3 2 2 1 2 2 2 | 16 |
| 1 1 1 2 1 3 1 2 3 1 2 1 2 1 1 3 2 3 1 3 1 1 2 3 | 17 |
| 1 2 1 1 3 2 2 1 2 1 1 3 2 3 2 2 1 2 3 2 3 1 3 2 | 18 |
| 2 1 2 1 3 1 2 1 1 1 3 1 3 1 2 3 1 2 2 2 3 2 2 3 | 19 |
| 1 3 1 3 2 2 3 1 3 1 1 2 3 2 1 2 1 3 2 1 2 2 1 2 | 20 |
| 1 1 3 2 1 3 2 2 2 3 2 1 1 3 1 1 2 3 1 2 2 3 2 1 | 21 |
| 2 2 1 2 3 1 1 1 2 2 3 1 3 2 3 1 1 3 1 2 2 3 1 2 | 22 |
| 3 2 1 2 1 2 3 2 1 1 1 2 2 3 2 2 2 1 2 3 2 2 3 1 3 | 23 |
| 3 1 1 2 2 3 2 1 2 1 1 1 3 2 1 2 2 1 3 1 2 3 2 3 | 24 |
| 2 1 3 1 2 3 1 3 1 2 2 1 1 3 2 3 2 2 1 2 2 2 3 1 | 25 |
| 3 2 2 1 1 3 2 2 2 3 2 2 2 1 2 3 2 1 2 1 3 1 1 3 | 26 |
| 3 1 3 2 1 2 2 2 1 3 2 1 1 1 3 2 3 1 2 1 2 3 1 2 1 | 27 |
| 3 2 3 1 1 2 3 1 2 2 2 1 3 2 1 1 1 2 3 1 2 2 3 1 | 28 |
| 3 1 2 2 3 1 1 1 3 2 2 1 2 1 3 1 1 1 2 3 1 2 2 1 3 | 29 |
| 1 3 2 3 1 2 1 1 1 2 3 2 2 1 3 2 2 3 1 1 2 2 3 2 | 30 |
| 2 1 2 1 2 1 3 2 1 1 1 2 3 2 2 2 3 2 3 2 3 2 2 3 | 31 |
| 2 2 1 1 3 2 3 2 2 1 3 2 2 1 2 2 2 3 2 2 3 2 1 3 | 32 |
| 3 2 1 3 2 1 1 2 1 2 3 1 1 3 2 3 1 3 1 1 2 1 2 1 | 33 |
| 2 1 3 2 3 2 1 2 1 3 1 1 2 3 2 1 3 1 2 2 2 1 3 2 | 34 |
| 2 2 3 2 1 3 1 2 2 1 3 1 2 3 2 3 2 2 2 3 2 1 1 1 | 35 |
| 2 1 3 2 1 2 1 3 1 3 2 1 3 1 3 1 2 3 1 2 1 2 2 2 | 36 |
| 1 2 2 3 2 3 1 1 1 3 1 1 1 3 1 3 1 1 3 1 1 1 2 2 | 37 |
| 2 3 2 3 1 3 1 1 2 2 1 1 3 1 2 2 1 1 3 1 1 2 3 2 | 38 |
| 1 2 1 2 2 1 3 2 2 1 1 3 1 1 1 3 1 1 3 1 3 2 2 3 | 39 |

TABLE IA-continued

Numeric sequences corresponding to nucleotide base patterns of a set of oligonucleotides

| Numeric Pattern | Sequence Identifier |
|---|---|
| 2 2 3 2 1 3 2 2 3 1 3 1 1 1 2 1 2 3 2 1 3 2 2 2 | 40 |
| 2 1 3 1 3 2 2 3 2 2 1 1 1 3 1 3 2 3 2 1 1 1 2 1 | 41 |
| 3 2 2 1 2 3 1 2 3 2 3 2 1 2 1 1 3 2 1 1 2 1 2 3 | 42 |
| 2 2 2 3 2 2 1 3 1 1 2 3 1 3 1 1 3 1 2 2 2 1 2 3 | 43 |
| 1 3 2 1 2 1 3 2 2 2 1 1 1 3 1 1 3 2 1 3 2 1 3 1 | 44 |
| 3 2 3 1 3 1 2 1 2 1 3 1 2 2 2 1 3 1 1 1 3 2 1 1 | 45 |
| 2 2 3 2 2 2 1 2 1 3 2 3 1 1 3 2 3 1 1 2 1 3 2 1 | 46 |
| 1 1 3 2 1 1 3 2 1 3 2 1 1 2 1 3 2 3 2 3 2 2 1 1 | 47 |
| 1 2 2 2 3 2 3 1 3 2 2 1 2 3 1 1 1 3 1 2 1 1 3 1 | 48 |
| 3 1 1 1 3 2 1 3 1 3 1 1 2 1 1 1 3 1 2 1 1 3 1 1 | 49 |
| 1 2 2 2 1 1 3 1 2 2 3 2 2 1 1 3 1 3 2 1 3 1 1 3 | 50 |
| 3 2 2 2 1 1 1 3 1 2 2 3 2 1 1 3 1 1 2 3 2 3 2 1 | 51 |
| 2 2 2 3 2 3 1 1 3 1 2 3 1 1 3 2 1 2 2 2 3 2 1 2 | 52 |
| 2 3 2 3 2 2 2 1 3 1 1 2 2 2 1 3 2 1 2 3 2 3 2 1 | 53 |
| 3 1 2 1 1 2 3 1 2 2 1 2 1 3 1 1 1 3 2 3 2 2 2 3 | 54 |
| 3 2 2 1 2 2 2 3 2 1 1 3 2 2 1 1 3 1 2 1 3 2 1 3 | 55 |
| 1 3 2 2 2 1 2 2 3 1 1 1 3 1 3 2 2 2 3 1 1 2 1 3 | 56 |
| 2 2 3 2 3 2 2 2 1 2 2 3 2 3 2 1 3 2 2 2 1 1 1 3 | 57 |
| 1 2 2 3 2 3 1 3 1 1 1 3 1 2 1 2 3 1 1 1 3 2 2 1 2 | 58 |
| 2 3 1 3 1 1 2 3 2 1 1 1 3 1 1 2 3 2 2 2 1 2 2 3 | 59 |
| 1 2 3 2 3 1 1 1 3 2 2 1 2 3 1 2 3 2 2 1 1 2 2 3 | 60 |
| 3 2 2 2 1 3 2 1 2 2 1 3 2 2 3 2 2 1 1 3 1 2 2 3 | 61 |
| 3 1 2 2 3 1 2 1 2 2 2 3 1 1 2 3 2 2 2 3 2 2 2 3 | 62 |
| 2 3 1 1 2 2 3 1 1 1 3 2 3 2 1 1 2 3 2 2 3 2 1 2 | 63 |
| 3 1 2 2 3 2 1 2 2 3 2 2 3 1 3 1 1 2 1 3 1 1 2 1 | 64 |
| 1 1 1 2 2 2 3 1 3 1 2 2 2 3 2 3 1 2 1 3 1 3 2 1 | 65 |
| 3 2 1 1 2 2 1 3 1 2 2 2 3 2 2 2 3 2 2 3 2 2 3 2 | 66 |
| 3 2 2 2 3 2 1 2 2 3 2 2 1 3 2 3 1 1 2 1 2 1 3 2 | 67 |
| 1 2 3 2 1 3 2 1 3 2 1 3 1 2 3 2 2 2 1 2 3 1 1 2 | 68 |
| 2 3 2 2 2 1 1 1 3 1 2 3 1 2 2 3 1 1 3 1 1 1 2 3 | 69 |
| 2 3 2 3 1 2 1 1 2 3 1 2 3 2 2 1 2 2 2 3 2 3 2 1 | 70 |
| 1 2 1 3 2 2 3 2 3 1 3 1 1 2 2 2 3 2 1 1 2 2 1 3 | 71 |
| 1 2 1 3 1 2 3 2 1 1 3 1 3 1 1 1 2 2 3 2 3 1 1 1 | 72 |
| 1 3 1 2 2 1 1 3 1 3 1 1 3 2 2 1 1 2 1 3 1 3 2 1 | 73 |
| 3 1 1 3 2 1 1 1 2 2 3 2 3 1 1 2 3 1 1 1 3 1 1 1 | 74 |
| 1 1 2 3 2 1 1 3 1 1 1 3 1 1 3 1 2 2 3 2 2 3 2 1 | 75 |
| 2 2 2 3 1 2 2 2 1 2 3 2 3 2 2 1 2 3 2 2 3 1 3 2 | 76 |

TABLE IA-continued

Numeric sequences corresponding to nucleotide base patterns of a set of oligonucleotides

| Numeric Pattern | Sequence Identifier |
|---|---|
| 3 2 1 2 2 3 1 3 1 1 1 2 2 2 3 1 1 3 1 1 2 3 1 1 | 77 |
| 3 1 1 2 2 3 2 1 2 3 1 1 1 2 3 1 1 2 2 3 2 1 1 3 | 78 |
| 2 1 2 2 3 2 1 3 1 1 3 2 1 1 1 3 2 2 1 3 1 1 3 2 | 79 |
| 2 2 2 1 2 3 2 1 1 2 3 1 2 1 1 3 2 3 2 1 3 2 2 3 | 80 |
| 1 2 1 2 1 3 2 2 3 1 1 1 2 2 3 2 3 1 2 1 3 2 3 2 | 81 |
| 1 2 1 1 3 1 1 1 2 2 1 3 1 3 1 3 2 2 3 2 1 1 1 3 | 82 |
| 3 1 1 2 2 3 2 3 1 1 1 2 3 2 3 1 2 2 3 1 2 1 2 1 | 83 |
| 1 1 1 2 1 1 3 2 1 3 2 2 2 1 1 2 3 1 3 1 3 1 1 3 | 84 |
| 3 1 2 2 1 1 1 3 1 1 3 2 1 1 3 2 3 1 1 2 3 2 2 2 | 85 |
| 2 1 2 3 2 3 2 3 2 2 3 2 2 2 1 3 2 3 2 2 1 2 2 1 | 86 |
| 3 1 3 2 2 1 2 1 2 3 2 1 3 2 2 1 3 1 3 2 2 1 2 1 | 87 |
| 3 1 1 1 3 1 1 1 3 1 1 3 2 3 2 2 1 1 3 2 2 1 1 1 | 88 |
| 2 1 3 2 1 2 2 1 3 2 1 1 3 2 1 2 3 2 3 1 2 2 3 2 | 89 |
| 2 2 3 2 3 2 3 1 2 2 3 1 1 2 1 2 2 3 2 3 1 1 1 2 | 90 |
| 1 2 3 2 3 1 1 1 3 1 3 2 2 1 1 3 2 3 1 2 2 1 1 1 | 91 |
| 3 1 2 2 3 1 1 2 3 1 2 2 3 1 3 1 2 1 2 3 2 1 1 1 | 92 |
| 1 1 3 1 2 3 1 2 1 3 2 2 1 1 3 2 3 2 1 1 3 2 2 1 | 93 |
| 2 1 3 2 2 3 2 2 1 2 2 3 1 3 1 1 2 2 2 1 3 1 1 3 | 94 |
| 2 2 2 1 2 1 3 2 3 1 1 2 2 1 2 3 1 3 2 3 1 1 1 3 | 95 |
| 3 1 2 1 3 1 2 2 2 1 3 1 1 1 2 3 1 1 2 2 1 1 3 2 3 | 96 |
| 2 2 2 3 1 1 3 1 1 3 1 3 1 2 2 2 3 1 1 1 2 2 3 1 | 97 |
| 1 2 3 1 1 2 1 1 3 1 3 2 2 3 1 2 1 1 1 2 3 2 3 1 | 98 |
| 2 3 2 2 2 1 2 3 2 1 3 2 3 2 1 3 1 2 2 3 1 1 2 2 | 99 |
| 2 2 2 1 1 3 2 3 1 3 2 2 1 2 1 3 1 1 3 2 1 3 2 1 | 100 |
| 3 1 2 2 2 1 2 3 2 3 2 2 2 3 1 1 3 2 2 1 1 3 1 2 | 101 |
| 2 1 3 2 2 1 3 1 3 1 1 1 3 2 3 1 2 1 1 1 3 2 2 1 | 102 |
| 3 2 1 1 2 3 1 2 1 1 2 3 1 1 3 2 3 2 1 2 1 2 1 3 | 103 |
| 1 1 2 3 1 1 3 2 3 2 2 1 3 2 1 2 1 3 1 2 1 3 2 1 | 104 |
| 2 1 1 1 2 2 3 1 3 2 2 2 3 2 2 2 3 1 2 2 3 2 1 3 | 105 |
| 2 1 1 2 3 1 1 3 1 1 2 1 1 3 2 1 2 3 1 3 2 3 2 2 | 106 |
| 1 1 1 2 3 2 1 1 2 1 3 2 3 2 2 3 2 2 1 3 2 2 1 3 | 107 |
| 1 3 1 3 2 2 1 3 2 3 1 1 1 2 3 2 2 3 2 2 1 1 1 2 | 108 |
| 3 1 1 1 2 1 3 1 1 1 2 3 2 1 2 2 3 2 2 2 3 2 3 1 | 109 |
| 1 3 2 2 1 2 1 1 1 3 2 2 2 3 2 3 1 3 1 1 2 2 1 1 3 | 110 |
| 3 1 3 2 2 2 1 2 1 3 2 2 1 3 1 1 1 2 1 2 3 2 2 3 2 | 111 |
| 1 3 1 3 2 2 1 2 2 1 3 1 1 3 1 1 3 1 2 2 2 1 1 3 | 112 |

TABLE IA-continued

Numeric sequences corresponding to nucleotide base patterns of a set of oligonucleotides

| Numeric Pattern | Sequence Identifier |
|---|---|
| 3 1 3 2 2 1 1 2 3 1 1 1 2 1 1 3 2 1 2 2 2 3 2 3 | 113 |
| 1 2 3 1 2 3 1 1 2 1 3 2 2 3 1 1 3 2 1 2 1 2 1 3 | 114 |
| 1 2 1 3 1 2 1 2 3 1 3 1 2 3 1 1 1 3 2 2 1 3 2 1 | 115 |
| 2 1 2 3 2 1 1 3 1 1 1 3 2 3 1 1 1 3 1 1 3 1 1 | 116 |
| 2 3 1 1 2 3 2 1 3 1 1 1 2 3 1 1 2 3 2 2 3 1 1 1 | 117 |
| 1 1 2 2 3 1 1 2 1 3 2 3 2 3 2 3 1 3 2 2 2 1 1 2 | 118 |
| 1 3 1 2 1 2 2 3 2 2 2 3 1 2 2 1 1 2 3 1 1 3 1 3 | 119 |
| 1 1 1 3 2 2 3 2 1 1 1 3 2 2 3 1 1 3 1 2 1 1 1 3 | 120 |
| 3 2 2 1 1 3 1 3 1 2 2 1 2 3 1 3 1 2 3 2 1 2 2 1 | 121 |
| 1 3 1 1 3 1 2 1 2 1 1 3 1 1 3 1 2 2 3 1 1 2 2 3 | 122 |
| 3 2 1 3 1 1 1 2 2 2 3 1 1 2 2 3 1 2 3 2 3 1 1 1 | 123 |
| 1 1 3 1 3 2 1 3 1 2 2 3 1 2 1 1 3 2 1 2 1 2 3 1 | 124 |
| 2 3 1 2 1 2 1 3 2 1 3 2 3 1 1 3 1 1 1 2 1 1 3 2 | 125 |
| 1 3 1 2 1 1 2 3 1 2 3 1 3 1 1 1 2 3 1 1 3 1 2 1 | 126 |
| 1 2 3 2 3 1 1 1 3 2 1 2 2 2 3 2 3 1 2 1 2 1 3 2 | 127 |
| 1 1 2 1 1 3 1 3 1 1 2 2 3 1 2 1 2 3 1 1 3 1 2 3 | 128 |
| 2 1 1 3 2 3 2 1 2 2 2 1 3 2 1 3 1 1 2 3 1 1 3 2 | 129 |
| 2 1 2 3 2 2 1 3 1 2 2 2 3 2 2 3 1 3 1 2 2 3 1 2 | 130 |
| 1 3 2 2 2 3 2 1 2 3 1 1 3 1 3 1 2 1 3 2 1 2 2 2 | 131 |
| 3 1 3 1 1 1 2 3 2 2 1 2 3 2 1 2 2 2 1 3 2 1 3 2 | 132 |
| 2 1 2 3 2 3 1 3 1 1 2 3 2 3 2 2 2 3 1 2 2 2 1 1 | 133 |
| 3 2 1 2 3 2 2 2 3 2 2 2 1 2 1 3 1 1 2 3 2 1 2 3 | 134 |
| 3 1 3 2 1 2 1 2 1 3 1 1 3 1 1 1 3 1 1 1 2 2 2 3 | 135 |
| 1 2 3 1 3 2 3 1 1 3 2 1 1 1 2 3 2 1 3 2 2 1 2 2 | 136 |
| 2 2 1 1 3 1 1 1 3 2 3 1 3 2 2 1 2 2 3 2 3 1 2 1 2 | 137 |
| 1 2 3 1 1 1 2 3 1 3 1 1 2 1 2 2 3 2 2 3 2 2 2 3 | 138 |
| 3 1 2 2 1 1 2 3 1 2 2 1 2 3 2 3 1 1 2 2 3 1 2 3 | 139 |
| 3 1 1 1 2 3 2 2 1 1 1 3 1 2 1 2 3 1 1 1 3 2 1 3 | 140 |
| 2 1 2 2 3 2 2 3 1 2 2 2 3 1 2 1 2 2 1 3 2 3 2 3 | 141 |
| 2 2 2 1 2 3 2 2 2 3 2 3 2 1 2 3 2 1 1 3 2 1 3 2 | 142 |
| 1 1 2 2 3 1 1 1 3 1 1 2 2 3 2 3 2 3 1 1 2 2 3 1 | 143 |
| 2 3 1 3 2 2 2 3 1 1 2 2 2 3 2 2 2 3 1 3 2 1 1 2 | 144 |
| 3 1 2 3 2 1 2 1 1 2 3 1 2 3 2 3 2 3 2 1 1 1 2 2 | 145 |
| 1 2 3 2 3 1 3 1 1 1 3 1 1 2 2 2 3 2 2 2 1 2 2 | 146 |
| 3 2 3 1 2 1 1 1 3 2 1 2 2 2 3 2 2 2 3 1 2 1 3 1 1 1 | 147 |
| 3 1 1 3 2 1 3 1 1 2 1 3 1 1 1 3 2 2 1 1 2 1 3 1 | 148 |
| 2 2 3 2 3 2 1 3 2 2 1 1 3 1 3 2 2 3 2 2 2 1 1 2 | 149 |

TABLE IA-continued

Numeric sequences corresponding to nucleotide
base patterns of a set of oligonucleotides

| Numeric Pattern | Sequence Identifier |
|---|---|
| 2 1 3 2 1 3 2 1 1 3 2 2 3 2 2 1 3 1 1 2 1 3 2 2 | 150 |
| 1 1 2 2 2 3 1 1 3 2 1 2 1 1 2 3 1 1 2 3 2 3 2 3 | 151 |
| 2 1 3 1 1 1 2 2 3 2 1 3 2 1 2 2 2 3 1 3 1 3 1 1 | 152 |
| 2 3 2 1 2 1 2 3 2 2 1 1 2 3 1 3 1 2 3 2 2 3 2 1 | 153 |
| 2 1 2 2 2 3 1 2 1 1 3 1 3 1 1 2 3 1 1 3 1 1 3 2 | 154 |
| 2 2 3 1 1 2 1 3 2 3 2 1 1 2 3 1 1 2 1 2 3 1 2 3 | 155 |
| 3 2 1 3 2 2 2 3 2 3 1 1 2 1 3 1 1 2 2 1 3 2 2 2 | 156 |
| 1 1 1 3 1 2 3 1 2 2 3 2 1 1 2 2 2 3 2 3 2 3 1 1 | 157 |
| 3 1 1 3 1 2 2 3 2 2 3 1 3 2 2 1 1 2 1 3 1 2 1 1 | 158 |
| 1 3 1 2 2 1 2 3 2 1 3 2 3 1 2 3 2 1 1 1 2 3 2 2 | 159 |
| 3 1 1 2 2 2 1 3 1 2 3 2 1 3 1 2 1 2 3 1 1 2 3 2 | 160 |
| 3 1 2 1 3 1 1 3 2 3 2 1 2 2 1 1 3 2 1 1 3 2 2 1 | 161 |
| 2 1 2 3 1 1 2 2 1 2 3 1 3 1 1 3 1 1 2 1 3 1 3 2 | 162 |
| 2 2 2 3 2 2 1 2 3 1 1 3 2 3 1 2 2 2 3 2 2 2 3 2 | 163 |
| 3 2 1 1 1 3 1 2 2 3 2 3 2 2 1 2 1 2 3 1 1 1 2 3 | 164 |
| 2 2 3 2 3 1 2 1 3 2 1 3 2 2 1 3 1 2 1 2 2 2 3 2 | 165 |
| 3 1 1 2 2 1 1 3 1 2 1 1 1 3 1 1 3 1 3 1 1 3 2 1 | 166 |
| 3 1 2 2 3 2 1 3 1 1 2 3 1 1 2 2 2 3 2 1 3 2 1 2 | 167 |
| 1 1 1 2 1 1 3 1 3 1 3 1 3 1 1 2 3 1 2 2 2 1 3 2 | 168 |
| 1 1 2 2 1 2 3 2 3 1 1 2 1 3 1 2 2 3 2 2 3 1 1 3 | 169 |
| 2 2 1 1 3 1 2 2 2 1 2 3 2 3 1 2 1 3 2 1 3 1 3 2 | 170 |
| 2 2 1 1 1 3 1 2 1 3 2 3 2 2 2 3 2 2 3 2 3 2 2 1 | 171 |
| 2 1 2 2 3 1 2 2 2 1 2 3 1 1 3 1 3 2 1 2 1 3 2 3 | 172 |
| 1 1 1 2 2 2 3 1 2 3 1 3 2 1 3 2 2 2 1 1 3 1 3 1 | 173 |
| 1 2 1 1 1 3 2 2 3 2 2 2 3 1 2 3 2 2 2 3 1 1 2 3 | 174 |
| 3 1 2 2 3 2 3 1 2 3 1 1 2 1 1 2 3 2 2 1 2 2 3 1 | 175 |
| 3 1 2 3 1 1 3 1 1 1 2 1 2 3 1 2 1 2 3 1 1 2 1 3 | 176 |
| 2 2 1 1 1 3 2 2 1 2 2 3 1 1 3 2 3 1 1 3 2 2 3 1 | 177 |
| 2 2 3 2 1 1 3 1 1 1 2 1 3 1 3 1 2 2 2 3 2 3 2 2 | 178 |
| 3 1 3 1 2 2 3 1 3 2 2 2 1 1 3 2 1 2 2 1 3 1 2 2 | 179 |
| 1 3 2 3 1 2 1 1 2 1 3 1 1 2 3 1 2 1 1 1 2 3 2 3 | 180 |
| 3 1 2 1 1 2 1 3 2 3 1 1 2 2 2 3 1 3 2 2 3 2 1 2 | 181 |
| 1 3 1 2 1 2 2 2 3 2 1 3 2 1 3 1 1 1 3 2 1 2 3 2 | 182 |
| 3 2 2 1 2 3 1 1 2 3 2 2 3 1 1 2 2 2 3 1 1 2 3 2 | 183 |
| 1 2 3 1 1 1 3 1 2 2 2 1 3 2 2 3 2 3 1 3 1 2 1 2 | 184 |
| 1 1 1 2 1 3 1 3 1 1 3 2 2 1 2 3 1 2 3 2 3 1 2 1 | 185 |

TABLE IA-continued

Numeric sequences corresponding to nucleotide base patterns of a set of oligonucleotides

| Numeric Pattern | Sequence Identifier |
|---|---|
| 2 2 1 3 2 3 1 3 1 1 1 2 3 2 2 2 1 1 2 3 2 3 1 2 | 186 |
| 2 3 1 1 3 1 1 2 1 2 3 2 3 1 1 1 2 2 1 3 2 2 2 3 | 187 |
| 3 2 2 2 3 1 2 1 3 2 2 2 1 1 2 3 1 3 2 1 2 2 3 1 | 188 |
| 3 2 2 3 2 1 1 3 2 1 1 2 3 1 2 1 1 1 3 2 1 2 3 1 | 189 |
| 2 1 1 3 1 3 2 1 3 2 1 1 2 2 3 2 2 3 2 2 2 1 3 1 | 190 |
| 2 2 2 3 1 3 1 3 1 3 2 1 2 3 2 1 2 3 1 2 2 1 2 2 | 191 |
| 1 2 2 3 1 2 2 2 3 2 3 1 2 1 2 1 3 1 2 1 3 1 1 3 1 | 192 |
| 3 1 2 2 1 3 2 1 2 2 2 1 3 2 1 3 2 1 1 2 1 3 1 3 | 193 |
| 2 1 2 3 2 1 2 2 1 3 1 3 1 2 1 2 2 3 1 1 1 3 2 3 | 194 |
| 2 1 2 3 2 3 1 1 1 3 2 1 1 2 3 1 2 1 1 1 2 3 1 3 | 195 |
| 3 2 1 1 2 2 1 3 2 1 1 2 3 1 2 2 2 3 1 1 2 3 1 3 | 196 |
| 3 2 2 2 1 2 2 3 2 1 1 1 3 1 2 3 2 1 1 3 2 3 1 1 | 197 |
| 2 1 3 2 1 3 1 1 2 2 3 2 2 3 2 2 1 1 1 3 1 1 2 3 | 198 |
| 2 1 2 2 3 2 2 1 3 2 2 1 2 3 2 1 3 2 3 2 3 2 1 1 | 199 |
| 3 1 3 2 3 1 1 1 3 2 2 1 2 1 2 3 1 1 1 3 2 1 2 1 | 200 |
| 1 2 1 2 1 3 1 1 3 2 2 3 1 2 3 1 3 2 2 2 1 2 3 1 | 201 |
| 2 2 2 1 3 1 1 3 2 1 1 3 2 1 1 2 1 3 2 3 1 3 2 1 | 202 |
| 2 3 2 3 2 1 2 1 1 3 1 2 1 2 2 2 3 2 1 1 3 1 1 3 | 203 |
| 2 1 3 1 1 3 1 3 2 2 3 2 1 2 2 3 2 2 1 2 1 1 3 2 | 204 |
| 3 2 3 2 2 1 2 2 1 3 2 2 2 1 1 3 2 2 1 3 1 3 2 1 | 205 |
| 1 1 2 1 2 1 3 2 3 1 2 3 2 3 1 1 1 2 2 3 1 1 2 3 | 206 |
| 2 2 1 3 1 3 1 1 2 1 3 1 3 2 3 1 2 2 1 2 1 3 2 2 | 207 |
| 3 1 1 3 2 3 1 3 2 2 1 1 2 3 1 2 2 2 3 2 1 1 1 2 | 208 |
| 1 1 2 3 2 1 1 1 3 2 1 1 1 3 1 1 1 3 2 3 1 2 3 1 | 209 |
| 3 2 2 1 3 2 2 1 2 3 1 2 3 1 1 2 1 2 2 2 3 2 3 2 1 | 210 |
| 1 1 1 2 3 1 3 2 2 1 3 1 3 2 1 3 1 1 2 2 1 2 3 2 | 211 |
| 3 1 2 1 2 1 3 1 1 3 1 2 2 1 3 2 2 1 3 2 3 1 2 1 | 212 |
| 1 2 1 3 2 2 2 3 2 2 3 1 3 1 2 2 2 1 2 3 1 3 2 1 | 213 |
| 2 1 3 1 1 2 1 3 2 2 1 3 2 1 3 2 1 1 3 1 3 2 1 2 | 214 |
| 3 1 1 2 2 2 3 2 1 2 2 3 2 3 1 1 1 3 2 2 2 1 3 2 1 | 215 |
| 3 2 1 3 2 1 1 3 1 1 1 3 1 3 1 1 2 2 1 3 1 2 2 1 1 | 216 |
| 1 1 2 3 2 3 2 2 1 2 3 2 1 2 3 2 1 1 1 2 1 3 2 3 | 217 |
| 3 1 1 2 2 1 3 2 2 1 3 1 3 2 1 1 1 2 2 3 2 2 2 3 | 218 |
| 3 1 1 1 2 2 3 1 1 3 1 2 1 3 2 1 1 3 1 1 1 2 3 1 | 219 |
| 3 2 3 2 1 2 2 2 1 2 3 2 3 1 2 2 2 1 2 3 1 2 1 3 1 | 220 |
| 2 1 2 2 2 1 2 3 1 3 1 1 1 3 2 2 3 1 1 2 1 3 2 1 3 | 221 |
| 2 1 2 3 2 1 2 2 3 2 1 2 2 3 1 3 2 1 3 1 2 3 1 1 | 222 |

TABLE IA-continued

Numeric sequences corresponding to nucleotide base patterns of a set of oligonucleotides

| Numeric Pattern | Sequence Identifier |
|---|---|
| 3 2 3 1 2 2 3 1 1 2 1 3 2 1 3 1 2 2 3 2 2 2 1 1 | 223 |
| 1 3 2 1 1 3 2 2 3 2 2 2 3 1 2 2 3 1 2 1 2 2 2 3 | 224 |
| 3 1 1 3 2 2 2 3 1 2 2 2 1 1 3 2 2 2 1 1 3 1 1 3 | 225 |
| 3 1 3 1 1 3 1 2 1 1 1 2 3 1 2 1 2 2 3 2 2 1 2 3 | 226 |
| 1 2 3 1 2 3 1 3 2 2 3 2 2 1 1 2 1 3 2 2 1 3 2 2 | 227 |
| 2 1 2 3 1 2 1 2 2 2 3 1 1 3 1 3 2 3 2 2 1 1 3 1 | 228 |
| 3 1 3 1 2 3 1 2 2 1 1 1 3 2 3 1 2 2 2 1 2 3 1 1 | 229 |
| 1 2 1 3 2 2 1 1 3 1 3 2 3 1 2 3 1 3 1 1 2 1 1 1 | 230 |
| 2 2 2 1 2 2 3 2 2 1 3 1 2 1 1 1 3 1 3 2 2 3 1 3 | 231 |
| 1 3 1 1 2 1 2 2 3 1 2 1 3 2 2 3 1 1 3 2 2 3 1 1 | 232 |
| 2 1 3 2 3 2 1 1 1 3 2 3 2 1 3 1 2 2 3 2 1 1 1 2 | 233 |
| 1 3 2 1 3 2 3 1 2 1 2 3 1 2 2 2 3 1 1 2 1 2 2 3 | 234 |
| 2 3 2 1 2 2 3 1 1 2 2 1 3 1 1 2 1 3 2 3 1 3 1 1 | 235 |
| 2 3 1 2 1 2 3 1 3 1 2 1 3 1 1 3 2 2 2 1 1 2 3 2 | 236 |
| 3 1 1 3 1 1 3 2 1 1 3 2 1 2 1 1 1 3 2 1 1 1 2 3 | 237 |
| 2 2 2 1 1 3 2 3 2 3 1 2 1 1 3 1 1 1 3 1 2 1 3 1 | 238 |
| 2 1 2 2 3 2 2 3 1 1.2 3 2 3 2 2 2 1 1 1 3 1 3 1 | 239 |
| 3 1 1 2 1 1 2 3 1 2 3 1 3 1 2 3 1 2 2 1 2 2 3 1 | 240 |
| 2 1 3 1 3 1 1 1 3 1 3 1 3 1 1 2 2 3 2 1 2 2 1 1 | 241 |
| 1 2 3 2 1 2 1 1 2 1 3 1 3 2 1 2 3 2 2 2 3 2 3 1 | 242 |
| 1 1 2 1 3 1 2 1 1 3 1 2 2 3 1 2 2 3 2 3 2 2 2 3 | 243 |
| 2 2 2 3 1 2 3 1 2 1 1 2 1 3 1 1 3 1 3 1 1 2 3 1 | 244 |
| 1 3 1 2 3 1 1 2 1 1 3 2 2 3 2 3 1 1 2 3 2 2 2 1 | 245 |
| 1 3 1 2 3 1 1 1 3 1 1 1 3 2 3 2 1 3 1 1 2 1 2 2 | 246 |
| 2 3 2 2 1 1 1 2 3 2 1 2 3 2 1 3 2 1 1 2 2 3 1 3 | 247 |
| 2 1 3 2 1 3 2 3 2 3 1 1 3 2 2 1 2 2 2 3 2 2 1 2 | 248 |
| 1 3 2 3 1 1 2 3 2 2 2 3 2 1 1 1 3 1 3 2 2 2 1 1 | 249 |
| 3 1 2 1 1 1 2 3 1 3 1 1 2 2 3 1 3 2 1 1 2 2 3 2 | 250 |
| 2 3 1 2 3 1 3 1 1 1 2 2 3 2 2 2 1 1 3 2 3 2 2 2 | 251 |
| 1 1 1 2 1 1 3 2 1 3 2 3 2 3 1 3 2 1 1 2 1 3 2 1 | 252 |
| 2 1 2 3 1 1 1 2 1 2 3 2 3 1 2 1 3 2 1 1 3 1 3 1 | 253 |
| 1 2 2 3 2 1 1 3 1 3 2 3 1 2 2 1 2 1 3 1 2 3 1 2 | 254 |
| 1 3 1 3 2 1 1 3 1 1 2 3 1 1 1 3 1 3 1 2 1 1 2 1 | 255 |
| 2 1 1 3 2 1 1 3 2 1 3 1 2 3 2 2 1 1 1 3 1 3 1 2 | 256 |
| 1 1 1 2 1 3 1 1 1 3 1 1 2 2 3 2 1 3 1 3 2 1 3 2 | 257 |
| 1 2 1 3 1 2 2 2 1 1 3 2 3 1 1 3 1 3 1 3 2 2 1 2 | 258 |

TABLE IA-continued

Numeric sequences corresponding to nucleotide base patterns of a set of oligonucleotides

| Numeric Pattern | Sequence Identifier |
|---|---|
| 3 1 1 2 3 2 2 2 3 2 1 1 1 2 3 2 1 2 1 3 1 2 1 3 | 259 |
| 1 1 1 2 1 3 1 1 2 3 1 3 2 1 3 2 3 1 1 1 2 1 2 3 | 260 |
| 2 2 3 1 1 2 2 1 2 3 2 1 3 1 3 1 1 1 3 2 1 1 1 3 | 261 |
| 2 1 3 2 1 1 1 2 2 3 1 3 1 3 2 1 3 2 2 3 1 1 2 2 | 262 |
| 2 3 2 1 1 1 1 3 2 3 2 2 2 1 2 1 3 2 3 2 3 2 1 1 2 | 263 |
| 1 2 1 2 3 1 2 2 2 3 1 3 1 2 3 1 3 1 1 2 3 2 1 1 | 264 |
| 1 1 2 1 2 2 3 1 2 1 2 3 2 3 2 2 3 2 3 1 1 1 3 2 1 | 265 |
| 1 3 2 3 1 3 1 2 2 1 2 3 1 3 2 1 2 2 3 1 2 2 2 1 | 266 |
| 2 2 3 2 1 2 2 2 1 3 1 2 1 3 2 3 1 3 1 2 2 1 2 3 | 267 |
| 1 2 1 3 1 1 1 2 3 1 1 1 3 1 2 1 3 1 2 1 3 1 1 3 | 268 |
| 3 1 2 2 3 2 1 2 1 2 3 2 1 1 1 3 2 1 3 2 2 2 1 3 | 269 |
| 2 1 2 3 1 1 2 3 2 2 1 2 2 3 2 3 2 3 2 2 3 1 2 2 | 270 |
| 3 1 2 1 2 2 1 3 2 1 3 1 3 2 1 1 3 2 1 2 1 2 2 3 | 271 |
| 2 3 1 3 1 2 3 1 1 2 2 2 3 2 3 2 2 1 2 3 1 2 1 2 | 272 |
| 2 1 2 3 1 1 2 3 1 1 3 2 1 1 1 3 1 3 1 2 3 2 1 1 | 273 |
| 3 1 3 2 3 1 1 2 2 2 3 2 2 3 2 1 1 2 2 2 3 2 2 2 | 274 |
| 1 3 1 1 1 2 2 3 2 1 3 1 3 2 2 1 1 2 2 3 2 3 2 1 | 275 |
| 3 2 3 2 2 1 1 2 3 1 1 1 3 2 2 3 2 3 1 1 2 1 1 2 | 276 |
| 2 3 2 3 1 2 2 2 3 2 2 1 1 3 1 1 1 3 1 2 2 1 1 2 3 | 277 |
| 1 3 2 1 3 2 1 2 2 3 2 1 1 1 3 2 1 2 1 1 1 3 1 3 | 278 |
| 2 3 1 2 2 3 2 2 3 2 1 2 1 3 2 2 1 2 2 3 2 3 2 1 | 279 |
| 3 1 2 2 3 2 1 3 2 2 2 1 1 2 3 2 2 1 1 3 1 1 2 3 | 280 |
| 1 2 3 1 1 1 2 1 1 3 1 1 1 2 2 3 1 3 2 1 3 1 3 1 | 281 |
| 2 1 2 3 1 2 3 1 2 1 2 2 2 3 2 2 3 2 1 2 3 2 3 2 | 282 |
| 2 2 2 1 3 1 3 2 2 2 3 1 2 2 1 3 2 1 2 3 2 2 2 3 | 283 |
| 1 1 2 1 1 3 1 3 1 2 2 3 2 3 1 2 3 1 3 1 1 1 2 1 | 284 |
| 1 1 2 3 1 1 2 1 3 1 1 2 1 3 1 3 1 1 2 3 2 1 3 1 | 285 |
| 3 2 1 3 2 1 3 2 1 1 2 2 2 3 1 1 2 3 2 2 2 3 1 1 | 286 |
| 1 3 2 3 1 3 2 1 1 2 2 3 1 2 2 3 1 2 2 3 2 2 1 1 | 287 |
| 3 1 1 2 1 1 2 3 2 2 2 1 3 2 3 2 3 2 2 2 3 1 1 1 | 288 |
| 1 2 1 2 3 1 1 1 3 2 1 3 1 3 1 1 1 3 2 3 2 2 1 2 | 289 |
| 2 3 1 3 2 2 1 2 2 3 2 1 2 2 2 1 3 2 2 2 3 1 1 3 | 290 |
| 2 1 3 2 2 3 1 3 2 2 2 1 1 1 3 2 2 3 1 1 1 3 1 1 | 291 |
| 2 1 1 1 3 1 3 2 3 1 2 3 2 1 1 1 2 1 3 1 1 3 2 2 | 292 |
| 2 3 2 1 3 2 3 2 2 2 2 1 3 1 3 2 1 1 3 2 2 1 2 2 1 | 293 |
| 1 3 1 3 1 2 2 1 1 2 3 2 3 2 2 3 1 1 1 3 1 2 2 1 | 294 |
| 3 2 1 1 2 1 1 3 2 2 2 3 2 3 1 1 1 3 1 1 3 1 2 2 1 | 295 |

TABLE IA-continued

Numeric sequences corresponding to nucleotide base patterns of a set of oligonucleotides

| Numeric Pattern | Sequence Identifier |
|---|---|
| 3 1 3 1 2 3 2 2 1 2 1 3 1 2 1 1 2 3 1 1 1 3 1 1 | 296 |
| 2 2 2 1 3 2 2 3 1 2 2 3 2 2 3 1 1 2 1 3 1 3 2 1 | 297 |
| 1 2 2 1 2 2 3 1 1 1 3 2 1 3 1 2 3 2 2 1 3 1 2 3 | 298 |
| 2 2 2 1 2 3 2 3 2 3 1 2 2 3 1 3 2 3 2 2 2 1 1 2 | 299 |
| 2 1 2 2 2 1 3 2 2 1 3 1 2 1 3 1 2 1 3 1 3 1 3 2 | 300 |
| 1 2 3 2 3 2 2 2 1 2 3 2 3 1 1 1 3 1 2 2 2 3 2 1 | 301 |
| 1 2 1 3 2 1 1 2 2 1 3 1 1 3 1 3 1 1 3 1 1 2 3 2 | 302 |
| 2 1 2 3 1 3 2 3 1 2 2 1 3 1 1 2 2 3 2 1 2 2 2 3 | 303 |
| 2 2 1 1 2 3 2 1 2 2 3 2 2 2 1 1 1 3 1 3 2 3 2 3 | 304 |
| 1 2 1 3 1 3 1 1 2 2 1 1 3 1 1 2 2 3 2 2 2 3 1 3 | 305 |
| 3 2 2 1 2 1 1 3 2 1 3 1 1 1 2 3 2 1 2 1 3 1 1 3 | 306 |
| 1 3 2 1 1 2 2 1 3 2 2 2 3 1 1 1 2 3 2 3 2 1 3 2 | 307 |
| 3 1 1 1 3 1 2 2 1 2 3 1 2 2 3 2 1 1 1 3 2 3 1 2 | 308 |
| 3 2 1 1 3 1 2 2 1 3 1 1 3 2 2 1 1 2 3 1 1 3 1 1 | 309 |
| 3 1 3 1 1 2 3 2 2 3 1 1 2 1 1 3 1 1 3 2 1 1 2 2 | 310 |
| 2 2 1 1 3 1 3 2 3 2 2 2 3 1 1 2 1 3 2 3 2 2 2 1 | 311 |
| 1 2 1 1 1 3 1 1 1 3 1 3 2 1 2 3 1 3 1 2 2 1 2 3 | 312 |
| 1 3 2 2 1 2 2 3 1 2 2 3 1 1 3 1 2 3 1 3 1 1 1 2 | 313 |
| 3 2 2 2 3 2 3 2 2 2 3 2 1 2 1 1 3 2 2 3 2 2 1 1 | 314 |
| 2 2 3 2 1 2 3 2 3 1 3 2 2 2 1 3 1 2 2 1 1 2 3 1 | 315 |
| 2 1 3 2 2 1 1 1 3 2 1 2 1 3 2 2 3 2 2 2 3 1 3 2 | 316 |
| 1 1 1 2 2 2 3 2 3 2 2 3 1 3 1 2 2 2 3 2 1 2 1 3 | 317 |
| 2 1 2 2 1 3 2 3 2 2 1 2 3 1 2 1 1 1 3 1 3 1 1 3 | 318 |
| 2 1 2 1 1 3 1 1 3 2 1 1 2 2 2 3 1 3 1 1 3 1 3 2 | 319 |
| 2 1 1 3 2 2 3 1 3 1 2 3 2 2 2 3 2 2 2 3 1 2 1 1 | 320 |
| 3 2 3 2 1 3 1 2 2 2 1 2 3 1 1 2 2 3 1 3 2 1 1 2 | 321 |
| 2 1 2 1 3 1 3 1 1 3 2 3 2 2 2 1 3 2 2 3 2 1 2 1 | 322 |
| 1 2 1 1 1 3 1 1 3 1 1 2 1 3 2 2 3 2 2 3 2 3 2 1 | 323 |
| 1 3 1 2 2 3 1 1 1 2 1 3 1 2 2 1 3 1 1 1 3 2 2 3 | 324 |
| 3 2 2 3 2 2 1 2 1 1 3 1 1 1 2 1 3 2 2 2 3 2 2 3 | 325 |
| 1 3 1 1 1 2 1 3 1 3 2 1 1 3 1 3 2 3 2 2 2 1 1 1 | 326 |
| 1 3 1 3 1 2 1 3 2 1 3 2 1 1 1 2 1 3 2 2 1 2 2 3 | 327 |
| 1 1 1 2 3 1 2 2 3 2 3 2 1 1 3 2 2 1 2 3 2 1 2 3 | 328 |
| 1 1 3 1 1 3 2 1 1 3 1 3 1 3 1 1 1 2 2 2 3 1 1 2 | 329 |
| 3 2 3 2 3 2 1 2 2 2 1 3 2 2 3 1 2 1 1 2 2 3 1 2 | 330 |
| 1 2 2 3 2 2 3 2 2 3 2 2 3 1 3 1 1 1 2 3 2 1 2 2 | 331 |

TABLE IA-continued

Numeric sequences corresponding to nucleotide base patterns of a set of oligonucleotides

| Numeric Pattern | Sequence Identifier |
|---|---|
| 1 3 1 2 1 1 3 2 2 1 1 1 3 2 1 1 1 3 1 3 1 1 2 3 | 332 |
| 2 1 3 2 2 3 1 1 3 2 2 1 3 2 2 2 1 1 3 2 3 2 2 1 | 333 |
| 1 3 2 1 1 3 1 1 2 3 2 1 1 2 1 2 3 1 2 3 1 2 1 3 | 334 |
| 1 2 3 1 3 1 2 2 3 1 1 1 3 1 2 2 2 1 2 3 1 1 2 3 | 335 |
| 2 3 1 2 2 3 1 1 2 2 1 3 1 3 1 3 1 1 2 3 2 1 2 1 | 336 |
| 1 3 2 2 1 3 2 1 1 3 1 3 1 1 2 1 2 1 3 2 3 1 1 2 | 337 |
| 1 2 2 1 1 3 1 2 2 3 2 1 2 1 3 2 2 1 3 2 3 1 2 3 | 338 |
| 3 1 3 1 2 1 1 1 3 1 1 2 2 3 1 1 1 2 1 3 1 1 3 1 | 339 |
| 1 3 1 3 2 1 1 1 2 3 2 2 1 1 3 1 1 1 3 1 1 3 2 2 | 340 |
| 1 1 1 3 2 2 2 3 2 2 1 2 3 2 3 2 3 1 1 3 1 1 2 2 | 341 |
| 1 2 2 3 2 3 2 2 2 1 1 3 1 1 1 2 1 2 3 1 2 3 1 3 | 342 |
| 2 1 2 2 3 1 1 1 2 3 1 3 1 2 3 2 1 2 3 2 1 3 2 2 | 343 |
| 1 2 2 2 3 2 3 2 3 1 2 3 2 2 2 3 1 1 1 2 1 2 3 1 | 344 |
| 2 1 1 3 1 2 1 1 2 1 3 2 3 1 3 1 3 1 1 1 2 2 3 1 | 345 |
| 1 2 2 2 1 2 3 1 2 2 1 3 2 3 2 1 1 3 2 3 2 2 3 2 | 346 |
| 3 1 2 2 1 1 3 1 1 2 1 1 1 3 2 3 2 3 1 1 3 1 1 2 | 347 |
| 3 2 1 1 2 2 3 1 2 3 1 1 3 1 3 2 2 1 3 2 2 2 1 2 | 348 |
| 2 3 2 3 2 2 1 2 3 2 2 1 2 1 1 3 1 1 3 2 3 1 2 1 | 349 |
| 1 3 1 3 1 1 1 2 2 3 1 1 2 2 2 1 3 1 1 1 2 3 2 3 | 350 |
| 2 2 1 2 2 3 1 1 2 3 2 3 1 3 1 1 1 3 2 1 2 2 2 3 | 351 |
| 2 3 2 2 1 1 2 3 1 3 1 1 3 1 2 1 1 2 3 1 2 1 3 2 | 352 |
| 3 1 1 1 3 2 1 2 2 2 3 2 2 3 1 2 2 1 2 2 3 2 2 3 | 353 |
| 2 1 3 2 2 2 1 2 3 2 1 3 2 2 1 1 2 2 3 2 2 3 1 3 | 354 |
| 3 2 2 3 1 1 1 3 1 2 1 3 2 2 2 3 1 2 1 2 3 2 1 2 | 355 |
| 2 2 1 3 1 1 3 1 2 1 3 1 2 2 1 2 2 3 1 3 1 1 1 3 | 356 |
| 1 1 2 1 1 1 2 3 2 2 3 2 3 1 1 1 2 1 3 1 2 3 2 3 1 | 357 |
| 1 3 2 1 1 3 1 1 1 3 2 2 2 1 3 2 2 2 1 3 2 2 1 3 | 358 |
| 2 1 3 2 2 2 1 1 2 3 1 3 1 2 3 2 2 2 3 1 2 1 2 3 | 359 |
| 2 2 1 1 1 3 1 2 3 2 2 1 1 1 3 1 1 2 3 1 3 2 3 1 | 360 |
| 1 1 1 3 2 3 2 3 2 1 2 1 2 3 2 2 1 3 1 1 1 3 2 1 | 361 |
| 1 2 2 1 1 3 2 2 1 2 3 2 3 2 2 2 1 2 3 2 3 2 2 3 | 362 |
| 2 2 2 3 1 1 3 1 1 3 2 3 2 2 2 3 2 1 2 2 1 2 3 2 | 363 |
| 2 3 2 2 1 1 3 1 1 3 2 2 2 1 3 2 2 1 1 1 3 2 2 3 | 364 |
| 2 2 2 1 1 3 2 1 2 1 1 3 1 2 2 3 2 3 2 3 1 3 1 2 | 365 |
| 1 3 1 2 1 2 2 2 3 1 2 1 3 1 2 1 3 1 1 3 1 1 1 3 | 366 |
| 1 2 2 2 1 3 1 3 2 2 3 2 1 1 3 1 1 3 1 2 1 2 2 3 | 367 |
| 3 1 3 1 1 1 1 2 2 3 2 1 1 2 2 3 2 2 1 3 1 3 2 1 2 | 368 |

TABLE IA-continued

Numeric sequences corresponding to nucleotide
base patterns of a set of oligonucleotides

| Numeric Pattern | Sequence Identifier |
|---|---|
| 3 1 1 3 2 1 2 1 2 3 2 2 1 1 3 1 2 3 2 1 1 2 1 3 | 369 |
| 1 1 2 1 2 2 3 1 1 3 1 2 3 2 1 3 2 3 1 3 2 2 1 2 | 370 |
| 3 1 3 2 2 2 1 3 1 1 1 2 3 1 2 1 1 1 3 1 1 2 2 3 | 371 |
| 2 1 1 3 1 1 1 2 3 1 3 2 2 1 2 1 2 3 2 2 3 1 3 1 | 372 |
| 2 2 3 1 2 1 2 1 1 3 1 1 3 2 2 3 2 3 1 2 1 1 3 2 | 373 |
| 1 1 3 2 3 2 2 2 1 1 2 3 2 1 1 3 1 3 1 1 2 3 1 1 | 374 |
| 3 2 2 3 2 3 1 3 1 1 2 2 1 3 1 1 1 2 1 3 2 1 2 1 | 375 |
| 2 2 2 1 3 2 2 2 3 1 2 3 2 3 2 2 2 1 2 3 1 3 1 2 | 376 |
| 3 2 1 1 2 2 3 1 1 1 3 2 1 2 3 1 3 2 1 3 2 1 1 2 | 377 |
| 2 1 3 2 2 3 1 1 2 1 1 3 1 2 2 3 1 3 1 3 1 1 1 2 | 378 |
| 2 2 1 1 3 2 3 1 1 3 2 3 2 2 3 2 2 2 1 2 2 3 1 1 | 379 |
| 1 2 2 3 1 2 2 2 3 2 2 3 1 1 1 2 1 1 3 2 3 2 2 3 | 380 |
| 2 3 1 1 2 2 3 2 2 3 1 2 1 1 3 2 2 1 2 3 1 1 3 1 | 381 |
| 3 2 2 2 3 2 2 1 2 2 3 1 3 2 1 1 3 2 2 3 1 1 2 2 | 382 |
| 2 3 1 2 2 2 1 3 2 1 2 3 2 1 2 2 1 3 1 3 2 2 3 1 | 383 |
| 2 1 1 1 2 1 3 1 3 1 2 3 1 3 1 1 2 1 1 3 1 1 1 3 | 384 |
| 1 3 1 1 2 3 2 2 1 2 1 2 3 2 1 3 1 3 1 1 1 2 2 3 | 385 |
| 1 2 2 2 1 2 3 2 1 3 2 2 3 1 3 1 3 2 3 1 2 1 1 1 | 386 |
| 3 2 1 1 1 3 1 2 1 3 2 2 2 3 1 3 2 1 1 2 2 2 3 1 | 387 |
| 3 1 1 1 2 1 3 2 1 2 1 1 2 3 2 2 1 1 3 2 3 1 3 1 | 388 |
| 1 2 2 3 2 1 2 1 2 2 3 2 3 2 2 3 1 1 3 1 1 1 3 2 | 389 |
| 3 1 3 2 2 1 1 3 2 3 2 1 1 1 2 3 1 1 1 2 3 2 1 1 | 390 |
| 1 2 1 3 1 2 2 3 2 3 2 3 1 1 1 3 1 1 1 3 1 1 2 2 | 391 |
| 2 2 1 1 2 1 3 1 1 3 2 2 2 3 2 1 3 2 1 2 3 1 2 3 | 392 |
| 2 2 3 2 1 2 3 2 3 1 3 1 1 2 1 1 1 3 2 2 2 1 3 2 | 393 |
| 3 2 3 1 2 2 1 3 1 2 1 2 3 1 2 3 1 2 1 2 3 1 1 2 | 394 |
| 2 3 1 1 3 1 1 3 1 1 2 2 2 1 3 1 2 2 2 3 2 1 1 3 | 395 |
| 2 3 2 1 2 3 1 2 2 1 2 2 3 1 2 2 1 3 2 3 2 3 2 2 | 396 |
| 2 3 2 3 1 1 1 3 1 3 1 1 2 3 1 2 1 3 1 2 1 2 2 2 | 397 |
| 1 1 2 2 3 1 1 1 2 3 1 3 2 3 2 3 2 2 2 1 1 3 1 1 | 398 |
| 1 2 2 1 2 1 3 1 3 2 2 1 3 2 2 2 1 3 1 1 2 3 1 3 | 399 |
| 1 1 1 3 1 2 1 3 1 1 1 2 2 3 1 3 2 3 2 1 2 3 1 2 | 400 |
| 3 2 1 3 2 2 2 3 2 2 1 1 2 3 2 2 3 2 1 2 1 1 2 3 | 401 |
| 1 3 1 3 1 2 1 2 2 1 3 1 1 2 3 2 1 1 3 1 1 2 1 3 | 402 |
| 1 3 1 1 3 2 2 2 3 1 1 1 2 1 2 3 1 2 1 3 1 1 2 3 | 403 |
| 2 1 3 1 1 2 3 2 1 1 1 3 2 2 2 1 3 2 1 2 1 3 1 3 | 404 |

TABLE IA-continued

Numeric sequences corresponding to nucleotide base patterns of a set of oligonucleotides

| Numeric Pattern | Sequence Identifier |
|---|---|
| 1 3 2 1 3 1 2 3 2 1 2 3 2 2 1 1 2 3 2 3 1 1 2 1 | 405 |
| 2 3 1 1 1 3 2 3 1 1 1 2 1 2 3 1 1 1 2 3 2 2 3 2 | 406 |
| 1 2 1 3 2 1 2 1 2 2 3 1 3 2 2 2 3 2 1 2 3 1 1 3 | 407 |
| 3 1 1 3 1 1 1 2 3 2 2 2 3 2 1 3 1 1 2 1 1 3 2 1 | 408 |
| 1 1 2 3 1 3 2 1 2 2 3 1 1 3 1 1 1 2 3 2 1 2 1 3 | 409 |
| 3 2 3 1 2 1 3 1 1 2 2 2 3 2 3 2 2 2 1 1 2 3 1 1 | 410 |
| 2 3 2 1 3 2 1 2 3 1 1 3 1 1 2 1 1 2 3 1 1 1 2 3 | 411 |
| 1 2 1 3 1 1 3 2 2 1 1 2 3 1 2 1 1 2 2 3 2 3 2 3 | 412 |
| 3 2 3 1 2 2 3 2 1 1 3 2 1 1 3 2 1 1 1 3 1 2 1 1 | 413 |
| 2 1 2 3 2 1 3 2 2 2 3 2 3 2 2 1 2 2 2 3 1 1 3 1 | 414 |
| 2 3 1 3 2 1 1 3 2 2 2 3 2 1 2 3 2 2 2 1 1 3 2 1 | 415 |
| 2 1 1 1 2 3 2 1 2 3 1 3 2 3 2 3 2 1 1 1 3 1 1 1 | 416 |
| 3 2 1 1 3 1 3 2 1 2 2 3 1 1 1 2 2 1 3 2 1 1 3 1 | 417 |
| 3 2 2 3 1 3 2 3 2 1 1 1 3 1 2 2 1 2 2 3 1 2 1 1 | 418 |
| 1 3 2 1 2 3 1 3 2 2 1 2 2 1 3 1 2 1 1 1 3 2 3 1 | 419 |
| 1 2 2 2 3 2 1 2 1 3 1 3 2 2 2 3 2 3 2 2 3 2 1 2 | 420 |
| 2 1 1 2 2 1 3 2 1 3 2 3 2 3 2 2 3 1 1 1 2 2 2 3 | 421 |
| 2 3 2 1 2 2 3 1 3 1 2 2 3 2 2 1 2 2 3 2 1 2 2 3 | 422 |
| 3 2 2 1 2 2 2 1 3 1 1 1 3 1 3 1 2 1 1 2 2 3 1 3 2 2 | 423 |
| 2 2 3 1 3 2 2 3 2 3 1 2 2 1 1 3 2 1 3 2 1 2 1 2 | 424 |
| 3 1 2 1 3 2 1 2 1 1 1 2 3 1 2 2 3 1 1 3 2 1 1 2 3 | 425 |
| 3 2 3 1 1 1 3 1 2 1 2 2 2 3 1 3 1 3 1 2 1 1 1 2 | 426 |
| 1 3 2 2 1 2 3 1 2 2 2 3 1 1 3 1 1 1 2 2 3 2 2 3 | 427 |
| 3 2 1 1 3 2 1 2 2 2 3 1 1 2 2 2 3 1 2 3 1 3 2 2 | 428 |
| 2 1 1 2 1 3 2 3 2 2 1 2 1 1 3 2 3 1 1 1 1 3 1 3 2 | 429 |
| 1 1 1 2 3 1 1 2 2 3 1 2 3 2 3 2 1 2 1 2 3 1 1 3 | 430 |
| 1 3 1 1 1 3 2 3 1 3 2 2 3 2 2 1 1 3 2 1 2 2 2 1 | 431 |
| 2 2 2 1 2 3 2 3 2 3 1 1 2 2 3 2 3 2 1 2 1 2 1 3 | 432 |
| 3 2 1 1 2 1 2 3 1 2 1 3 1 1 1 2 3 2 1 1 1 3 1 3 | 433 |
| 3 1 3 1 1 2 2 3 2 2 2 1 1 1 3 1 2 1 3 2 2 3 2 1 | 434 |
| 3 1 1 2 2 2 3 2 2 1 1 3 1 1 2 3 1 3 2 2 2 3 1 2 | 435 |
| 1 2 1 3 2 3 1 2 3 1 2 2 1 1 1 3 1 3 1 1 2 2 2 3 | 436 |
| 1 2 1 3 1 2 3 2 2 2 1 3 2 2 3 1 3 1 2 2 1 2 2 3 | 437 |
| 1 1 3 1 3 2 3 2 1 1 1 2 1 3 1 1 1 3 2 3 1 2 1 2 | 438 |
| 2 3 2 2 3 2 1 2 2 3 1 2 2 3 2 2 2 3 1 3 1 2 1 1 1 2 | 439 |
| 2 1 3 2 1 2 1 3 2 3 1 3 1 1 1 3 1 3 2 2 1 1 1 2 | 440 |
| 1 1 1 3 1 2 1 1 3 1 1 1 3 1 3 1 2 3 1 2 3 2 2 2 | 441 |

TABLE IA-continued

Numeric sequences corresponding to nucleotide base patterns of a set of oligonucleotides

| Numeric Pattern | Sequence Identifier |
|---|---|
| 3 1 1 3 2 2 1 2 2 3 1 1 1 2 1 3 1 3 1 1 3 2 1 2 | 442 |
| 1 2 3 2 1 2 3 2 1 2 1 3 1 1 1 3 1 3 2 1 1 1 2 3 | 443 |
| 3 1 2 3 2 2 2 3 2 1 1 1 3 1 2 2 3 1 1 1 2 2 3 1 | 444 |
| 1 1 2 2 2 1 3 1 3 1 3 2 1 2 2 2 3 2 3 2 2 3 2 1 | 445 |
| 1 1 2 2 2 3 2 2 2 3 1 1 1 3 1 1 1 3 2 1 1 3 2 3 | 446 |
| 1 1 1 3 1 3 2 1 3 2 3 2 2 1 2 2 3 2 2 1 3 1 2 1 | 447 |
| 3 2 1 2 3 2 2 3 2 1 2 1 2 3 2 2 3 2 2 3 1 2 1 2 | 448 |
| 3 2 1 3 1 1 2 2 2 3 2 2 3 1 3 2 1 2 2 2 3 2 1 1 | 449 |
| 1 2 3 1 1 2 2 2 1 3 2 2 1 3 2 3 2 1 1 3 1 1 1 3 | 450 |
| 1 2 3 1 2 1 1 3 1 1 1 2 3 2 2 3 1 2 3 1 1 3 2 1 | 451 |
| 2 2 3 1 2 3 1 2 3 1 1 3 1 2 1 1 2 3 2 1 3 1 2 1 | 452 |
| 1 3 1 2 3 1 2 1 2 3 1 2 1 2 1 3 1 2 2 1 3 1 2 3 | 453 |
| 2 2 3 1 1 1 3 2 2 1 3 1 1 1 3 1 2 1 3 1 2 3 2 2 | 454 |
| 3 2 2 2 1 1 2 3 2 2 1 3 2 2 1 3 1 1 1 3 2 1 1 3 | 455 |
| 3 1 3 1 2 2 2 1 1 3 2 2 2 3 1 1 3 2 3 1 1 1 2 1 | 456 |
| 2 2 2 3 2 2 1 3 2 1 3 2 2 3 2 2 1 2 1 1 3 1 3 1 | 457 |
| 2 1 2 3 1 3 1 1 2 1 3 2 2 2 3 2 2 1 3 2 3 1 1 2 | 458 |
| 2 2 3 1 1 1 3 2 2 2 1 1 1 3 1 1 3 1 3 1 2 1 1 3 | 459 |
| 1 1 3 2 3 1 3 2 2 3 1 1 1 2 3 1 1 1 2 1 2 3 2 2 | 460 |
| 3 2 2 1 3 1 1 1 2 3 1 1 1 2 3 1 3 2 1 3 2 2 1 2 | 461 |
| 2 1 1 3 2 1 2 2 3 2 1 2 2 2 3 2 3 2 3 2 3 2 1 2 | 462 |
| 2 3 2 1 2 2 1 3 2 1 1 1 3 1 1 3 1 3 1 3 1 1 2 1 | 463 |
| 3 1 3 1 1 3 1 3 1 1 1 2 1 1 3 2 2 3 1 1 1 2 1 1 | 464 |
| 3 2 1 1 1 3 2 1 3 1 1 1 2 1 3 1 1 2 2 3 1 3 2 2 | 465 |
| 3 2 3 2 3 2 2 1 2 2 2 3 2 2 2 3 2 1 1 1 3 2 1 2 | 466 |
| 2 2 2 3 1 2 3 2 1 2 3 1 1 2 1 2 1 3 2 1 2 3 1 3 | 467 |
| 1 1 3 1 2 2 3 2 3 2 3 1 1 2 1 3 2 2 3 1 1 1 2 2 | 468 |
| 2 1 2 1 1 1 3 2 2 2 3 1 1 3 1 2 3 1 3 2 3 1 2 1 | 469 |
| 1 3 1 2 1 1 1 3 1 3 1 2 2 2 1 1 3 1 2 3 2 1 2 3 | 470 |
| 3 1 1 3 1 1 2 2 1 1 3 2 2 3 1 3 1 1 2 2 1 1 3 1 | 471 |
| 2 1 3 1 3 1 1 1 2 2 2 3 1 2 1 1 1 3 1 1 1 3 1 3 | 472 |
| 1 1 1 3 2 2 2 1 2 3 1 1 3 2 2 1 2 2 3 1 3 2 1 3 | 473 |
| 1 1 1 2 1 3 2 3 2 1 1 3 2 1 1 1 3 1 3 1 2 3 1 2 | 474 |
| 2 1 2 3 1 2 3 1 2 2 2 1 3 2 2 1 2 1 1 3 1 3 2 3 | 475 |
| 2 1 3 1 2 1 1 1 2 3 2 2 1 2 3 1 2 3 1 3 2 1 1 3 | 476 |
| 1 3 1 2 2 3 1 2 2 3 2 3 1 2 3 1 2 2 2 3 2 1 2 1 | 477 |

TABLE IA-continued

Numeric sequences corresponding to nucleotide base patterns of a set of oligonucleotides

| Numeric Pattern | Sequence Identifier |
|---|---|
| 2 2 1 1 3 1 1 3 1 1 2 2 3 2 1 2 1 2 3 1 3 1 3 2 | 478 |
| 3 2 1 3 1 1 2 3 2 2 2 1 3 1 3 2 2 3 1 1 2 1 2 1 | 479 |
| 3 1 3 1 1 1 2 1 3 2 1 1 3 1 1 3 2 1 1 1 2 1 3 1 | 480 |
| 1 2 2 3 1 1 3 2 2 3 2 2 1 2 3 2 3 1 1 3 1 2 2 2 | 481 |
| 2 1 1 1 2 3 2 2 3 2 3 2 1 3 1 3 2 1 1 2 2 1 3 1 | 482 |
| 1 1 1 2 1 1 3 1 3 2 2 2 3 1 3 1 1 3 2 2 3 2 2 2 | 483 |
| 1 3 2 2 3 2 1 1 2 1 1 3 1 1 3 2 3 1 2 2 2 1 1 3 | 484 |
| 3 2 2 1 3 1 1 1 2 3 2 1 2 1 2 1 3 1 3 2 2 1 3 1 2 | 485 |
| 2 2 3 1 2 1 2 2 3 1 1 1 3 1 3 1 1 1 3 2 2 1 2 3 | 486 |
| 2 2 1 1 1 3 1 3 1 3 1 1 1 2 3 2 2 2 3 1 2 2 1 3 | 487 |
| 2 3 2 3 1 1 2 2 2 3 1 3 2 1 2 2 1 3 2 1 1 3 1 1 | 488 |
| 2 1 1 2 2 2 3 1 1 2 3 2 3 1 1 1 3 2 2 3 2 2 1 3 | 489 |
| 1 2 3 2 3 2 2 2 3 1 1 1 3 1 2 3 1 2 3 1 2 2 2 1 | 490 |
| 1 1 3 2 2 1 2 3 2 2 3 1 2 1 2 2 3 1 3 2 3 1 1 1 | 491 |
| 2 1 3 1 2 1 1 1 3 1 1 3 1 2 1 3 1 3 1 2 2 2 1 3 | 492 |
| 3 1 2 3 1 1 2 3 2 1 3 1 2 1 2 1 2 3 2 1 1 2 3 1 | 493 |
| 3 1 1 3 1 1 2 1 3 2 2 2 1 2 3 2 1 1 1 2 3 1 2 3 | 494 |
| 3 2 1 3 2 1 2 1 2 1 3 2 2 1 1 1 3 1 2 3 1 3 2 2 | 495 |
| 3 2 2 1 2 2 2 3 2 3 2 1 2 3 1 2 2 1 2 3 1 2 2 3 | 496 |
| 1 3 1 3 1 2 2 1 3 1 1 1 2 2 3 1 3 1 3 1 1 2 2 1 | 497 |
| 3 2 1 2 3 1 2 1 3 1 3 2 2 2 1 2 1 3 2 3 1 2 1 1 | 498 |
| 3 2 2 1 3 1 1 1 3 1 1 2 3 1 1 1 2 2 3 1 1 3 2 1 | 499 |
| 1 1 3 1 1 2 3 1 3 1 1 2 1 2 1 3 1 3 1 2 3 1 1 2 | 500 |
| 1 1 1 3 1 3 1 1 2 1 3 2 3 2 2 2 1 1 3 1 1 3 1 2 | 501 |
| 3 1 2 3 2 3 2 2 1 2 2 3 1 2 1 3 1 1 1 2 2 1 3 1 | 502 |
| 2 1 3 1 3 2 2 1 2 1 3 1 3 1 2 1 2 2 3 2 1 2 3 1 | 503 |
| 3 1 3 1 3 2 2 3 1 1 2 1 1 3 2 2 1 1 1 3 1 2 1 2 | 504 |
| 1 3 1 2 1 2 3 1 1 1 2 1 3 1 2 2 3 2 2 1 3 1 3 1 | 505 |
| 3 1 3 2 3 1 1 2 1 3 1 1 1 3 1 2 1 2 3 2 2 1 1 2 | 506 |
| 1 1 1 3 1 3 1 2 1 2 2 3 1 1 3 1 3 1 1 2 1 1 1 3 | 507 |
| 3 2 2 1 2 1 3 1 1 2 1 1 3 2 2 3 2 1 1 1 3 2 3 2 | 508 |
| 2 3 1 2 1 3 2 1 2 3 1 2 1 1 2 3 2 3 2 2 2 1 2 3 | 509 |
| 2 2 2 3 2 2 3 2 2 1 1 3 2 1 2 3 2 3 1 2 2 2 1 3 | 510 |
| 2 1 1 1 3 2 3 2 2 2 3 2 3 2 2 1 1 1 3 1 2 2 1 1 3 | 511 |
| 2 3 2 3 2 2 2 3 1 2 2 3 1 2 2 1 1 2 3 2 2 1 2 3 | 512 |
| 1 2 2 1 1 2 3 1 1 2 3 1 3 2 3 2 2 3 2 1 1 2 3 2 | 513 |
| 2 1 3 1 2 3 2 2 2 2 3 2 3 1 3 2 2 2 3 1 2 1 2 2 1 | 514 |

TABLE IA-continued

Numeric sequences corresponding to nucleotide
base patterns of a set of oligonucleotides

| Numeric Pattern | Sequence Identifier |
|---|---|
| 3 1 1 2 3 1 1 2 1 3 2 1 1 2 1 3 1 2 3 1 2 2 2 3 | 515 |
| 1 1 2 1 3 2 3 2 3 2 2 3 2 2 1 2 1 2 3 1 2 2 1 3 | 516 |
| 2 1 3 1 2 2 1 3 1 1 3 1 2 3 2 2 3 2 3 2 1 2 2 1 | 517 |
| 1 1 2 3 2 3 2 3 2 3 2 2 1 1 1 2 3 1 1 2 2 2 3 2 | 518 |
| 3 1 1 2 2 1 1 3 2 1 2 1 2 3 1 3 2 3 2 1 3 1 1 1 | 519 |
| 2 2 1 2 2 3 2 3 2 3 2 1 1 3 2 1 3 2 3 2 1 1 1 2 | 520 |
| 3 2 1 3 2 1 1 1 3 1 3 1 1 2 2 3 2 2 2 1 3 2 1 2 | 521 |
| 1 1 3 2 2 2 3 2 1 1 3 1 1 3 2 1 3 2 2 3 1 1 2 1 | 522 |
| 1 3 2 2 1 2 1 3 2 1 2 1 3 2 1 3 2 1 2 1 3 1 3 1 | 523 |
| 3 1 1 1 3 1 1 1 2 3 2 3 2 1 2 1 3 2 2 2 1 1 2 3 | 524 |
| 2 2 3 2 3 1 3 2 1 1 2 3 1 1 2 3 1 2 3 2 1 2 2 1 | 525 |
| 3 2 1 3 1 3 2 2 3 2 1 1 1 2 1 3 1 3 1 1 2 1 1 1 | 526 |
| 1 2 2 1 1 2 3 2 1 3 1 2 2 3 2 1 1 3 1 3 1 2 1 3 | 527 |
| 2 2 1 3 2 3 2 3 2 2 2 3 2 1 3 1 2 1 3 1 1 2 2 1 | 528 |
| 1 3 1 3 1 3 2 2 2 3 2 3 2 1 2 1 2 3 2 1 2 1 1 1 | 529 |
| 2 2 1 1 3 2 2 2 1 3 2 3 1 3 1 2 2 2 3 2 2 1 1 3 | 530 |
| 1 2 3 1 1 3 2 2 2 1 2 2 3 1 1 2 1 3 2 1 3 2 3 1 | 531 |
| 1 2 1 2 2 2 3 2 3 2 2 3 2 1 2 3 2 2 2 3 2 3 1 1 | 532 |
| 1 1 1 3 2 3 2 2 2 1 2 1 3 1 1 3 1 2 2 2 3 1 2 3 | 533 |
| 1 1 3 1 3 1 2 1 2 3 1 2 2 2 3 2 2 1 3 2 2 3 2 1 | 534 |
| 1 1 3 1 1 3 1 1 1 2 3 1 3 2 3 1 2 1 1 2 3 2 1 1 | 535 |
| 2 1 3 2 3 2 2 2 3 1 2 1 2 3 2 2 1 1 3 1 1 3 2 2 | 536 |
| 3 2 1 3 1 1 1 3 2 3 1 2 1 3 1 2 2 1 3 2 1 1 2 1 | 537 |
| 3 1 2 1 1 1 2 3 2 2 1 1 3 2 2 1 3 2 1 2 3 1 2 3 | 538 |
| 1 3 1 2 2 1 3 1 1 3 1 1 2 2 3 2 2 2 1 3 1 1 2 3 | 539 |
| 1 2 1 2 2 2 3 1 3 1 1 1 3 2 3 2 3 1 1 1 2 3 1 1 2 | 540 |
| 2 3 1 3 2 1 1 1 2 1 3 2 2 2 1 2 3 1 3 2 1 3 2 1 | 541 |
| 2 2 1 3 1 3 1 3 2 1 3 1 2 1 1 1 3 1 2 2 2 3 1 2 | 542 |
| 1 2 2 3 2 2 2 1 1 3 2 2 3 2 2 3 1 2 1 1 3 1 2 3 | 543 |
| 3 2 2 3 2 1 1 1 3 2 2 1 1 1 3 2 3 2 3 1 1 2 2 2 | 544 |
| 1 2 1 3 1 2 2 3 2 3 2 3 2 2 2 3 2 2 1 2 1 3 2 1 | 545 |
| 3 2 1 1 3 2 2 1 2 2 3 1 3 1 1 2 3 1 2 1 1 2 1 3 | 546 |
| 2 1 3 1 2 2 1 3 2 2 3 1 2 1 1 1 3 2 3 2 3 2 1 1 2 | 547 |
| 1 1 1 2 3 2 1 1 1 2 3 1 1 3 1 3 2 3 2 2 2 3 2 2 | 548 |
| 3 1 2 1 3 1 1 1 3 1 1 1 2 3 2 1 2 1 2 1 3 2 3 1 2 | 549 |
| 2 1 2 1 3 1 3 2 3 2 1 2 3 2 2 1 2 3 1 2 1 1 1 3 | 550 |

TABLE IA-continued

Numeric sequences corresponding to nucleotide
base patterns of a set of oligonucleotides

| Numeric Pattern | Sequence Identifier |
|---|---|
| 2 1 2 3 1 1 3 2 3 1 2 1 1 3 1 2 3 1 1 3 1 1 2 2 | 551 |
| 2 3 2 2 3 1 3 1 1 2 1 3 2 1 1 3 1 3 1 1 2 2 2 1 | 552 |
| 2 1 3 1 2 1 1 2 3 2 3 1 1 3 2 1 1 2 1 1 3 2 3 1 | 553 |
| 3 2 1 2 2 1 2 3 1 2 3 1 2 1 3 2 1 3 2 1 1 3 2 1 | 554 |
| 1 3 1 2 1 2 3 1 2 2 2 1 3 2 1 2 2 3 1 1 2 3 2 3 | 555 |
| 1 1 2 2 1 1 3 2 2 2 3 2 1 3 1 3 2 3 1 2 2 2 3 1 | 556 |
| 1 1 3 1 1 1 2 1 3 1 2 3 2 1 3 2 1 1 3 1 2 3 2 2 | 557 |
| 2 2 3 1 3 1 1 3 2 2 3 2 2 3 2 1 1 2 1 1 3 1 1 2 | 558 |
| 1 3 2 3 2 3 1 1 1 2 1 3 2 3 1 1 1 3 2 2 2 1 1 1 | 559 |
| 2 2 2 1 2 3 2 1 3 2 1 3 1 2 2 2 1 2 3 2 3 1 1 3 | 560 |
| 1 2 2 1 1 2 3 1 3 1 1 1 2 2 1 3 2 3 2 3 2 2 1 3 | 561 |
| 1 2 3 2 2 1 1 2 1 3 2 3 1 2 1 3 2 1 1 1 3 2 3 1 | 562 |
| 2 1 2 3 2 2 3 1 2 1 1 1 2 3 1 2 2 1 2 3 1 3 2 3 | 563 |
| 2 2 1 2 2 1 3 1 3 2 2 3 2 3 2 3 2 3 1 2 1 2 1 2 | 564 |
| 2 3 2 2 3 2 2 1 2 3 1 2 2 3 1 3 2 2 1 3 1 1 2 1 | 565 |
| 1 1 2 2 2 3 1 3 2 2 1 1 3 1 1 3 1 1 3 2 3 2 1 1 | 566 |
| 1 1 1 3 1 2 1 1 1 3 2 2 1 1 3 2 3 2 2 2 3 2 1 3 | 567 |
| 2 3 2 2 3 1 3 1 2 3 1 2 1 2 2 3 2 1 2 1 1 3 2 2 | 568 |
| 2 1 1 1 2 1 3 2 3 1 1 2 3 1 3 2 2 1 2 1 3 1 3 2 | 569 |
| 1 2 1 3 1 2 3 2 2 1 2 3 1 2 1 3 2 2 1 3 2 2 1 3 | 570 |
| 3 2 2 1 1 3 2 3 1 1 3 1 2 1 2 3 2 1 2 2 3 2 2 1 | 571 |
| 2 1 1 3 1 1 1 3 2 1 1 1 3 2 2 2 3 2 1 3 1 2 3 2 | 572 |
| 1 1 3 1 3 1 1 1 3 2 2 2 3 1 2 2 3 1 1 2 1 1 1 3 | 573 |
| 1 2 1 2 2 1 3 1 2 3 2 3 1 3 2 2 1 2 1 2 3 2 3 2 | 574 |
| 1 3 2 2 2 3 1 3 2 2 2 1 3 2 1 2 2 3 2 3 1 1 2 1 | 575 |
| 1 2 3 2 2 1 1 1 2 3 1 3 1 3 1 2 2 3 2 3 2 1 2 1 | 576 |
| 2 1 1 1 2 3 2 2 3 2 3 1 2 2 1 2 2 3 2 3 1 3 1 2 | 577 |
| 2 1 1 3 1 1 2 2 3 1 1 3 2 1 1 3 1 3 2 2 1 2 2 3 | 578 |
| 1 3 1 3 1 2 1 3 1 1 2 2 1 1 3 2 2 2 3 2 2 2 3 1 2 | 579 |
| 3 1 1 3 2 1 2 3 2 2 1 1 3 1 1 1 2 1 2 3 2 1 1 3 | 580 |
| 2 1 2 2 2 3 2 3 1 2 2 1 1 3 1 1 3 2 2 3 1 3 1 1 | 581 |
| 1 3 2 2 1 3 1 1 2 2 2 3 2 3 2 1 3 2 1 3 1 1 2 2 | 582 |
| 1 1 3 2 2 2 1 2 2 3 2 2 3 1 2 3 2 2 3 2 1 2 2 3 | 583 |
| 3 1 1 2 3 1 3 2 2 2 1 1 3 1 3 2 2 2 1 2 1 3 2 1 | 584 |
| 1 3 2 3 1 1 3 1 2 2 3 2 2 2 3 2 1 3 2 1 2 1 1 1 | 585 |
| 1 3 2 2 3 1 1 1 2 3 1 3 2 1 2 2 1 1 3 2 1 1 2 3 | 586 |
| 1 2 3 2 3 2 2 2 1 2 2 2 3 1 3 1 2 3 1 3 2 1 1 2 2 | 587 |

TABLE IA-continued

Numeric sequences corresponding to nucleotide base patterns of a set of oligonucleotides

| Numeric Pattern | Sequence Identifier |
|---|---|
| 1 1 1 2 1 3 2 3 2 2 3 2 2 3 1 1 3 2 2 3 2 2 1 2 | 588 |
| 3 2 1 3 1 3 1 1 1 3 1 2 1 2 1 2 3 2 1 3 2 2 2 1 | 589 |
| 3 1 3 1 3 2 1 2 2 2 3 1 2 3 1 1 2 3 1 2 2 1 2 1 | 590 |
| 3 1 3 2 1 2 1 1 3 2 2 2 1 3 2 3 2 1 2 1 2 2 3 1 | 591 |
| 1 2 1 1 2 3 2 3 1 2 2 1 2 2 3 1 2 2 3 1 3 1 3 1 | 592 |
| 2 2 1 3 2 2 3 2 2 1 2 3 2 3 1 3 1 3 2 1 1 2 1 1 | 593 |
| 1 1 1 2 3 1 3 2 1 2 1 2 2 3 1 1 2 2 3 2 3 1 2 3 | 594 |
| 1 1 2 2 1 3 1 1 3 2 1 1 3 2 1 3 1 3 2 2 2 1 1 3 | 595 |
| 2 3 2 1 1 3 2 2 2 1 1 1 3 2 1 1 3 1 1 1 2 3 2 3 | 596 |
| 3 1 1 1 2 3 1 2 1 1 3 2 2 3 1 2 1 2 1 1 3 1 1 3 | 597 |
| 1 1 2 3 1 3 2 1 3 2 2 2 3 2 1 2 2 2 3 1 3 2 2 2 | 598 |
| 1 3 2 3 1 1 2 3 2 1 1 3 1 2 2 1 2 3 2 1 2 2 2 3 | 599 |
| 3 2 1 1 2 2 3 1 1 2 2 3 1 1 1 3 1 2 1 1 3 2 3 2 | 600 |
| 2 1 2 3 2 2 2 1 1 3 2 1 3 2 3 1 1 1 2 1 3 1 3 2 | 601 |
| 3 2 1 2 2 3 1 1 1 2 2 3 1 1 2 2 1 3 1 1 3 2 1 3 | 602 |
| 1 1 2 1 2 3 2 1 1 2 3 2 1 3 2 2 3 1 1 1 3 2 3 1 | 603 |
| 2 3 1 1 2 1 2 2 3 1 3 1 1 2 2 1 2 3 1 3 1 3 2 2 | 604 |
| 2 1 3 2 3 2 1 1 1 2 3 1 2 3 1 1 3 1 1 1 3 2 1 2 | 605 |
| 3 2 1 2 3 2 3 2 1 1 1 3 1 1 1 2 2 2 3 1 2 3 2 1 | 606 |
| 1 1 2 2 3 2 2 2 3 1 1 1 3 2 2 2 3 2 2 3 1 3 1 1 | 607 |
| 1 1 2 2 3 2 2 2 3 1 3 2 1 3 2 1 2 2 1 3 2 1 3 2 | 608 |
| 2 1 1 2 2 3 1 3 2 2 2 3 1 1 2 1 1 3 1 3 1 3 2 2 | 609 |
| 2 3 2 2 3 1 2 2 3 2 1 1 3 2 3 2 2 2 1 2 2 3 2 2 | 610 |
| 3 1 1 1 2 2 2 3 2 3 1 3 2 1 2 3 2 1 2 2 2 3 1 1 | 611 |
| 2 1 1 3 1 1 2 3 1 1 2 3 2 3 1 1 3 2 3 1 1 2 1 2 | 612 |
| 2 1 1 2 3 2 3 1 1 3 2 2 2 3 2 3 1 1 1 3 1 2 1 2 | 613 |
| 2 2 3 2 1 2 1 2 3 1 1 1 3 2 1 1 3 1 1 3 1 1 3 2 | 614 |
| 2 1 3 1 3 1 3 1 1 3 1 1 3 1 1 1 2 1 1 3 1 1 2 1 | 615 |
| 1 2 2 2 3 1 1 1 2 3 2 2 1 1 2 3 1 3 1 3 1 3 1 2 | 616 |
| 2 2 3 2 3 2 3 2 1 2 1 2 1 3 2 1 2 2 1 3 1 1 2 3 | 617 |
| 1 2 2 3 2 2 1 3 2 1 2 2 3 1 2 3 2 3 1 1 3 2 2 1 | 618 |
| 2 3 2 2 2 3 2 1 2 2 2 3 1 1 2 3 1 1 1 2 3 1 1 3 | 619 |
| 2 3 2 2 1 3 1 2 2 2 3 2 3 2 2 1 1 1 2 3 2 1 3 2 2 | 620 |
| 2 1 2 1 3 1 3 2 1 2 2 2 3 2 1 2 1 3 1 3 1 3 1 1 1 | 621 |
| 1 1 1 2 1 3 2 1 1 3 1 2 2 3 2 1 3 2 2 3 2 2 3 1 | 622 |
| 2 3 1 3 2 3 2 3 1 2 2 2 1 2 3 1 2 2 1 1 3 2 2 1 | 623 |

TABLE IA-continued

Numeric sequences corresponding to nucleotide
base patterns of a set of oligonucleotides

| Numeric Pattern | Sequence Identifier |
|---|---|
| 1 3 1 1 2 2 2 3 2 2 3 2 1 3 2 3 2 2 1 2 3 1 2 2 | 624 |
| 3 1 2 2 3 1 1 3 1 1 1 3 1 1 1 2 1 3 2 2 2 3 1 1 | 625 |
| 3 1 2 1 1 2 1 3 1 3 1 1 2 1 3 2 1 3 1 3 2 2 1 1 | 626 |
| 3 1 2 2 3 1 1 1 2 2 2 3 2 1 3 2 2 1 2 1 3 2 3 1 | 627 |
| 3 1 2 2 2 1 1 3 1 1 3 1 2 3 1 1 2 1 1 2 3 2 1 3 | 628 |
| 2 2 2 3 1 3 1 3 1 1 1 3 2 1 3 1 1 2 1 1 3 1 2 1 | 629 |
| 3 1 2 2 1 1 3 1 3 2 1 1 1 2 3 1 3 2 1 2 1 1 3 1 | 630 |
| 2 2 2 3 1 2 1 3 1 1 2 2 3 1 1 1 2 2 2 3 1 3 1 3 | 631 |
| 2 3 1 1 3 1 1 3 1 3 2 3 2 2 1 2 1 1 3 1 2 2 2 1 | 632 |
| 3 2 3 1 1 1 1 2 3 1 2 2 2 1 3 1 3 2 1 1 2 1 1 3 2 | 633 |
| 1 1 1 2 1 1 3 1 1 2 1 3 1 3 1 3 1 3 1 1 1 3 2 2 | 634 |
| 3 2 2 3 2 1 1 1 3 2 1 1 2 1 3 1 3 1 1 1 2 2 1 2 | 635 |
| 1 3 2 3 1 2 2 2 1 3 1 2 2 1 2 3 2 3 1 2 3 1 2 2 | 636 |
| 1 3 1 3 2 1 2 1 3 2 2 2 1 3 1 2 2 2 1 2 3 2 1 3 | 637 |
| 1 2 3 1 2 2 1 3 1 2 1 3 2 3 1 1 1 2 2 3 2 2 1 3 | 638 |
| 1 2 3 1 1 1 1 2 3 2 1 2 2 1 3 2 2 2 1 3 1 3 2 2 3 | 639 |
| 1 2 1 2 2 3 1 3 2 3 1 3 1 3 2 2 1 2 2 3 2 2 1 1 | 640 |
| 1 3 1 2 3 2 3 2 1 2 2 3 1 1 2 2 1 1 3 1 1 3 2 2 | 641 |
| 2 1 1 2 3 2 3 2 2 3 1 2 1 3 1 1 2 1 3 1 3 1 2 1 | 642 |
| 1 1 1 2 2 1 3 2 2 3 1 1 1 3 2 1 2 3 1 3 1 1 1 3 | 643 |
| 2 2 2 1 3 1 3 2 2 3 1 1 3 1 1 1 2 3 2 2 1 1 2 3 | 644 |
| 3 1 2 2 3 2 2 3 1 2 2 1 2 2 3 1 2 3 1 1 2 2 2 3 | 645 |
| 2 3 2 2 3 2 2 3 2 2 3 1 1 2 2 3 1 1 3 1 1 2 2 1 | 646 |
| 1 2 2 1 1 3 2 1 1 3 1 1 2 2 3 1 3 1 3 2 2 2 3 1 | 647 |
| 3 2 1 2 3 2 2 3 2 1 1 2 3 2 1 2 2 1 1 3 1 1 1 3 | 648 |
| 2 1 3 2 2 3 2 3 1 2 2 2 1 2 3 2 1 1 2 3 1 2 2 3 | 649 |
| 2 3 1 2 1 1 1 2 3 1 1 1 3 2 2 2 1 2 1 3 1 3 1 3 1 | 650 |
| 3 2 1 1 3 1 2 2 3 2 2 2 3 2 1 2 3 1 2 1 1 3 1 2 | 651 |
| 2 2 3 1 1 2 2 1 1 3 1 3 2 1 1 3 1 2 3 2 2 2 1 3 | 652 |
| 1 1 3 2 3 2 2 2 3 2 2 2 1 3 1 3 2 1 1 1 3 1 2 1 | 653 |
| 1 3 1 3 1 3 1 2 1 1 1 3 2 1 2 1 3 1 1 3 2 2 1 1 | 654 |
| 1 2 2 1 2 3 1 1 2 1 3 2 2 1 3 1 1 1 3 1 3 1 3 2 | 655 |
| 2 2 3 2 2 3 1 2 1 2 2 1 3 1 3 1 1 2 3 2 3 2 2 2 | 656 |
| 2 2 2 1 2 2 3 1 3 1 3 2 2 2 3 2 2 1 2 2 2 3 2 3 | 657 |
| 1 3 2 3 2 2 1 1 3 1 1 1 3 2 2 3 1 2 2 1 2 2 3 1 2 | 658 |
| 3 1 3 1 1 1 2 3 1 2 2 3 1 1 2 3 2 2 3 1 2 1 1 2 | 659 |
| 3 1 2 1 1 3 2 1 2 2 1 3 2 1 2 3 1 3 2 3 2 1 1 2 | 660 |

TABLE IA-continued

Numeric sequences corresponding to nucleotide base patterns of a set of oligonucleotides

| Numeric Pattern | Sequence Identifier |
|---|---|
| 2 2 2 3 1 2 2 2 1 1 3 1 3 2 3 2 2 3 1 1 2 3 2 1 | 661 |
| 1 1 3 2 2 1 3 2 1 1 1 2 1 3 1 3 2 1 3 1 1 1 3 1 | 662 |
| 3 2 1 1 1 3 2 1 2 3 1 1 2 1 2 3 2 3 1 1 1 2 3 2 | 663 |
| 2 1 1 2 1 1 3 2 3 2 3 2 2 3 2 3 1 1 2 3 2 1 1 2 | 664 |
| 1 1 1 3 1 2 2 2 1 3 1 3 2 1 3 1 1 1 3 1 3 1 1 2 | 665 |
| 2 2 1 3 2 2 2 3 1 3 2 2 3 1 1 1 2 1 3 2 1 1 1 3 | 666 |
| 2 1 1 2 1 3 2 1 2 3 1 3 2 1 1 3 1 2 2 3 1 1 1 3 | 667 |
| 3 1 1 3 1 2 2 1 3 1 2 2 3 1 2 3 2 2 1 3 2 2 1 1 | 668 |
| 2 1 1 1 3 1 3 1 3 1 1 3 2 2 1 3 2 1 1 2 1 3 1 1 | 669 |
| 2 1 1 3 2 1 2 3 1 3 1 1 1 2 3 1 2 3 2 3 2 2 1 2 | 670 |
| 3 1 3 2 2 2 3 2 2 2 3 2 2 1 3 2 2 1 2 2 3 1 2 1 | 671 |
| 1 1 3 2 1 1 1 3 1 1 1 2 3 2 2 1 1 3 1 3 2 1 3 2 | 672 |
| 1 2 3 1 3 1 1 1 2 2 3 2 2 3 2 2 3 1 1 1 2 3 2 1 1 | 673 |
| 2 2 1 3 1 2 2 1 3 1 3 2 1 3 2 1 3 1 1 3 1 1 2 1 | 674 |
| 2 1 3 2 3 1 2 3 1 1 3 1 1 3 2 2 1 3 1 1 1 2 2 1 | 675 |
| 2 1 1 2 3 2 1 3 2 1 1 2 3 2 3 1 2 3 1 2 1 1 3 2 | 676 |
| 2 2 3 1 3 1 1 1 3 1 1 2 1 1 3 2 1 3 2 3 2 1 1 1 | 677 |
| 2 1 1 2 3 1 3 2 3 1 3 1 2 2 1 2 1 3 1 2 2 3 2 2 | 678 |
| 3 2 1 2 1 1 3 1 1 1 2 3 2 3 2 3 2 2 2 3 1 2 2 1 | 679 |
| 3 2 3 1 1 2 3 2 3 2 2 1 1 2 3 1 1 3 1 2 1 2 1 2 | 680 |
| 3 1 1 1 3 2 2 1 2 2 1 3 2 1 3 2 2 1 1 1 3 1 2 3 | 681 |
| 2 1 3 1 1 2 2 3 2 3 2 2 2 3 1 2 1 1 3 2 3 1 2 1 | 682 |
| 2 3 1 2 2 2 1 3 1 2 2 3 2 3 1 3 2 2 1 1 1 2 3 1 | 683 |
| 1 2 2 1 2 2 3 1 3 2 2 2 3 1 1 2 3 2 2 3 1 2 1 3 | 684 |
| 1 2 1 3 2 1 3 2 2 1 2 3 2 2 2 3 1 2 2 2 1 3 2 3 | 685 |
| 1 2 1 3 1 1 3 1 1 3 1 1 1 2 1 1 1 3 2 2 1 3 1 3 1 | 686 |
| 3 1 2 3 2 2 3 1 1 1 3 2 1 1 2 3 1 1 2 2 2 3 2 1 | 687 |
| 3 1 3 1 2 2 3 1 2 1 3 2 1 3 1 1 1 2 3 1 2 1 1 1 | 688 |
| 2 3 1 3 1 3 1 1 2 1 1 1 3 2 1 2 3 1 1 2 2 2 3 1 | 689 |
| 2 1 2 1 1 1 3 1 2 3 1 2 3 2 3 1 1 2 2 1 3 2 1 3 | 690 |
| 2 2 1 2 3 2 1 1 3 1 1 1 2 3 2 2 2 3 1 3 1 3 1 1 1 | 691 |
| 1 3 2 1 1 1 2 3 1 2 3 1 1 2 3 1 2 1 2 3 1 2 3 1 | 692 |
| 3 1 1 1 2 2 2 3 2 3 2 2 1 1 1 3 2 2 3 1 1 2 3 1 | 693 |
| 3 1 2 3 1 1 2 3 1 2 2 3 2 3 2 2 2 1 1 3 2 1 2 1 | 694 |
| 3 1 1 1 2 1 1 3 2 3 1 3 1 3 2 2 1 1 2 3 1 1 1 2 | 695 |
| 2 3 2 2 3 1 1 1 2 1 3 2 2 1 2 2 1 3 2 2 2 3 2 3 | 696 |

TABLE IA-continued

Numeric sequences corresponding to nucleotide
base patterns of a set of oligonucleotides

| Numeric Pattern | Sequence Identifier |
|---|---|
| 2 2 2 3 1 3 1 3 2 1 2 1 2 2 3 1 2 1 2 3 1 3 1 1 | 697 |
| 1 2 2 3 2 3 2 3 2 1 1 1 3 2 1 1 3 1 2 2 2 1 1 3 | 698 |
| 2 1 2 1 3 2 2 2 3 1 1 3 2 3 2 3 1 2 3 2 1 2 2 2 | 699 |
| 3 2 3 1 1 3 2 2 1 2 1 3 2 3 2 1 2 1 1 1 3 1 1 2 | 700 |
| 3 2 1 2 3 2 2 3 1 1 2 1 3 2 1 1 1 2 1 3 1 2 2 3 | 701 |
| 2 2 1 3 1 1 1 3 2 3 2 3 1 2 2 2 3 2 3 2 1 2 2 2 | 702 |
| 2 2 2 1 3 2 1 1 2 1 2 3 2 1 1 3 1 3 1 2 3 2 3 1 | 703 |
| 1 3 2 1 2 3 2 1 2 1 3 1 2 3 1 2 3 2 2 2 3 2 2 2 | 704 |
| 1 2 2 2 1 1 3 2 1 1 1 3 2 3 2 1 3 1 3 1 2 1 1 3 | 705 |
| 1 2 2 2 3 2 3 2 2 2 3 1 1 2 2 3 2 1 1 1 3 2 3 1 1 | 706 |
| 1 2 3 2 2 1 2 2 1 3 1 2 2 3 2 3 1 2 3 1 1 2 3 1 | 707 |
| 2 1 3 2 1 3 2 1 3 1 1 2 1 2 3 1 1 1 2 2 1 3 1 3 | 708 |
| 2 2 2 1 1 2 3 1 3 1 1 3 1 3 2 2 1 3 1 3 2 1 2 1 | 709 |
| 1 1 1 3 2 2 2 1 3 2 1 3 1 3 2 3 2 1 2 3 2 1 1 1 | 710 |
| 1 2 1 2 1 2 3 1 2 1 3 2 1 3 1 3 2 1 3 1 2 2 1 3 | 711 |
| 2 3 1 3 1 1 3 2 2 1 1 2 2 3 2 1 2 1 3 1 2 2 3 1 | 712 |
| 2 1 2 1 3 1 3 1 2 3 2 2 1 2 1 2 3 1 1 3 2 2 3 2 | 713 |
| 1 1 1 2 2 2 3 2 2 1 1 3 2 2 3 2 2 3 2 2 3 2 2 3 | 714 |
| 2 2 3 2 2 3 1 1 3 1 2 3 1 1 1 3 2 1 3 1 1 2 2 1 | 715 |
| 1 1 3 1 3 1 2 1 1 3 2 1 3 2 3 2 2 2 1 2 3 2 2 2 | 716 |
| 1 1 2 1 1 3 1 1 3 1 1 3 2 3 1 1 1 3 1 2 2 3 1 2 | 717 |
| 2 1 1 3 2 2 1 1 1 3 2 2 3 1 2 3 1 2 2 3 1 2 1 3 | 718 |
| 1 2 1 2 1 1 3 1 2 1 1 3 1 3 2 3 2 1 1 3 2 3 1 2 | 719 |
| 3 2 2 1 1 1 2 3 2 2 3 2 2 3 2 2 2 1 1 3 2 3 1 2 | 720 |
| 3 1 3 2 2 1 1 3 2 2 1 2 2 1 3 2 2 1 1 3 1 1 3 2 | 721 |
| 2 1 2 2 1 3 1 3 2 2 2 3 1 3 1 1 2 1 1 3 2 1 3 2 | 722 |
| 2 1 1 2 3 2 2 3 2 2 1 2 3 2 3 2 2 1 3 1 1 1 3 2 2 | 723 |
| 3 1 1 1 3 2 2 3 1 2 1 3 1 1 2 3 2 1 1 2 3 2 2 2 | 724 |
| 2 3 1 2 1 3 1 2 3 1 1 2 2 3 1 2 2 3 1 2 2 1 3 2 | 725 |
| 1 2 3 1 2 1 3 1 3 2 1 1 1 3 1 1 2 1 1 3 2 2 3 2 | 726 |
| 1 3 2 1 1 3 2 3 2 2 1 3 1 2 1 3 2 1 2 2 3 1 1 2 | 727 |
| 1 2 3 2 1 3 1 2 2 1 1 1 3 2 1 3 2 3 2 1 2 3 2 2 | 728 |
| 2 2 1 2 2 3 1 2 1 1 2 3 1 3 1 3 1 3 2 2 1 1 1 3 | 729 |
| 1 2 2 2 3 2 2 1 2 3 1 2 1 1 1 2 3 2 3 2 1 3 2 3 | 730 |
| 2 2 3 1 1 3 1 1 1 2 1 1 3 1 3 2 1 1 2 1 1 3 1 3 | 731 |
| 2 3 2 3 2 1 1 2 1 1 3 2 1 3 2 1 1 3 1 2 2 1 3 1 | 732 |
| 1 2 3 1 1 1 3 2 2 1 3 1 3 2 2 2 1 2 3 1 2 1 1 3 | 733 |

TABLE IA-continued

Numeric sequences corresponding to nucleotide
base patterns of a set of oligonucleotides

| Numeric Pattern | Sequence Identifier |
|---|---|
| 1 2 2 1 3 2 2 1 1 3 1 3 1 3 2 2 2 3 2 1 3 1 2 2 | 734 |
| 2 3 2 1 3 2 1 2 2 3 2 1 2 3 1 2 2 1 1 1 3 2 3 2 | 735 |
| 1 3 2 2 3 1 2 1 1 1 3 1 1 3 1 1 3 1 3 2 1 2 1 2 | 736 |
| 3 2 1 1 2 3 1 3 1 2 1 1 1 3 1 3 1 3 1 2 1 1 2 2 | 737 |
| 2 3 2 3 2 2 3 1 1 3 1 2 1 1 1 3 2 2 2 1 2 3 1 2 | 738 |
| 1 1 3 1 1 3 1 3 2 1 3 2 2 1 3 1 1 2 2 3 1 2 2 1 | 739 |
| 3 1 1 2 3 1 1 3 1 2 3 1 1 3 2 2 2 3 2 2 1 1 2 1 | 740 |
| 1 1 1 2 2 3 2 2 3 1 3 1 2 1 1 3 1 2 1 3 2 3 1 2 | 741 |
| 2 3 1 2 2 3 2 2 2 1 1 2 3 1 2 3 2 3 2 3 1 2 2 1 | 742 |
| 1 2 3 1 1 3 2 1 2 2 3 2 2 3 1 3 2 3 1 2 2 2 1 1 | 743 |
| 3 2 3 2 1 1 1 2 3 2 2 2 3 1 3 1 2 3 2 1 2 1 2 2 | 744 |
| 1 1 2 2 3 1 2 3 1 3 2 2 2 1 1 1 3 1 3 2 2 3 1 2 | 745 |
| 2 2 2 3 2 3 2 1 1 2 1 2 3 1 2 2 3 1 3 1 3 2 2 2 | 746 |
| 3 2 1 3 2 1 3 1 2 3 1 2 2 1 1 3 1 1 3 1 2 1 1 1 | 747 |
| 2 2 2 1 1 2 3 2 3 1 1 1 2 2 2 3 2 2 3 2 3 1 3 2 | 748 |
| 3 2 1 1 1 3 1 1 2 2 1 3 1 2 1 1 1 3 1 3 2 3 1 2 | 749 |
| 1 1 2 1 3 2 2 1 1 3 2 2 2 1 1 3 1 3 2 2 3 2 3 2 | 750 |
| 3 2 3 2 3 1 2 3 2 2 2 1 2 1 3 1 2 2 2 3 2 2 1 2 | 751 |
| 3 2 1 2 1 3 2 3 2 3 1 2 2 1 3 1 2 2 2 3 2 1 1 1 | 752 |
| 3 2 2 3 2 1 1 3 1 1 1 3 1 2 1 2 3 2 1 1 3 1 1 1 | 753 |
| 1 2 1 2 2 1 3 1 2 2 3 2 1 1 1 3 1 3 1 3 2 3 1 1 | 754 |
| 3 1 3 2 3 1 2 1 2 2 3 1 1 1 2 2 1 3 1 2 2 3 2 1 | 755 |
| 2 1 1 3 1 1 3 2 2 1 1 1 3 1 1 3 1 3 1 3 2 2 2 1 | 756 |
| 3 1 2 3 2 2 1 3 1 2 1 1 1 1 3 2 2 2 1 1 3 2 1 3 2 | 757 |
| 3 2 3 1 2 2 3 2 1 2 3 1 3 1 1 1 2 3 2 2 1 1 1 2 | 758 |
| 2 3 1 2 2 1 2 2 3 2 1 1 3 1 1 1 3 1 2 2 3 1 3 1 | 759 |
| 1 1 3 1 1 2 2 3 2 3 2 1 1 3 2 2 2 1 2 3 1 3 2 1 | 760 |
| 2 2 3 2 1 2 2 2 1 3 1 1 3 1 2 2 2 3 2 1 3 1 2 3 | 761 |
| 2 1 2 1 2 3 2 2 2 3 2 3 2 1 1 3 1 1 3 1 1 1 2 3 | 762 |
| 3 1 2 1 1 2 3 2 3 2 3 1 1 2 2 2 3 2 3 1 1 2 1 1 | 763 |
| 2 2 1 3 1 1 1 2 3 2 3 1 3 1 2 2 2 1 1 3 1 3 2 2 | 764 |
| 1 3 2 3 2 1 3 1 1 2 2 2 3 2 1 2 2 2 1 3 2 2 3 2 | 765 |
| 2 1 3 2 2 1 1 3 1 2 1 3 1 3 2 1 1 1 2 3 1 2 1 3 | 766 |
| 3 1 1 3 2 3 1 2 1 2 2 3 2 1 1 1 2 2 3 1 2 1 1 3 | 767 |
| 3 2 1 1 2 2 3 2 3 2 2 1 3 1 2 2 2 1 1 3 1 1 3 2 | 768 |
| 2 3 1 2 1 2 2 2 3 2 3 1 1 2 2 3 1 2 1 3 2 1 2 3 | 769 |

TABLE IA-continued

Numeric sequences corresponding to nucleotide base patterns of a set of oligonucleotides

| Numeric Pattern | Sequence Identifier |
|---|---|
| 1 1 3 2 1 1 1 3 1 3 1 2 1 2 1 3 2 2 1 1 3 2 2 3 | 770 |
| 1 2 2 1 3 2 2 1 1 3 2 2 1 2 2 2 3 2 3 1 3 2 3 1 | 771 |
| 1 3 1 2 3 1 1 3 2 1 3 2 2 2 1 2 3 1 1 2 2 1 3 1 | 772 |
| 2 3 1 3 2 2 1 3 2 2 1 1 3 2 3 1 2 1 3 2 2 1 1 1 | 773 |
| 2 2 1 2 2 3 2 1 3 1 2 2 2 1 3 1 3 1 1 3 1 2 3 1 | 774 |
| 2 1 2 2 2 3 2 3 2 2 2 3 2 2 3 1 2 2 1 3 1 2 1 3 | 775 |
| 3 2 1 2 1 1 1 2 3 2 3 2 3 2 3 1 1 1 3 2 2 1 2 1 1 | 776 |
| 2 1 2 1 2 3 2 2 3 1 3 2 1 2 1 1 1 3 1 3 1 3 1 1 | 777 |
| 2 2 1 3 2 2 1 3 2 2 2 1 1 1 3 1 2 2 3 2 3 1 3 2 | 778 |
| 2 2 2 1 3 1 1 2 1 1 3 2 3 1 2 3 2 3 1 2 3 1 1 1 | 779 |
| 1 3 1 3 2 1 1 2 3 2 3 2 1 1 1 2 1 3 2 2 1 3 1 2 | 780 |
| 2 3 2 3 1 2 1 1 1 3 1 3 1 1 1 2 2 1 3 2 2 3 2 2 | 781 |
| 3 1 1 2 2 2 1 3 2 3 1 1 2 3 2 2 2 3 1 3 1 2 2 1 | 782 |
| 2 3 2 3 1 2 3 2 3 2 1 1 3 2 1 2 1 2 3 1 1 1 2 2 | 783 |
| 2 2 3 2 3 1 1 2 3 1 2 2 1 1 2 3 1 1 2 1 3 1 1 3 | 784 |
| 1 1 2 3 2 2 3 2 2 2 1 3 1 2 2 3 1 3 1 1 1 3 2 2 | 785 |
| 1 3 1 2 2 3 2 3 2 2 1 3 2 1 2 2 1 3 2 1 2 1 1 3 | 786 |
| 2 2 3 1 2 3 2 1 2 2 1 3 1 1 1 3 2 2 2 1 2 3 2 3 | 787 |
| 2 1 2 3 1 2 2 3 2 3 2 3 2 2 1 3 1 3 1 1 2 2 2 1 | 788 |
| 2 1 3 2 3 2 1 3 1 2 1 2 2 2 3 1 2 1 3 2 2 1 2 3 | 789 |
| 1 3 2 2 2 1 1 2 3 2 3 2 2 2 1 3 2 2 3 2 2 1 2 3 | 790 |
| 2 3 2 3 2 1 1 1 3 2 1 3 1 1 1 1 3 2 1 1 1 3 1 2 2 | 791 |
| 3 2 2 1 2 3 1 2 1 2 1 3 2 3 1 3 2 2 3 2 2 1 2 2 | 792 |
| 2 2 2 3 1 2 2 3 1 1 2 3 2 2 1 1 2 1 3 2 3 2 3 2 | 793 |
| 1 3 1 3 2 1 2 2 1 3 2 1 3 2 2 1 2 2 3 2 1 1 3 2 | 794 |
| 2 1 1 3 2 1 3 1 1 1 3 1 1 3 1 1 3 1 2 1 2 2 2 3 | 795 |
| 1 3 1 1 1 3 1 3 1 1 2 2 1 2 3 2 1 1 2 3 1 1 1 3 | 796 |
| 2 2 1 3 1 2 2 2 3 2 2 1 3 2 3 2 3 1 2 2 2 1 1 3 | 797 |
| 3 1 2 3 1 2 2 1 1 3 1 2 1 2 1 3 1 3 1 2 1 3 2 2 | 798 |
| 1 2 1 2 2 2 3 1 3 2 3 1 2 2 1 1 3 1 3 2 1 1 2 3 | 799 |
| 2 3 2 1 2 2 3 2 3 1 3 2 2 1 1 3 2 1 2 1 1 3 2 2 | 800 |
| 1 1 2 2 2 1 3 2 1 3 1 1 1 3 2 3 2 2 3 2 3 2 2 2 | 801 |
| 3 2 2 1 3 1 1 1 3 1 2 2 1 1 3 2 2 3 1 1 2 1 1 2 3 | 802 |
| 2 1 1 1 3 2 1 2 3 2 3 1 3 1 2 3 1 2 2 2 1 2 3 2 | 803 |
| 2 3 1 1 1 2 3 1 2 2 1 1 1 3 1 2 3 1 1 3 1 2 3 1 | 804 |
| 2 2 1 2 2 1 3 1 2 3 2 2 3 1 3 2 3 2 2 2 3 2 2 2 | 805 |
| 2 1 3 2 3 2 2 2 1 1 1 3 1 3 2 1 3 2 1 2 1 2 3 1 | 806 |

TABLE IA-continued

Numeric sequences corresponding to nucleotide base patterns of a set of oligonucleotides

| Numeric Pattern | Sequence Identifier |
|---|---|
| 1 3 2 2 1 2 1 1 3 2 1 1 1 2 3 1 2 3 2 2 3 1 2 3 | 807 |
| 2 2 1 1 3 1 3 1 3 1 1 1 2 1 1 3 2 3 2 1 2 2 3 2 | 808 |
| 3 1 2 1 2 2 3 1 1 1 2 3 2 3 2 1 1 1 2 3 1 2 3 1 | 809 |
| 1 2 3 1 2 3 1 1 2 2 1 1 3 1 1 1 3 1 1 1 3 1 3 1 | 810 |
| 3 1 1 2 1 3 2 2 2 3 1 2 2 2 3 2 3 2 2 2 3 2 2 1 | 811 |
| 1 3 2 2 3 2 2 2 1 3 1 2 2 2 3 1 2 2 2 3 2 1 1 3 | 812 |
| 3 2 1 2 3 1 3 1 2 2 2 3 1 2 1 2 1 1 3 1 2 2 1 3 | 813 |
| 2 2 2 1 2 1 3 2 3 1 3 2 1 2 1 3 2 3 1 2 3 1 2 2 | 814 |
| 2 1 2 1 2 3 2 3 1 1 3 1 2 1 2 1 1 3 2 3 2 2 2 3 | 815 |
| 1 2 2 3 1 2 1 3 1 2 3 1 2 1 3 2 1 1 2 2 3 1 3 2 | 816 |
| 2 3 1 2 1 3 1 2 3 2 3 1 1 3 1 1 2 2 2 3 1 2 2 2 | 817 |
| 3 1 1 3 1 2 1 2 2 3 1 1 1 3 1 1 2 2 2 3 1 2 3 2 | 818 |
| 3 1 2 3 2 2 2 1 3 2 3 2 1 3 1 2 1 2 1 3 1 2 2 2 | 819 |
| 3 1 1 2 1 2 2 3 1 3 2 2 1 2 1 1 3 2 1 3 2 1 3 2 | 820 |
| 1 3 2 3 1 3 2 1 1 3 2 1 1 2 1 3 1 1 1 3 1 2 2 2 | 821 |
| 3 2 1 3 1 1 2 1 1 3 2 1 1 2 2 2 3 2 3 1 3 1 2 1 | 822 |
| 3 1 3 2 2 1 2 2 2 3 1 3 1 2 2 2 1 3 1 2 3 2 2 2 | 823 |
| 3 1 1 1 2 3 1 2 3 1 2 2 3 1 1 2 2 2 1 3 1 3 1 2 | 824 |
| 1 1 1 2 1 3 2 3 2 3 1 3 1 1 2 1 3 2 2 1 1 3 2 1 | 825 |
| 1 2 3 2 3 2 2 1 1 3 2 2 3 2 1 3 1 1 3 1 1 2 1 1 | 826 |
| 1 2 1 1 2 3 1 3 2 2 1 1 2 1 3 2 3 2 1 1 3 1 1 3 | 827 |
| 1 2 1 1 3 1 3 1 2 3 2 2 2 1 1 3 2 2 1 3 1 1 1 3 | 828 |
| 2 3 2 2 1 3 2 3 2 2 1 3 1 1 1 2 1 2 3 1 1 1 3 1 | 829 |
| 2 2 2 1 3 1 1 1 3 1 2 2 3 2 2 1 3 1 2 1 1 3 2 2 3 | 830 |
| 3 2 3 2 1 1 2 3 2 1 2 1 1 3 1 2 1 3 2 2 1 1 3 2 | 831 |
| 2 1 2 2 1 3 1 3 1 3 1 1 1 2 2 3 2 1 3 1 3 1 2 2 | 832 |
| 2 1 3 2 3 1 3 1 2 1 1 1 3 2 1 1 1 3 2 2 2 1 2 3 | 833 |
| 2 2 3 2 3 1 1 1 3 2 2 1 1 3 2 1 1 3 2 2 1 3 2 2 | 834 |
| 1 1 1 3 2 3 2 1 1 3 2 2 3 1 1 3 1 1 2 1 2 2 3 1 | 835 |
| 3 1 1 2 1 3 1 3 2 3 2 2 1 2 2 2 3 1 1 1 2 1 3 1 | 836 |
| 2 1 2 1 1 3 1 3 1 3 1 3 1 2 1 1 3 2 1 1 2 1 1 3 | 837 |
| 2 3 1 3 2 3 1 1 1 2 2 3 1 2 1 3 1 3 2 1 1 1 2 2 | 838 |
| 3 1 2 3 1 1 2 1 1 3 2 2 2 1 1 3 2 3 1 3 1 1 1 2 | 839 |
| 3 2 3 2 3 1 2 1 2 3 2 2 2 1 2 2 3 1 2 2 1 1 3 2 | 840 |
| 2 1 1 1 3 2 3 1 3 2 3 2 1 1 1 2 3 1 2 1 1 2 3 1 | 841 |
| 3 2 1 3 1 3 2 2 2 3 1 2 2 2 3 1 1 1 3 1 1 2 1 2 | 842 |

TABLE IA-continued

Numeric sequences corresponding to nucleotide
base patterns of a set of oligonucleotides

| Numeric Pattern | Sequence Identifier |
|---|---|
| 3 1 1 2 1 2 2 3 2 2 1 2 3 2 2 2 3 2 2 1 2 3 1 3 | 843 |
| 3 2 3 2 1 1 1 2 1 1 3 1 2 3 2 1 2 2 3 2 2 3 2 2 2 | 844 |
| 2 1 1 1 2 2 3 1 2 2 3 2 3 1 3 2 2 3 1 1 3 1 1 2 | 845 |
| 2 3 1 3 1 2 1 3 2 2 1 2 1 3 2 2 1 1 3 2 2 2 1 3 | 846 |
| 1 3 2 2 2 3 2 2 1 1 3 1 2 2 1 2 3 2 1 3 1 1 1 3 | 847 |
| 3 1 1 2 3 2 3 2 1 3 1 1 2 1 1 3 1 3 1 2 2 1 1 1 | 848 |
| 3 2 1 2 2 1 2 3 1 1 1 3 1 1 3 2 2 3 2 2 3 2 2 2 | 849 |
| 3 2 3 2 2 1 2 1 3 1 1 1 3 2 2 1 1 1 2 3 2 2 1 1 3 | 850 |
| 2 2 1 1 3 1 3 2 1 3 2 3 1 1 2 1 2 3 1 2 1 3 2 1 | 851 |
| 1 1 2 3 2 2 1 2 1 1 1 3 1 2 3 1 3 1 3 2 2 2 1 3 2 | 852 |
| 1 2 1 2 1 1 1 3 1 2 2 2 3 1 2 3 2 1 3 2 3 2 1 3 2 | 853 |
| 2 1 2 3 2 2 2 3 2 2 3 2 2 3 2 2 1 1 3 2 2 2 3 1 | 854 |
| 3 1 2 1 3 2 2 2 1 3 2 1 2 1 3 1 1 3 1 2 1 1 1 3 | 855 |
| 3 2 2 3 1 1 2 1 2 1 3 1 3 1 2 1 3 2 1 1 1 2 1 3 | 856 |
| 1 3 1 3 1 1 1 3 1 2 2 2 1 3 2 1 1 3 1 1 2 3 1 2 1 | 857 |
| 2 3 1 1 2 3 1 3 1 1 1 3 1 2 1 2 2 3 1 3 2 1 2 2 | 858 |
| 2 3 1 1 3 1 2 2 1 2 1 3 2 1 3 2 2 3 2 1 2 1 3 1 | 859 |
| 3 1 2 2 1 3 2 1 3 2 1 2 2 3 1 1 3 1 2 2 1 2 3 2 | 860 |
| 2 3 1 1 1 2 3 2 3 2 1 2 2 2 3 2 1 2 3 2 2 2 1 3 | 861 |
| 1 2 2 1 1 1 3 2 2 3 1 2 1 2 3 1 1 1 3 1 1 3 2 3 | 862 |
| 1 1 2 3 2 1 3 1 3 1 2 2 3 2 1 3 2 3 1 1 2 1 2 2 | 863 |
| 2 2 1 2 2 2 3 2 2 3 1 3 2 3 2 1 1 1 2 3 2 3 1 2 | 864 |
| 1 2 3 2 1 1 2 2 3 2 3 1 1 2 1 1 2 3 2 1 2 3 2 3 | 865 |
| 3 1 2 2 2 3 2 1 2 1 3 1 3 1 2 2 1 3 2 1 1 3 2 1 | 866 |
| 1 1 2 1 2 2 3 2 2 3 2 2 2 1 3 1 3 1 1 1 3 1 1 3 | 867 |
| 1 2 3 1 2 3 1 2 3 2 1 2 2 2 3 2 1 1 1 3 1 3 2 1 | 868 |
| 1 1 2 3 2 1 2 2 2 3 2 3 2 3 1 2 2 3 2 3 2 1 1 1 | 869 |
| 1 3 2 3 2 2 1 2 3 1 1 3 1 1 2 1 3 2 1 1 3 1 1 2 | 870 |
| 3 2 2 1 2 3 2 1 3 1 3 1 2 3 1 1 1 3 1 1 1 2 2 1 | 871 |
| 3 2 2 2 3 2 1 2 2 1 3 1 2 1 1 1 2 3 1 3 2 2 3 2 | 872 |
| 2 3 1 2 2 2 1 2 3 1 3 1 2 2 1 1 3 1 3 1 1 1 3 1 | 873 |
| 2 2 2 3 2 3 2 3 2 2 1 2 2 3 2 1 1 2 2 3 1 3 1 2 | 874 |
| 3 1 2 3 2 3 2 3 1 2 1 2 3 1 2 2 1 1 1 3 1 1 1 2 | 875 |
| 1 3 1 2 2 1 2 1 3 1 2 2 2 3 2 1 3 1 3 1 1 1 3 2 | 876 |
| 3 1 1 3 1 3 2 1 2 3 2 1 1 2 1 3 2 1 2 2 3 2 1 2 | 877 |
| 2 2 2 3 2 1 1 2 3 2 2 3 2 2 3 1 3 2 2 2 1 1 3 1 | 878 |
| 1 3 2 1 1 1 2 1 3 2 1 3 2 1 2 3 1 1 2 1 1 3 1 3 | 879 |

TABLE IA-continued

Numeric sequences corresponding to nucleotide base patterns of a set of oligonucleotides

| Numeric Pattern | Sequence Identifier |
|---|---|
| 3 1 1 2 3 2 2 3 1 1 2 2 3 1 1 1 2 1 2 3 1 3 2 2 | 880 |
| 1 3 2 1 3 2 2 1 1 2 2 3 1 2 1 3 2 1 1 3 2 2 2 3 | 881 |
| 1 3 2 3 2 1 1 1 3 1 1 1 2 3 1 1 2 3 1 1 2 1 1 3 | 882 |
| 2 3 2 2 1 3 1 2 1 2 2 2 3 2 3 1 1 1 2 3 2 3 1 1 | 883 |
| 2 3 2 1 2 3 2 2 3 1 3 2 2 2 3 1 1 2 2 3 2 2 1 2 | 884 |
| 2 3 1 3 2 3 1 1 2 2 1 3 2 2 1 2 3 2 2 3 2 2 1 2 | 885 |
| 3 1 1 3 1 1 1 3 1 1 1 2 3 1 3 1 1 1 3 1 2 2 1 2 | 886 |
| 2 2 1 1 3 2 1 1 3 2 2 3 2 3 2 2 3 1 2 1 2 2 1 3 | 887 |
| 1 2 3 1 2 3 2 3 2 2 2 3 1 2 2 2 3 1 1 2 2 3 1 1 | 888 |
| 1 1 3 2 1 1 3 2 3 1 1 1 2 2 3 2 2 3 2 2 2 3 1 1 | 889 |
| 1 2 3 1 1 3 2 3 2 1 1 1 3 2 2 2 3 1 1 1 3 1 1 1 | 890 |
| 1 3 1 3 1 3 2 1 1 3 1 2 1 1 2 2 3 2 1 2 1 3 2 1 | 891 |
| 2 2 2 1 2 3 1 3 1 2 1 3 1 2 3 1 1 1 2 1 1 3 2 3 | 892 |
| 1 3 1 1 1 2 2 1 3 2 1 3 2 1 1 2 3 1 2 2 2 3 2 3 | 893 |
| 3 1 2 2 2 3 1 3 1 2 2 3 1 1 2 3 1 3 1 1 2 1 2 1 | 894 |
| 3 1 2 2 1 3 1 1 1 3 1 2 3 1 1 2 1 1 1 3 1 2 3 1 | 895 |
| 2 1 3 1 2 1 3 1 1 1 3 2 1 2 1 2 3 2 2 3 2 1 3 2 | 896 |
| 3 1 1 3 1 2 1 3 2 1 1 1 3 2 1 1 1 3 2 1 1 3 2 2 | 897 |
| 1 1 1 2 3 2 3 2 2 2 1 3 2 1 3 2 2 3 2 1 1 1 | 898 |
| 2 2 3 2 2 3 1 1 3 2 1 1 3 1 3 1 2 3 1 1 2 1 1 1 | 899 |
| 2 1 2 2 2 3 1 3 1 3 1 1 1 3 1 1 1 3 1 3 2 2 2 1 | 900 |
| 2 1 2 2 2 1 3 2 3 1 2 3 1 1 2 2 2 3 2 3 1 2 3 2 | 901 |
| 2 2 1 2 1 3 2 3 1 2 3 1 2 3 1 2 1 1 3 2 2 3 1 2 | 902 |
| 2 1 1 1 3 1 2 1 1 2 2 3 2 1 3 1 1 1 3 2 1 3 2 3 | 903 |
| 3 2 2 2 1 3 2 1 2 2 3 1 2 1 2 2 3 2 3 2 3 2 1 1 | 904 |
| 3 2 3 2 2 2 3 2 3 1 1 2 1 1 3 1 2 2 3 1 1 1 2 1 2 | 905 |
| 1 1 1 3 1 1 1 3 2 1 2 1 1 1 3 2 3 1 3 1 2 1 3 1 | 906 |
| 2 1 2 2 2 3 2 1 1 3 1 1 3 2 3 2 1 3 1 2 1 2 2 3 | 907 |
| 2 1 3 1 1 3 1 2 3 1 1 1 2 2 3 2 3 1 2 2 2 3 2 2 | 908 |
| 1 2 1 1 2 1 3 2 1 1 3 2 3 1 1 2 3 1 2 3 1 3 1 2 | 909 |
| 1 1 2 3 2 3 1 1 2 1 1 3 1 2 1 1 1 3 2 3 2 3 2 1 | 910 |
| 1 2 2 3 1 1 3 1 2 1 1 1 3 1 2 3 2 2 3 2 2 2 1 3 | 911 |
| 2 3 1 1 1 2 1 3 1 1 1 3 2 3 1 3 1 2 2 1 2 1 3 2 1 | 912 |
| 1 3 2 2 1 2 2 3 2 3 1 1 1 3 1 3 2 2 2 1 2 3 1 2 | 913 |
| 1 1 1 2 1 3 2 1 3 2 3 1 2 1 3 1 3 1 1 3 1 2 2 2 | 914 |
| 1 3 2 3 2 1 2 3 1 1 3 2 3 2 1 1 2 1 1 3 1 2 2 1 | 915 |

TABLE IA-continued

Numeric sequences corresponding to nucleotide
base patterns of a set of oligonucleotides

| Numeric Pattern | Sequence Identifier |
|---|---|
| 2 3 1 2 2 1 1 3 1 2 2 3 2 3 2 1 3 2 3 2 2 1 2 1 | 916 |
| 1 3 2 2 2 1 2 3 1 2 1 2 2 2 3 2 1 3 1 2 3 1 3 2 | 917 |
| 2 1 2 3 2 3 2 1 2 3 1 1 3 1 2 2 1 2 1 3 2 2 1 3 | 918 |
| 3 1 1 1 2 2 3 2 2 3 2 1 2 1 3 1 3 2 3 1 2 1 2 1 | 919 |
| 2 1 3 1 1 1 2 1 3 2 2 2 1 1 3 2 1 2 1 3 2 3 2 3 | 920 |
| 2 3 1 2 2 2 1 3 1 2 3 2 2 2 1 2 2 3 2 3 1 3 1 1 | 921 |
| 1 1 3 2 2 3 1 2 1 2 2 2 3 2 2 3 2 2 1 3 1 2 3 1 | 922 |
| 2 3 1 2 3 2 3 1 2 1 1 2 3 1 3 1 1 2 1 1 1 3 1 1 | 923 |
| 1 1 1 3 2 2 2 1 3 2 2 2 3 2 1 2 2 1 3 2 1 3 1 3 | 924 |
| 1 3 2 2 2 3 1 2 3 2 3 1 2 1 3 2 1 1 1 2 1 3 1 1 | 925 |
| 1 1 3 2 3 2 2 1 2 2 3 1 1 2 3 2 3 1 2 3 2 2 1 2 | 926 |
| 1 1 1 2 2 3 1 1 3 2 3 2 3 1 2 1 1 2 3 2 2 2 3 2 | 927 |
| 3 2 2 2 1 3 2 3 1 2 2 1 1 1 3 1 2 1 3 1 2 2 1 3 | 928 |
| 1 2 1 1 3 2 3 2 1 2 1 1 3 1 3 1 1 3 2 3 2 2 1 1 | 929 |
| 1 2 3 1 1 2 2 2 3 2 2 2 3 2 3 1 2 3 1 1 3 2 2 1 | 930 |
| 1 1 1 3 1 1 2 2 3 1 3 1 1 1 2 3 1 1 1 3 2 2 1 3 | 931 |
| 1 3 2 3 2 1 1 3 1 3 2 1 2 1 1 1 3 2 1 2 2 2 3 1 | 932 |
| 3 1 1 2 2 1 1 3 1 2 2 3 2 2 1 2 1 2 3 2 3 1 3 2 | 933 |
| 2 1 2 3 1 1 1 3 2 3 2 2 3 2 2 2 1 1 3 2 1 1 3 1 | 934 |
| 2 1 1 1 3 2 1 1 1 2 3 2 2 1 2 3 2 3 1 3 1 3 1 1 | 935 |
| 1 1 1 3 1 2 1 2 2 3 1 2 2 3 1 3 1 2 1 3 1 3 2 2 | 936 |
| 1 1 3 2 3 1 2 1 2 3 1 1 2 1 2 3 2 3 1 3 1 1 1 2 | 937 |
| 1 1 1 2 1 3 1 3 2 2 2 3 2 2 1 1 2 3 2 1 1 3 2 3 | 938 |
| 3 1 2 2 2 1 3 1 2 3 1 3 2 2 1 1 3 1 1 2 2 2 1 3 | 939 |
| 2 2 3 2 1 1 1 2 3 1 3 2 3 2 3 1 1 2 1 2 2 3 2 1 | 940 |
| 1 3 2 1 3 2 3 2 1 2 2 2 3 1 3 1 2 1 1 2 1 3 1 1 | 941 |
| 2 3 1 3 2 2 1 1 1 3 1 3 2 2 3 2 2 2 3 1 2 1 2 2 2 | 942 |
| 1 1 1 3 1 3 2 3 2 1 2 2 1 3 1 1 1 2 1 3 2 2 2 3 | 943 |
| 3 2 2 2 1 3 2 2 1 2 2 2 3 1 2 3 1 3 1 2 1 1 2 3 | 944 |
| 1 1 3 2 3 2 1 1 1 2 3 1 1 2 1 1 1 3 1 3 2 2 3 2 | 945 |
| 1 1 2 1 1 1 3 2 3 1 3 2 1 3 1 1 1 3 2 3 2 1 1 2 2 | 946 |
| 2 1 2 2 3 1 3 2 2 2 3 2 3 2 1 1 1 3 1 1 3 1 2 1 | 947 |
| 2 2 2 1 2 1 3 2 2 3 2 2 3 2 3 2 2 3 1 1 1 3 2 2 | 948 |
| 1 2 3 1 1 1 2 1 2 3 1 2 2 3 2 3 2 2 2 3 2 2 3 2 | 949 |
| 1 1 1 3 1 3 1 2 3 2 1 1 1 3 2 3 1 3 2 2 1 2 2 1 | 950 |
| 2 2 3 1 1 3 1 1 1 3 2 2 1 3 1 2 3 1 2 3 1 1 2 2 | 951 |
| 1 2 3 2 2 1 2 2 2 3 2 2 2 1 3 2 2 2 3 2 3 2 3 1 | 952 |

TABLE IA-continued

Numeric sequences corresponding to nucleotide base patterns of a set of oligonucleotides

| Numeric Pattern | Sequence Identifier |
|---|---|
| 1 1 1 2 1 2 3 1 1 2 2 2 3 1 1 3 1 3 1 1 3 2 3 1 | 953 |
| 3 1 2 2 1 3 1 2 1 2 1 3 1 1 2 1 2 2 3 1 1 3 1 3 | 954 |
| 2 2 1 3 1 1 2 1 1 3 1 3 1 1 1 2 3 2 1 2 3 2 3 2 | 955 |
| 2 2 2 1 2 3 1 1 1 3 1 3 1 1 3 2 3 2 1 2 2 1 2 3 | 956 |
| 3 2 1 1 3 2 1 2 2 1 1 3 2 3 2 3 1 2 2 2 1 3 2 1 | 957 |
| 1 2 1 1 1 3 1 3 1 1 3 2 1 1 1 3 1 3 2 1 1 1 3 2 | 958 |
| 1 2 2 3 2 2 1 1 2 2 3 1 1 3 2 3 2 1 2 3 1 1 1 3 | 959 |
| 2 1 2 1 2 1 3 2 2 3 1 3 2 2 3 1 3 2 1 1 3 1 2 2 | 960 |
| 2 1 3 1 2 3 1 3 1 2 1 2 1 2 3 1 1 1 3 1 2 1 3 2 | 961 |
| 1 2 1 1 3 1 1 3 1 2 3 1 2 2 2 3 2 3 2 1 1 1 2 3 | 962 |
| 2 2 1 3 2 1 1 2 1 1 3 1 1 1 3 1 2 3 1 1 3 1 3 1 | 963 |
| 3 1 2 2 2 3 2 3 1 3 2 1 1 1 3 2 1 1 1 2 1 3 1 1 | 964 |
| 1 1 1 2 1 3 1 2 3 2 1 3 1 1 2 2 2 3 2 3 2 3 2 2 | 965 |
| 3 1 1 1 2 2 1 3 2 3 2 2 2 3 2 3 2 3 2 1 2 2 1 2 | 966 |
| 1 2 2 2 3 1 3 2 1 2 3 1 2 1 3 1 1 3 1 2 2 3 2 2 | 967 |
| 1 2 1 3 1 3 2 2 3 1 1 3 2 1 2 3 2 1 1 1 3 2 2 2 | 968 |
| 2 1 1 2 2 2 3 2 3 1 1 2 3 2 2 3 2 2 1 2 2 3 2 3 | 969 |
| 2 2 1 3 2 2 2 1 2 3 1 3 1 3 2 3 1 3 1 2 2 2 1 1 | 970 |
| 3 2 2 3 2 2 1 3 1 3 2 3 2 2 2 1 2 3 1 1 1 2 2 2 | 971 |
| 2 2 2 1 2 2 3 2 3 1 2 3 2 3 1 1 1 2 1 1 3 1 3 1 | 972 |
| 3 2 1 1 3 2 1 1 2 1 2 3 1 2 1 3 2 3 1 2 2 1 1 3 | 973 |
| 2 3 1 3 1 2 3 1 2 3 2 1 2 1 2 3 2 1 3 2 1 1 2 1 | 974 |
| 1 1 2 2 3 1 3 1 1 1 3 1 3 1 2 1 1 1 2 3 1 2 1 3 | 975 |
| 2 2 2 3 1 1 1 3 2 3 1 2 3 2 2 1 3 1 1 2 3 2 2 2 1 | 976 |
| 1 3 2 2 3 2 2 2 3 2 3 2 1 1 2 2 3 2 2 1 3 2 1 1 1 | 977 |
| 1 2 1 3 2 3 1 3 1 1 3 2 3 1 2 1 1 3 1 2 1 2 2 2 | 978 |
| 3 2 3 2 3 1 2 1 1 3 2 1 1 2 2 3 1 3 2 2 1 1 1 2 | 979 |
| 2 1 3 2 2 1 2 2 3 2 2 2 3 2 3 1 1 2 2 2 3 1 3 1 | 980 |
| 1 2 1 3 2 2 3 1 1 2 1 3 2 1 1 2 2 2 3 1 1 3 1 3 | 981 |
| 1 2 3 2 2 2 3 2 3 2 2 2 3 1 1 2 1 3 1 3 1 1 2 1 | 982 |
| 2 3 1 2 1 1 1 3 1 2 1 2 3 1 3 1 3 1 2 2 3 2 1 1 | 983 |
| 2 1 1 1 3 1 2 3 1 3 1 2 3 2 2 3 2 2 1 1 1 3 2 2 | 984 |
| 1 1 3 2 3 1 1 1 2 2 2 3 2 1 1 3 1 1 2 2 1 3 2 3 | 985 |
| 3 1 1 1 2 3 1 3 1 3 2 2 1 2 2 3 1 2 1 3 2 2 2 1 | 986 |
| 2 2 2 3 2 1 1 1 2 3 1 3 1 2 1 2 1 3 2 3 2 2 1 3 | 987 |
| 3 2 2 1 1 2 2 3 2 3 1 2 1 2 2 2 3 1 2 2 1 3 2 3 | 988 |

TABLE IA-continued

Numeric sequences corresponding to nucleotide
base patterns of a set of oligonucleotides

| Numeric Pattern | Sequence Identifier |
|---|---|
| 1 3 1 3 2 3 2 2 3 1 2 1 1 1 3 1 2 3 2 2 2 1 2 1 | 989 |
| 1 1 2 2 3 2 3 1 3 1 1 1 2 2 3 1 2 1 1 3 1 1 3 1 | 990 |
| 2 2 1 1 1 3 1 3 1 1 2 2 3 1 3 1 1 3 1 3 1 1 1 2 | 991 |
| 2 2 3 2 2 1 3 1 1 3 1 1 2 2 3 1 1 2 3 2 1 2 3 2 | 992 |
| 1 3 2 2 1 1 3 1 2 1 2 3 2 3 2 3 1 2 3 2 2 2 1 1 | 993 |
| 2 3 1 3 2 2 1 2 3 2 2 3 2 1 1 2 1 3 1 1 1 2 2 3 | 994 |
| 2 2 1 3 1 2 1 1 3 2 2 2 1 3 1 3 1 2 2 3 1 3 1 1 | 995 |
| 1 2 3 1 3 2 1 1 2 1 1 3 1 3 2 1 2 2 2 3 1 1 3 2 | 996 |
| 2 3 2 2 2 1 1 3 2 3 2 1 1 2 3 1 2 2 2 3 2 2 1 3 | 997 |
| 2 2 3 1 1 3 1 1 3 1 2 2 3 2 2 1 2 2 3 2 2 3 1 1 | 998 |
| 2 1 2 1 3 1 1 1 3 1 2 2 1 1 1 3 1 3 2 3 1 1 2 3 | 999 |
| 2 1 1 1 2 2 3 2 2 1 3 1 1 1 2 2 2 3 1 3 2 3 2 3 | 1000 |
| 1 2 2 3 2 2 1 3 2 3 2 3 2 2 1 2 2 3 1 2 2 1 2 3 | 1001 |
| 3 1 3 1 1 2 2 1 2 3 2 3 2 3 1 1 2 1 2 1 3 1 1 1 | 1002 |
| 2 2 3 1 2 2 3 1 2 1 1 1 3 2 1 1 1 3 1 3 2 3 2 1 | 1003 |
| 3 2 3 2 3 2 1 1 1 2 2 3 1 1 2 1 2 3 2 2 1 1 2 3 | 1004 |
| 1 1 1 3 2 1 1 1 3 1 1 1 3 1 1 3 2 2 2 3 1 1 1 3 | 1005 |
| 2 2 2 1 3 2 2 3 1 1 3 1 1 2 1 3 1 1 1 3 1 1 1 3 | 1006 |
| 3 2 3 2 1 1 2 1 1 3 1 3 2 3 1 1 2 1 3 2 1 1 2 2 | 1007 |
| 2 1 2 2 3 1 1 1 2 1 1 3 1 3 1 3 1 2 2 2 3 2 3 1 | 1008 |
| 1 2 3 1 3 1 1 1 3 1 1 3 1 1 3 2 2 1 1 3 1 2 2 2 | 1009 |
| 1 1 3 1 3 2 3 1 3 2 1 2 1 2 2 3 2 2 1 1 1 3 1 1 | 1010 |
| 2 2 2 3 2 1 1 1 3 2 3 1 2 3 1 2 3 2 1 1 3 1 2 1 | 1011 |
| 3 1 2 3 2 2 1 2 3 2 3 1 2 3 1 1 1 2 1 2 3 2 1 2 | 1012 |
| 3 2 1 3 1 1 2 1 1 1 3 2 3 2 2 1 1 1 3 2 3 2 2 1 | 1013 |
| 1 1 1 3 1 3 2 1 2 3 2 3 2 3 2 1 2 3 1 2 1 2 2 2 | 1014 |
| 1 1 1 3 1 2 1 1 3 1 3 2 2 1 3 2 1 1 1 2 2 3 2 3 | 1015 |
| 1 1 3 1 1 2 2 1 3 1 3 1 1 2 1 1 3 2 3 2 3 1 2 1 | 1016 |
| 3 1 2 1 1 3 1 1 1 3 2 3 1 1 1 2 3 2 1 1 2 2 2 3 | 1017 |
| 3 2 3 1 1 1 3 1 2 3 2 2 2 1 2 1 1 3 2 2 2 3 2 2 | 1018 |
| 1 3 2 3 2 1 1 3 2 1 1 2 1 1 3 2 2 2 3 1 3 1 1 1 | 1019 |
| 3 2 2 3 1 3 1 1 2 2 1 3 1 1 2 2 2 3 1 2 1 1 1 3 | 1020 |
| 2 2 1 1 3 1 1 1 2 2 2 3 2 1 2 3 2 3 2 2 3 2 2 3 | 1021 |
| 1 3 1 1 3 1 2 2 2 1 3 1 2 3 1 1 1 2 3 1 3 2 2 2 | 1022 |
| 2 1 1 3 2 2 2 3 1 3 1 2 1 1 1 3 1 2 3 1 2 1 2 3 | 1023 |
| 2 3 1 3 1 2 1 3 2 2 2 3 2 1 1 2 1 2 3 2 2 2 3 2 | 1024 |
| 1 3 2 2 2 3 1 1 1 2 2 3 2 1 1 3 2 2 2 3 1 2 3 1 | 1025 |

TABLE IA-continued

Numeric sequences corresponding to nucleotide base patterns of a set of oligonucleotides

| Numeric Pattern | Sequence Identifier |
|---|---|
| 2 1 3 1 1 2 2 3 1 2 2 1 1 2 3 1 2 3 1 3 2 1 3 2 | 1026 |
| 1 3 1 3 1 2 2 2 3 2 1 1 2 1 1 3 2 1 2 2 3 1 1 3 | 1027 |
| 1 2 1 1 2 3 1 2 3 2 1 1 2 3 2 1 1 3 2 1 3 2 3 2 | 1028 |
| 2 3 1 1 1 2 2 2 3 1 2 3 1 3 1 3 1 2 1 2 3 2 2 1 | 1029 |
| 2 3 2 3 2 1 1 1 3 2 1 2 1 3 2 2 2 1 2 3 2 2 1 3 | 1030 |
| 2 3 1 1 2 1 1 3 2 3 1 1 1 2 1 3 1 1 2 3 1 1 2 3 | 1031 |
| 1 1 1 3 1 1 1 3 1 2 2 3 2 1 1 2 1 1 3 2 1 3 1 3 | 1032 |
| 1 1 2 3 1 1 1 2 1 3 2 3 2 2 1 1 1 2 3 1 3 2 3 2 | 1033 |
| 3 2 1 3 1 2 1 1 1 3 1 2 3 2 3 1 1 2 2 1 2 3 1 2 | 1034 |
| 3 1 2 1 3 2 1 2 1 2 3 2 3 2 3 2 1 2 2 2 3 2 2 2 | 1035 |
| 1 2 3 2 2 2 3 2 1 3 1 1 1 2 3 2 2 2 3 1 1 3 1 2 | 1036 |
| 1 1 1 2 2 2 3 2 1 3 1 3 1 3 1 1 1 2 2 2 3 2 2 3 | 1037 |
| 2 1 3 1 1 2 1 1 3 1 2 2 1 3 2 1 1 3 2 3 2 1 3 1 | 1038 |
| 2 3 1 2 2 2 1 3 1 3 1 1 1 2 1 2 3 1 3 2 1 3 1 1 | 1039 |
| 1 1 2 1 3 1 3 2 1 2 3 2 2 3 2 2 2 1 2 3 1 3 1 1 | 1040 |
| 3 1 2 3 1 2 3 1 1 3 1 3 2 2 2 1 2 2 3 2 1 1 1 2 | 1041 |
| 1 1 3 2 1 1 1 3 1 1 3 1 1 3 1 1 1 2 3 2 3 2 2 1 | 1042 |
| 2 2 3 1 1 3 1 1 2 2 1 1 3 2 3 2 2 2 1 3 2 3 2 1 | 1043 |
| 1 3 1 1 1 3 1 1 2 3 2 2 3 1 2 2 2 1 2 3 1 2 3 2 | 1044 |
| 3 1 2 2 1 1 1 3 1 3 1 2 3 2 2 3 1 2 2 3 1 1 1 2 | 1045 |
| 1 1 2 3 1 2 1 1 2 2 3 2 2 3 1 3 1 3 1 3 2 1 1 2 | 1046 |
| 3 2 2 2 3 2 2 3 1 1 1 3 2 3 2 1 1 1 3 2 1 2 1 2 | 1047 |
| 2 3 1 3 2 2 1 2 1 2 3 1 3 1 1 1 3 2 3 2 1 1 2 2 | 1048 |
| 2 2 3 2 3 1 3 1 1 1 3 1 1 3 2 1 2 1 2 1 3 1 1 2 | 1049 |
| 3 2 1 1 3 2 2 2 1 3 1 3 2 2 1 2 1 3 1 3 2 2 2 1 | 1050 |
| 3 1 2 1 3 1 2 1 3 1 2 1 1 3 2 2 1 1 2 2 3 1 1 3 | 1051 |
| 1 3 1 3 1 2 3 1 2 2 3 2 2 2 1 2 3 2 1 2 2 1 2 3 | 1052 |
| 1 1 1 3 2 2 1 1 3 1 1 1 2 2 3 2 1 3 2 3 1 2 1 3 | 1053 |
| 2 2 2 3 1 2 1 2 2 3 2 2 2 3 2 3 1 3 2 3 2 1 2 1 | 1054 |
| 1 2 2 2 3 2 1 3 1 1 1 3 2 2 3 2 2 1 2 3 1 3 2 2 | 1055 |
| 3 1 2 2 2 3 1 3 2 1 1 3 2 2 2 1 2 1 3 1 2 3 1 1 | 1056 |
| 1 1 3 1 2 1 1 1 3 2 3 1 3 2 2 3 1 2 2 2 1 3 1 2 | 1057 |
| 3 1 2 1 2 2 3 2 1 1 3 1 2 1 2 3 2 2 3 2 1 1 1 3 | 1058 |
| 3 2 1 1 3 1 3 2 3 2 1 2 2 3 2 2 1 1 3 2 2 1 1 2 2 | 1059 |
| 3 2 3 2 3 1 2 2 1 3 2 1 1 2 3 1 1 3 2 1 2 2 2 1 | 1060 |
| 3 2 1 1 3 1 1 1 3 1 2 2 1 1 3 2 3 2 2 2 1 3 2 1 1 | 1061 |

TABLE IA-continued

Numeric sequences corresponding to nucleotide
base patterns of a set of oligonucleotides

| Numeric Pattern | Sequence Identifier |
|---|---|
| 1 3 2 1 3 1 1 1 3 2 2 3 1 1 1 2 2 3 1 2 2 1 2 3 | 1062 |
| 2 1 1 3 1 3 1 1 3 2 2 3 1 3 2 1 1 2 3 2 1 2 2 2 | 1063 |
| 3 2 2 1 1 3 1 1 1 2 1 3 2 1 3 1 2 1 1 3 2 3 1 1 | 1064 |
| 2 1 1 3 2 1 1 1 2 2 3 1 1 1 3 2 3 2 1 2 1 3 2 3 | 1065 |
| 1 1 3 1 2 3 2 1 2 3 2 2 2 1 2 2 3 2 2 3 2 3 2 1 | 1066 |
| 1 2 2 2 1 3 1 1 2 1 2 1 3 2 3 1 1 3 1 3 1 2 1 3 | 1067 |
| 3 2 2 1 2 3 1 1 1 3 1 3 2 1 2 3 2 3 2 2 1 1 1 2 | 1068 |
| 2 1 2 2 1 2 3 2 3 1 1 3 1 1 3 1 1 2 3 1 2 2 1 3 | 1069 |
| 2 1 1 2 1 1 3 2 2 3 1 1 3 1 3 1 1 2 2 3 2 2 3 2 | 1070 |
| 2 3 1 2 3 2 2 2 3 1 2 3 2 1 1 2 2 3 2 2 1 1 1 3 | 1071 |
| 3 2 3 1 1 1 3 1 2 2 2 3 1 3 2 2 2 3 2 1 2 1 1 2 | 1072 |
| 1 3 1 3 1 1 2 1 2 1 3 1 2 2 3 1 3 1 2 2 2 3 2 2 | 1073 |
| 2 2 2 3 1 3 1 2 3 2 3 1 2 3 1 2 1 1 1 3 2 2 1 1 | 1074 |
| 3 2 2 3 2 1 1 1 2 2 3 2 1 3 2 1 1 1 3 1 1 3 2 1 | 1075 |
| 3 2 3 2 2 1 2 3 1 2 3 2 2 3 2 2 2 3 2 1 2 2 1 2 | 1076 |
| 1 2 2 1 2 2 3 2 3 2 1 3 1 2 3 2 1 2 2 1 1 3 1 3 | 1077 |
| 3 2 2 1 3 1 1 1 3 1 2 2 2 1 3 1 1 3 2 2 1 3 2 2 | 1078 |
| 2 2 3 2 3 2 1 2 2 1 1 3 1 3 1 3 2 3 1 1 1 2 1 2 | 1079 |
| 3 2 2 2 1 1 3 1 2 1 3 1 1 1 3 1 3 2 3 1 2 2 2 1 | 1080 |
| 1 1 2 3 1 3 1 1 1 2 1 3 1 2 1 3 2 2 1 2 2 3 2 3 | 1081 |
| 2 3 1 1 2 2 3 1 1 2 1 1 3 1 1 2 2 2 3 2 2 3 2 3 | 1082 |
| 1 1 2 1 1 3 1 2 2 3 1 1 2 2 1 3 2 3 1 3 2 1 1 3 | 1083 |
| 1 1 2 3 2 2 2 3 1 3 1 3 1 2 2 2 1 3 2 1 1 1 3 1 | 1084 |
| 1 3 2 2 2 1 3 1 1 2 1 3 1 1 1 2 3 2 3 2 2 2 3 1 | 1085 |
| 2 1 2 1 1 3 2 1 1 3 2 3 2 2 1 1 3 1 2 2 2 3 1 3 | 1086 |
| 3 2 1 3 2 3 1 1 2 1 1 3 2 2 1 3 2 3 2 2 1 1 2 1 | 1087 |
| 1 1 3 2 3 2 3 2 2 1 1 1 3 2 1 1 1 2 3 2 1 3 1 2 | 1088 |
| 1 3 1 3 1 2 3 2 2 2 1 2 3 2 2 3 2 3 1 1 2 2 1 1 | 1089 |
| 1 3 2 2 3 1 1 2 1 2 2 3 1 2 3 1 2 1 1 3 1 1 3 1 | 1090 |
| 2 3 1 1 2 3 2 3 1 3 1 2 3 2 2 2 1 3 1 1 2 1 1 2 | 1091 |
| 1 1 2 1 1 2 3 1 2 3 2 1 1 3 2 2 2 3 1 3 2 2 2 3 | 1092 |
| 1 1 1 3 1 3 2 3 1 1 2 1 3 1 1 1 2 1 1 3 1 3 1 1 | 1093 |
| 1 1 2 1 1 1 3 2 2 1 2 2 3 1 3 1 3 1 3 2 2 2 1 3 | 1094 |
| 1 3 2 1 3 2 3 2 2 2 3 2 1 3 2 2 2 1 3 2 1 2 1 2 1 | 1095 |
| 3 2 1 1 3 1 1 1 2 3 2 1 2 2 1 3 1 2 1 2 2 2 3 2 3 | 1096 |
| 3 1 2 1 1 1 2 3 2 2 2 3 1 2 1 1 1 3 2 1 3 2 2 3 | 1097 |
| 1 2 1 3 2 1 2 3 2 1 2 3 2 3 2 3 1 1 3 1 2 2 2 1 | 1098 |

TABLE IA-continued

Numeric sequences corresponding to nucleotide
base patterns of a set of oligonucleotides

| Numeric Pattern | Sequence Identifier |
|---|---|
| 1 2 3 1 1 2 3 2 1 3 1 3 2 3 1 2 2 1 3 2 2 2 1 1 | 1099 |
| 3 2 1 3 2 1 2 2 2 1 3 2 3 1 2 3 2 1 1 3 1 1 2 1 | 1100 |
| 1 3 1 1 2 2 3 2 1 2 2 3 1 1 3 1 1 3 1 1 2 1 2 3 | 1101 |
| 2 2 2 1 2 1 3 1 1 2 2 3 1 3 1 3 1 1 3 2 2 1 1 3 | 1102 |
| 1 1 1 3 2 1 3 2 1 3 1 3 1 2 2 2 3 1 3 1 1 2 2 1 | 1103 |
| 2 2 2 1 1 1 3 1 1 1 3 2 1 2 2 3 2 1 1 3 1 3 2 3 | 1104 |
| 1 1 1 2 2 3 1 3 1 1 1 3 2 3 1 1 2 3 1 1 3 2 2 2 | 1105 |
| 1 1 3 1 1 1 2 1 1 3 2 1 2 3 1 2 1 3 2 1 3 2 1 3 | 1106 |
| 1 2 2 2 3 1 1 2 2 3 2 1 2 2 3 2 1 3 2 2 2 3 2 3 | 1107 |
| 1 1 3 1 3 1 1 2 1 1 2 3 2 1 3 1 3 1 2 1 2 1 1 3 | 1108 |
| 2 3 2 3 2 1 1 2 1 3 2 2 3 2 2 1 1 2 3 1 3 2 1 1 | 1109 |
| 2 1 2 1 3 2 2 3 2 1 3 2 2 2 1 3 1 2 3 1 1 2 3 2 | 1110 |
| 1 2 2 3 2 3 2 2 1 3 1 1 2 3 1 2 3 2 2 1 1 2 1 3 | 1111 |
| 3 2 2 2 3 2 1 2 1 3 2 1 2 2 2 3 1 2 2 3 1 2 3 2 | 1112 |
| 1 3 1 3 2 1 1 1 3 2 1 2 3 1 3 2 2 1 2 3 1 1 2 1 | 1113 |
| 3 1 1 1 3 2 2 2 1 1 3 2 3 1 2 3 2 1 2 1 2 2 3 2 | 1114 |
| 2 2 1 1 1 2 3 1 2 1 1 1 3 1 3 2 1 3 2 3 1 1 3 2 | 1115 |
| 2 2 1 1 1 2 3 2 3 2 3 1 3 1 1 3 1 2 3 1 1 2 1 1 | 1116 |
| 1 2 2 2 3 2 1 2 1 1 1 3 2 3 1 1 3 1 1 3 1 3 1 1 | 1117 |
| 2 3 1 2 2 1 3 2 1 2 2 2 3 2 3 1 1 3 1 3 1 2 2 2 | 1118 |
| 2 2 2 3 1 1 2 3 1 1 1 2 2 3 1 2 3 1 2 1 3 1 2 3 | 1119 |
| 1 3 1 3 2 1 1 3 1 2 2 1 1 3 1 1 2 1 1 3 1 1 1 3 | 1120 |
| 1 2 2 3 1 1 2 2 3 1 3 1 1 1 3 2 3 1 1 3 2 1 1 1 2 | 1121 |
| 2 2 2 1 3 1 3 1 1 3 2 1 2 2 3 2 2 2 3 1 1 1 3 1 | 1122 |
| 2 1 1 1 3 2 3 1 1 1 3 1 2 2 2 3 1 1 1 2 3 1 2 3 | 1123 |
| 3 1 1 1 3 2 2 2 1 3 1 3 1 1 1 2 3 2 1 3 1 1 1 2 2 | 1124 |
| 3 2 3 1 1 2 1 1 2 3 1 1 3 1 1 3 2 2 1 2 3 2 2 1 | 1125 |
| 2 2 3 2 3 1 1 2 1 1 1 3 2 1 3 1 2 3 2 3 2 2 1 2 | 1126 |
| 2 2 1 2 1 2 3 1 2 1 2 3 1 3 2 2 2 3 2 3 2 2 3 1 | 1127 |
| 2 2 3 1 2 2 2 3 2 3 2 3 1 3 2 1 2 2 1 3 2 2 1 2 | 1128 |
| 1 1 1 3 2 3 1 2 2 1 1 3 2 2 1 3 2 2 2 3 1 3 1 2 | 1129 |
| 2 2 3 2 1 2 2 2 3 2 1 2 1 1 2 3 2 2 1 1 3 1 1 3 | 1130 |
| 3 2 2 2 3 1 1 1 2 2 1 3 2 3 2 3 1 3 1 1 1 2 1 2 | 1131 |
| 1 1 2 3 2 2 3 1 3 1 2 2 3 1 2 1 1 2 3 2 2 3 1 1 | 1132 |
| 2 1 3 2 1 3 2 1 3 2 1 2 2 3 2 2 2 3 2 1 1 2 1 1 3 | 1133 |
| 3 2 2 3 2 1 1 2 2 2 3 1 3 2 3 2 2 1 3 2 2 1 2 2 | 1134 |

TABLE IA-continued

Numeric sequences corresponding to nucleotide
base patterns of a set of oligonucleotides

| Numeric Pattern | Sequence Identifier |
|---|---|
| 2 3 1 1 2 1 2 3 1 2 1 3 2 2 1 3 2 1 1 2 2 3 2 3 | 1135 |
| 2 3 1 2 1 3 2 1 2 3 2 2 2 3 2 3 1 2 2 1 1 1 3 1 | 1136 |
| 3 1 2 3 2 1 2 1 1 1 3 1 3 2 1 2 3 2 2 1 2 1 1 3 | 1137 |
| 1 3 2 3 1 3 1 2 2 2 1 3 1 1 3 1 2 3 2 2 1 2 2 1 | 1138 |
| 1 2 3 1 3 1 1 2 2 2 3 2 2 1 1 1 3 1 3 1 1 1 3 2 | 1139 |
| 1 1 1 3 1 1 2 2 1 3 2 1 2 3 1 2 1 3 1 2 3 1 3 1 | 1140 |
| 2 1 3 1 3 2 2 3 2 1 2 1 3 2 2 2 1 2 1 3 2 2 3 1 | 1141 |
| 3 2 1 3 1 1 2 3 1 2 2 3 2 2 2 1 3 1 1 3 1 2 2 2 | 1142 |
| 3 2 2 2 1 2 3 2 2 2 3 1 3 1 1 3 1 3 2 2 1 2 2 2 | 1143 |
| 2 1 3 1 1 3 2 2 2 3 1 1 1 3 2 2 1 2 2 3 1 2 2 3 | 1144 |
| 3 1 2 3 1 1 3 1 3 2 1 2 2 2 3 2 2 1 2 1 2 3 2 1 | 1145 |
| 3 1 2 3 1 1 2 1 2 1 3 2 1 1 3 2 1 2 2 3 1 3 2 1 | 1146 |
| 2 1 3 2 3 1 2 3 1 1 1 2 2 2 3 1 3 1 2 1 3 1 2 1 | 1147 |
| 3 1 1 1 3 1 1 1 2 2 3 1 1 3 1 3 2 2 2 3 1 2 1 2 | 1148 |
| 1 2 2 2 3 1 3 2 1 2 2 2 3 2 3 2 1 2 2 3 1 1 2 3 | 1149 |
| 1 2 3 1 3 2 2 3 1 1 1 2 2 2 3 1 1 3 2 1 2 2 3 2 | 1150 |
| 2 2 1 1 2 1 3 2 3 1 3 1 3 1 3 2 1 2 1 2 3 2 1 1 | 1151 |
| 1 2 2 1 1 3 1 3 1 3 2 3 1 3 2 1 1 1 2 3 2 1 1 1 | 1152 |
| 1 1 3 1 1 2 1 3 1 2 3 1 3 1 2 2 1 3 1 1 1 2 1 3 | 1153 |
| 1 3 2 2 2 1 1 1 3 1 3 2 2 1 3 1 1 2 2 3 1 1 1 3 | 1154 |
| 3 2 1 1 3 1 2 2 2 3 2 2 3 1 1 2 1 1 1 3 1 1 3 1 | 1155 |
| 1 3 1 3 1 1 1 3 1 1 3 2 2 1 1 1 3 2 3 1 2 1 2 2 | 1156 |
| 2 1 1 2 1 3 1 3 1 1 3 1 3 1 2 3 2 1 2 3 1 1 2 1 | 1157 |
| 2 2 1 2 2 1 3 2 3 1 2 1 1 3 2 3 1 1 3 2 2 2 1 3 | 1158 |
| 1 2 1 1 2 3 2 1 1 1 3 1 2 3 1 3 2 2 2 1 2 3 1 3 | 1159 |
| 2 2 3 1 2 2 2 3 1 3 1 3 2 2 3 1 2 1 1 3 1 2 2 2 | 1160 |
| 1 2 3 1 2 2 1 2 2 3 2 3 2 3 2 1 3 1 1 2 2 1 3 1 | 1161 |
| 2 1 2 1 1 1 3 1 2 1 2 1 3 2 1 3 1 2 3 1 2 3 2 3 | 1162 |
| 2 2 2 1 3 2 2 3 1 3 1 2 3 1 1 3 2 2 1 2 2 1 3 1 | 1163 |
| 1 2 2 3 1 1 2 2 3 1 2 1 2 1 3 2 3 2 1 1 1 3 2 3 | 1164 |
| 3 1 1 3 1 1 1 3 1 2 2 1 2 2 3 2 1 2 2 3 1 3 2 2 | 1165 |
| 1 2 2 3 1 3 2 3 2 1 3 2 3 1 2 2 2 1 3 1 1 1 2 1 | 1166 |
| 1 1 2 1 1 1 1 3 2 3 2 2 2 1 1 3 1 3 2 1 3 1 3 2 1 | 1167 |
| 3 2 1 3 1 3 1 2 1 1 2 2 3 1 2 3 2 3 2 1 1 2 2 2 | 1168 |

In Table IA, each of the numerals 1 to 3 (numeric identifiers) represents a nucleotide base and the pattern of numerals 1 to 3 of the sequences in the above list corresponds to the pattern of nucleotide bases present in the oligonucleotides of Table I, which oligonucleotides have been found to be non-cross-hybridizing, as described further in the detailed examples. Each nucleotide base is selected from the group of nucleotide bases consisting of A, C, G, and T/U. A particularly preferred embodiment of the invention, in which a specific base is assigned to each numeric identifier is shown in Table I, below.

In one broad aspect, the invention is a composition comprising molecules for use as tags or tag complements wherein each molecule comprises an oligonucleotide selected from a set of oligonucleotides based on a group of sequences as specified by numeric identifiers set out in Table IA. In the sequences, each of 1 to 3 is a nucleotide base selected to be different from the others of 1 to 3 with the proviso that up to three nucleotide bases of each sequence can be substituted with any nucleotide base provided that:
  for any pair of sequences of the set:
    $M1 \leq 16$, $M2 \leq 13$, $M3 \leq 20$, $M4 \leq 16$, and $M5 \leq 19$, where:
      M1 is the maximum number of matches for any alignment in which there are no internal indels;
      M2 is the maximum length of a block of matches for any alignment;
      M3 is the maximum number of matches for any alignment having a maximum score;
      M4 is the maximum sum of the lengths of the longest two blocks of matches for any alignment of maximum score; and
      M5 is the maximum sum of the lengths of all the blocks of matches having a length of at least 3, for any alignment of maximum score; wherein:
        the score of an alignment is determined according to the equation $(A \times m)-(B \times mm)-(C \times (og+eg))-(D \times eg))$, wherein:
          for each of (i) to (iv):
            (i) M=6, mm=6, og=0 and eg=6,
            (ii) M=6, mm=6, og=5 and eg=1,
            (iii) M=6, mm=2, og=5 and eg=1, and
            (iv) M=6, mm=6, og=6 and eg=0,
          A is the total number of matched pairs of bases in the alignment;
          B is the total number of internal mismatched pairs in the alignment;
          C is the total number of internal gaps in the alignment; and
          D is the total number of internal indels in the alignment minus the total number of internal gaps in the alignment; and
        wherein the maximum score is determined separately for each of (i), (ii), (iii) and (iv).

An explanation of the meaning of the parameters set out above is given in the section describing detailed embodiments.

In another broad aspect, the invention is a composition containing molecules for use as tags or tag complements wherein each molecule comprises an oligonucleotide selected from a set of oligonucleotides based on a group of sequences as set out in Table IA wherein each of 1 to 3 is a nucleotide base selected to be different from the others of 1 to 3 with the proviso that up to three nucleotide bases of each sequence can be substituted with any nucleotide base provided that:
  for any pair of sequences of the set:
    $M1 \leq 19$, $M2 \leq 17$, $M3 \leq 21$, $M4 \leq 18$, and $M5 \leq 20$, where:
      M1 is the maximum number of matches for any alignment in which there are no internal indels;
      M2 is the maximum length of a block of matches for any alignment;
      M3 is the maximum number of matches for any alignment having a maximum score;
      M4 is the maximum sum of the lengths of the longest two blocks of matches for any alignment of maximum score; and
      M5 is the maximum sum of the lengths of all the blocks of matches having a length of at least 3, for any alignment of maximum score; wherein
        the score of an alignment is determined according to the equation $(A \times m)-(B \times mm)-(C \times (og+eg))-(D \times eg))$, wherein:
          for each of (i) to (iv):
            (i) M=6, mm=6, og=0 and eg=6,
            (ii) M=6, mm=6, og=5 and eg=1,
            (iii) M=6, mm=2, og=5 and eg=1, and
            (iv) M=6, mm=6, og=6 and eg=0,
          A is the total number of matched pairs of bases in the alignment;
          B is the total number of internal mismatched pairs in the alignment;
          C is the total number of internal gaps in the alignment; and
          D is the total number of internal indels in the alignment minus the total number of internal gaps in the alignment; and
        wherein the maximum score is determined separately for each of (i), (ii), (iii) and (iv).

In another broad aspect, the invention is a composition comprising molecules for use as tags or tag complements wherein each molecule comprises an oligonucleotide selected from a set of oligonucleotides based on a group of sequences set out in Table IA wherein each of 1 to 3 is a nucleotide base selected to be different from the others of 1 to 3 with the proviso that up to three nucleotide bases of each sequence can be substituted with any nucleotide base provided that:
  for any pair of sequences of the set:
    $M1 \leq 19$, $M2 \leq 17$, $M3 \leq 21$, $M4 \leq 18$, and $M5 \leq 20$, where:
      M1 is the maximum number of matches for any alignment in which there are no internal indels;
      M2 is the maximum length of a block of matches for any alignment;
      M3 is the maximum number of matches for any alignment having a maximum score;
      M4 is the maximum sum of the lengths of the longest two blocks of matches for any alignment of maximum score; and
      M5 is the maximum sum of the lengths of all the blocks of matches having a length of at least 3, for any alignment of maximum score, wherein:
        the score of an alignment is determined according to the equation $3A-B-3C-D$, wherein:
          A is the total number of matched pairs of bases in the alignment;
          B is the total number of internal mismatched pairs in the alignment;
          C is the total number of internal gaps in the alignment; and
          D is the total number of internal indels in the alignment minus the total number of internal gaps in the alignment.

In preferred aspects, the invention provides a composition in which, for the group of 24mer sequences in which 1=A, 2=T and 3=G, under a defined set of conditions in which the maximum degree of hybridization between a sequence and any complement of a different sequence of the group of 24mer sequences does not exceed 30% of the degree of hybridization between said sequence and its complement, for all said oligonucleotide of the composition, the maximum degree of hybridization between an oligonucleotide and a complement of any other oligonucleotide of the composition does not exceed 50% of the degree of hybridization of the oligonucleotide and its complement.

More preferably, the maximum degree of hybridization between a sequence and any complement of a different sequence does not exceed 30% of the degree of hybridization between said sequence and its complement, the degree of hybridization between each sequence and its complement varies by a factor of between 1 and up to 10, more preferably between 1 and up to 9, more preferably between 1 and up to 8, more preferably between 1 and up to 7, more preferably between 1 and up to 6, and more preferably between 1 and up to 5.

It is also preferred that the maximum degree of hybridization between a sequence and any complement of a different sequence does not exceed 25%, more preferably does not exceed 20%, more preferably does not exceed 15%, more preferably does not exceed 10%, more preferably does not exceed 5%.

Even more preferably, the above-referenced defined set of conditions results in a level of hybridization that is the same as the level of hybridization obtained when hybridization conditions include 0.2 M NaCl, 0.1 M Tris, 0.08% Triton X-100, pH 8.0 at 37° C.

In the composition, the defined set of conditions can include the group of 24mer sequences being covalently linked to beads.

In a particular preferred aspect, for the group of 24mers the maximum degree of hybridization between a sequence and any complement of a different sequence does not exceed 15% of the degree of hybridization between said sequence and its complement and the degree of hybridization between each sequence and its complement varies by a factor of between 1 and up to 9, and for all oligonucleotides of the set, the maximum degree of hybridization between an oligonucleotide and a complement of any other oligonucleotide of the set does not exceed 20% of the degree of hybridization of the oligonucleotide and its complement.

It is possible that each 1 is one of A, T/U, G and C; each 2 is one of A, T/U, G and C; and each 3 is one of A, T/U, G and C; and each of 1, 2 and 3 is selected so as to be different from all of the others of 1, 2 and 3. More preferably, 1 is A or T/U, 2 is A or T/U and 3 is G or C. Even more preferably, 1 is A, 2 is T/U, and 3 is G.

In certain preferred composition, each of the oligonucleotides is from twenty-two to twenty-six bases in length, or from twenty-three to twenty-five, and preferably, each oligonucleotide is of the same length as every other said oligonucleotide.

In a particularly preferred embodiment, each oligonucleotide is twenty-four bases in length.

It is preferred that no oligonucleotide contains more than four contiguous bases that are identical to each other.

It is also preferred that the number of G's in each oligonucleotide does not exceed L/4 where L is the number of bases in said sequence.

For reasons described below, the number of G's in each said oligonucleotide is preferred not to vary from the average number of G's in all of the oligonucleotides by more than one Even more preferably, the number of G's in each said oligonucleotide is the same as every other said oligonucleotide. In the embodiment disclosed below in which oligonucleotides were tested, the sequence of each was twenty-four bases in length and each oligonucleotide contained 6 G's.

It is also preferred that, for each nucleotide, there is at most six bases other than G between every pair of neighboring pairs of G's.

Also, it is preferred that, at the 5'-end of each oligonucleotide at least one of the first, second, third, fourth, fifth, sixth and seventh bases of the sequence of the oligonucleotide is a G. Similarly, it is preferred, at the 3'-end of each oligonucleotide that at least one of the first, second, third, fourth, fifth, sixth and seventh bases of the sequence of the oligonucleotide is a G.

It is possible to have sequence compositions that include one hundred and sixty said molecules, or that include one hundred and seventy said molecules, or that include one hundred and eighty said molecules, or that include one hundred and ninety said molecules, or that include two hundred said molecules, or that include two hundred and twenty said molecules, or that include two hundred and forty said molecules, or that include two hundred and sixty said molecules, or that include two hundred and eighty said molecules, or that include three hundred said molecules, or that include four hundred said molecules, or that include five hundred said molecules, or that include six hundred said molecules, or that include seven hundred said molecules, or that include eight hundred said molecules, or that include nine hundred said molecules, or that include one thousand said molecules.

It is possible, in certain applications, for each molecule to be linked to a solid phase support so as to be distinguishable from a mixture containing other of the molecules by hybridization to its complement. Such a molecule can be linked to a defined location on a solid phase support such that the defined location for each molecule is different than the defined location for different others of the molecules.

In certain embodiments, each solid phase support is a microparticle and each said molecule is covalently linked to a different microparticle than each other different said molecule.

In another broad aspect, the invention is a composition comprising a set of 150 molecules for use as tags or tag complements wherein each molecule includes an oligonucleotide having a sequence of at least sixteen nucleotide bases wherein for any pair of sequences of the set:

$M1 \leq 19/24 \times L1$, $M2 \leq 17/24 \times L1$, $M3 \leq 21/24 \times L1$, $M4 \leq 18/24 \times L1$, $M5 \leq 20/24 \times L1$, where L1 is the length of the shortest sequence of the pair, where:

M1 is the maximum number of matches for any alignment of the pair of sequences in which there are no internal indels;

M2 is the maximum length of a block of matches for any alignment of the pair of sequences;

M3 is the maximum number of matches for any alignment of the pair of sequences having a maximum score;

M4 is the maximum sum of the lengths of the longest two blocks of matches for any alignment of the pair of sequences of maximum score; and M5 is the maximum sum of the lengths of all the blocks of matches having a length of at least 3, for any alignment of the pair of sequences of maximum score, wherein:

the score of an alignment is determined according to the equation (A×m)−(B×mm)−(C×(og+eg))−(D×eg)), wherein:

for each of (i) to (iv):
(i) m=6, mm=6, og=0 and eg=6,
(ii) m=6, mm=6, og=5 and eg=1,
(iii) m=6, mm=2, og=5 and eg=1, and
(iv) m=6, mm=6, og=6 and eg=0,
A is the total number of matched pairs of bases in the alignment;
B is the total number of internal mismatched pairs in the alignment;
C is the total number of internal gaps in the alignment; and
D is the total number of internal indels in the alignment minus the total number of internal gaps in the alignment; and wherein the maximum score is determined separately for each of (i), (ii), (iii) and (iv).

In yet another broad aspect, the invention is a composition that includes a set of 150 molecules for use as tags or tag complements wherein each molecule has an oligonucleotide having a sequence of at least sixteen nucleotide bases wherein for any pair of sequences of the set:

M1≦19, M2≦17, M3≦21, M4≦18, and M5≦20, where:
M1 is the maximum number of matches for any alignment of the pair of sequences in which there are no internal indels;
M2 is the maximum length of a block of matches for any alignment of the pair of sequences;
M3 is the maximum number of matches for any alignment of the pair of sequences having a maximum score;
M4 is the maximum sum of the lengths of the longest two blocks of matches for any alignment of the pair of sequences of maximum score; and
M5 is the maximum sum of the lengths of all the blocks of matches having a length of at least 3, for any alignment of the pair of sequences of maximum score, wherein:

the score of a said alignment is determined according to the equation 3A−B−3C−D, wherein:
A is the total number of matched pairs of bases in the alignment;
B is the total number of internal mismatched pairs in the alignment;
C is the total number of internal gaps in the alignment; and
D is the total number of internal indels in the alignment minus the total number of internal gaps in the alignment.

In certain embodiments of the invention, each sequence of a composition has up to fifty bases. More preferably, however, each sequence is between sixteen and forty bases in length, or between sixteen and thirty-five bases in length, or between eighteen and thirty bases in length, or between twenty and twenty-eight bases in length, or between twenty-one and twenty-seven bases in length, or between twenty-two and twenty-six bases in length.

Often, each sequence is of the same length as every other said sequence. In particular embodiments disclosed herein, each sequence is twenty-four bases in length.

Again, it can be preferred that no sequence contains more than four contiguous bases that are identical to each other, etc., as described above.

In certain preferred embodiments, the composition is such that, under a defined set of conditions, the maximum degree of hybridization between an oligonucleotide and any complement of a different oligonucleotide of the composition does not exceed about 30% of the degree of hybridization between said oligonucleotide and its complement, more preferably 20%, more preferably 15%, more preferably 10%, more preferably 6%.

Preferably, the set of conditions results in a level of hybridization that is the same as the level of hybridization obtained when hybridization conditions include 0.2 M NaCl, 0.1 M Tris, 0.08% Triton X-100, pH 8.0 at 37° C., and the oligonucleotides are covalently linked to microparticles. Of course it is possible that these specific conditions be used for determining the level of hybridization.

It is also preferred that under such a defined set of conditions, the degree of hybridization between each oligonucleotide and its complement varies by a factor of between 1 and up to 8, more preferably up to 7, more preferably up to 6, more preferably up to 5. In a particular disclosed embodiment, the observed variance in the degree of hybridization was a factor of only 5.3, i.e., the degree of hybridization between each oligonucleotide and its complement varied by a factor of between 1 and 5.6.

In certain preferred embodiments, under the defined set of conditions, the maximum degree of hybridization between a said oligonucleotide and any complement of a different oligonucleotide of the composition does not exceed about 15%, more preferably 10%, more preferably 6%.

In one preferred embodiment, the set of conditions results in a level of hybridization that is the same as the level of hybridization obtained when hybridization conditions include 0.2 M NaCl, 0.1 M Tris, 0.08% Triton X-100, pH 8.0 at 37° C., and the oligonucleotides are covalently linked to microparticles.

Also, under the defined set of conditions, it is preferred that the degree of hybridization between each oligonucleotide and its complement varies by a factor of between 1 and up to 8, more preferably up to 7, more preferably up to 6, more preferably up to 5.

Any composition of the invention can include one hundred and sixty of the oligonucleotide molecules, or one hundred and seventy of the oligonucleotide molecules, or one hundred and eighty of the oligonucleotide molecules, or one hundred and ninety of the oligonucleotide molecules, or two hundred of the oligonucleotide molecules, or two hundred and twenty of the oligonucleotide molecules, or two hundred and forty of the oligonucleotide molecules, or two hundred and sixty of the oligonucleotide molecules, or two hundred and eighty of the oligonucleotide molecules, or three hundred of the oligonucleotide molecules, or four hundred of the oligonucleotide molecules, or five hundred of the oligonucleotide molecules, or six hundred of the oligonucleotide molecules, or seven hundred of the oligonucleotide molecules, or eight hundred of the oligonucleotide molecules, or nine hundred of the oligonucleotide molecules, or one thousand or more of the oligonucleotide molecules.

A composition of the invention can be a family of tags, or it can be a family of tag complements.

An oligonucleotide molecule belonging to a family of molecules of the invention can have incorporated thereinto one more analogues of nucleotide bases, preference being given those that undergo normal Watson-Crick base pairing.

The invention includes kits for sorting and identifying polynucleotides. Such a kit can include one or more solid phase supports each having one or more spatially discrete regions, each such region having a uniform population of substantially identical tag complements covalently attached. The tag complements are made up of a set of oligonucleotides of the invention.

The one or more solid phase supports can be a planar substrate in which the one or more spatially discrete regions is a plurality of spatially addressable regions.

The tag complements can also be coupled to microparticles. Microparticles preferably each have a diameter in the range of from 5 to 40 μm.

Such a kit preferably includes microparticles that are spectrophotometrically unique, and therefore distinguishable from each other according to conventional laboratory techniques. Of course for such kits to work, each type of microparticle would generally have only one tag complement associated with it, and usually there would be a different oligonucleotide tag complement associated with (attached to) each type of microparticle.

The invention includes methods of using families of oligonucleotides of the invention.

One such method is of analyzing a biological sample containing a biological sequence for the presence of a mutation or polymorphism at a locus of the nucleic acid. The method includes:

(A) amplifying the nucleic acid molecule in the presence of a first primer having a 5'-sequence having the sequence of a tag complementary to the sequence of a tag complement belonging to a family of tag complements of the invention to form an amplified molecule with a 5'-end with a sequence complementary to the sequence of the tag;

(B) extending the amplified molecule in the presence of a polymerase and a second primer having 5'-end complementary the 3'-end of the amplified sequence, with the 3'-end of the second primer extending to immediately adjacent said locus, in the presence of a plurality of nucleoside triphosphate derivatives each of which is: (i) capable of incorporation during transciption by the polymerase onto the 3'-end of a growing nucleotide strand; (ii) causes termination of polymerization; and (iii) capable of differential detection, one from the other, wherein there is a said derivative complementary to each possible nucleotide present at said locus of the amplified sequence;

(C) specifically hybridizing the second primer to a tag complement having the tag complement sequence of (A); and (D) detecting the nucleotide derivative incorporated into the second primer in (B) so as to identify the base located at the locus of the nucleic acid.

In another method of the invention, a biological sample containing a plurality of nucleic acid molecules is analyzed for the presence of a mutation or polymorphism at a locus of each nucleic acid molecule, for each nucleic acid molecule. This method includes steps of:

(A) amplifying the nucleic acid molecule in the presence of a first primer having a 5'-sequence having the sequence of a tag complementary to the sequence of a tag complement belonging to a family of tag complements of the invention to form an amplified molecule with a 5'-end with a sequence complementary to the sequence of the tag;

(B) extending the amplified molecule in the presence of a polymerase and a second primer having 5'-end complementary the 3'-end of the amplified sequence, the 3'-end of the second primer extending to immediately adjacent said locus, in the presence of a plurality of nucleoside triphosphate derivatives each of which is: (i) capable of incorporation during transciption by the polymerase onto the 3'-end of a growing nucleotide strand; (ii) causes termination of polymerization; and (iii) capable of differential detection, one from the other, wherein there is a said derivative complementary to each possible nucleotide present at said locus of the amplified molecule;

(C) specifically hybridizing the second primer to a tag complement having the tag complement sequence of (A); and (D) detecting the nucleotide derivative incorporated into the second primer in (B) so as to identify the base located at the locus of the nucleic acid;

wherein each tag of (A) is unique for each nucleic acid molecule and steps (A) and (B) are carried out with said nucleic molecules in the presence of each other.

Another method includes analyzing a biological sample that contains a plurality of double stranded complementary nucleic acid molecules for the presence of a mutation or polymorphism at a locus of each nucleic acid molecule, for each nucleic acid molecule. The method includes steps of:

(A) amplifying the double stranded molecule in the presence of a pair of first primers, each primer having an identical 5'-sequence having the sequence of a tag complementary to the sequence of a tag complement belonging to a family of tag complements of the invention to form amplified molecules with 5'-ends with a sequence complementary to the sequence of the tag;

(B) extending the amplified molecules in the presence of a polymerase and a pair of second primers each second primer having a 5'-end complementary a 3'-end of the amplified sequence, the 3'-end of each said second primer extending to immediately adjacent said locus, in the presence of a plurality of nucleoside triphosphate derivatives each of which is: (i) capable of incorporation during transciption by the polymerase onto the 3'-end of a growing nucleotide strand; (ii) causes termination of polymerization; and (iii) capable of differential detection, one from the other;

(C) specifically hybridizing each of the second primers to a tag complement having the tag complement sequence of (A); and (D) detecting the nucleotide derivative incorporated into the second primers in (B) so as to identify the base located at said locus;

wherein the sequence of each tag of (A) is unique for each nucleic acid molecule and steps (A) and (B) are carried out with said nucleic molecules in the presence of each other.

In yet another aspect, the invention is a method of analyzing a biological sample containing a plurality of nucleic acid molecules for the presence of a mutation or polymorphism at a locus of each nucleic acid molecule, for each nucleic acid molecule, the method including steps of:

(a) hybridizing the molecule and a primer, the primer having a 5'-sequence having the sequence of a tag complementary to the sequence of a tag complement belonging to a family of tag complements of the invention and a 3'-end extending to immediately adjacent the locus;

(b) enzymatically extending the 3'-end of the primer in the presence of a plurality of nucleoside triphosphate derivatives each of which is: (i) capable of enzymatic incorporation onto the 3'-end of a growing nucleotide strand; (ii) causes termination of said extension; and (iii) capable of differential detection, one from the other, wherein there is a said derivative complementary to each possible nucleotide present at said locus;

(c) specifically hybridizing the extended primer formed in step (b) to a tag complement having the tag complement sequence of (a); and (d) detecting the nucleotide derivative incorporated into the primer in step (b) so as to identify the base located at the locus of the nucleic acid molecule;

wherein each tag of (a) is unique for each nucleic acid molecule and steps (a) and (b) are carried out with said nucleic molecules in the presence of each other.

The derivative can be a dideoxy nucleoside triphosphate.

Each respective complement can be attached as a uniform population of substantially identical complements in spatially discrete regions on one or more solid phase support(s).

Each tag complement can include a label, each such label being different for respective complements, and step (d) can include detecting the presence of the different labels for respective hybridization complexes of bound tags and tag complements.

Another aspect of the invention includes a method of determining the presence of a target suspected of being contained in a mixture. The method includes the steps of:
(i) labelling the target with a first label;
(ii) providing a first detection moiety capable of specific binding to the target and including a first tag;
(iii) exposing a sample of the mixture to the detection moiety under conditions suitable to permit (or cause) said specific binding of the molecule and target;
(iv) providing a family of suitable tag complements of the invention wherein the family contains a first tag complement having a sequence complementary to that of the first tag;
(v) exposing the sample to the family of tag complements under conditions suitable to permit (or cause) specific hybridization of the first tag and its tag complement;
(vi) determining whether a said first detection moiety hybridized to a first said tag complement is bound to a said labelled target in order to determine the presence or absence of said target in the mixture.

Preferably, the first tag complement is linked to a solid support at a specific location of the support and step (vi) includes detecting the presence of the first label at said specified location.

Also, the first tag complement can include a second label and step (vi) includes detecting the presence of the first and second labels in a hybridized complex of the moiety and the first tag complement.

Further, the target can be selected from the group consisting of organic molecules, antigens, proteins, polypeptides, antibodies and nucleic acids. The target can be an antigen and the first molecule can be an antibody specific for that antigen.

The antigen is usually a polypeptide or protein and the labelling step can include conjugation of fluorescent molecules, digoxigenin, biotinylation and the like.

The target can be a nucleic acid and the labelling step can include incorporation of fluorescent molecules, radiolabelled nucleotide, digoxigenin, biotinylation and the like.

DETAILED DESCRIPTION OF THE INVENTION

Figures

Reference is made to the attached figures in which.

Figure 2:
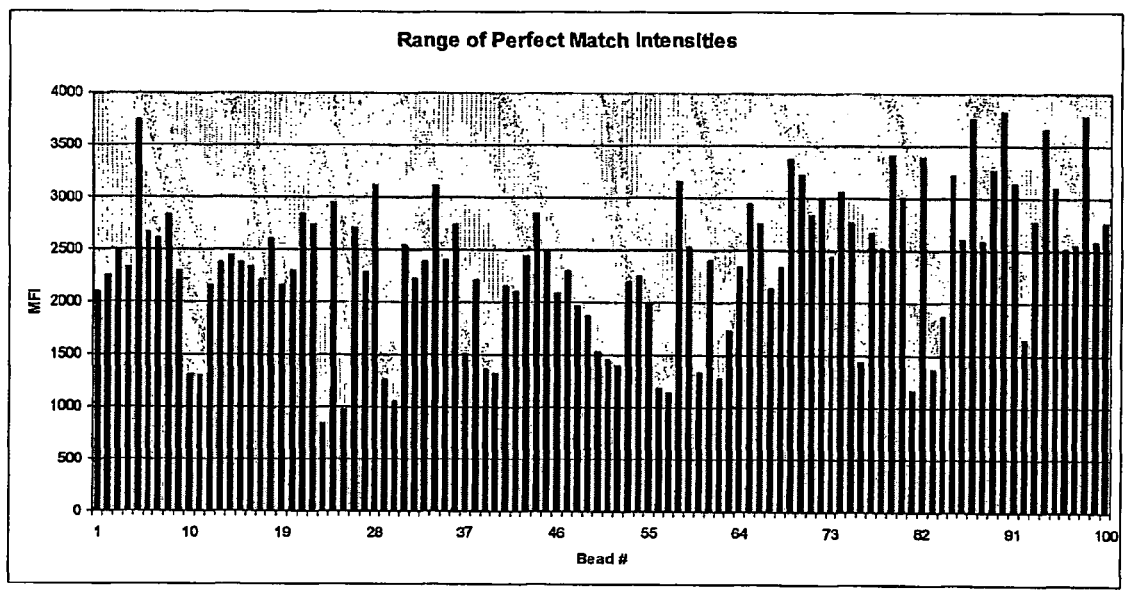
FIG. 2 shows the intensity of the signal (MFI) for each perfectly matched sequence (probe sequences indicated in Table I) and its complement (target, at 50 fmol) obtained as described in Example 1.
Figure 3:
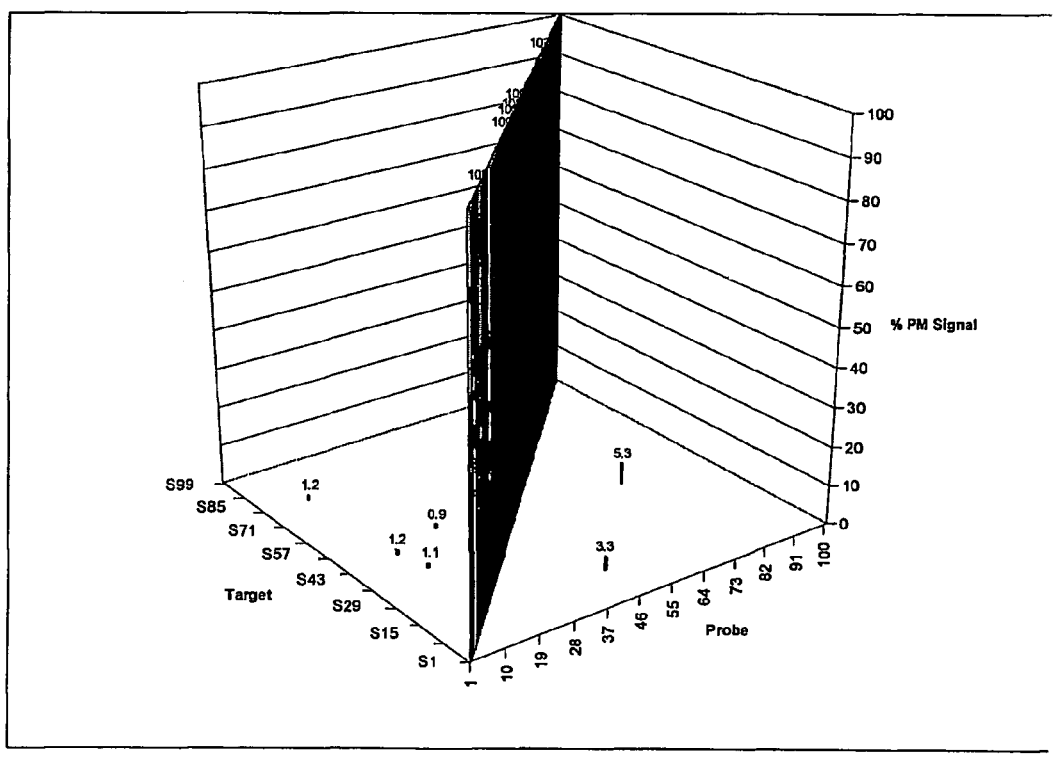
Figure 4:
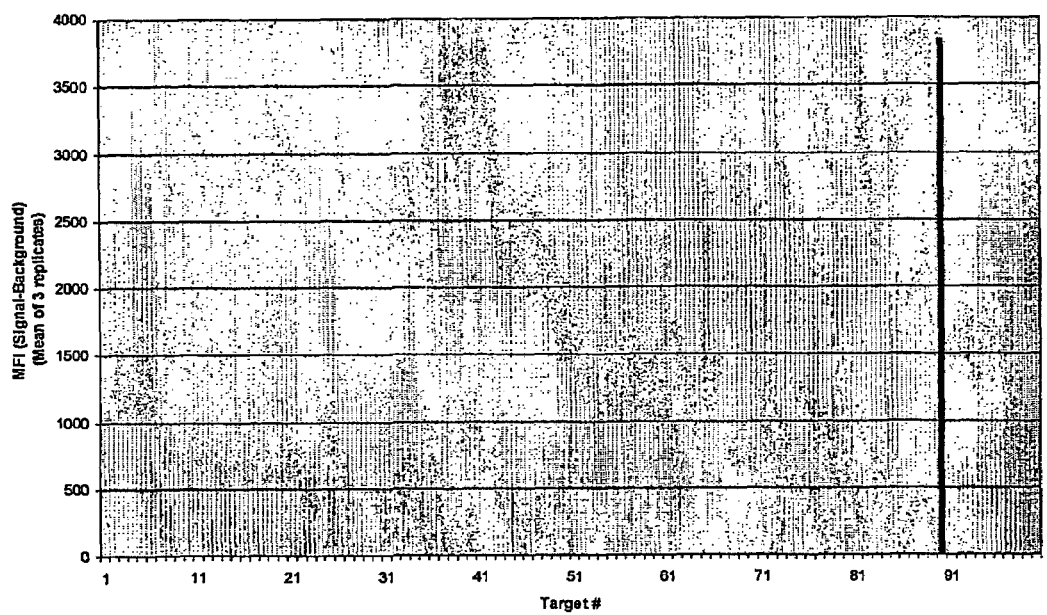

FIG. 3 is a three dimensional representation showing cross-hybridization observed for the sequences of FIG. 2 as described in Example 1. The results shown in FIG. 2 are reproduced along the diagonal of the drawing; and FIG. 4 is illustrative of results obtained for an individual target (SEQ ID NO:90, target No. 90) when exposed to the 100 probes of Example 1. The MFI for each bead is plotted.

DETAILED EMBODIMENTS

The invention provides a method for sorting complex mixtures of molecules by the use of families of oligonucleotide sequence tags. The families of oligonucleotide sequence tags are designed so as to provide minimal cross hybridization during the sorting process. Thus any sequence within a family of sequences will not significantly cross-hybridize with any other sequence derived from that family under appropriate hybridization conditions known by those skilled in the art. The invention is particularly useful in highly parallel processing of analytes.

Families of Oligonucleotide Sequence Tags

The present invention includes a family of 24mer polynucleotides that have been demonstrated to be minimally cross-hybridizing with each other. This family of polynucleotides is thus useful as a family of tags, and their complements as tag complements.

In order to be considered for inclusion into the family, a sequence had to satisfy a certain number of rules regarding its composition. For example, repetitive regions that present potential hybridization problems such as four or more of a similar base (e.g., AAAA or TTTT) or pairs of Gs were forbidden. Another rule is that each sequence contains exactly six Gs and no Cs, in order to have sequences that are more or less isothermal. Also required for a 24mer to be included is that there must be at most six bases between every neighboring pair of Gs. Another way of putting this is that there are at most six non-Gs between any two consecutive Gs. Also, each G nearest the 5'-end (resp. 3'-end) of its oligonucleotide (the left-hand (resp. right-hand) side as written in Table I) was required to occupy one of the first to seventh positions (counting the 5'-terminal (resp. 3'-terminal) position as the first position.)

Figure 1:
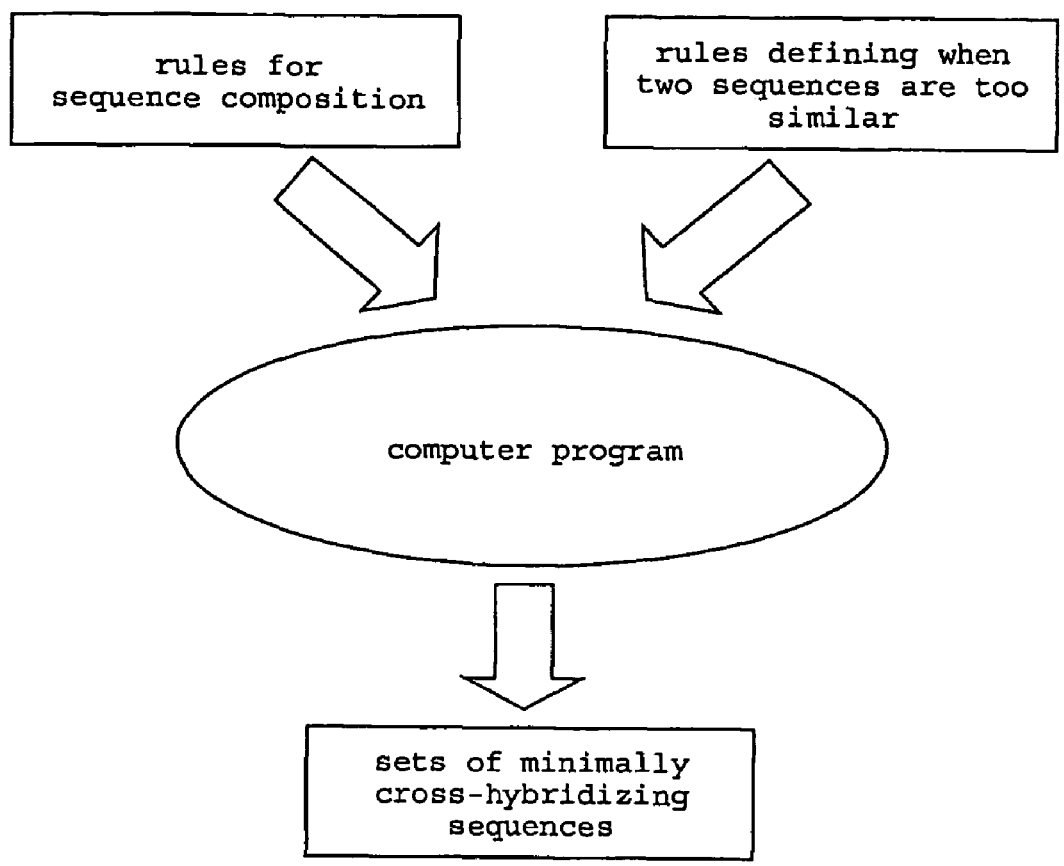
FIG. 1 illustrates generally the steps followed to obtain a family of sequences of the present invention.

The process used to design families of sequences that do not exhibit cross-hybridization behavior is illustrated generally in FIG. 1). Depending on the application for which these families of sequences will be used, various rules are designed. A certain number of rules can specify constraints for sequence composition (such as the ones described in the previous paragraph). The other rules are used to judge whether two sequences are too similar. Based on these rules, a computer program can derive families of sequences that exhibit minimal or no cross-hybridization behavior. The exact method used by the computer program is not crucial since various computer programs can derive similar families based on these rules. Such a program is for example described in international patent application No. PCT/CA 01/00141 published under WO 01/59151 on Aug. 16, 2001. Other programs can use different methods, such as the ones summarized below.

A first method of generating a maximum number of minimally cross-hybridizing polynucleotide sequences starts with any number of non-cross-hybridizing sequences, for example just one sequence, and increases the family as follows. A certain number of sequences is generated and compared to the sequences already in the family. The generated sequences that exhibit too much similarity with sequences already in the family are dropped. Among the "candidate sequences" that remain, one sequence is selected and added to the family. The other candidate sequences are then compared to the selected sequence, and the ones that show too much similarity are dropped. A new sequence is selected from the remaining candidate sequences, if any, and added to the family, and so on until there are no candidate sequences left. At this stage, the process can be repeated (generating a certain number of sequences and comparing them to the sequences in the family, etc.) as often as desired. The family obtained at the end of this method contains only minimally cross-hybridizing sequences.

A second method of generating a maximum number of minimally cross-hybridizing polynucleotide sequences starts with a fixed-size family of polynucleotide sequences. The sequences of this family can be generated randomly or designed by some other method. Many sequences in this family may not be compatible with each other, because they show too much similarity and are not minimally cross-hybridizing. Therefore, some sequences need to be replaced by new ones, with less similarity. One way to achieve this consists of repeatedly replacing a sequence of the family by the best (that is, lowest similarity) sequence among a certain number of (for example, randomly generated) sequences that are not part of the family. This process can be repeated until the family of sequences shows minimal similarity, hence minimal cross-hybridizing, or until a set number of replacements has occurred. If, at the end of the process, some sequences do not obey the similarity rules that have been set, they can be taken out of the family, thus providing a somewhat smaller family that only contains minimally cross-hybridizing sequences. Some additional rules can be added to this method in order to make it more efficient, such as rules to determine which sequence will be replaced.

Such methods have been used to obtain the 1168 non-cross-hybridizing tags of Table I that are the subject of this patent application.

One embodiment of the invention is a composition comprising molecules for use as tags or tag complements wherein each molecule comprises an oligonucleotide selected from a set of oligonucleotides based on the group of sequences set out in Table IA, wherein each of the numeric identifiers 1 to 3 (see the Table) is a nucleotide base selected to be different from the others of 1 to 3. According to this embodiment, several different families of specific sets of oligonucleotide sequences are described, depending upon the assignment of bases made to the numeric identifiers 1 to 3.

The sequences contained in Table I have a mathematical relationship to each other, described as follows.

Let S and T be two DNA sequences of lengths s and t respectively. While the term "alignment" of nucleotide sequences is widely used in the field of biotechnology, in the context of this invention the term has a specific meaning illustrated here. An alignment of S and T is a 2xp matrix A (with $p \geq s$ and $p \geq t$) such that the first (or second) row of A contains the characters of S (or T respectively) in order, interspersed with p−s (or p−t respectively) spaces. It assumed that no column of the alignment matrix contains two spaces, i.e., that any alignment in which a column contains two spaces is ignored and not considered here. The columns containing the same base in both rows are called matches, while the columns containing different bases are called mismatches. Each column of an alignment containing a space in its first row is called an insertion and each column containing a space in its second row is called a deletion while a column of the alignment containing a space in either row is called an indel. Insertions and deletions within a sequence are represented by the character '−'. A gap is a continuous sequence of spaces in one of the rows (that is neither immediately preceded nor immediately followed by another space in the same row), and the length of a gap is the number of spaces in that gap. An internal gap is one in which its first space is preceded by a base and its last space is followed by a base and an internal indel is an indel belonging to an internal gap. Finally, a block is a continuous sequence of matches (that is neither immediately preceded nor immediately followed by another match), and the length of a block is the number of matches in that block. In order to illustrate these definitions, two sequences S=TGATCGTAGCTACGCCGCG (of length s=19; SEQ ID NO:1169) and T=CGTACGATTGCAACGT (of length t=16; SEQ ID NO:1170) are considered. Exemplary alignment $R_1$ of S and T (with p=23) is:

Alignment $R_1$

| – | – | – | – | T | G | A | T | C | G | T | A | G | C | T | A | C | G | C | C | G | C | G |
|---|---|---|---|---|---|---|---|---|---|---|---|---|---|---|---|---|---|---|---|---|---|---|
| C | G | T | A | C | G | A | T | – | – | T | – | G | C | A | A | C | G | T | – | – | – | – |
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |

Columns 1 to 4, 9, 10, 12 and 20 to 23 are indels, columns 6, 7, 8, 11, 13, 14, 16, 17 and 18 are matches, and columns 5, 15 and 19 are mismatches. Columns 9 and 10 form a gap of length 2, while columns 16 to 18 form a block of length 3. Columns 9, 10 and 12 are internal indels.

A score is assigned to the alignment A of two sequences by assigning weights to each of matches, mismatches and gaps as follows:
the reward for a match m,
the penalty for a mismatch mm,
the penalty for opening a gap og,
the penalty for extending a gap eg.

Once these values are set, a score to each column of the alignment is assigned according to the following rules:
1. assign 0 to each column preceding the first match and to each column following the last match.
2. for each of the remaining columns, assign m if it is a match, −mm if it is a mismatch, −og−eg if it is the first indel of a gap, −eg if it is an indel but not the first indel of a gap.

The score of the alignment A is the sum of the scores of its columns. An alignment is said to be of maximum score if no other alignment of the same two sequences has a higher score (with the same values of m, mm, og and eg). A person knowledgeable in the field will recognize this method of scoring an alignment as scoring a local (as opposed to global) alignment with affine gap penalties (that is, gap penalties that can distinguish between the first indel of a gap and the other indels). It will be appreciated that the total number of indels that open a gap is the same as the total number of gaps and that an internal indel is not one of those assigned a 0 in rule (1) above.

It will also be noted that foregoing rule (1) assigns a 0 for non-internal mismatches. An internal mismatch is a mismatch that is preceded and followed (not necessarily immediately) by a match.

As an illustration, if the values of m, mm, og and eg are set to 3, 1, 2 and 1 respectively, alignment $R_1$ has a score of 19, determined as shown below:

Scoring of Alignment $R_1$

| — | — | — | — | T | G | A | T | C | G | T | A | G | C | T | A | C | G | C | C | G | C | G |
|---|---|---|---|---|---|---|---|---|---|---|---|---|---|---|---|---|---|---|---|---|---|---|
| C | G | T | A | C | G | A | T | — | — | T | — | G | C | A | A | C | G | T | — | — | — | — |
| 0 | 0 | 0 | 0 | 0 | 3 | 3 | 3 | -3 | -1 | 3 | -3 | 3 | 3 | -1 | 3 | 3 | 3 | 0 | 0 | 0 | 0 | 0 |

Note that for two given sequences S and T, there are numerous alignments. There are often several alignments of maximum score.

Based on these alignments, five sequence similarity measures are defined as follows. For two sequences S and T, and weights {m, mm, og, eg}:

M1 is the maximum number of matches over all alignments free of internal indels;

M2 is the maximum length of a block over all alignments;

M3 is the maximum number of matches over all alignments of maximum score;

M4 is the maximum sum of the lengths of the longest two blocks over all alignments of maximum score;

M5 is the maximum sum of the lengths of all the blocks of length at least 3, over all alignments of maximum score.

Notice that, by definition, the following inequalities between these similarity measures are obtained: $M4 \leq M3$ and $M5 \leq M3$. Also, in order to determine M2 it is sufficient to determine the maximum length of a block over all alignments free of internal indels. For two given sequences, the values of M3 to M5 can vary depending on the values of the weights {m, mm, og, eg}, but not M1 and M2.

For weights {3, 1, 2, 1}, the illustrated alignment is not a maximum score alignment of the two example sequences. But for weights {6, 6, 0, 6} it is; hence this alignment shows that for these two example sequences, and weights {6, 6, 0, 6}, $M2 \geq 3$, $M3 \geq 9$, $M4 \geq 6$ and $M5 \geq 6$. In order to determine the exact values of M1 to M5, all the necessary alignments need to be considered. M1 and M2 can be found by looking at the s+t−1 alignments free of internal indels, where s and t are the lengths of the two sequences considered. Mathematical tools known as dynamic programming can be implemented on a computer and used to determine M3 to M5 in a very quick way. Using a computer program to do these calculations, it was determined that:

with the weights {6, 6, 0, 6}, M1=8, M2=4, M3=10, M4=6 and M5=6;

with the weights {3, 1, 2, 1}, M1=8, M2=4, M3=10, M4=6 and M5=4.

According to the preferred embodiment of this invention, two sequences S and T each of length 24 are too similar if at least one of the following happens:

M1>16 or

M2>13 or

M3>20 or

M4>16 or

M5>19 when using either weights {6, 6, 0, 6}, or {6, 6, 5, 1}, or {6, 2, 5, 1}, or {6, 6, 6, 0}. In other words, the five similarity measures between S and T are determined for each of the above four sets of weights, and checked against these thresholds (for a total of 20 tests).

The above thresholds of 16, 13, 20, 16 and 19, and the above sets of weights, were used to obtain the sequences listed in Table I. Additional sequences can thus be added to those of Table I as long as the above alignment rules are obeyed for all sequences.

It is also possible to alter thresholds M1, M2, etc., while remaining within the scope of this invention. It is thus possible to substitute or add sequences to those of Table I, or more generally to those of Table IA to obtain other sets of sequences that would also exhibit reasonably low cross-hybridization. More specifically, a set of 24mer sequences in which there are no two sequences that are too similar, where too similar is defined as:

M1>19 or

M2>17 or

M3>21 or

M4>18 or

M5>20 when using either weights {6, 6, 0, 6}, or {6, 6, 5, 1}, or {6, 2, 5, 1}, or {6, 6, 6, 0}, would also exhibit low cross-hybridization. Reducing any of the threshold values provides sets of sequences with even lower cross-hybridization. Alternatively, 'too similar' can also be defined as:

M1>19 or

M2>17 or

M3>21 or

M4>18 or

M5>20 when using either weights {3, 1, 2, 1}. Alternatively, other combinations of weights will lead to sets of sequences with low cross-hybridization.

Notice that using weights {6, 6, 0, 6} is equivalent to using weights {1, 1, 0, 1}, or weights {2, 2, 0, 2}, . . . (that is, for any two sequences, the values of M1 to M5 are exactly the same whether weights {6, 6, 0, 6} or {1, 1, 0, 1} or {2, 2, 0, 2} or any other multiple of {1, 1, 0, 1} is used).

When dealing with sequences of length other than 24, or sequences of various lengths, the definition of similarity can be adjusted. Such adjustments are obvious to the persons skilled in the art. For example, when comparing a sequence of length L1 with a sequence of length L2 (with $L1 \leq L2$), they can be considered as too similar when

M1>19/24×L1

M2>17/24×L1

M3>21/24×L1

M4>18/24×L1

M5>20/24×L1 when using either weights {6, 6, 0, 6}, or {6, 6, 5, 1}, or {6, 2, 5, 1} or {6, 6, 6, 0}.

Polynucleotide sequences can be composed of a subset of natural bases most preferably A, T and G. Sequences that are deficient in one base possess useful characteristics, for example, in reducing potential secondary structure formation or reduced potential for cross hybridization with nucleic acids in nature. Also, it is preferable to have tag sequences that behave isothermally. This can be achieved for example by maintaining a constant base composition for all sequences such as six Gs and eighteen As or Ts for each sequence. Additional sets of sequences can be designed by extrapolating on the original family of non-cross-hybridizing sequences by simple methods known to those skilled in the art.

In order to validate the sequence set, a subset of sequences from the family of 1168 sequence tags was selected and characterized, in terms of the ability of these sequences to form specific duplex structures with their complementary sequences, and the potential for cross-hybridization within the sequence set. See Example 1, below. The subset of 100 sequences was randomly selected, and analyzed using the Luminex[100] LabMAP™ platform. The 100 sequences were chemically immobilized onto the set of 100 different Luminex microsphere populations, such that each specific sequence was coupled to one spectrally distinct microsphere population. The pool of 100 microsphere-immobilized probes was then hybridized with each of the 100 corresponding complementary sequences. Each sequence was examined individually for its specific hybridization with its complementary sequence, as well as for its non-specific hybridization with the other 99 sequences present in the reaction. This analysis demonstrated the propensity of each sequence to hybridize only to its complement (perfect match), and not to cross-hybridize appreciably with any of the other oligonucleotides present in the hybridization reaction.

It is within the capability of a person skilled in the art, given the family of sequences of Table I, to modify the sequences, or add other sequences while largely retaining the property of minimal cross-hybridization which the polynucleotides of Table I have been demonstrated to have.

There are 1168 polynucleotide sequences given in Table I. Since all 1168 of this family of polynucleotides can work with each other as a minimally cross-hybridizing set, then any plurality of polynucleotides that is a subset of the 1168 can also act as a minimally cross-hybridizing set of polynucleotides. An application in which, for example, 30 molecules are to be sorted using a family of polynucleotide tags and tag complements could thus use any group of 30 sequences shown in Table I. This is not to say that some subsets may be found in a practical sense to be more preferred than others. For example, it may be found that a particular subset is more tolerant of a wider variety of conditions under which hybridization is conducted before the degree of cross-hybridization becomes unacceptable.

It may be desirable to use polynucleotides that are shorter in length than the 24 bases of those in Table I. A family of subsequences (i.e., subframes of the sequences illustrated) based on those contained in Table I having as few as 10 bases per sequence could be chosen, so long as the subsequences are chosen to retain homological properties between any two of the sequences of the family important to their non cross-hybridization.

The selection of sequences using this approach would be amenable to a computerized process. Thus for example, a string of 10 contiguous bases of the first 24mer of Table I could be selected: AAATTGTGAAAGATTGTTTGTGTA (SEQ ID NO:1).

The same string of contiguous bases from the second 24mer could then be selected and compared for similarity against the first chosen sequence: GTTAGAGTTAATTGTATTTGATGA (SEQ ID NO:2). A systematic pairwise comparison could then be carried out to determine if the similarity requirements are violated. If the pair of sequences does not violate any set property, a 10mer subsequence can be selected from the third 24mer sequence of Table I, and compared to each of the first two 10mer sequences (in a pairwise fashion to determine its compatibility therewith, etc. In this way a family of 10mer sequences may be developed.

It is within the scope of this invention, to obtain families of sequences containing 11mer, 12mer, 13mer, 14mer, 15mer, 16mer, 17mer, 18mer, 19mer, 20mer, 21mer, 22mer and 23mer sequences by analogy to that shown for 10mer sequences.

It may be desirable to have a family of sequences in which there are sequences greater in length than the 24mer sequences shown in Table I. It is within the capability of a person skilled in the art, given the family of sequences shown in Table I, to obtain such a family of sequences. One possible approach would be to insert into each sequence at one or more locations a nucleotide, non-natural base or analogue such that the longer sequence should not have greater similarity than any two of the original non-cross-hybridizing sequences of Table I and the addition of extra bases to the tag sequences should not result in a major change in the thermodynamic properties of the tag sequences of that set for example the GC content must be maintained between 10%-40% with a variance from the average of 20%. This method of inserting bases could be used to obtain, for example, a family of sequences up to 40 bases long.

Given a particular family of sequences that can be used as a family of tags (or tag complements), e.g., those of Table I, a skilled person will readily recognize variant families that work equally as well.

Again taking the sequences of Table I for example, every T could be converted to an A and vice versa and no significant change in the cross-hybridization properties would be expected to be observed. This would also be true if every G were converted to a C.

Also, all of the sequences of a family could be taken to be constructed in the 5'-3' direction, as is the convention, or all of the constructions of sequences could be in the opposition direction (3'-5').

There are additional modifications that can be carried out. For example, C has not been used in the family of sequences. Substitution of C in place of one or more G's of a particular sequence would yield a sequence that is at least as low in homology with every other sequence of the family as was the particular sequence chosen for modification. It is thus possible to substitute C in place of one or more G's in any of the sequences shown in Table I. Analogously, substituting of C in place of one or more A's is possible, or substituting C in place of one or T's is possible.

It is preferred that the sequences of a given family are of the same, or roughly the same length. Preferably, all the sequences of a family of sequences of this invention have a length that is within five bases of the base-length of the average of the family. More preferably, all sequences are within four bases of the average base-length. Even more preferably, all or almost all sequences are within three bases of the average base-length of the family. Better still, all or almost all sequences have a length that is within two of the base-length of the average of the family, and even better still, within one of the base-length of the average of the family.

It is also possible for a person skilled in the art to derive sets of sequences from the family of sequences described in this specification and remove sequences that would be expected to have undesirable hybridization properties.

Methods for Synthesis of Oligonucleotide Families

Preferably oligonucleotide sequences of the invention are synthesized directly by standard phosphoramidite synthesis approaches and the like (Caruthers et al, Methods in Enzymology; 154, 287-313: 1987; Lipshutz et al, Nature Genet.; 21, 20-24: 1999; Fodor et al, Science; 251, 763-773: 1991). Alternative chemistries involving non natural bases such as peptide nucleic acids or modified nucleosides that offer advantages in duplex stability may also be used (Hacia et al; Nucleic Acids Res; 27: 4034-4039, 1999; Nguyen et al, Nucleic Acids Res.; 27, 1492-1498: 1999; Weiler et al, Nucleic Acids Res.; 25, 2792-2799:1997). It is also possible to synthesize the oligonucleotide sequences of this invention with alternate nucleotide backbones such as phosphorothioate or phosphoroamidate nucleotides. Methods involving synthesis through the addition of blocks of sequence in a stepwise manner may also be employed (Lyttle et al, Biotechniques, 19: 274-280 (1995). Synthesis may be carried out directly on the substrate to be used as a solid phase support for the application or the oligonucleotide can be cleaved from the support for use in solution or coupling to a second support.

Solid Phase Supports

There are several different solid phase supports that can be used with the invention. They include but are not limited to slides, plates, chips, membranes, beads, microparticles and the like. The solid phase supports can also vary in the materials that they are composed of including plastic, glass, silicon, nylon, polystyrene, silica gel, latex and the like. The surface of the support is coated with the complementary tag sequences by any conventional means of attachment.

In preferred embodiments, the family of tag complement sequences is derivatized to allow binding to a solid support. Many methods of derivatizing a nucleic acid for binding to a solid support are known in the art (Hermanson G., Bioconjugate Techniques; Acad. Press: 1996). The sequence tag may be bound to a solid support through covalent or non-covalent bonds (Iannone et al, Cytometry; 39: 131-140, 2000; Matson et al, Anal. Biochem.; 224: 110-106, 1995; Proudnikov et al, Anal Biochem; 259: 34-41, 1998; Zammatteo et al, Analytical Biochemistry; 280:143-150, 2000). The sequence tag can be conveniently derivatized for binding to a solid support by incorporating modified nucleic acids in the terminal 5' or 3' locations.

A variety of moieties useful for binding to a solid support (e.g., biotin, antibodies, and the like), and methods for attaching them to nucleic acids, are known in the art. For example, an amine-modified nucleic acid base (available from, e.g., Glen Research) may be attached to a solid support (for example, Covalink-NH, a polystyrene surface grafted with secondary amino groups, available from Nunc) through a bifunctional crosslinker (e.g., bis(sulfosuccinimidyl suberate), available from Pierce). Additional spacing moieties can be added to reduce steric hindrance between the capture moiety and the surface of the solid support.

Attaching Tags to Analytes for Sorting

A family of oligonucleotide tag sequences can be conjugated to a population of analytes most preferably polynucleotide sequences in several different ways including but not limited to direct chemical synthesis, chemical coupling, ligation, amplification, and the like. Sequence tags that have been synthesized with primer sequences can be used for enzymatic extension of the primer on the target for example in PCR amplification.

Detection of Single Nucleotide Polymorphisms Using Primer Extension

There are a number of areas of genetic analysis where families of non-cross-hybridizing sequences can be applied including disease diagnosis, single nucleotide polymorphism analysis, genotyping, expression analysis and the like. One such approach for genetic analysis, referred to as the primer extension method (also known as Genetic Bit Analysis (Nikiforov et al, Nucleic Acids Res.; 22, 4167-4175: 1994; Head et al Nucleic Acids Res.; 25, 5065-5071: 1997)), is an extremely accurate method for identification of the nucleotide located at a specific polymorphic site within genomic DNA. In standard primer extension reactions, a portion of genomic DNA containing a defined polymorphic site is amplified by PCR using primers that flank the polymorphic site. In order to identify which nucleotide is present at the polymorphic site, a third primer is synthesized such that the polymorphic position is located immediately 3' to the primer. A primer extension reaction is set up containing the amplified DNA, the primer for extension, up to 4 dideoxynucleoside triphosphates (each labeled with a different fluorescent dye) and a DNA polymerase such as the Klenow subunit of DNA Polymerase 1. The use of dideoxy nucleotides ensures that a single base is added to the 3' end of the primer, a site corresponding to the polymorphic site. In this way the identity of the nucleotide present at a specific polymorphic site can be determined by the identity of the fluorescent dye-labeled nucleotide that is incorporated in each reaction. One major drawback to this approach is its low throughput. Each primer extension reaction is carried out independently in a separate tube.

Universal sequences can be used to enhance the throughput of primer extension assay as follows. A region of genomic DNA containing multiple polymorphic sites is amplified by PCR. Alternatively, several genomic regions containing one or more polymorphic sites each are amplified together in a multiplexed PCR reaction. The primer extension reaction is carried out as described above except that the primers used are chimeric, each containing a unique universal tag at the 5' end and the sequence for extension at the 3' end. In this way, each gene-specific sequence would be associated with a specific universal sequence. The chimeric primers would be hybridized to the amplified DNA and primer extension is carried out as described above. This would result in a mixed pool of extended primers, each with a specific fluorescent dye characteristic of the incorporated nucleotide. Following the primer extension reaction, the mixed extension reactions are hybridized to an array containing probes that are reverse complements of the universal sequences on the primers. This would segregate the products of a number of primer extension reactions into discrete spots. The fluorescent dye present at each spot would then identify the nucleotide incorporated at each specific location. A number of additional methods for the detection of single nucleotide polymorphisms, including but not limited to, allele specific polymerase chain reaction (ASPCR), allele specific primer extension (ASPE) and oligonucleotide ligation assay (OLA) can be performed by someone skilled in the art in combination with the tag sequences described herein.

Kits Using Families of Tag Sequences

The families of non cross-hybridizing sequences may be provided in kits for use in for example genetic analysis. Such kits include at least one set of non-cross-hybridizing sequences in solution or on a solid support. Preferably the sequences are attached to microparticles and are provided with buffers and reagents that are appropriate for the application. Reagents may include enzymes, nucleotides, fluorescent labels and the like that would be required for specific applications. Instructions for correct use of the kit for a given application will be provided.

EXAMPLES

Example 1

Cross Talk Behavior of Sequence on Beads

A group of 100 sequences, randomly selected from Table I, was tested for feasibility for use as a family of minimally cross-hybridizing oligonucleotides. The 100 sequences selected are separately indicated in Table I along with the numbers assigned to the sequences in the tests.

The tests were conducted using the Luminex LabMAP™ platform available from Luminex Corporation, Austin, Tex., U.S.A. The one hundred sequences, used as probes, were synthesized as oligonucleotides by Integrated DNA Technologies (IDT, Coralville, Iowa, U.S.A.). Each probe included a $C_6$ aminolink group coupled to the 5'-end of the oligonucleotide through a $C_{12}$ ethylene glycol spacer. The $C_6$ aminolink molecule is a six carbon spacer containing an amine group that can be used for attaching the oligonucleotide to a solid support. One hundred oligonucleotide targets (probe complements), the sequence of each being the reverse complement of the 100 probe sequences, were also synthesized by IDT. Each target was labelled at its 5'-end with biotin. All oligonucleotides were purified using standard desalting procedures, and were reconstituted to a concentration of approximately 200 µm in sterile, distilled water for use. Oligonucleotide concentrations were determined spectrophotometrically using extinction coefficients provided by the supplier.

Each probe was coupled by its amino linking group to a carboxylated fluorescent microsphere of the LapMAP system according to the Luminex[100] protocol. The microsphere, or bead, for each probe sequence has unique, or spectrally distinct, light absorption characteristics which permits each probe to be distinguished from the other probes. Stock bead pellets were dispersed by sonication and then vortexing. For each bead population, five million microspheres (400 µL) were removed from the stock tube using barrier tips and added to a 1.5 mL Eppendorf tube (USA Scientific). The microspheres were then centrifuged, the supernatant was removed, and beads were resuspended in 25 µL of 0.2 M MES (2-(N-morpholino)ethane sulfonic acid) (Sigma), pH 4.5, followed by vortexing and sonication. One nmol of each probe (in a 25 µL volume) was added to its corresponding bead population. A volume of 2.5 µL of EDC cross-linker (1-ethyl-3-(3-dimethylaminopropyl) carbodiimide hydrochloride (Pierce), prepared immediately before use by adding 1.0 mL of sterile ddH$_2$O to 10 mg of EDC powder, was added to each microsphere population. Bead mixes were then incubated for 30 minutes at room temperature in the dark with periodic vortexing. A second 2.5 µL aliquot of freshly prepared EDC solution was then added followed by an additional 30 minute incubation in the dark. Following the second EDC incubation, 1.0 mL of 0.02% Tween-20 (BioShop) was added to each bead mix and vortexed. The microspheres were centrifuged, the supernatant was removed, and the beads were resuspended in 1.0 mL of 0.1% sodium dodecyl sulfate (Sigma). The beads were centrifuged again and the supernatant removed. The coupled beads were resuspended in 100 µL of 0.1 M MES pH 4.5. Bead concentrations were then determined by diluting each preparation 100-fold in ddH$_2$O and enumerating using a Neubauer BrightLine Hemacytometer. Coupled beads were stored as individual populations at 8° C. protected from light.

The relative oligonucleotide probe density on each bead population was assessed by Terminal Deoxynucleotidyl Transferase (TdT) end-labelling with biotin-ddUTPs. TdT was used to label the 3'-ends of single-stranded DNA with a labeled ddNTP. Briefly, 180 µL of the pool of 100 bead populations (equivalent to about 4000 of each bead type) to be used for hybridizations was pipetted into an Eppendorf tube and centrifuged. The supernatant was removed, and the beads were washed in 1× TdT buffer. The beads were then incubated with a labelling reaction mixture, which consisted of 5× TdT buffer, 25 mM CoCl$_2$, and 1000 pmol of biotin-16-ddUTP (all reagents were purchased from Roche). The total reaction volume was brought up to 85.5 µL with sterile, distilled H$_2$O, and the samples were incubated in the dark for 1 hour at 37° C. A second aliquot of enzyme was added, followed by a second 1 hour incubation. Samples were run in duplicate, as was the negative control, which contained all components except the TdT. In order to remove unincorporated biotin-ddUTP, the beads were washed 3 times with 200 µL of hybridization buffer, and the beads were resuspended in 50 µL of hybridization buffer following the final wash. The biotin label was detected spectrophotometrically using SA-PE (streptavidin-phycoerythrin conjugate). The streptavidin binds to biotin and the phycoerythrin is spectrally distinct from the probe beads. The 10 mg/mL stock of SA-PE was diluted 100-fold in hybridization buffer, and 15 µL of the diluted SA-PE was added directly to each reaction and incubated for 15 minutes at 37° Celsius. The reactions were analyzed on the Luminex[100] LabMAP. Acquisition parameters were set to measure 100 events per bead using a sample volume of 50 µL.

The results obtained are shown in FIG. 2. As can be seen the Mean Fluorescent Intensity (MFI) of the beads varies from 840.3 to 3834.9, a range of 4.56-fold. Assuming that the labelling reactions are complete for all of the oligonucleotides, this illustrates the signal intensity that would be obtained for each type of bead at this concentration if the target (i.e., labelled complement) was bound to the probe sequence to the full extent possible.

The cross-hybridization of targets to probes was evaluated as follows. 100 oligonucleotide probes linked to 100 different bead populations, as described above, were combined to generate a master bead mix, enabling multiplexed reactions to be carried out. The pool of microsphere-immobilized probes was then hybridized individually with each biotinylated target. Thus, each target was examined individually for its specific hybridization with its complementary bead-immobilized sequence, as well as for its non-specific hybridization with the other 99 bead-immobilized universal sequences present in the reaction. For each hybridization reaction, 25 µL bead mix (containing about 2500 of each bead population in hybridization buffer) was added to each well of a 96-well Thermowell PCR plate and equilibrated at 37° C. Each target was diluted to a final concentration of 0.002 fmol/µL in hybridization buffer, and 25 µL (50 fmol) was added to each well, giving a final reaction volume of 50 µL. Hybridization buffer consisted of 0.2 M NaCl, 0.1 M Tris, 0.08% Triton X-100, pH 8.0 and hybridizations were performed at 37° C. for 30 minutes. Each target was analyzed in triplicate and six background samples (i.e. no target) were included in each plate. A SA-PE conjugate was used as a reporter, as described above. The 10 mg/mL stock of SA-PE was diluted 100-fold in hybridization buffer, and 15 µL of the diluted SA-PE was added directly to each reaction, without removal of unbound target, and incubated for 15 minutes at 37° C. Finally, an additional 35 µL of hybridization buffer was added to each well, resulting in a final volume of 100 µL per well prior to analysis on the Luminex[100] LabMAP. Acquisition parameters were set to measure 100 events per bead using a sample volume of 80 µL.

The percent hybridization was calculated for any event in which the NET MFI was at least 3 times the zero target background. In other words, a calculation was made for any sample where $(MFI_{sample} - MFI_{zero\ target\ background})/MFI_{zero\ target\ background} \geq 3$.

The net median fluorescent intensity $(MFI_{sample} - MFI_{zero\ target\ background})$ generated for all of the 10,000 possible target/probe combinations was calculated. As there are 100 probes and 100 targets, there are 100×100=10,0000 possible different interactions possible of which 100 are the result of perfect hybridizations. The remaining 9900 result from hybridization of a target with a mismatched probe. A cross-hybridization event is then defined as a non-specific event whose net median fluorescent intensity exceeds 3 times the zero target background. In other words, a cross-talk calculation is only be made for any sample where $(MFI_{sample} - MFI_{zero\ target\ background})/MFI_{zero\ target\ background} \geq 3$. Cross-hybridization events were quantified by expressing the value of the cross-hybridization signal as a percentage of the perfect match hybridization signal with the same probe.

The results obtained are illustrated in FIG. 3. The ability of each target to be specifically recognized by its matching probe is shown of the possible 9900 non-specific hybridization events that could have occurred when the 100 targets were each exposed to the pool of 100 probes, 6 events were observed. Of these 6 events, the highest non-specific event generated a signal equivalent to 5.3% of the signal observed for the perfectly matched pair (i.e. specific hybridization event).

Each of the 100 targets was thus examined individually for specific hybridization with its complement sequence as incorporated onto a microsphere, as well as for non-specific hybridization with the complements of the other 99 target sequences. Representative hybridization results for target (complement of probe 90, Table I) are shown in FIG. 4. Probe 90 was found to hybridize only to its perfectly-matched target. No cross-hybridization with any of the other 99 targets was observed.

The foregoing results demonstrate the possibility of incorporating the 1168 sequences of Table I, or any subset thereof, into a multiplexed system with the expectation that most if not all sequences can be distinguished from the others by hybridization. That is, it is possible to distinguish each target from the other targets by hybridization of the target with its precise complement and minimal hybridization with complements of the other targets.

Example 2

Tag Sequences Used in Sorting Polynucleotides

The family of non cross hybridizing sequence tags or a subset thereof can be attached to oligonucleotide probe sequences during synthesis and used to generate amplified probe sequences. In order to test the feasibility of PCR amplification with non cross hybridizing sequence tags and subsequently addressing each respective sequence to its appropriate location on two-dimensional or bead arrays, the following experiment was devised. A 24mer tag sequence can be connected in a 5'-3' specific manner to a p53 exon specific sequence (20mer reverse primer). The connecting p53 sequence represents the inverse complement of the nucleotide gene sequence. To facilitate the subsequent generation of single stranded DNA post-amplification the tag-Reverse primer can be synthesized with a phosphate modification ($PO_4$) on the 5'-end. A second PCR primer can also be generated for each desired exon, represented by the Forward (5'-3') amplification primer. In this instance the Forward primer can be labeled with a 5'-biotin modification to allow detection with Cy3-avidin or equivalent.

A practical example of the aforementioned description is as follows: For exon 1 of the human p53 tumor suppressor gene sequence the following tag-Reverse primer (SEQ ID NO:1171) can be generated:

```
              222087                              222063
5'-PO4-ATGTTAAAGTAAGTGTTGAAATGT -TCCAGGGAAGCGTGTCACCGTCGT-3'
              Tag Sequence # 3                Exon 1 Reverse
```

The numbering above the Exon-1 reverse primer represents the genomic nucleotide positions of the indicated bases.

The corresponding Exon-1 Forward primer sequence (SEQ ID NO:1172) is as follows:

```
       221873                 221896
5'-Biotin-TCATGGCGACTGTCCAGCTTTGTG-3'
```

In combination these primers will amplify a product of 214 bp plus a 24 bp tag extension yielding a total size of 238 bp.

Once amplified, the PCR product can be purified using a QIAquick PCR purification kit and the resulting DNA can be quantified. To generate single stranded DNA, the DNA is subjected to λ-exonuclease digestion thereby resulting in the exposure of a single stranded sequence (anti-tag) complementary to the tag-sequence covalently attached to the solid phase array. The resulting product is heated to 95° C. for 5 minutes and then directly applied to the array at a concentration of 10-50 nM. Following hybridization and concurrent sorting, the tag-Exon 1 sequences are visualized using Cy3-streptavidin. In addition to direct visualization of the biotinylated product, the product itself can now act as a substrate for further analysis of the amplified region, such as SNP detection and haplotype determination.

DEFINITIONS

Non-cross-hybridization: Describes the absence of hybridization between two sequences that are not perfect complements of each other.

Cross-hybridization: The hydrogen bonding of a single-stranded DNA sequence that is partially but not entirely complementary to a single-stranded substrate.

Homology or Similarity: How closely related two or more separate strands of DNA are to each other, based on their base sequences.

Analogue: The symbols A, G, T/U, C take on their usual meaning in the art here. In the case of T and U, a person skilled in the art would understand that these are equivalent to each other with respect to the inter-strand hydrogen-bond (Watson-Crick) binding properties at work in the context of this invention. The two bases are thus interchangeable and hence the designation of T/U. A chemical, which resembles a nucleotide base is an analogue thereof. A base that does not normally appear in DNA but can substitute for the ones, which do, despite minor differences in structure. Analogues particularly useful in this invention are of the naturally occurring bases can be inserted in their respective places where desired. Such an analogue is any non-natural base, such as peptide nucleic acids and the like that undergoes normal Watson-Crick pairing in the same way as the naturally occurring nucleotide base to which it corresponds.

Complement: The opposite or "mirror" image of a DNA sequence. A complementary DNA sequence has an "A" for every "T" and a "C" for every "G". Two complementary strands of single stranded DNA, for example a tag sequence and its complement, will join to form a double-stranded molecule.

Complementary DNA (cDNA): DNA that is synthesized from a messenger RNA template; the single-stranded form is often used as a probe in physical mapping.

Oligonucleotide: Refers to a short nucleotide polymer whereby the nucleotides may be natural nucleotide bases or analogues thereof.

Tag: Refers to an oligonucleotide that can be used for specifically sorting analytes with at least one other oligonucleotide that when used together do not cross hybridize.

TABLE I

| Sequence | SEQ ID NO: | No. in Ex 1 |
|---|---|---|
| A A A T T G T G A A A G A T T G T T T G T G T A | 1 | 1 |
| G T T A G A G T T A A T T G T A T T T G A T G A | 2 | — |
| A T G T T A A A G T A A G T G T T G A A A T G T | 3 | — |
| T G A T G T T A G A A G T A T A T T G T G A A T | 4 | — |
| T T T G T G T A G A A T A T G T G T T G T T A A | 5 | — |
| A T A A G T G T A A G T G A A A T A A G A A G A | 6 | — |
| A A G A G T A T T T G T T G T G A G T T A A A T | 7 | — |
| G T G T T T A T G T T A T A T G T G A A G T T T | 8 | — |
| A A A G A G A A T A G A A T A T G T G T A A G T | 9 | — |
| T A T G A A A G A G T G A G A T A A T G T T T A | 10 | — |
| A T G A G A A A T A T G T T A G A A T G T G A T | 11 | — |
| T T A G T T G T T G A T G T T T A G T A G T T T | 12 | — |
| G T A A A G A G T A T A A G T T T G A T G A T A | 13 | — |
| A A A G T A A G A A T G A T G T A A T A A G T G | 14 | — |
| G T A G A A A T A G T T T A T T G A T G A T T G | 15 | — |
| T G T A A G T G A A A T A G T G A G T T A T T T | 16 | 2 |
| A A A T A G A T G A T A T A A G T G A G A A T G | 17 | — |
| A T A A G T T A T A A G T G T T A T G T G A G T | 18 | — |
| T A T A G A T A A A G A G A T G A T T T G T T G | 19 | — |
| A G A G T T G A G A A T G T A T A G T A T T A T | 20 | — |
| A A G T A G T T T G T A A G A A T G A T T G T A | 21 | — |
| T T A T G A A A T T G A G T G A A G A T T G A T | 22 | — |
| G T A T A T G T A A A T T G T T A T G T T G A G | 23 | — |
| G A A T T G T A T A A A G T A T T A G A T G T G | 24 | 4 |
| T A G A T G A G A T T A A G T G T T A T T T G A | 25 | — |
| G T T A A G T T T G T T T A T G T A T A G A A G | 26 | — |

TABLE I-continued

| Sequence | SEQ ID NO: | No. in Ex 1 |
|---|---|---|
| GAGTATTAGTAAAGTGATATGATA | 27 | — |
| GTGAATGATTTAGTAAATGATTGA | 28 | — |
| GATTGAAGTTATAGAAATGATTAG | 29 | — |
| AGTGATAAATGTTAGTTGAATTGT | 30 | — |
| TATATAGTAAATGTTTGTGTGTTG | 31 | — |
| TTAAGTGTTAGTTATTTGTTGTAG | 32 | — |
| GTAGTAATATGAAGTGAGAATATA | 33 | — |
| TAGTGTATAGAATGTAGATTTAGT | 34 | — |
| TTGTAGATTAGATGTGTTTGTAAA | 35 | — |
| TAGTATAGAGTAGAGATGATATTT | 36 | — |
| ATTGTGAAAGAAAGAGAAGAAATT | 37 | 7 |
| TGTGAGAATTAAGATTAAGAATGT | 38 | — |
| ATATTAGTTAAGAAAGAAGAGTTG | 39 | — |
| TTGTAGTTGAGAAATATGTAGTTT | 40 | — |
| TAGAGTTGTTAAAGAGTGTAAATA | 41 | — |
| GTTATGATGTGTATAAGTAATATG | 42 | — |
| TTTGTTAGAATGAGAAGATTTATG | 43 | 10 |
| AGTATAGTTTAAAGAAGTAGTAGA | 44 | — |
| GTGAGATATAGATTTAGAAAGTAA | 45 | — |
| TTGTTTATAGTGAAGTGAATAGTA | 46 | — |
| AAGTAAGTAGTAATAGTGTGTTAA | 47 | — |
| ATTTGTGAGTTATGAAAGATAAGA | 48 | — |
| GAAAGTAGAGAATAAAGATAAGAA | 49 | — |
| ATTAAGATTGTTAAGAGTAGAAG | 50 | — |
| GTTTAAAGATTGTAAGAATGTGTA | 51 | — |
| TTTGTGAAGATGAAGTATTTGTAT | 52 | — |
| TGTGTTTAGAATTTAGTATGTGTA | 53 | — |
| GATAATGATTATAGAAAGTGTTTG | 54 | — |
| GTTATTTGTAAGTTAAGATAGTAG | 55 | — |
| AGTTTATTGAAAGAGTTTGAATAG | 56 | — |
| TTGTGTTTATTGTGTAGTTTAAAG | 57 | — |
| ATTGTGAAGATATGAAAGTTAT | 58 | — |
| TGAGAATGTAAAGAATGTTTATTG | 59 | 13 |
| ATGTGAAAGTTATGATGTTAATTG | 60 | — |
| GTTTAGTATTAGTTGTTAAGATTG | 61 | — |
| GATTGATATTTGAATGTTTGTTTG | 62 | 14 |
| TGAATTGAAAGTGTAATGTTGTAT | 63 | — |
| GATTGTATTGTTGAGAATAGAATA | 64 | — |

TABLE I-continued

| Sequence | SEQ ID NO: | No. in Ex 1 |
|---|---|---|
| A A A T T T G A G A T T T G T G A T A G A G T A | 65 | — |
| G T A A T T A G A T T T G T T T G T T G T T G T | 66 | — |
| G T T T G T A T T G T T A G T G A A T A T A G T | 67 | — |
| A T G T A G T A G T A G A T G T T T A T G A A T | 68 | — |
| T G T T T A A A G A T G A T T G A A G A A A T G | 69 | — |
| T G T G A T A A T G A T G T T A T T T G T G T A | 70 | — |
| A T A G T T G T G A G A A T T T G T A A T T A G | 71 | — |
| A T A G A T G T A A G A G A A A T T G T G A A A | 72 | — |
| A G A T T A A G A G A A G T T A A T A G A G T A | 73 | — |
| G A A G T A A A T T G T G A A T G A A A G A A A | 74 | — |
| A A T G T A A G A A A G A A G A T T G T T G T A | 75 | — |
| T T T G A T T T A T G T G T T A T G T T G A G T | 76 | — |
| G T A T T G A G A A A T T T G A A G A A T G A A | 77 | — |
| G A A T T G T A T G A A A T G A A T T G T A A G | 78 | — |
| T A T T G T A G A A G T A A A G T T A G A A G T | 79 | — |
| T T T A T G T A A T G A T A A G T G T A G T T G | 80 | — |
| A T A T A G T T G A A A T T G T G A T A G T G T | 82 | — |
| A T A A G A A A T T A G A G A G T T G T A A A G | 82 | — |
| G A A T T G T G A A A T G T G A T T G A T A T A | 83 | — |
| A A A T A A G T A G T T T A A T G A G A G A A G | 84 | — |
| G A T T A A A G A A G T A A G T G A A T G T T T | 85 | — |
| T A T G T G T G T T G T T T A G T G T T A T T A | 86 | — |
| G A G T T A T A T G T A G T T A G A G T T A T A | 87 | — |
| G A A A G A A A G A A G T G T T A A G T T A A A | 88 | — |
| T A G T A T T A G T A A G T A T G T G A T T G T | 89 | — |
| T T G T G T G A T T G A A T A T T G T G A A A T | 90 | — |
| A T G T G A A A G A G T T A A G T G A T T A A A | 91 | — |
| G A T T G A A T G A T T G A G A T A T G T A A A | 92 | — |
| A A G A T G A T A G T T A A G T G T A A G T T A | 93 | 17 |
| T A G T T G T T A T T G A G A A T T T A G A A G | 94 | — |
| T T T A T A G T G A A T T A T G A G T G A A A G | 95 | — |
| G A T A G A T T T A G A A T G A A T T A A G T G | 96 | 18 |
| T T T G A A G A A G A G A T T T G A A A T T G A | 97 | — |
| A T G A A T A A G A G T T G A T A A A T G T G A | 98 | — |
| T G T T T A T G T A G T G T A G A T T G A A T T | 99 | — |
| T T T A A G T G A G T T A T A G A A G T A G T A | 100 | 19 |
| G A T T T A T G T G T T T G A A G T T A A G A T | 101 | — |
| T A G T T A G A G A A A G T G A T A A A G T T A | 102 | — |

TABLE I-continued

| Sequence | SEQ ID NO: | No. in Ex 1 |
|---|---|---|
| GTAATGATAATGAAGTGTATATAG | 103 | — |
| AATGAAGTGTTAGTATAGATAGTA | 104 | — |
| TAAATTGAGTTTGTTTGATTGTAG | 105 | — |
| TAATGAAGAATAAGTATGAGTGTT | 106 | — |
| AAATGTAATAGTGTTGTTAGTTAG | 107 | — |
| AGAGTTAGTGAAATGTTGTTAAAT | 108 | — |
| GAAATAGAAATGTATTGTTTGTGA | 109 | — |
| AGTTATAAGTTTGTGAGAATTAAG | 110 | — |
| GAGTTTATAGTTAGAATATGTTGT | 111 | — |
| AGAGTTATTAGAAGAAGATTTAAG | 112 | — |
| GAGTTAATGAAATAAGTATTTGTG | 113 | — |
| ATGATGAATAGTTGAAGTATATAG | 114 | — |
| ATAGATATGAGATGAAAGTTAGTA | 115 | — |
| TATGTAAAGAAAGTGAAAGAAGAA | 116 | — |
| TGAATGTAGAAATGAATGTTGAAA | 117 | — |
| AATTGAATAGTGTGTGAGTTTAAT | 118 | — |
| AGATATTGTTTGATTAATGAAGAG | 119 | — |
| AAAGTTGTAAAGTTGAAGATAAAG | 120 | — |
| GTTAAGAGATTATGAGATGTATTA | 121 | — |
| AGAAGATATAAGAAGATTGAATTG | 122 | — |
| GTAGAAATTTGAATTGATGTGAAA | 123 | — |
| AAGAGTAGATTGATAAGTATATGA | 124 | — |
| TGATATAGTAGTGAAGAAATAAGT | 125 | 22 |
| AGATAATGATGAGAAATGAAGATA | 126 | — |
| ATGTGAAAGTATTTGTGATATAGT | 127 | — |
| AATAAGAGAATTGATATGAAGATG | 128 | 23 |
| TAAGTGTATTAGTAGAATGGAAGT | 129 | — |
| TATGTTAGATTTGTTGAGATTGAT | 130 | — |
| AGTTTGTATGAAGAGATAGTATTT | 131 | — |
| GAGAAATGTTATGTATTTAGTAGT | 132 | — |
| TATGTGAGAATGTGTTTGATTTAA | 133 | — |
| GTATGTTTGTTTATAGAATGTATG | 134 | — |
| GAGTATATAGAAGAAGAAATTTG | 135 | — |
| ATGAGTGAAGTAAATGTAGTTATT | 136 | — |
| TTAAGAAGTGAGTTATTGTGATAT | 137 | — |
| ATGAAATGAGAATATTGTTGTTTG | 138 | — |
| GATTAATGATTATGTGAATTGATG | 139 | — |
| GAAATGTTAAAGATATGAAAGTAG | 140 | — |

TABLE I-continued

| Sequence | SEQ ID NO: | No. in Ex 1 |
|---|---|---|
| TATTGTTGATTTGATATTAGTGTG | 141 | — |
| TTTATGTTTGTGTATGTAAGTAGT | 142 | — |
| AATTGAAAGAATTGTGTGAATTGA | 143 | — |
| TGAGTTTGAATTTGTTTGAGTAAT | 144 | — |
| GATGTATAATGATGTGTGTAAATT | 145 | — |
| ATGTGAGAGAAGAATTTGTTTATT | 146 | — |
| GTGATAAAGTATTGTTGATAGAAA | 147 | — |
| GAAGTAGAATAGAAAGTTAATAGA | 148 | — |
| TTGTGTAGTTAAGAGTTGTTTAAT | 149 | 24 |
| TAGTAGTAAGTTGTTAGAATAGTT | 150 | — |
| AATTGAAGTATAATGAATGTGTG | 151 | — |
| TAGAAATTGTAGTATTTGAGAGAA | 152 | — |
| TGTATATGTTAATGAGATGTTGTA | 153 | 25 |
| TATTTGATAAGAGAATGAAGAAGT | 154 | 26 |
| TTGAATAGTGTAATGAATATGATG | 155 | — |
| GTAGTTTGTGAATAGAATTAGTTT | 156 | — |
| AAAGATGATTGTAATTTGTGTGAA | 157 | — |
| GAAGATTGTTGAGTTAATAGATAA | 158 | — |
| AGATTATGTAGTGATGTAAATGTT | 159 | — |
| GAATTTAGATGTAGATATGAATGT | 160 | — |
| GATAGAAGTGTATTAAGTAAGTTA | 161 | — |
| TATGAATTATGAGAAGAATAGAGT | 162 | — |
| TTTGTTATGAAGTGATTTGTTTGT | 163 | — |
| GTAAAGATTGTGTTATATGAAATG | 164 | — |
| TTGTGATAGTAGTTAGATATTTGT | 165 | 28 |
| GAATTAAGATAAAGAAGAGAAGTA | 166 | — |
| GATTGTAGAATGAATTTGTAGTAT | 167 | — |
| AAATAAGAGAGAATGATTTAGT | 168 | — |
| AATTATGTGAATAGATTGTTGAAG | 169 | — |
| TTAAGATTTATGTGATAGTAGAGT | 170 | — |
| TTAAAGATAGTGTTTGTTGTGTTA | 171 | — |
| TATTGATTTATGAAGAGTATAGTG | 172 | — |
| AAATTTGATGAGTAGTTTAAGAGA | 173 | — |
| ATAAAGTTGTTTGATGTTTGAATG | 174 | — |
| GATTGTGATGAATAATGTTATTGA | 175 | — |
| GATGAAGAAATATGATATGAATAG | 176 | — |
| TTAAAGTTATTGAAGTGAAGTTGA | 177 | — |
| TTGTAAGAAATAGAGATTTGTGTT | 178 | — |

TABLE I-continued

| Sequence | SEQ ID NO: | No. in Ex 1 |
|---|---|---|
| GAGATTGAGTTTAAGTATTAGATT | 179 | — |
| AGTGATAATAGAATGATAAATGTG | 180 | — |
| GATAATAGTGAATTTGAGTTGTAT | 181 | — |
| AGATATTTGTAGTAGAAAGTATGT | 182 | — |
| GTTATGAATGTTGAATTTGAATGT | 183 | — |
| ATGAAAGATTTAGTTGTGAGATAT | 184 | 30 |
| AAATAGAGAAGTTATGATGTGATA | 185 | — |
| TTAGTGAGAAATGTTTAATGTGAT | 186 | — |
| TGAAGAATATGTGAAATTAGTTTG | 187 | — |
| GTTTGATAGTTTAATGAGTATTGA | 188 | — |
| GTTGTAAGTAATGATAAAGTATGA | 189 | — |
| TAAGAGTAGTAATTGTTGTTTAGA | 190 | — |
| TTTGAGAGTATGTATGATTATT | 191 | — |
| ATTGATTGTGAATTAGATAGAAGA | 192 | — |
| GATTAGTATTTAGTAGTAATAGAG | 193 | 31 |
| TATGTATTAGAGATATTGAAAGTG | 194 | — |
| TATGTGAAAGTAATGATAAATGAG | 195 | — |
| GTAATTAGTAATGATTTGAATGAG | 196 | — |
| GTTTATTGTAAAGATGTAAGTGAA | 197 | — |
| TAGTAGAATTGTTGTTAAAGAATG | 198 | 32 |
| TATTGTTAGTTATGTAGTGTGTAA | 199 | — |
| GAGTGAAAGTTATATGAAAGTATA | 200 | — |
| ATATAGAAGTTGATGAGTTTATGA | 201 | — |
| TTTAGAAGTAAGAATAAGTGAGTA | 202 | — |
| TGTGTATAAGATATTTGTAAGAAG | 203 | — |
| TAGAAGAGTTGTATTGTTATAAGT | 204 | — |
| GTGTTATTAGTTTAAGTTAGAGTA | 205 | — |
| AATATAGTCATGTGAAATTGAATG | 206 | — |
| TTAGAGAATAGAGTGATTATAGTT | 207 | — |
| GAAGTGAGTTAATGATTTGTAAAT | 208 | — |
| AATGTAAAGTAAAGAAAGTGATGA | 209 | 33 |
| GTTAGTTATGATGAATATTGTGTA | 210 | 34 |
| AAATGAGTTAGAGTAGAATTATGT | 211 | — |
| GATATAGAAGATTAGTTAGTGATA | 212 | — |
| ATAGTTTGTTGAGATTTATGAGTA | 213 | — |
| TAGAATAGTTAGTAGTAAGAGTAT | 214 | — |
| GAATTTGTATTGTGAAGTTTAGTA | 215 | — |
| GTAGTAAGAAGAGAATTAGATTAA | 216 | — |

TABLE I-continued

| Sequence | SEQ ID NO: | No. in Ex 1 |
|---|---|---|
| AATGTGTTATGTATGTAAATAGTG | 217 | — |
| GAATTAGTTAGAGTAAATTGTTTG | 218 | — |
| GAAATTGAAGATAGTAAGAAATGA | 219 | — |
| GTGTATTATGTGATTTATGATAGA | 220 | — |
| TATTATGAGAAAGTTGAATAGTAG | 221 | 35 |
| TATGTATTGTATTGAGTAGATGAA | 222 | — |
| GTGATTGAATAGTAGATTGTTTAA | 223 | 36 |
| AGTAAGTTGTTTGATTGAAATTTG | 224 | — |
| GAAGTTTGATTTAAGTTTAAGAAG | 225 | — |
| GAGAAGATAAATGATATTGTTATG | 226 | — |
| ATGATGAGTTGTTAATAGTTAGTT | 227 | — |
| TATGATATTTGAAGAGTGTTAAGA | 228 | — |
| GAGATGATTAAAGTGATTTATGAA | 229 | — |
| ATAGTTAAGAGTGATGAGAATAAA | 230 | — |
| TTTATTGTTAGATAAAGAGTTGAG | 231 | — |
| AGAATATTGATAGTTGAAGTTGAA | 232 | — |
| TAGTGTAAAGTGTAGATTGTAAAT | 233 | — |
| AGTAGTGATATGATTTGAATATTG | 234 | — |
| TGTATTGAATTAGAATAGTGAGAA | 235 | — |
| TGATATGAGATAGAAGTTTAATGT | 236 | — |
| GAAGAAGTAAGTATAAAGTAAATG | 237 | — |
| TTTAAGTGTGATAAGAAAGATAGA | 238 | — |
| TATTGTTGAATGTGTTTAAAGAGA | 239 | 38 |
| GAATAATGATGAGATGATTATTGA | 240 | — |
| TAGAGAAGAGAGAATTGTATTAA | 241 | 39 |
| ATGTATAATGAGATATGTTTGTGA | 242 | — |
| AATAGATAAGATTGATTGTGTTTG | 243 | 40 |
| TTTGATGATAATAGAAGAGAATGA | 244 | — |
| AGATGAATAAGTTGTGAATGTTTA | 245 | — |
| AGATGAAAGAAAGTGTAGAATATT | 246 | — |
| TGTTAAATGTATGTAGTAATTGAG | 247 | 41 |
| TAGTAGTGTGAAGTTATTTGTTAT | 248 | — |
| AGTGAATGTTTGTAAAGAGTTTAA | 249 | — |
| GATAAATGAGAATTGAGTAATTGT | 250 | — |
| TGATGAGAAATTGTTTAAGTGTTT | 251 | — |
| AAATAAGTAGTGTGAGTAATAGTA | 252 | — |
| TATGAAATATGTGATAGTAAGAGA | 253 | — |
| ATTGTAAGAGTGATTATAGATGAT | 254 | — |

TABLE I-continued

| Sequence | SEQ ID NO: | No. in Ex 1 |
|---|---|---|
| A G A G T A A G A A T G A A A G A G A T A A T A | 255 | — |
| T A A G T A A G T A G A T G T T A A A G A G A T | 256 | — |
| A A A T A G A A A G A A T T G T A G A G T A G T | 257 | — |
| A T A G A T T T A A G T G A A G A G A G T T A T | 258 | 42 |
| G A A T G T T T G T A A A T G T A T A G A T A G | 259 | 43 |
| A A A T A G A A T G A G T A G T G A A A T A T G | 260 | — |
| T T G A A T T A T G T A G A G A A A G T A A A G | 261 | — |
| T A G T A A A T T G A G A G T A G T T G A A T T | 262 | — |
| T G T A A A G T G T T T A T A G T G T G T A A T | 263 | — |
| A T A T G A T T T G A G A T G A G A A T G T A A | 264 | — |
| A A T A T T G A T A T G T G T T G T G A A G T A | 265 | — |
| A G T G A G A T T A T G A G T A T T G A T T T A | 266 | 44 |
| T T G T A T T T A G A T A G T G A G A T T A T G | 267 | — |
| A T A G A A A T G A A A G A T A G A T A G A A G | 268 | — |
| G A T T G T A T A T G T A A A G T A G T T T A G | 269 | — |
| T A T G A A T G T T A T T G T G T G T T G A T T | 270 | 45 |
| G A T A T T A G T A G A G T A A G T A T A T T G | 271 | — |
| T G A G A T G A A T T T G T G T T A T G A T A T | 272 | — |
| T A T G A A T G A A G T A A A G A G A T G T A A | 273 | — |
| G A G T G A A T T T G T T G T A A T T T G T T T | 274 | — |
| A G A A A T T G T A G A G T T A A T T G T G T A | 275 | — |
| G T G T T A A T G A A A G T T G T G A A T A A T | 276 | — |
| T G T G A T T T G T T A A G A A G A T T A A T G | 277 | — |
| A G T A G T A T T G T A A A G T A T A A A G A G | 278 | — |
| T G A T T G T T G T A T A G T T A T T G T G T A | 279 | — |
| G A T T G T A G T T T A A T G T T A A G A A T G | 280 | — |
| A T G A A A T A A G A A A T T G A G T A G A G A | 281 | — |
| T A T G A T G A T A T T T G T T G T A T G T G T | 282 | — |
| T T T A G A G T T T G A T T A G T A T G T T T G | 283 | — |
| A A T A A G A G A T T G T G A T G A G A A A T A | 284 | — |
| A A T G A A T A G A A T A G A G A A T G T A G A | 285 | — |
| G T A G T A G T A A T T T G A A T G T T T G A A | 286 | 47 |
| A G T G A G T A A T T G A T T G A T T G T T A A | 287 | — |
| G A A T A A T G T T T A G T G T G T T T G A A A | 288 | — |
| A T A T G A A A G T A G A G A A A G T G T T A T | 289 | — |
| T G A G T T A T T G T A T T T A G T T T G A A G | 290 | — |
| T A G T T G A G T T T A A A G T T G A A A G A A | 291 | — |
| T A A A G A G T G A T G T A A A T A G A A G T T | 292 | — |

TABLE I-continued

| Sequence | SEQ ID NO: | No. in Ex 1 |
|---|---|---|
| TGTAGTGTTTAGAGTAAGTTATTA | 293 | — |
| AGAGATTAATGTGTTGAAAGATTA | 294 | — |
| GTAATAAGTTGTGAAAGAAGATTA | 295 | — |
| GAGATGTTATAGATAATGAAAGAA | 296 | — |
| TTTAGTTGATTGTTGAATAGAGTA | 297 | — |
| ATTATTGAAAGTAGATGTTAGATG | 298 | — |
| TTTATGTGTGATTGAGTGTTTAAT | 299 | — |
| TATTTAGTTAGATAGATAGAGAGT | 300 | — |
| ATGTGTTTATGTGAAAGATTTGTA | 301 | — |
| ATAGTAATTAGAAGAGAAGAATGT | 302 | — |
| TATGAGTGATTAGAATTGTATTTG | 303 | — |
| TTAATGTATTGTTTAAAGAGTGTG | 304 | — |
| ATAGAGAATTAAGAATTGTTTGAG | 305 | — |
| GTTATAAGTAGAAATGTATAGAAG | 306 | — |
| AGTAATTAGTTTGAAATGTGTAGT | 307 | — |
| GAAAGATTATGATTGTAAAGTGAT | 308 | — |
| GTAAGATTAGAAGTTAATGAAGAA | 309 | 48 |
| GAGAATGTTGAATAAGAAGTAATT | 310 | — |
| TTAAGAGTGTTTGAATAGTGTTTA | 311 | — |
| ATAAAGAAGAGTATGAGATTATG | 312 | — |
| AGTTATTGATTGAAGATGAGAAAT | 313 | — |
| GTTTGTGTTTGTATAAGTTGTTAA | 314 | 50 |
| TTGTATGTGAGTTTAGATTAATGA | 315 | — |
| TAGTTAAAGTATAGTTGTTTGAGT | 316 | — |
| AAATTTGTGTTGAGATTTGTATAG | 317 | — |
| TATTAGTGTTATGATAAAGAGAAG | 318 | — |
| TATAAGAAGTAATTTGAGAAGAGT | 319 | — |
| TAAGTTGAGATGTTTGTTTGATAA | 320 | — |
| GTGTAGATTTATGAATTGAGTAAT | 321 | — |
| TATAGAGAAGTGTTTAGTTGTATA | 322 | — |
| ATAAAGAAGAATAGTTGTTGTGTA | 323 | — |
| AGATTGAAATAGATTAGAAAGTTG | 324 | — |
| GTTGTTATAAGAAATAGTTTGTTG | 325 | — |
| AGAAATAGAGTAAGAGTGTTTAAA | 326 | — |
| AGAGATAGTAGTAAATAGTTATTG | 327 | — |
| AAATGATTGTGTAAGTTATGTATG | 328 | — |
| AAGAAGTAAGAGAGAAATTTGAAT | 329 | — |
| GTGTGTATTTAGTTGATAATTGAT | 330 | — |

TABLE I-continued

| Sequence | SEQ ID NO: | No. in Ex 1 |
|---|---|---|
| ATTGTTGTTGTTGAGAAATGTATT | 331 | — |
| AGATAAGTTAAAGTAAAGAGAATG | 332 | — |
| TAGTTGAAGTTAGTTTAAGTGTTA | 333 | — |
| AGTAAGAATGTAATATGATGATAG | 334 | — |
| ATGAGATTGAAAGATTTATGAATG | 335 | — |
| TGATTGAATTAGAGAGAATGTATA | 336 | — |
| AGTTAGTAAGAGAATATAGTGAAT | 337 | — |
| ATTAAGATTGTATAGTTAGTGATG | 338 | — |
| GAGATAAAGAATTGAAATAGAAGA | 339 | — |
| AGAGTAAATGTTAAGAAAGAAGTT | 340 | — |
| AAAGTTTGTTATGTGTGAAGAATT | 341 | — |
| ATTGTGTTTAAGAAATATGATGAG | 342 | — |
| TATTGAAATGAGATGTATGTAGTT | 343 | — |
| ATTTGTGTGATGTTTGAAATATGA | 344 | — |
| TAAGATAATAGTGAGAGAAATTGA | 345 | — |
| ATTTATGATTAGTGTAAGTGTTGT | 346 | — |
| GATTAAGAATAAAGTGTGAAGAAT | 347 | — |
| GTAATTGATGAAGAGTTAGTTTAT | 348 | — |
| TGTGTTATGTTATAAGAAGTGATA | 349 | — |
| AGAGAAATTGAATTTAGAAATGTG | 350 | — |
| TTATTGAATGTGAGAAAGTATTTG | 351 | — |
| TGTTAATGAGAAGATAATGATAGT | 352 | — |
| GAAAGTATTTGTTGATTATTGTTG | 353 | — |
| TAGTTTATGTAGTTAATTGTTGAG | 354 | — |
| GTTGAAAGATAGTTTGATATGTAT | 355 | — |
| TTAGAAGATAGATTATTGAGAAAG | 356 | — |
| AATAATGTTGTGAAATAGATGTGA | 357 | 56 |
| AGTAAGAAAGTTTAGTTTAGTTAG | 358 | — |
| TAGTTTAATGAGATGTTTGATATG | 359 | — |
| TTAAAGATGTTAAAGAATGAGTGA | 360 | — |
| AAAGTGTGTATATGTTAGAAAGTA | 361 | — |
| ATTAAGTTATGTGTTTATGTGTTG | 362 | — |
| TTTGAAGAAGTGTTTGTATTATGT | 363 | — |
| TGTTAAGAAGTTTAGTTAAAGTTG | 364 | — |
| TTTAAGTATAAGATTGTGTGAGAT | 365 | — |
| AGATATTTGATAGATAGAAGAAAG | 366 | — |
| ATTTAGAGTTGTAAGAAGATATTG | 367 | — |
| GAGAAATTGTAATTGTTAGAGTAT | 368 | |

TABLE I-continued

| Sequence | SEQ ID NO: | No. in Ex 1 |
|---|---|---|
| G A A G T A T A T G T T A A G A T G T A A T A G | 369 | — |
| A A T A T T G A A G A T G T A G T G A G T T A T | 370 | — |
| G A G T T T A G A A A T G A T A A A G A A T T G | 371 | — |
| T A A G A A A T G A G T T A T A T G T T G A G A | 372 | 60 |
| T T G A T A T A A G A A G T T G T G A T A A G T | 373 | — |
| A A G T G T T T A A T G T A A G A G A A T G A A | 374 | 61 |
| G T T G T G A G A A T T A G A A A T A G T A T A | 375 | — |
| T T T A G T T T G A T G T G T T T A T G A G A T | 376 | — |
| G T A A T T G A A A G T A T G A G T A G T A A T | 377 | — |
| T A G T T G A A T A A G A T T G A G A G A A A T | 378 | — |
| T T A A G T G A A G T G T T G T T T A T T G A A | 379 | — |
| A T T G A T T T G T T G A A A T A A G T G T T G | 380 | — |
| T G A A T T G T T G A T A A G T T A T G A A G A | 381 | — |
| G T T T G T T A T T G A G T A A G T T G A A T T | 382 | — |
| T G A T T T A G T A T G T A T T A G A G T T G A | 383 | — |
| T A A A T A G A G A T G A G A A T A A G A A A G | 384 | — |
| A G A A T G T T A T A T G T A G A G A A A T T G | 385 | — |
| A T T T A T G T A G T T G A G A G T G A T A A A | 386 | — |
| G T A A A G A T A G T T T G A G T A A T T T G A | 387 | — |
| G A A A T A G T A T A A T G T T A A G T G A G A | 388 | — |
| A T T G T A T A T T G T G T T G A A G A A A G T | 389 | — |
| G A G T T A A G T G T A A A T G A A A T G T A A | 390 | — |
| A T A G A T T G T G T G A A A G A A A G A A T T | 391 | — |
| T T A A T A G A A G T T T G T A G T A T G A T G | 392 | — |
| T T G T A T G T G A G A A T A A A G T T T A G T | 393 | — |
| G T G A T T A G A T A T G A T G A T A T G A A T | 394 | — |
| T G A A G A A G A A T T T A G A T T T G T A A G | 395 | — |
| T G T A T G A T T A T T G A T T A G T G T G T T | 396 | — |
| T G T G A A A G A G A A T G A T A G A T A T T T | 397 | — |
| A A T T G A A A T G A G T G T G T T T A A G A A | 398 | — |
| A T T A T A G A G T T A G T T T A G A A T G A G | 399 | — |
| A A A G A T A G A A A T T G A G T G T A T G A T | 400 | — |
| G T A G T T T G T T A A T G T T G T A T A A T G | 401 | — |
| A G A G A T A T T A G A A T G T A A G A A T A G | 402 | 64 |
| A G A A G T T T G A A A T A T G A T A G A A T G | 403 | — |
| T A G A A T G T A A A G T T T A G T A T A G A G | 404 | — |
| A G T A G A T G T A T G T T A A T G T G A A T A | 405 | — |
| T G A A A G T G A A A T A T G A A A T G T T G T | 406 | — |

TABLE I-continued

| Sequence | SEQ ID NO: | No. in Ex 1 |
|---|---|---|
| ATAGTATATTGAGTTTGTATGAAG | 407 | — |
| GAAGAAATGTTTGTAGAATAAGTA | 408 | — |
| AATGAGTATTGAAGAAATGTATAG | 409 | — |
| GTGATAGAATTTGTGTTTAATGAA | 410 | 66 |
| TGTAGTATGAAGAATAATGAAATG | 411 | — |
| ATAGAAGTTAATGATAATTGTGTG | 412 | — |
| GTGATTGTAAGTAAGTAAAGATAA | 413 | — |
| TATGTAGTTTGTGTTATTTGAAGA | 414 | — |
| TGAGTAAGTTTGTATGTTTAAGTA | 415 | 67 |
| TAAATGTATGAGTGTGTAAAGAAA | 416 | — |
| GTAAGAGTATTGAAATTAGTAAGA | 417 | 68 |
| GTTGAGTGTAAAGATTATTGATAA | 418 | — |
| AGTATGAGTTATTAGATAAAGTGA | 419 | — |
| ATTTGTTATAGAGTTGTGTTGTAT | 420 | — |
| TAATTAGTAGTGTGTTGAAATTTG | 421 | — |
| TGTATTGAGATTGTTATTGTATTG | 422 | — |
| GTTATTAGAAGAGATAATTGAGTT | 423 | — |
| TTGAGTTGTGATTAAGTAGTATAT | 424 | — |
| GATAGTATAATGATTGAAGTAATG | 425 | — |
| GTGAAAGATATTTGAGAGATAAAT | 426 | — |
| AGTTATGATTTGAAGAAATTGTTG | 427 | — |
| GTAAGTATTTGAATTTGATGAGTT | 428 | — |
| TAATAGTGTTATAAGTGAAAGAGT | 429 | — |
| AAATGAATTGATGTGTATATGAAG | 430 | — |
| AGAAAGTGAGTTGTTAAGTATTTA | 431 | — |
| TTTATGTGTGAATTGTGTATATAG | 432 | — |
| GTAATATGATAGAAATGTAAAGAG | 433 | — |
| GAGAATTGTTTAAAGATAGTTGTA | 434 | — |
| GAATTTGTTAAGAATGAGTTTGAT | 435 | — |
| ATAGTGATGATTAAAGAGAATTTG | 436 | — |
| ATAGATGTTTAGTTGAGATTATTG | 437 | — |
| AAGAGTGTAAATAGAAAGTGATAT | 438 | — |
| TGTGTATTGATTGTTGAGATAAAT | 439 | — |
| TAGTATAGTGAGAAAGAGTTAAAT | 440 | — |
| AAAGATAAGAAAGAGATGATGTTT | 441 | — |
| GAAGTTATTGAAATAGAAGTAT | 442 | — |
| ATGTATGTATAGAAAGAGTAAATG | 443 | — |
| GATGTTTGTAAAGATTGAAATTGA | 444 | — |

TABLE I-continued

| Sequence | SEQ ID NO: | No. in Ex 1 |
|---|---|---|
| AATTTAGAGAGTATTTGTGTTGTA | 445 | — |
| AATTTGTTTGAAAGAAAGTAAGTG | 446 | — |
| AAAGAGTAGTGTTATTGTTAGATA | 447 | — |
| GTATGTTGTATATGTTGTTGATAT | 448 | — |
| GTAGAATTTGTTGAGTATTTGTAA | 449 | — |
| ATGAATTTAGTTAGTGTAAGAAAG | 450 | — |
| ATGATAAGAAATGTTGATGAAGTA | 451 | — |
| TTGATGATGAAGATAATGTAGATA | 452 | — |
| AGATGATATGATATAGATTAGATG | 453 | — |
| TTGAAAGTTAGAAAGATAGATGTT | 454 | — |
| GTTTAATGTTAGTTAGAAAGTAAG | 455 | — |
| GAGATTTAAGTTTGAAGTGAAATA | 456 | — |
| TTTGTTAGTAGTTGTTATAAGAGA | 457 | — |
| TATGAGAATAGTTTGTTAGTGAAT | 458 | — |
| TTGAAAGTTTAAAGAAGAGATAAG | 459 | — |
| AAGTGAGTTGAAATGAAATATGTT | 460 | — |
| GTTAGAAATGAAATGAGTAGTTAT | 461 | — |
| TAAGTATTGTATTTGTGTGTGTAT | 462 | — |
| TGTATTAGTAAAGAAGAGAGAATA | 463 | — |
| GAGAAGAGAAATAAGTTGAAATAA | 464 | — |
| GTAAAGTAGAAATAGAATTGAGTT | 465 | — |
| GTGTGTTATTTGTTTGTAAAGTAT | 466 | 69 |
| TTTGATGTATGAATATAGTATGAG | 467 | — |
| AAGATTGTGTGAATAGTTGAAATT | 468 | — |
| TATAAAGTTTGAAGATGAGTGATA | 469 | — |
| AGATAAAGAGATTTAAGATGTATG | 470 | 71 |
| GAAGAATTAAGTTGAGAATTAAGA | 471 | — |
| TAGAGAAATTTGATAAAGAAAGAG | 472 | — |
| AAAGTTTATGAAGTTATTGAGTAG | 473 | — |
| AAATAGTGTAAGTAAAGAGATGAT | 474 | — |
| TATGATGATTTAGTTATAAGAGTG | 475 | — |
| TAGATAAATGTTATGATGAGTAAG | 476 | — |
| AGATTGATTGTGATGATTTGTATA | 477 | — |
| TTAAGAAGAATTGTATATGAGAGT | 478 | 73 |
| GTAGAATGTTTAGAGTTGAATATA | 479 | — |
| GAGAAATAGTAAGAAGTAAATAGA | 480 | — |
| ATTGAAGTTGTTATGTGAAGATTT | 481 | — |
| TAAATGTTGTGTAGAGTAATTAGA | 482 | — |

TABLE I-continued

| Sequence | SEQ ID NO: | No. in Ex 1 |
|---|---|---|
| AAATAAGAGTTTGAGAAGTTGTTT | 483 | — |
| AGTTGTAATAAGAAGTGATTTAAG | 484 | — |
| GTTAGAATGTATATAGAGTTAGAT | 485 | 74 |
| TTGATATTGAAAGAGAAAGTTATG | 486 | — |
| TTAAAGAGAAATGTTTGATTAG | 487 | — |
| TGTGAATTTGAGTATTAGTAAGAA | 488 | — |
| TAATTTGAATGTGAAAGTTGTTAG | 489 | — |
| ATGTGTTTGAAAGATGATGATTTA | 490 | — |
| AAGTTATGTTGATATTGAGTGAAA | 491 | — |
| TAGATAAAGAAGATAGAGATTTAG | 492 | — |
| GATGAATGTAGATATATGTAATGA | 493 | — |
| GAAGAATAGTTTATGTAAATGATG | 494 | — |
| GTAGTATATAGTTAAAGATGAGTT | 495 | — |
| GTTATTTGTGTATGATTATGATTG | 496 | — |
| AGAGATTAGAAATTGAGAGAATTA | 497 | — |
| GTATGATAGAGTTTATAGTGATAA | 498 | — |
| GTTAGAAAGAATGAAATTGAAGTA | 499 | — |
| AAGAATGAGAATATAGAGATGAAT | 500 | — |
| AAAGAGAATAGTGTTTAAGAAGAT | 501 | — |
| GATGTGTTATTGATAGAAATTAGA | 502 | — |
| TAGAGTTATAGAGATATTGTATGA | 503 | — |
| GAGAGTTGAATAAGTTAAAGATAT | 504 | — |
| AGATATGAAATAGATTGTTAGAGA | 505 | — |
| GAGTGAATAGAAAGATATGTTAAT | 506 | — |
| AAAGAGATATTGAAGAGAATAAAG | 507 | — |
| GTTATAGAATAAGTTGTAAAGTGT | 508 | — |
| TGATAGTATGATAATGTGTTTATG | 509 | — |
| TTTGTTGTTAAGTATGTGATTTAG | 510 | 77 |
| TAAAGTGTTGTGTTAAAGATTAAG | 511 | — |
| TGTGTTTGATTGATTAATGTTATG | 512 | — |
| ATTAATGAATGAGTGTTGTAATGT | 513 | — |
| TAGATGTTTGTGAGTTTGATATTA | 514 | — |
| GAATGAATAGTAATAGATGATTTG | 515 | — |
| AATAGTGTGTTGTTATATGATTAG | 516 | — |
| TAGATTAGAAGATGTTGTGTATTA | 517 | — |
| AATGTGTGTGTTAAATGAATTTGT | 518 | — |
| GAATTAAGTATATGAGTGTAGAAA | 519 | — |
| TTATTGTGTGTAAGTAGTGTAAAT | 520 | — |

TABLE I-continued

| Sequence | SEQ ID NO: | No. in Ex 1 |
|---|---|---|
| GTAGTAAAGAGAATTGTTTAGTAT | 521 | 80 |
| AAGTTTGTAAGAAGTAGTTGAATA | 522 | — |
| AGTTATAGTATAGTAGTATAGAGA | 523 | — |
| GAAAGAAATGTGTATAGTTTAATG | 524 | — |
| TTGTGAGTAATGAATGATGTATTA | 525 | — |
| GTAGAGTTGTAAATAGAGAATAAA | 526 | — |
| ATTAATGTAGATTGTAAGAGATAG | 527 | — |
| TTAGTGTGTTTGTAGATAGAATTA | 528 | — |
| AGAGAGTTTGTGTATATGTATAAA | 529 | 81 |
| TTAAGTTTAGTGAGATTTGTTAAG | 530 | — |
| ATGAAGTTTATTGAATAGTAGTGA | 531 | — |
| ATATTTGTGTTGTATGTTTGTGAA | 532 | — |
| AAAGTGTTTATAGAAGATTTGATG | 533 | — |
| AAGAGATATGATTTGTTAGTTGTA | 534 | — |
| AAGAAGAAATGAGTGATAATGTAA | 535 | — |
| TAGTGTTTGATATGTTAAGAAGTT | 536 | — |
| GTAGAAAGTGATAGATTAGTAATA | 537 | — |
| GATAAATGTTAAGTTAGTATGATG | 538 | — |
| AGATTAGAAGAATTGTTTAGAATG | 539 | — |
| ATATTTGAGAAGTGTGAAATGAAT | 540 | — |
| TGAGTAAATAGTTTATGAGTAGTA | 541 | — |
| TTAGAGTAGATAAAGATTTGAT | 542 | — |
| ATTGTTTAAGTTGTTGATAAGATG | 543 | — |
| GTTGTAAAGTTAAAGTGTGAATTT | 544 | — |
| ATAGATTGTGTGTTTGTTATAGTA | 545 | — |
| GTAAGTTATTGAGAATGATAATAG | 546 | — |
| TAGATTAGTTGATAAGTGTGTAAT | 547 | 83 |
| AAATGTAAATGAAGAGTGTTTGTT | 548 | — |
| GATAGAAGAAATGTATATAGTGAT | 549 | — |
| TATAGAGTGTATGTTATGATAAAG | 550 | — |
| TATGAAGTGATAAGATGAAGAATT | 551 | — |
| TGTTGAGAATAGTAAGAGAATTTA | 552 | — |
| TAGATAATGTGAAGTAATAAGTGA | 553 | 84 |
| GTATTATGATGATAGTAGTAAGTA | 554 | — |
| AGATATGATTTAGTATTGAATGTG | 555 | — |
| AATTAAGTTTGTAGAGTTATTTGA | 556 | — |
| AAGAAATAGATGTAGTAAGATGTT | 557 | — |
| TTGAGAAGTTGTTGTAATAAGAAT | 558 | — |

TABLE I-continued

| Sequence | SEQ ID NO: | No. in Ex 1 |
|---|---|---|
| A G T G T G A A A T A G T G A A A G T T T A A A | 559 | — |
| T T T A T G T A G T A G A T T T A T G T G A A G | 560 | — |
| A T T A A T G A G A A A T T A G T G T G T T A G | 561 | — |
| A T G T T A A T A G T G A T A G T A A A G T G A | 562 | — |
| T A T G T T G A T A A A T G A T T A T G A G T G | 563 | — |
| T T A T T A G A G T T G T G T G T G A T A T A T | 564 | — |
| T G T T G T T A T G A T T G A G T T A G A A T A | 565 | — |
| A A T T T G A G T T A A G A A G A A G T G T A A | 566 | — |
| A A A G A T A A A G T T A A G T G T T T G T A G | 567 | 88 |
| T G T T G A G A T G A T A T T G T A T A A G T T | 568 | — |
| T A A A T A G T G A A T G A G T T A T A G A G T | 569 | — |
| A T A G A T G T T A T G A T A G T T A G T T A G | 570 | — |
| G T T A A G T G A A G A T A T G T A T T G T T A | 571 | — |
| T A A G A A A G T A A A G T T T G T A G A T G T | 572 | — |
| A A G A G A A A G T T T G A T T G A A T A A A G | 573 | — |
| A T A T T A G A T G T G A G T T A T A T G T G T | 574 | — |
| A G T T T G A G T T T A G T A T T G T G A A T A | 575 | — |
| A T G T T A A A T G A G A G A T T G T G T A T A | 576 | — |
| T A A A T G T T G T G A T T A T T G T G A G A T | 577 | — |
| T A A G A A T T G A A G T A A G A G T T A T T G | 578 | — |
| A G A G A T A G A A T T A A G T T T G T T G A T | 579 | — |
| G A A G A A T G T T A A G A A A T A T G T A A G | 580 | — |
| T A T T T G T G A T T A A G A A G T T G A G A A | 581 | — |
| A G T T A G A A T T T G T G T A G T A G A A T T | 582 | — |
| A A G T T T A T T G T T G A T G T T G T A T T G | 583 | — |
| G A A T G A G T T T A A G A G T T T A T A G T A | 584 | — |
| A G T G A A G A T T G T A T G T A G T A T A A A | 585 | — |
| A G T T G A A A T G A G T A T T A A G T A A T G | 586 | — |
| A T G T T A T T T G A G A T G A G T A A T T | 587 | — |
| A A A T A G T G T T G T T G A A G T T G T T A T | 588 | — |
| G T A G A G A A A G A T A T A T G T A G T T T A | 589 | — |
| G A G A G T A T T T G A T G A A T G A T T A T A | 590 | — |
| G A G T A T A A G T T T A G T G T A T A T T G A | 591 | — |
| A T A A T G T G A T T A T T G A T T G A G A G A | 592 | — |
| T T A G T T G T T A T G T G A G A G T A A T A A | 593 | — |
| A A A T G A G T A T A T T G A A T T G T G A T G | 594 | — |
| A A T T A G A A G T A A G T A G A G T T T A A G | 595 | 3 |
| T G T A A G T T T A A A G T A A G A A A T G T G | 596 | 5 |

TABLE I-continued

| Sequence | SEQ ID NO: | No. in Ex 1 |
|---|---|---|
| G A A A T G A T A A G T T G A T A T A A G A A G | 597 | — |
| A A T G A G T A G T T T G T A T T T G A G T T T | 598 | — |
| A G T G A A T G T A A G A T T A T G T A T T T G | 599 | 6 |
| G T A A T T G A A T T G A A A G A T A A G T G T | 600 | 8 |
| T A T G T T T A A G T A G T G A A A T A G A G T | 601 | — |
| G T A T T G A A A T T G A A T T A G A A G T A G | 602 | — |
| A A T A T G T A A T G T A G T T G A A A G T G A | 603 | — |
| T G A A T A T T G A G A A T T A T G A G A G T T | 604 | — |
| T A G T G T A A A T G A T G A A G A A A G T A T | 605 | — |
| G T A T G T G T A A A G A A A T T T G A T G T A | 606 | — |
| A A T T G T T T G A A A G T T T G T T G A G A A | 607 | — |
| A A T T G T T T G A G T A G T A T T A G T A G T | 608 | — |
| T A A T T G A G T T T G A A T A A G A G A G T T | 609 | — |
| T G T T G A T T G T A A G T G T T T A T T G T T | 610 | — |
| G A A A T T T G T G A G T A T G T A T T T G A A | 611 | — |
| T A A G A A T G A A T G T G A A G T G A A T A T | 612 | — |
| T A A T G T G A A G T T T G T G A A A G A T A T | 613 | — |
| T T G T A T A T G A A A G T A A G A A G A A G T | 614 | — |
| T A G A G A G A A G A A G A A A T A A G A A T A | 615 | — |
| A T T T G A A A T G T T A A T G A G A G A G A T | 616 | — |
| T T G T G T G T A T A T A G T A T T A G A A T G | 617 | — |
| A T T G T T A G T A T T G A T G T G A A G T T A | 618 | — |
| T G T T T G T A T T T G A A T G A A A T G A A G | 619 | — |
| T G T T A G A T T G T G T T A A A T G T A G T T | 620 | — |
| T A T A G A G T A T T G T A T A G A G A G A A A | 621 | — |
| A A A T A G T A A G A A T G T A G T T G T T G A | 622 | — |
| T G A G T G T G A T T T A T G A T T A A G T T A | 623 | — |
| A G A A T T T G T T G T A G T G T T A T G A T T | 624 | — |
| G A T T G A A G A A A G A A A T A G T T T G A A | 625 | — |
| G A T A A T A G A G A A T A G T A G A G T T A A | 626 | — |
| G A T T G A A A T T T G T A G T T A T A G T G A | 627 | — |
| G A T T T A A G A A G A T G A A T A A T G T A G | 628 | — |
| T T T G A G A G A A A G T A G A A T A A G A T A | 629 | — |
| G A T T A A G A G T A A A T G A G T A T A A G A | 630 | — |
| T T T G A T A G A A T T G A A A T T T G A G A G | 631 | — |
| T G A A G A A G A G T G T T A T A A G A T T T A | 632 | — |
| G T G A A A T G A T T T A G A G T A A T A A G T | 633 | — |
| A A A T A A G A A T A G A G A G A G A A A G T T | 634 | 9 |

TABLE I-continued

| Sequence | SEQ ID NO: | No. in Ex 1 |
|---|---|---|
| GTTGTAAAGTAATAGAGAAATTAG | 635 | — |
| AGTGATTTAGATTATGTGATGATT | 636 | — |
| AGAGTATAGTTTAGATTTATGTAG | 637 | — |
| ATGATTAGATAGTGAAATTGTTAG | 638 | — |
| ATGAAATGTATTAGTTTAGAGTTG | 639 | — |
| ATATTGAGTGAGAGTTATTGTTAA | 640 | — |
| AGATGTGTATTGAATTAAGAAGTT | 641 | — |
| TAATGTGTTGATAGAATAGAGATA | 642 | — |
| AAATTAGTTGAAAGTATGAGAAAG | 643 | 11 |
| TTTAGAGTTGAAGAAATGTTAATG | 644 | — |
| GATTGTTGATTATTGATGAATTTG | 645 | — |
| TGTTGTTGTTGAATTGAAGAATTA | 646 | — |
| ATTAAGTAAGAATTGAGAGTTTGA | 647 | 12 |
| GTATGTTGTAATGTATTAAGAAAG | 648 | 15 |
| TAGTTGTGATTTATGTAATGATTG | 649 | — |
| TGATAATGAAAGTTTATAGAGAGA | 650 | — |
| GTAAGATTGTTTGTATGATAAGAT | 651 | — |
| TTGAATTAAGAGTAAGATGTTTAG | 652 | — |
| AAGTGTTTGTTTAGAGTAAAGATA | 653 | — |
| AGAGAGATAAAGTATAGAAGTTAA | 654 | — |
| ATTATGAATAGTTAGAAAGAGAGT | 655 | — |
| TTGTTGATATTAGAGAATGTGTTT | 656 | — |
| TTTATTGAGAGTTTGTTATTTGTG | 657 | — |
| AGTGTTAAGAAGTTGATTATTGAT | 658 | — |
| GAGAAATGATTGAATGTTGATAAT | 659 | — |
| GATAAGTATTAGTATGAGTGTAAT | 660 | — |
| TTTGATTTAAGAGTGTTGAATGTA | 661 | 16 |
| AAGTTAGTAAATAGAGTAGAAAGA | 662 | — |
| GTAAAGTATGAATATGTGAAATGT | 663 | — |
| TAATAAGTGTGTTGTGAAGGTAAT | 664 | — |
| AAAGATTTAGAGTAGAAAGAGAAT | 665 | — |
| TTAGTTTGAGTTGAAATAGTAAAG | 666 | — |
| TAATAGTATGAGTAAGATTGAAAG | 667 | — |
| GAAGATTAGATTGATGTTAGTTAA | 668 | — |
| TAAAGAGAAGTTAGTAATAGAA | 669 | — |
| TAAGTATGAGAAATGATGTGTTAT | 670 | — |
| GAGTTTGTTTGTTAGTTATTGATA | 671 | — |
| AAGTAAAGAAATGTTAAGAGTAGT | 672 | — |

TABLE I-continued

| Sequence | SEQ ID NO: | No. in Ex 1 |
|---|---|---|
| ATGAGAATTGTTGTTGAAATGTAA | 673 | — |
| TTAGATTAGAGTAGTAGAAGAATA | 674 | — |
| TAGTGATGAAGAAGTTAGAAATTA | 675 | — |
| TAATGTAGTAATGTGATGATAAGT | 676 | — |
| TTGAGAAAGAATAAGTAGTGTAAA | 677 | — |
| TAATGAGTGAGATTATAGATTGTT | 678 | — |
| GTATAAGAAATGTGTTTGATTA | 679 | — |
| GTGAATGTGTTAATGAAGATATAT | 680 | — |
| GAAAGTTATTAGTAGTTAAAGATG | 681 | — |
| TAGAATTGTGTTTGATAAGTGATA | 682 | — |
| TGATTTAGATTGAGAGTTAAATGA | 683 | — |
| ATTATTGAGTTTGAATGTTGATAG | 684 | — |
| ATAGTAGTTATGTTTGATTTAGTG | 685 | — |
| ATAGAAGAAGAATAAAGTTAGAGA | 686 | — |
| GATGTTGAAAGTAATGAATTTGTA | 687 | — |
| GAGATTGATAGTAGAAATGATAAA | 688 | — |
| TGAGAGAATAAAGTATGAATTTGA | 689 | — |
| TATAAAGATGATGTGAATTAGTAG | 690 | — |
| TTATGTAAGAATGTTTGAGAGAAA | 691 | — |
| AGTAAATGATGAATGATATGATGA | 692 | — |
| GAAATTTGTGTTAAAGTTGAATGA | 693 | — |
| GATGAATGATTGTGTTTAAGTATA | 694 | — |
| GAAATAAGTGAGAGTTAATGAAAT | 695 | — |
| TGTTGAAATAGTTATTAGTTTGTG | 696 | — |
| TTTGAGAGTATATTGATATGAGAA | 697 | — |
| ATTGTGTGTAAAGTAAGATTTAAG | 698 | — |
| TATAGTTTGAAGTGTGATGTATTT | 699 | — |
| GTGAAGTTATAGTGTATAAAGAAT | 700 | — |
| GTATGTTGAATAGTAAATAGATTG | 701 | — |
| TTAGAAAGTGTGATTTGTGTATTT | 702 | — |
| TTTAGTAATATGTAAGAGATGTGA | 703 | — |
| AGTATGTATAGATGATGTTTGTTT | 704 | — |
| ATTTAAGTAAAGTGTAGAGATAAG | 705 | 20 |
| ATTTGTGTTGAATTGTAAAGTGAA | 706 | — |
| ATGTTATTAGATTGTGATGAATGA | 707 | — |
| TAGTAGTAGAATATGAAATTAGAG | 708 | — |
| TTTAATGAGAAGAGTTAGAGTATA | 709 | — |
| AAAGTTTAGTAGAGTGTATGTAAA | 710 | — |

TABLE I-continued

| Sequence | SEQ ID NO: | No. in Ex 1 |
|---|---|---|
| A T A T A T G A T A G T A G A G T A G A T T A G | 711 | — |
| T G A G A A G T T A A T T G T A T A G A T T G A | 712 | — |
| T A T A G A G A T G T T A T A T G A A G T T G T | 713 | — |
| A A A T T T G T T A A G T T G T T G T T G T T G | 714 | — |
| T T G T T G A A G A T G A A A G T A G A A T T A | 715 | — |
| A A G A G A T A A G T A G T G T T T A T G T T T | 716 | — |
| A A T A A G A A G A A G T G A A A G A T T G A T | 717 | — |
| T A A G T T A A A G T T G A T G A T T G A T A G | 718 | — |
| A T A T A A G A T A A G A G T G T A A G T G A T | 719 | — |
| G T T A A A T G T T G T T G T T T A A G T G A T | 720 | — |
| G A G T T A A G T T A T T A G T T A A G A A G T | 721 | — |
| T A T T A G A G T T T G A G A A T A A G T A G T | 722 | 21 |
| T A A T G T T G T T A T G T G T T A G A T G T T | 723 | — |
| G A A A G T T G A T A G A A T G T A A T G T T T | 724 | — |
| T G A T A G A T G A A T T G A T T G A T T A G T | 725 | — |
| A T G A T A G A G T A A A G A A T A A G T T G T | 726 | — |
| A G T A A G T G T T A G A T A G T A T T G A A T | 727 | 27 |
| A T G T A G A T T A A A G T A G T G T A T G T T | 728 | — |
| T T A T T G A T A A T G A G A G A G T T A A A G | 729 | — |
| A T T T G T T A T G A T A A A T G T G T A G T G | 730 | 29 |
| T T G A A G A A A T A A G A G T A A T A A G A G | 731 | — |
| T G T G T A A T A A G T A G T A A G A T T A G A | 732 | — |
| A T G A A A G T T A G A G T T T A T G A T A A G | 733 | 37 |
| A T T A G T T A A G A G A G T T T G T A G A T T | 734 | — |
| T G T A G T A T T G T A T G A T T A A A G T G T | 735 | — |
| A G T T G A T A A A G A A G A A G A G T A T A T | 736 | — |
| G T A A T G A G A T A A A G A G A G A T A A T T | 737 | — |
| T G T G T T G A A G A T A A A G T T T A T G A T | 738 | — |
| A A G A A G A G T A G T T A G A A T T G A T T A | 739 | — |
| G A A T G A A G A T G A A G T T T G T T A A T A | 740 | — |
| A A A T T G T T G A G A T A A G A T A G T G A T | 741 | — |
| T G A T T G T T T A A T G A T G T G T G A T T A | 742 | — |
| A T G A A G T A T T G T T G A G T G A T T T A A | 743 | — |
| G T G T A A A T G T T T G A G A T G T A T A T T | 744 | 46 |
| A A T T G A T G A G T T T A A A G A G T T G A T | 745 | — |
| T T T G T G T A A T A T G A T T G A G A G T T T | 746 | — |
| G T A G T A G A T G A T T A A G A A G A T A A A | 747 | — |
| T T T A A T G T G A A A T T T G T T G T G A G T | 748 | — |

TABLE I-continued

| Sequence | SEQ ID NO: | No. in Ex 1 |
|---|---|---|
| GTAAAGAATTAGATAAAGAGTGAT | 749 | — |
| AATAGTTAAGTTTAAGAGTTGTGT | 750 | — |
| GTGTGATGTTTATAGATTTGTTAT | 751 | — |
| GTATAGTGTGATTAGATTTGTAAA | 752 | 49 |
| GTTGTAAGAAAGATATGTAAGAAA | 753 | — |
| ATATTAGATTGTAAAGAGAGTGAA | 754 | — |
| GAGTGATATTGAAATTAGATTGTA | 755 | — |
| TAAGAAGTTAAAGAAGAGAGTTTA | 756 | — |
| GATGTTAGATAAAGTTTAAGTAGT | 757 | — |
| GTGATTGTATGAGAAATGTTAAAT | 758 | — |
| TGATTATTGTAAGAAAGATTGAGA | 759 | — |
| AAGAATTGTGTAAGTTTATGAGTA | 760 | — |
| TTGTATTTAGAAGATTTGTAGATG | 761 | — |
| TATATGTTTGTGTAAGAAGAAATG | 762 | — |
| GATAATGTGTGAATTTGTGAATAA | 763 | — |
| TTAGAAATGTGAGATTTAAGAGTT | 764 | — |
| AGTGTAGAATTTGTATTTAGTTGT | 765 | — |
| TAGTTAAGATAGAGTAAATGATAG | 766 | — |
| GAAGTGATATTGTAAATTGATAAG | 767 | — |
| GTAATTGTGTTAGATTTAAGAAGT | 768 | — |
| TGATATTTGTGAATTGATAGTATG | 769 | — |
| AAGTAAAGAGATATAGTTAAGTTG | 770 | — |
| ATTAGTTAAGTTATTTGTGAGTGA | 771 | — |
| AGATGAAGTAGTTTATGAATTAGA | 772 | — |
| TGAGTTAGTTAAGTGATAGTTAAA | 773 | — |
| TTATTGTAGATTTAGAGAAGATGA | 774 | — |
| TATTTGTGTTTGTTGATTAGATAG | 775 | — |
| GTATAATGTGTGAAAGTTATAA | 776 | — |
| TATATGTTGAGTATAAAGAGAGAA | 777 | — |
| TTAGTTAGTTTAAAGATTGTGAGT | 778 | — |
| TTTAGAATAAGTGATGTGATGAAA | 779 | — |
| AGAGTAATGTGTAAATAGTTAGAT | 780 | — |
| TGTGATAAAGAGAAATTAGTTGTT | 781 | — |
| GAATTTAGTGAATGTTTGAGATTA | 782 | — |
| TGTGATGTGTAAGTATATGAAATT | 783 | — |
| TTGTGAATGATTAATGAATAGAAG | 784 | 51 |
| AATGTTGTTTAGATTGAGAAAGTT | 785 | — |
| AGATTGTGTTAGTATTAGTATAAG | 786 | — |

TABLE I-continued

| Sequence | SEQ ID NO: | No. in Ex 1 |
|---|---|---|
| T T G A T G T A T T A G A A A G T T T A T G T G | 787 | — |
| T A T G A T T G T G T G T T A G A G A A T T T A | 788 | — |
| T A G T G T A G A T A T T T G A T A G T T A T G | 789 | 52 |
| A G T T T A A T G T G T T T A G T T G T T A T G | 790 | — |
| T G T G T A A A G T A G A A A G T A A A G A T T | 791 | — |
| G T T A T G A T A T A G T G A G T T G T T A T T | 792 | 53 |
| T T T G A T T G A A T G T T A A T A G T G T G T | 793 | — |
| A G A G T A T T A G T A G T T A T T G T A A G T | 794 | 54 |
| T A A G T A G A A A G A A G A A G A T A T T T G | 795 | — |
| A G A A A G A G A A T T A T G T A A T G A A A G | 796 | — |
| T T A G A T T T G T T A G T G T G A T T T A A G | 797 | — |
| G A T G A T T A A G A T A T A G A G A T A G T T | 798 | — |
| A T A T T T G A G T G A T T A A G A G T A A T G | 799 | — |
| T G T A T T G T G A G T T A A G T A T A A G T T | 800 | — |
| A A T T T A G T A G A A A G T G T T G T G T T T | 801 | — |
| G T T A G A A G A T T A A G T T G A A T A A T G | 802 | — |
| T A A A G T A T G T G A G A T G A T T T A T G T | 803 | — |
| T G A A A T G A T T A A A G A T G A A G A T G A | 804 | — |
| T T A T T A G A T G T T G A G T G T T T G T T T | 805 | — |
| T A G T G T T T A A A G A G T A G T A T A T G A | 806 | — |
| A G T T A T A A G T A A A T G A T G T T G A T G | 807 | — |
| T T A A G A G A G A A A T A A G T G T A T T G T | 808 | — |
| G A T A T T G A A A T G T G T A A A T G A T G A | 809 | — |
| A T G A T G A A T T A A G A A A G A A A G A G A | 810 | — |
| G A A T A G T T T G A T T T G T G T T T G T T A | 811 | — |
| A G T T G T T T A G A T T T G A T T T G T A A G | 812 | — |
| G T A T G A G A T T T G A T A T A A G A T T A G | 813 | — |
| T T T A T A G T G A G T A T A G T G A T G A T T | 814 | — |
| T A T A T G T G A A G A T A T A A G T G T T T G | 815 | — |
| A T T G A T A G A T G A T A G T A A T T G A G T | 816 | — |
| T G A T A G A T G T G A A G A A T T T G A T T T | 817 | — |
| G A A G A T A T T G A A A G A A T T T G A T G T | 818 | 55 |
| G A T G T T T A G T G T A G A T A T A G A T T T | 819 | — |
| G A A T A T T G A G T T A T A A G T A G T A G T | 820 | — |
| A G T G A G T A A G T A A T A G A A A G A T T T | 821 | — |
| G T A G A A T A A G T A A T T T G T G A G A T A | 822 | — |
| G A G T T A T T T G A G A T T T A G A T G T T T | 823 | — |
| G A A A T G A T G A T T G A A T T T A G A G A T | 824 | — |

TABLE I-continued

| Sequence | SEQ ID NO: | No. in Ex 1 |
|---|---|---|
| A A A T A G T G T G A G A A T A G T T A A G T A | 825 | — |
| A T G T G T T A A G T T G T A G A A G A A T A A | 826 | — |
| A T A A T G A G T T A A T A G T G T A A G A A G | 827 | — |
| A T A A G A G A T G T T T A A G T T A G A A A G | 828 | — |
| T G T T A G T G T T A G A A A T A T G A A A G A | 829 | — |
| T T T A G A A G A T T G T T A G A T A A G T T G | 830 | — |
| G T G T A A T G T A T A A G A T A G T T A A G T | 831 | — |
| T A T T A G A G A G A A T T G T A G A G A T T | 832 | 57 |
| T A G T G A G A T A A A G T A A A G T T T A T G | 833 | — |
| T T G T G A A A G T T A A G T A A G T T A G T T | 834 | — |
| A A A G T G T A A G T T G A A G A A T A T T G A | 835 | — |
| G A A T A G A G T G T T A T T T G A A A T A G A | 836 | — |
| T A T A A G A G A G A T A A G T A A T A A G | 837 | — |
| T G A G T G A A A T T G A T A G A G T A A A T T | 838 | — |
| G A T G A A T A A G T T T A A G T G A G A A A T | 839 | — |
| G T G T G A T A T G T T T A T T G A T T A A G T | 840 | — |
| T A A A G T G A G T G T A A A T G A T A A T G A | 841 | — |
| G T A G A G T T T G A T T T G A A A G A A T A T | 842 | — |
| G A A T A T T G T T A T G T T T G T T A T G A G | 843 | — |
| G T G T A A T A A G A T G T A T T G T T G T T T | 844 | — |
| T A A A T T G A T T G T G A G T T G A A G A A T | 845 | — |
| T G A G A T A G T T A T A G T T A A G T T T A G | 846 | — |
| A G T T T G T T A A G A T T A T G T A G A A A G | 847 | — |
| G A A T G T G T A G A A T A A G A G A T T A A A | 848 | — |
| G T A T T A T G A A A G A A G T T G T T G T T T | 849 | — |
| G T G T T A T A G A A G T T A A A T G T T A A G | 850 | 58 |
| T T A A G A G T A G T G A A T A T G A T A G T A | 851 | — |
| A A T G T T A T A A G A T G A G A G T T T A G T | 852 | — |
| A T A T A A G A T T T G A T G T A G T G T A G T | 853 | — |
| T A T G T T T G T T G T T G T T A A G T T T G A | 854 | — |
| G A T A G T T T A G T A T A G A A G A T A A A G | 855 | — |
| G T T G A A T A T A G A G A T A G T A A A T A G | 856 | — |
| A G A G A A G A T T T A G T A A G A A T G A T A | 857 | — |
| T G A A T G A G A A A G A T A T T G A G T A T T | 858 | — |
| T G A A G A T T A T A G T A G T T G T A T A G A | 859 | — |
| G A T T A G T A G T A T T G A A G A T T A T G T | 860 | — |
| T G A A A T G T G T A T T T G T A T G T T T A G | 861 | 59 |
| A T T A A A G T T G A T A T G A A A G A A G T G | 862 | — |

TABLE I-continued

| Sequence | SEQ ID NO: | No. in Ex 1 |
|---|---|---|
| A A T G T A G A G A T T G T A G T G A A T A T T | 863 | 62 |
| T T A T T T G T T G A G T G T A A A T G T G A T | 864 | — |
| A T G T A A T T G T G A A T A A T G T A T G T G | 865 | 63 |
| G A T T T G T A T A G A G A T T A G T A A G T A | 866 | — |
| A A T A T T G T T G T T T A G A G A A A G A A G | 867 | — |
| A T G A T G A T G T A T T T G T A A A G A G T A | 868 | — |
| A A T G T A T T T G T G T G A T T G T G T A A A | 869 | — |
| A G T G T T A T G A A G A A T A G T A A G A A T | 870 | — |
| G T T A T G T A G A G A T G A A A G A A A T T A | 871 | 65 |
| G T T T G T A T T A G A T A A A T G A G T T G T | 872 | — |
| T G A T T T A T G A G A T T A A G A G A A A G A | 873 | — |
| T T T G T G T G T T A T T G T A A T T G A G A T | 874 | 70 |
| G A T G T G T G A T A T G A T T A A A G A A A T | 875 | — |
| A G A T T A T A G A T T T G T A G A G A A A G T | 876 | — |
| G A A G A G T A T G T A A T A G T A T T G T A T | 877 | — |
| T T T G T A A T G T T G T T G A G T T T A A G A | 878 | — |
| A G T A A A T A G T A G T A T G A A T A A G A G | 879 | — |
| G A A T G T T G A A T T G A A A T A T G A G T T | 880 | — |
| A G T A G T T A A T T G A T A G T A A G T T T G | 881 | — |
| A G T G T A A A G A A A T G A A T G A A T A A G | 882 | — |
| T G T T A G A T A T T T G T G A A A T G T G A A | 883 | — |
| T G T A T G T T G A G T T T G A A T T G T T A T | 884 | — |
| T G A G T G A A T T A G T T A T G T T G T T A T | 885 | — |
| G A A G A A A G A A A T G A G A A A G A T T A T | 886 | — |
| T T A A G T A A G T T G T G T T G A T A T T A G | 887 | — |
| A T G A T G T G T T T G A T T T G A A T T G A A | 888 | 72 |
| A A G T A A G T G A A A T T G T T G T T T G A A | 889 | — |
| A T G A A G T G T A A A G T T T G A A A G A A A | 890 | — |
| A G A G A G T A A G A T A A T T G T A T A G T A | 891 | — |
| T T T A T G A G A T A G A T G A A A T A A G T G | 892 | — |
| A G A A A T T A G T A G T A A T G A T T T G T G | 893 | — |
| G A T T T G A G A T T G A A T G A G A A T A T A | 894 | — |
| G A T T A G A A A G A T G A A T A A A G A T G A | 895 | — |
| T A G A T A G A A A G T A T A T G T T G T A G T | 896 | — |
| G A A G A T A G T A A A G T A A A G T A A G T T | 897 | — |
| A A A T G T G T G T T T A G T A G T T G T A A A | 898 | 75 |
| T T G T T G A A G T A A G A G A T G A A T A A A | 899 | — |
| T A T T T G A G A G A A A G A A A G A G T T T A | 900 | — |

TABLE I-continued

| Sequence | SEQ ID NO: | No. in Ex 1 |
|---|---|---|
| TATTTAGTGATGAATTTGTGATGT | 901 | — |
| TTATAGTGATGATGATAAGTTGAT | 902 | — |
| TAAAGATAATTGTAGAAAGTAGTG | 903 | — |
| GTTTAGTATTGATATTGTGTGTAA | 904 | — |
| GTGTTGTGAATAAGATTGAAATAT | 905 | — |
| AAAGAAGTATAAAGTGAGATAGA | 906 | — |
| TATTTGTAAGAAGTGTAGATATTG | 907 | — |
| TAGAAGATGAAATTGTGATTTGTT | 908 | — |
| ATAATAGTAAGTGAATGATGAGAT | 909 | — |
| AATGTGAATAAGATAAAGTGTGTA | 910 | — |
| ATTGAAGATAAAGATGTTGTTTAG | 911 | — |
| TGAAATAGAAGTGAGATTATAGTA | 912 | 76 |
| AGTTATTGTGAAAGAGTTTATGAT | 913 | — |
| AAATAGTAGTGATAGAGAAGATTT | 914 | — |
| AGTGTATGAAGTGTAATAAGATTA | 915 | — |
| TGATTAAGATTGTGTAGTGTTATA | 916 | — |
| AGTTTATGATATTTGTAGATGAGT | 917 | — |
| TATGTGTATGAAGATTATAGTTAG | 918 | 78 |
| GAAATTGTTGTATAGAGTGATATA | 919 | — |
| TAGAAATAGTTTAAGTATAGTGTG | 920 | — |
| TGATTTAGATGTTTATTGTGAGAA | 921 | — |
| AAGTTGATATTTGTTGTTAGATGA | 922 | — |
| TGATGTGATAATGAGAATAAAGAA | 923 | 79 |
| AAAGTTTAGTTTGTATTAGTAGAG | 924 | — |
| AGTTTGATGTGATAGTAAATAGAA | 925 | — |
| AAGTGTTATTGAATGTGATGTTAT | 926 | — |
| AAATTGAAGTGTGATAATGTTTGT | 927 | — |
| GTTTAGTGATTAAAGATAGATTAG | 928 | 82 |
| ATAAGTGTATAAGAGAAGTGTTAA | 929 | — |
| ATGAATTTGTTTGTGATGAAGTTA | 930 | — |
| AAAGAATTGAGAAATGAAAGTTAG | 931 | — |
| AGTGTAAGAGTATAAAGTATTTGA | 932 | — |
| GAATTAAGATTGTTATATGTGAGT | 933 | — |
| TATGAAAGTGTTGTTTAAGTAAGA | 934 | — |
| TAAAGTAAATGTTATGTGAGAGAA | 935 | — |
| AAAGATATTGATTGAGATAGAGTT | 936 | — |
| AAGTGATATGAATATGTGAGAAAT | 937 | — |
| AAATAGAGTTTGTTAATGTAAGTG | 938 | — |

TABLE I-continued

| Sequence | SEQ ID NO: | No. in Ex 1 |
|---|---|---|
| GATTTAGATGAGTTAAGAATTTAG | 939 | — |
| TTGTAAATGAGTGTGAATATTGTA | 940 | — |
| AGTAGTGTATTTGAGATAATAGAA | 941 | — |
| TGAGTTAAAGAGTTGTTGATATTT | 942 | — |
| AAAGAGTGTATTAGAAATAGTTTG | 943 | — |
| GTTTAGTTATTTGATGAGATAATG | 944 | — |
| AAGTGTAAATGAATAAAGAGTTGT | 945 | — |
| AATAAAGTGAGTAGAAGTGTAATT | 946 | — |
| TATTGAGTTTGTGTAAAGAAGATA | 947 | — |
| TTTATAGTTGTTGTGTTGAAAGTT | 948 | — |
| ATGAAATATGATTGTGTTTGTTGT | 949 | — |
| AAAGAGATGTAAAGTGAGTTATTA | 950 | — |
| TTGAAGAAAGTTAGATGATGAATT | 951 | — |
| ATGTTATTTGTTTAGTTTGTGTGA | 952 | — |
| AAATATGAATTTGAAGAGAAGTGA | 953 | — |
| GATTAGATATAGAATATTGAAGAG | 954 | — |
| TTAGAATAAGAGAAATGTATGTGT | 955 | — |
| TTTATGAAAGAGAAGTGTATTATG | 956 | — |
| GTAAGTATTAAGTGTGATTTAGTA | 957 | — |
| ATAAAGAGAAGTAAAGAGTAAAGT | 958 | — |
| ATTGTTAATTGAAGTGTATGAAAG | 959 | — |
| TATATAGTTGAGTTGAGTAAGATT | 960 | — |
| TAGATGAGATATATGAAAGATAGT | 961 | — |
| ATAAGAAGATGATTTGTGTAAATG | 962 | — |
| TTAGTAATAAGAAAGATGAAGAGA | 963 | — |
| GATTTGTGAGTAAAGTAAATAGAA | 964 | — |
| AAATAGATGTAGAATTTGTGTGTT | 965 | — |
| GAAATTAGTGTTTGTGTGTATTAT | 966 | — |
| ATTTGAGTATGATAGAAGATTGTT | 967 | — |
| ATAGAGTTGAAGTATGTAAAGTTT | 968 | — |
| TAATTTGTGAATGTTGTTATTGTG | 969 | — |
| TTAGTTTATGAGAGTGAGATTTAA | 970 | — |
| GTTGTTAGAGTGTTTATGAAATTT | 971 | — |
| TTTATTGTGATGTGAAATAAGAGA | 972 | — |
| GTAAGTAATATGATAGTGATTAAG | 973 | — |
| TGAGATGATGTATATGTAGTAATA | 974 | — |
| AATTGAGAAAGAGATAAATGATAG | 975 | 85 |
| TTTGAAGTGATGTTAGAATGTTTA | 976 | — |

TABLE I-continued

| Sequence | SEQ ID NO: | No. in Ex 1 |
|---|---|---|
| A G T T G T T G T G T A A T T G T T A G T A A A | 977 | — |
| A T A G T G A G A A G T G A T A A G A T A T T T | 978 | — |
| G T G T G A T A A G T A A T T G A G T T A A A T | 979 | — |
| T A G T T A T T G T T T G T G A A T T T G A G A | 980 | — |
| A T A G T T G A A T A G T A A T T T G A A G A G | 981 | — |
| A T G T T T G T G T T T G A A T A G A G A A T A | 982 | — |
| T G A T A A A G A T A T G A G A G A T T G T A A | 983 | — |
| T A A A G A T G A G A T G T T G T T A A A G T T | 984 | — |
| A A G T G A A A T T T G T A A G A A T T A G T G | 985 | — |
| G A A A T G A G A G T T A T T G A T A G T T T A | 986 | — |
| T T T G T A A A T G A G A T A T A G T G T T A G | 987 | — |
| G T T A A T T G T G A T A T T T G A T T A G T G | 988 | — |
| A G A G T G T T G A T A A A G A T G T T T A T A | 989 | — |
| A A T T G T G A G A A A T T G A T A A G A A G A | 990 | — |
| T T A A A G A G A A T T G A G A A G A G A A A T | 991 | — |
| T T G T T A G A A G A A T T G A A T G T A T G T | 992 | — |
| A G T T A A G A T A T G T G T G A T G T T T A A | 993 | — |
| T G A G T T A T G T T G T A A T A G A A A T T G | 994 | — |
| T T A G A T A A G T T T A G A G A T T G A G A A | 995 | — |
| A T G A G T A A T A A G A G T A T T T G A A G T | 996 | — |
| T G T T T A A G T G T A A T G A T T T G T T A G | 997 | — |
| T T G A A G A A G A T T G T T A T T G T T G A A | 998 | — |
| T A T A G A A A G A T T A A A G A G T G A A T G | 999 | — |
| T A A A T T G T T A G A A A T T T G A G T G T G | 1000 | — |
| A T T G T T A G T G T G T T A T T G A T T A T G | 1001 | — |
| G A G A A T T A T G T G T G A A T A T A G A A A | 1002 | — |
| T T G A T T G A T A A A G T A A A G A G T G T A | 1003 | — |
| G T G T G T A A A T T G A A T A T G T T A A T G | 1004 | — |
| A A A G T A A A G A A A G A A G T T T G A A A G | 1005 | — |
| T T T A G T T G A A G A A T A G A A A G A A A G | 1006 | — |
| G T G T A A T A A G A G T G A A T A G T A A T T | 1007 | — |
| T A T T G A A A T A A G A G A G A T T T G T G A | 1008 | — |
| A T G A G A A G A A G A A G T T A A G A T T T | 1009 | — |
| A A G A G T G A G T A T A T T G T T A A A G A A | 1010 | — |
| T T T G T A A A G T G A T G A T G T A A G A T A | 1011 | — |
| G A T G T T A T G T G A T G A A A T A T G T A T | 1012 | — |
| G T A G A A T A A A G T G T T A A A G T G T T A | 1013 | — |
| A A A G A G T A T G T G T G T A T G A T A T T T | 1014 | — |

TABLE I-continued

| Sequence | SEQ ID NO: | No. in Ex 1 |
|---|---|---|
| AAAGATAAGAGTTAGTAAATTGTG | 1015 | — |
| AAGAATTAGAGAATAAGTGTGATA | 1016 | — |
| GATAAGAAAGTGAAATGTAAATTG | 1017 | 86 |
| GATGAAAGATGTTTAAAGTTTGTT | 1018 | — |
| AGTGTAAGTAATAAGTTTGAGAAA | 1019 | — |
| GTTGAGAATTAGAATTTGATAAAG | 1020 | 87 |
| TTAAGAAATTTGTATGTGTTGTTG | 1021 | — |
| AGAAGATTTAGATGAAATGAGTTT | 1022 | — |
| TAAGTTTGAGATAAAGATGATATG | 1023 | — |
| TGAGATAGTTTGTAATATGTTTGT | 1024 | — |
| AGTTTGAAATTGTAAGTTTGATGA | 1025 | — |
| TAGAATTGATTAATGATGAGTAGT | 1026 | — |
| AGAGATTTGTAATAAGTATTGAAG | 1027 | — |
| ATAATGATGTAATGTAAGTAGTGT | 1028 | — |
| TGAAATTTGATGAGAGATATGTTA | 1029 | — |
| TGTGTAAAGTATAGTTTATGTTAG | 1030 | — |
| TGAATAAGTGAAATAGAATGAATG | 1031 | — |
| AAAGAAGATTGTAATAAGTAGAG | 1032 | — |
| AATGAAATAGTGTTAAATGAGTGT | 1033 | 89 |
| GTAGATAAAGATGTGAATTATGAT | 1034 | — |
| GATAGTATATGTGTGTATTTGTTT | 1035 | — |
| ATGTTTGTAGAAATGTTTGAAGAT | 1036 | — |
| AAATTTGTAGAGAGAAATTTGTTG | 1037 | — |
| TAGAATAAGATTAGTAAGTGTAGA | 1038 | — |
| TGATTTAGAGAAATATGAGTAGAA | 1039 | — |
| AATAGAGTATGTTGTTTATGAGAA | 1040 | — |
| GATGATGAAGAGTTTATTGTAAAT | 1041 | — |
| AAGTAAAGAAGAAGAAATGTGTTA | 1042 | — |
| TTGAAGAATTAAGTGTTTAGTGTA | 1043 | — |
| AGAAAGAATGTTGATTTATGATGT | 1044 | — |
| GATTAAAGAGATGTTGATTGAAAT | 1045 | — |
| AATGATAATTGTTGAGAGAGTAAT | 1046 | — |
| GTTTGTTGAAAGTGTAAAGTATAT | 1047 | 90 |
| TGAGTTATATGAGAAAGTGTAATT | 1048 | — |
| TTGTGAGAAAGAAGTATATAGAAT | 1049 | — |
| GTAAGTTTAGAGTTATAGAGTTTA | 1050 | — |
| GATAGATAGATAAGTTAATTGAAG | 1051 | — |
| AGAGATGATTGTTTATGTATTATG | 1052 | — |

TABLE I-continued

| Sequence | SEQ ID NO: | No. in Ex 1 |
|---|---|---|
| A A A G T T A A G A A A T T G T A G T G A T A G | 1053 | — |
| T T T G A T A T T G T T T G T G A G T G T A T A | 1054 | — |
| A T T T G T A G A A A G T T G T T A T G A G T T | 1055 | — |
| G A T T T G A G T A A G T T T A T A G A T G A A | 1056 | — |
| A A G A T A A A G T G A G T T G A T T T A G A T | 1057 | — |
| G A T A T T G T A A G A T A T G T T G T A A A G | 1058 | — |
| G T A A G A G T G T A T T G T A A G T T A A T T | 1059 | — |
| G T G T G A T T A G T A A T G A A G T A T T T A | 1060 | 91 |
| G T A A G A A A G A T T A A G T G T T A G T A A | 1061 | — |
| A G T A G A A A G T T G A A A T T G A T T A T G | 1062 | 92 |
| T A A G A G A A G T T G A G T A A T G T A T T T | 1063 | — |
| G T T A A G A A A T A G T A G A T A A G T G A A | 1064 | — |
| T A A G T A A A T T G A A A G T G T A T A G T G | 1065 | — |
| A A G T G T A T G T T T A T T G T T G T G T A | 1066 | — |
| A T T T A G A A T A T A G T G A A G A G A T A G | 1067 | — |
| G T T A T G A A A G A G T A T G T G T T A A A T | 1068 | 93 |
| T A T T A T G T G A A G A A G A A T G A T T A G | 1069 | — |
| T A A T A A G T T G A A G A G A A T T G T T G T | 1070 | — |
| T G A T G T T T G A T G T A A T T G T T A A A G | 1071 | — |
| G T G A A A G A T T T G A G T T T G T A T A A T | 1072 | — |
| A G A G A A T A T A G A T T G A G A T T T G T T | 1073 | — |
| T T T G A G A T G T G A T G A T A A A G T T A A | 1074 | — |
| G T T G T A A A T T G T A G T A A A G A A G T A | 1075 | 94 |
| G T G T T A T G A T G T T G T T T G T A T T A T | 1076 | — |
| A T T A T T G T G T A G A T G T A T T A A G A G | 1077 | — |
| G T T A G A A A G A T T T A G A A G T T A G T T | 1078 | — |
| T T G T G T A T T A A G A G A G T G A A A T A T | 1079 | — |
| G T T T A A G A T A G A A A G A G T G A T T T A | 1080 | — |
| A A T G A G A A T A G A T A G T T A T T G T G | 1081 | — |
| T G A A T T G A A T A A G A A T T T G T T G T G | 1082 | 95 |
| A A T A A G A T T G A A T T A G T G A G T A A G | 1083 | — |
| A A T G T T T G A G A G A T T T A G T A A A G A | 1084 | — |
| A G T T T A G A A T A G A A A T G T G T T T G A | 1085 | — |
| T A T A A G T A A G T G T T A A G A T T T G A G | 1086 | — |
| G T A G T G A A T A A G T T A G T G T T A A T A | 1087 | — |
| A A G T G T G T T A A A G T A A A T G T A G A T | 1088 | — |
| A G A G A T G T T T A T G T T G T G A A T T A A | 1089 | — |
| A G T T G A A T A T T G A T G A T A A G A A G A | 1090 | — |

TABLE I-continued

| Sequence | SEQ ID NO: | No. in Ex 1 |
|---|---|---|
| TGAATGTGAGATGTTTAGAATAAT | 1091 | — |
| AATAATGATGTAAGTTTGAGTTTG | 1092 | — |
| AAAGAGTGAATAGAATAAGAGAA | 1093 | — |
| AATAAAGTTATTGAGAGAGTTTAG | 1094 | — |
| AGTAGTGTTGTAGTTTAGTATATA | 1095 | — |
| GTAAGAATGTATTAGATATTTGTG | 1096 | — |
| GATAAATGTTTGATAAAGTAGTTG | 1097 | — |
| ATAGTATGTATGTGTGAAGATTTA | 1098 | — |
| ATGAATGTAGAGTGATTAGTTTAA | 1099 | — |
| GTAGTATTTAGTGATGTAAGAATA | 1100 | — |
| AGAATTGTATTGAAGAAGAATATG | 1101 | — |
| TTTATAGAATTGAGAGAAGTTAAG | 1102 | — |
| AAAGTAGTAGAGATTTGAGAATTA | 1103 | — |
| TTTAAAGAAAGTATTGTAAGAGTG | 1104 | — |
| AAATTGAGAAAGTGAATGAAGTTT | 1105 | — |
| AAGAAATAAGTATGATAGTAGTAG | 1106 | — |
| ATTTGAATTGTATTGTAGTTTGTG | 1107 | — |
| AAGAGAATAATGTAGAGATATAAG | 1108 | — |
| TGTGTAATAGTTGTTAATGAGTAA | 1109 | — |
| TATAGTTGTAGTTTAGATGAATGT | 1110 | — |
| ATTGTGTTAGAATGATGTTAATAG | 1111 | — |
| GTTTGTATAGTATTTGATTGATGT | 1112 | — |
| AGAGTAAAGTATGAGTTATGAATA | 1113 | — |
| GAAAGTTTAAGTGATGTATATTGT | 1114 | 96 |
| TTAAATGATAAAGAGTAGTGAAGT | 1115 | — |
| TTAAATGTGTGAGAAGATGAATAA | 1116 | — |
| ATTTGTATAAAGTGAAGAAGAGAA | 1117 | 97 |
| TGATTAGTATTTGTGAAGAGATTT | 1118 | — |
| TTTGAATGAAATTGATGATAGATG | 1119 | — |
| AGAGTAAGATTAAGAATAAGAAAG | 1120 | — |
| ATTGAATTGAGAAGTGAAGTAAAT | 1121 | — |
| TTTAGAGAAGTATTGTTTGAAAGA | 1122 | — |
| TAAAGTGAAAGATTTGAAATGATG | 1123 | — |
| GAAAGTTAGAGAAATGTAGAAATT | 1124 | — |
| GTGAATAATGAAGAAGTTATGTTA | 1125 | 98 |
| TTGTGAATAAAGTAGATGTGTTAT | 1126 | — |
| TTATATGATATGAGTTTGTGTTGA | 1127 | — |
| TTGATTTGTGTGAGTATTAGTTAT | 1128 | — |

TABLE I-continued

| Sequence | SEQ ID NO: | No. in Ex 1 |
|---|---|---|
| AAAGTGATTAAGTTAGTTTGAGAT | 1129 | - |
| TTGTATTTGTATAATGTTGAAGAG | 1130 | - |
| GTTTGAAATTAGTGTGAGAAATAT | 1131 | - |
| AATGTTGAGATTGATAATGTTGAA | 1132 | - |
| TAGTAGTAGTATTGTTGTAATAAG | 1133 | - |
| GTTGTAATTTGAGTGTTAGTTATT | 1134 | - |
| TGAATATGATAGTTAGTAATTGTG | 1135 | - |
| TGATAGTATGTTTGTGATTAAAGA | 1136 | - |
| GATGTATAAAGAGTATGTTATAAG | 1137 | - |
| AGTGAGATTTAGAAGATGTTATTA | 1138 | - |
| ATGAGAATTTGTTAAAGAGAAAGT | 1139 | - |
| AAAGAATTAGTATGATAGATGAGA | 1140 | 99 |
| TAGAGTTGTATAGTTTATAGTTGA | 1141 | - |
| GTAGAATGATTGTTTAGAAGATTT | 1142 | - |
| GTTTATGTTTGAGAAGAGTTATTT | 1143 | - |
| TAGAAGTTTGAAAGTTATTGATTG | 1144 | - |
| GATGAAGAGTATTTGTTATATGTA | 1145 | - |
| GATGAATATAGTAAGTATTGAGTA | 1146 | 100 |
| TAGTGATGAAATTTGAGATAGATA | 1147 | - |
| GAAAGAAATTGAAGAGTTTGATAT | 1148 | - |
| ATTTGAGTATTTGTGTATTGAATG | 1149 | - |
| ATGAGTTGAAATTTGAAGTATTGT | 1150 | - |
| TTAATAGTGAGAGAGTATATGTAA | 1151 | - |
| ATTAAGAGAGTGAGTAAATGTAAA | 1152 | - |
| AAGAATAGATGAGATTAGAAATAG | 1153 | - |
| AGTTTAAAGAGTTAGAATTGAAAG | 1154 | - |
| GTAAGATTTGTTGAATAAAGAAGA | 1155 | - |
| AGAGAAGAAGTTAAAGTGATATT | 1156 | - |
| TAATAGAAGAGATGTATGAATA | 1157 | - |
| TTATTAGTGATAAGTGAAGTTTAG | 1158 | - |
| ATAATGTAAAGATGAGTTTATGAG | 1159 | - |
| TTGATTTGAGAGTTGATAAGATTT | 1160 | - |
| ATGATTATTGTGTGTAGAATTAGA | 1161 | - |
| TATAAAGATATAGTAGATGATGTG | 1162 | - |
| TTTAGTTGAGATGAAGTTATTAGA | 1163 | - |
| ATTGAATTGATATAGTGTAAAGTG | 1164 | - |
| GAAGAAAGATTATTGTATTGAGTT | 1165 | - |
| ATTGAGTGTAGTGATTTAGAAATA | 1166 | - |

TABLE I-continued

| Sequence | SEQ ID NO: | No. in Ex 1 |
|---|---|---|
| A A T A A A G T G T T T A A G A G T A G A G T A | 1167 | — |
| G T A G A G A T A A T T G A T G T G T A A T T T | 1168 | — |

All references referred to in this specification are incorporated herein by reference.

The scope of protection sought for the invention described herein is defined by the appended claims. It will also be understood that any elements recited above or in the claims, can be combined with the elements of any claim. In particular, elements of a dependent claim can be combined with any element of a claim from which it depends, or with any other compatible element of the invention.

The invention claimed is:

1. A set of minimally cross-hybridizing oligonucleotide tags or tag complements, the set of tags or tag complements being characterized in that:
   (a) each tag or tag complement either is free of cytosine residues and comprises guanosine residues or is free of guanosine residues and comprises cytosine residues;
   (b) in each tag or tag complement that comprises cytosine residues, the cytosine residues are separated by between one and six non-cytosine residues, and in each tag or tag complement that comprises guanosine residues, the guanosine residues are separated by between one and six non-guanosine residues;
   (c) the number of cytosine and guanosine residues present in each tag or tag complement does not exceed L/4 where L is the number of bases in the oligonucleotide;
   (d) the length of each oligonucleotide differs by no more than five bases from the average length of all oligonucleotides in the set;
   (e) each tag or tag complement contains no more than 4 contiguous identical nucleotides;
   (f) the number of guanosine and cytosine residues present in each tag or tag complement does not vary from the average number of guanosine and cytosine residues present in all other tags or tag complements of the set by more than one; and
   (g) when each tag or tag complement of the set is exposed to hybridization conditions comprising 0.2M NaCl, 0.1M Tris, 0.08% Triton X-100, pH 8.0 at 37° C., the degree of cross-hybridization between the tag or tag complement and an oligonucleotide of the set that is not fully complementary to the tag or tag complement does not exceed 30% of the degree of hybridization between the tag or tag complement and a fully complementary oligonucleotide to said tag or tag complement,
   wherein each tag or tag complement is between 10 and 50 nucleotides in length.

2. The set of oligonucleotide tags or tag complements of claim 1, further characterized in that, each tag or tag complement in the set contains either a cytosine or guanosine residue located within seven residues of an end of the tag or tag complement.

3. The set of oligonucleotide tags or tag complements of claim 1 or 2, wherein the length of each tag or tag complement in the set is identical.

4. The set of oligonucleotide tags or tag complements of claim 3, wherein the number of guanosine and cytosine residues present in each tag or tag complement is the same.

5. The set of oligonucleotide tags or tag complements of claim 1 or 2, wherein the degree of cross-hybridization between the tag or tag complement and an oligonucleotide of the set that is not fully complementary to the tag or tag complement does not exceed 20% of the degree of hybridization between the tag or tag complement and its fully complementary oligonucleotide.

6. The set of oligonucleotide tags or tag complements of claim 5, wherein the degree of cross-hybridization between the tag or tag complement and an oligonucleotide of the set that is not fully complementary to the tag or tag complement does not exceed 6% of the degree of hybridization between the tag or tag complement and its fully complementary oligonucleotide.

7. The set of oligonucleotide tags or tag complements of claim 1 or 2, wherein the tags or tag complements are attached to a solid phase support.

8. The set of oligonucleotide tags or tag complements of claim 7, wherein the support is a planar substrate comprising a plurality of spatially addressable regions.

9. The set of oligonucleotide tags or tag complements of claim 1 or 2, wherein the tags or tag complements are covalently linked to microparticles.

10. The set of oligonucleotide tags or tag complements of claim 9, wherein the microparticles are spectrophotometrically unique and each unique microparticle has a different tag or tag complement attached thereto.

11. The set of oligonucleotide tags or tag complements of claim 1, wherein the length of each oligonucleotide tag or tag complement is 24 residues.

12. The set of oligonucleotide tags or tag complements of claim 11, wherein each oligonucleotide tag or tag complement contains either 6 guanosine or 6 cytosine residues.

13. A composition comprising minimally cross-hybridizing molecules for use as tags or tag complements wherein each molecule comprises an oligonucleotide comprising a sequence of ten to fifty nucleotide bases in length, wherein each sequence comprises guanosine residues and, for each sequence, the number of guanosine residues does not exceed L/4 where L is the number of bases in said sequence, and for which,
   under a single set of hybridization conditions, the degree of cross-hybridization between a said oligonucleotide and any complement of a different oligonucleotide of the composition does not exceed about 15% of the degree of hybridization between said oligonucleotide and a complement to said oligonucleotide, and
   wherein the single set of hybridization conditions results in a level of hybridization that is the same as the level of hybridization obtained when hybridization conditions include 0.2 M NaCl, 0.1 M Tris, 0.08% Triton X-100, pH 8.0 at 37° C., and the oligonucleotides are covalently linked to microparticles.

14. The composition of claim 13, wherein each sequence does not comprise cytosine residues.

15. The composition of claim 13, wherein each sequence contains a guanosine residue located within seven residues of an end of the sequence.

16. The composition of claim 13, wherein the length of each sequence is identical.

17. The composition of claim 16, wherein the number of guanosine residues present in each sequence is the same.

18. The composition of claim 13, wherein the length of each sequence is 24 residues.

19. The composition of claim 18, wherein each sequence contains 6 guanosine residues.

20. The composition of claim 13, wherein the oligonucleotides are covalently linked to spectrophotometrically unique microparticles and each unique microparticle has a different oligonucleotide attached thereto.

21. A composition comprising minimally cross-hybridizing molecules for use as tags or tag complements wherein each molecule comprises an oligonucleotide comprising a sequence of ten to fifty nucleotide bases in length, wherein each sequence comprises cytosine residues and, for each sequence, the number of cytosine residues does not exceed L/4 where L is the number of bases in said sequence, and for which,
    under a single set of hybridization conditions, the degree of cross-hybridization between a said oligonucleotide and any complement of a different oligonucleotide of the composition does not exceed about 15% of the degree of hybridization between said oligonucleotide and a complement to said oligonucleotide, and
    wherein the single set of hybridization conditions results in a level of hybridization that is the same as the level of hybridization obtained when hybridization conditions include 0.2 M NaCl, 0.1 M Tris, 0.08% Triton X-100, pH 8.0 at 37° C., and the oligonucleotides are covalently linked to microparticles.

22. The composition of claim 21, wherein each sequence does not comprise guanosine residues.

23. The composition of claim 21, wherein each sequence contains a cytosine residue located within seven residues of an end of the sequence.

24. The composition of claim 21, wherein the length of each sequence is identical.

25. The composition of claim 24, wherein the number of cytosine residues present in each sequence is the same.

26. The composition of claim 21, wherein the length of each sequence is 24 residues.

27. The composition of claim 26, wherein each sequence contains 6 cytosine residues.

28. The composition of claim 21, wherein the oligonucleotides are covalently linked to spectrophotometrically unique microparticles and each unique microparticle has a different oligonucleotide attached thereto.

* * * * *

UNITED STATES PATENT AND TRADEMARK OFFICE
CERTIFICATE OF CORRECTION

PATENT NO. : 7,645,868 B2
APPLICATION NO. : 10/470073
DATED : January 12, 2010
INVENTOR(S) : Kobler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1193 days.

Signed and Sealed this

Twenty-eighth Day of December, 2010

David J. Kappos
*Director of the United States Patent and Trademark Office*

SEQUENCE LISTING

<160> NUMBER OF SEQ ID NOS: 1172

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1
aaattgtgaa agattgtttg tgta                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 2
gttagagtta attgtatttg atga                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 3
atgttaaagt aagtgttgaa atgt                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 4
tgatgttaga agtatattgt gaat                                              24

<210> SEQ ID NO 5
<211> LENGTH: 24

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 5
tttgtgtaga atatgtgttg ttaa                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 6
ataagtgtaa gtgaaataag aaga                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 7
aagagtattt gttgtgagtt aaat                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 8
gtgtttatgt tatatgtgaa gttt                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 9
aaagagaata gaatatgtgt aagt                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 10
tatgaaagag tgagataatg ttta                                              24

<210> SEQ ID NO 11
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 11
atgagaaata tgttagaatg tgat                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 12
ttagttgttg atgtttagta gttt                                            24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 13
gtaaagagta taagtttgat gata                                            24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 14
aaagtaagaa tgatgtaata agtg                                            24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 15
gtagaaatag tttattgatg attg                                            24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 16
tgtaagtgaa atagtgagtt attt                                            24

<210> SEQ ID NO 17
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 17
aaatagatga taaagtgag aatg                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 18
ataagttata agtgttatgt gagt                                             24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 19
tatagataaa gagatgattt gttg                                             24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 20
agagttgaga atgtatagta ttat                                             24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 21
aagtagtttg taagaatgat tgta                                             24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 22
ttatgaaatt gagtgaagat tgat                                             24

<210> SEQ ID NO 23
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 23
gtatatgtaa attgttatgt tgag                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 24
gaattgtata aagtattaga tgtg                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 25
tagatgagat taagtgttat ttga                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 26
gttaagtttg tttatgtata gaag                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 27
gagtattagt aaagtgatat gata                                              24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 28
gtgaatgatt tagtaaatga ttga                                              24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 29
gattgaagtt atagaaatga ttag                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 30
agtgataaat gttagttgaa ttgt                                          24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 31
tatatagtaa atgtttgtgt gttg                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 32
ttaagtgtta gttatttgtt gtag                                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 33
gtagtaatat gaagtgagaa tata                                          24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 34
tagtgtatag aatgtagatt tagt                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 35
ttgtagatta gatgtgtttg taaa                                              24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 36
tagtatagag tagagatgat attt                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 37
attgtgaaag aaagagaaga aatt                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 38
tgtgagaatt aagattaaga atgt                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 39
atattagtta agaaagaaga gttg                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 40
ttgtagttga gaaatatgta gttt                                              24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 41
tagagttgtt aaagagtgta aata                                       24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 42
gttatgatgt gtataagtaa tatg                                       24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 43
tttgttagaa tgagaagatt tatg                                       24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 44
agtatagttt aaagaagtag taga                                       24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 45
gtgagatata gatttagaaa gtaa                                       24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 46
ttgtttatag tgaagtgaat agta                                       24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 47
```

-continued aagtaagtag taatagtgtg ttaa                                              24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 48
atttgtgagt tatgaaagat aaga                                              24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 49
gaaagtagag aataaagata agaa                                              24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 50
atttaagatt gttaagagta gaag                                              24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 51
gtttaaagat tgtaagaatg tgta                                              24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 52
tttgtgaaga tgaagtattt gtat                                              24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 53

-continued

```
tgtgtttaga atttagtatg tgta                                              24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 54
gataatgatt atagaaagtg tttg                                              24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 55
gttatttgta agttaagata gtag                                              24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 56
agtttattga aagagtttga atag                                              24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 57
ttgtgtttat tgtgtagttt aaag                                              24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 58
attgtgagaa gatatgaaag ttat                                              24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 59
tgagaatgta aagaatgttt attg                                              24
```

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 60
atgtgaaagt tatgatgtta attg                                           24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 61
gtttagtatt agttgttaag attg                                           24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 62
gattgatatt tgaatgtttg tttg                                           24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 63
tgaattgaaa gtgtaatgtt gtat                                           24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 64
gattgtattg ttgagaatag aata                                           24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 65
aaatttgaga tttgtgatag agta                                           24

```
<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 66
gtaattagat tgtttgttg ttgt                                              24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 67
gtttgtattg ttagtgaata tagt                                             24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 68
atgtagtagt agatgtttat gaat                                             24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 69
tgtttaaaga tgattgaaga aatg                                             24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 70
tgtgataatg atgttatttg tgta                                             24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 71
atagttgtga gaatttgtaa ttag                                             24
```

```
<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 72
atagatgtaa gagaaattgt gaaa                                              24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 73
agattaagag aagttaatag agta                                              24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 74
gaagtaaatt gtgaatgaaa gaaa                                              24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 75
aatgtaagaa agaagattgt tgta                                              24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 76
tttgatttat gtgttatgtt gagt                                              24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 77
gtattgagaa atttgaagaa tgaa                                              24

<210> SEQ ID NO 78
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 78
gaattgtatg aaatgaattg taag                                           24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 79
tattgtagaa gtaaagttag aagt                                           24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 80
tttatgtaat gataagtgta gttg                                           24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 81
atatagttga aattgtgata gtgt                                           24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 82
ataagaaatt agagagttgt aaag                                           24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 83
gaattgtgaa atgtgattga tata                                           24

<210> SEQ ID NO 84
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 84
aaataagtag tttaatgaga gaag                                          24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 85
gattaaagaa gtaagtgaat gttt                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 86
tatgtgtgtt gtttagtgtt atta                                          24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 87
gagttatatg tagttagagt tata                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 88
gaaagaaaga agtgttaagt taaa                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 89
tagtattagt aagtatgtga ttgt                                          24

<210> SEQ ID NO 90
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 90
ttgtgtgatt gaatattgtg aaat                                              24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 91
atgtgaaaga gttaagtgat taaa                                              24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 92
gattgaatga ttgagatatg taaa                                              24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 93
aagatgatag ttaagtgtaa gtta                                              24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 94
tagttgttat tgagaattta gaag                                              24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 95
tttatagtga attatgagtg aaag                                              24

<210> SEQ ID NO 96
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 96
gatagattta gaatgaatta agtg                                              24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 97
tttgaagaag agatttgaaa ttga                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 98
atgaataaga gttgataaat gtga                                              24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 99
tgtttatgta gtgtagattg aatt                                              24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 100
tttaagtgag ttatagaagt agta                                              24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 101
gatttatgtg tttgaagtta agat                                              24

<210> SEQ ID NO 102
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 102
tagttagaga aagtgataaa gtta                                              24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 103
gtaatgataa tgaagtgtat atag                                              24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 104
aatgaagtgt tagtatagat agta                                              24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 105
taaattgagt ttgtttgatt gtag                                              24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 106
taatgaagaa taagtatgag tgtt                                              24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 107
aaatgtaata gtgttgttag ttag                                              24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 108
agagttagtg aaatgttgtt aaat                                          24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 109
gaaatagaaa tgtattgttt gtga                                          24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 110
agttataagt ttgtgagaat taag                                          24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 111
gagtttatag ttagaatatg ttgt                                          24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 112
agagttatta gaagaagatt taag                                          24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 113
gagttaatga aataagtatt tgtg                                          24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 114
atgatgaata gttgaagtat atag                                          24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 115
atagatatga gatgaaagtt agta                                          24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 116
tatgtaaaga aagtgaaaga agaa                                          24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 117
tgaatgtaga aatgaatgtt gaaa                                          24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 118
aattgaatag tgtgtgagtt taat                                          24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 119
agatattgtt tgattaatga agag                                          24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 120
aaagttgtaa agttgaagat aaag                                              24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 121
gttaagagat tatgagatgt atta                                              24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 122
agaagatata agaagattga attg                                              24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 123
gtagaaattt gaattgatgt gaaa                                              24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 124
aagagtagat tgataagtat atga                                              24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 125
tgatatagta gtgaagaaat aagt                                              24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 126
```
agataatgat gagaaatgaa gata                                    24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 127
atgtgaaagt atttgtgata tagt                                    24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 128
aataagagaa ttgatatgaa gatg                                    24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 129
taagtgtatt tagtagaatg aagt                                    24

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 130
tatgttagat ttgttgagat tgat                                    24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 131
agtttgtatg aagagatagt attt                                    24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 132

```
gagaaatgtt atgtatttag tagt                                              24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 133
tatgtgagaa tgtgtttgat ttaa                                              24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 134
gtatgtttgt ttatagaatg tatg                                              24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 135
gagtatatag aagaaagaaa tttg                                              24

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 136
atgagtgaag taaatgtagt tatt                                              24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 137
ttaagaagtg agttattgtg atat                                              24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 138
atgaaatgag aatattgttg tttg                                              24
```

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 139
gattaatgat tatgtgaatt gatg                                             24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 140
gaaatgttaa agatatgaaa gtag                                             24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 141
tattgttgat ttgatattag tgtg                                             24

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 142
tttatgtttg tgtatgtaag tagt                                             24

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 143
aattgaaaga attgtgtgaa ttga                                             24

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 144
tgagtttgaa tttgtttgag taat                                             24

-continued

```
<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 145
gatgtataat gatgtgtgta aatt                                              24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 146
atgtgagaga agaatttgtt tatt                                              24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 147
gtgataaagt attgttgata gaaa                                              24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 148
gaagtagaat agaaagttaa taga                                              24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 149
ttgtgtagtt aagagttgtt taat                                              24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 150
tagtagtaag ttgttagaat agtt                                              24
```

```
<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 151
aatttgaagt ataatgaatg tgtg                                              24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 152
tagaaattgt agtatttgag agaa                                              24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 153
tgtatatgtt aatgagatgt tgta                                              24

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 154
tatttgataa gagaatgaag aagt                                              24

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 155
ttgaatagtg taatgaatat gatg                                              24

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 156
gtagtttgtg aatagaatta gttt                                              24

<210> SEQ ID NO 157
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 157
aaagatgatt gtaatttgtg tgaa                                              24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 158
gaagattgtt gagttaatag ataa                                              24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 159
agattatgta gtgatgtaaa tgtt                                              24

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 160
gaatttagat gtagatatga atgt                                              24

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 161
gatagaagtg tattaagtaa gtta                                              24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 162
tatgaattat gagaagaata gagt                                              24

<210> SEQ ID NO 163
<211> LENGTH: 24
```

-continued

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 163
tttgttatga agtgatttgt ttgt                                             24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 164
gtaaagattg tgttatatga aatg                                             24

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 165
ttgtgatagt agttagatat ttgt                                             24

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 166
gaattaagat aaagaagaga agta                                             24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 167
gattgtagaa tgaatttgta gtat                                             24

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 168
aaataagaga gagaatgatt tagt                                             24

<210> SEQ ID NO 169
<211> LENGTH: 24
<212> TYPE: DNA
```

<213> ORGANISM: Artificial Sequence
<220> FEATURE:
<223> OTHER INFORMATION: Description of Artificial Sequence:Artificially
      Synthesized DNA Sequence

<400> SEQUENCE: 169
aattatgtga atagattgtt gaag                                              24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 170
ttaagattta tgtgatagta gagt                                              24

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 171
ttaaagatag tgtttgttgt gtta                                              24

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 172
tattgattta tgaagagtat agtg                                              24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 173
aaatttgatg agtagtttaa gaga                                              24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 174
ataaagttgt ttgatgtttg aatg                                              24

<210> SEQ ID NO 175
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 175
gattgtgatg aataatgtta ttga                                            24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 176
gatgaagaaa tatgatatga atag                                            24

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 177
ttaaagttat tgaagtgaag ttga                                            24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 178
ttgtaagaaa tagagatttg tgtt                                            24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 179
gagattgagt ttaagtatta gatt                                            24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 180
agtgataata gaatgataaa tgtg                                            24

<210> SEQ ID NO 181
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 181
gataatagtg aatttgagtt gtat                                           24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 182
agatatttgt agtagaaagt atgt                                           24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 183
gttatgaatg ttgaatttga atgt                                           24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 184
atgaaagatt tagttgtgag atat                                           24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 185
aaatagagaa gttatgatgt gata                                           24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 186
ttagtgagaa atgtttaatg tgat                                           24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 187
tgaagaatat gtgaaattag tttg                                    24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 188
gtttgatagt ttaatgagta ttga                                    24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 189
gttgtaagta atgataaagt atga                                    24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 190
taagagtagt aattgttgtt taga                                    24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 191
tttgagagag tatgtatgat tatt                                    24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 192
attgattgtg aattagatag aaga                                    24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 193
gattagtatt tagtagtaat agag                                              24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 194
tatgtattag agatattgaa agtg                                              24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 195
tatgtgaaag taatgataaa tgag                                              24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 196
gtaattagta atgatttgaa tgag                                              24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 197
gtttattgta aagatgtaag tgaa                                              24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 198
tagtagaatt gttgttaaag aatg                                              24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 199
tattgttagt tatgtagtgt gtaa                                          24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 200
gagtgaaagt tatatgaaag tata                                          24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 201
atatagaagt tgatgagttt atga                                          24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 202
tttagaagta agaataagtg agta                                          24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 203
tgtgtataag atatttgtaa gaag                                          24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 204
tagaagagtt gtattgttat aagt                                          24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 205
```
gtgttattag tttaagttag agta				24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 206
aatatagtga tgtgaaattg aatg				24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 207
ttagagaata gagtgattat agtt				24

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 208
gaagtgagtt aatgatttgt aaat				24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 209
aatgtaaagt aaagaaagtg atga				24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 210
gttagttatg atgaatattg tgta				24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 211

```
aaatgagtta gagtagaatt atgt                                          24
```

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 212

```
gatatagaag attagttagt gata                                          24
```

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 213

```
atagtttgtt gagatttatg agta                                          24
```

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 214

```
tagaatagtt agtagtaaga gtat                                          24
```

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 215

```
gaatttgtat tgtgaagttt agta                                          24
```

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 216

```
gtagtaagaa gagaattaga ttaa                                          24
```

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 217

```
aatgtgttat gtatgtaaat agtg                                          24
```

```
<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 218
gaattagtta gagtaaattg tttg                                          24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 219
gaaattgaag atagtaagaa atga                                          24

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 220
gtgtattatg tgatttatga taga                                          24

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 221
tattatgaga aagttgaata gtag                                          24

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 222
tatgtattgt attgagtaga tgaa                                          24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 223
gtgattgaat agtagattgt ttaa                                          24
```

```
<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 224
agtaagttgt tgattgaaa tttg                                              24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 225
gaagtttgat ttaagtttaa gaag                                             24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 226
gagaagataa atgatattgt tatg                                             24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 227
atgatgagtt gttaatagtt agtt                                             24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 228
tatgatattt gaagagtgtt aaga                                             24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 229
gagatgatta aagtgattta tgaa                                             24
```

```
<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 230
atagttaaga gtgatgagaa taaa                                            24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 231
tttattgtta gataaagagt tgag                                            24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 232
agaatattga tagttgaagt tgaa                                            24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 233
tagtgtaaag tgtagattgt aaat                                            24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 234
agtagtgata tgatttgaat attg                                            24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 235
tgtattgaat tagaatagtg agaa                                            24

<210> SEQ ID NO 236
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 236
tgatatgaga tagaagttta atgt                                          24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 237
gaagaagtaa gtataaagta aatg                                          24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 238
tttaagtgtg ataagaaaga taga                                          24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 239
tattgttgaa tgtgtttaaa gaga                                          24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 240
gaataatgat gagatgatta ttga                                          24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 241
tagagaaaga gagaattgta ttaa                                          24

<210> SEQ ID NO 242
<211> LENGTH: 24
```

<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 242
atgtataatg agatatgttt gtga                                              24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 243
aatagataag attgattgtg tttg                                              24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 244
tttgatgata atagaagaga atga                                              24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 245
agatgaataa gttgtgaatg ttta                                              24

<210> SEQ ID NO 246
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 246
agatgaaaga aagtgtagaa tatt                                              24

<210> SEQ ID NO 247
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 247
tgttaaatgt atgtagtaat tgag                                              24

<210> SEQ ID NO 248
<211> LENGTH: 24
<212> TYPE: DNA

<213> ORGANISM: Artificial Sequence
<220> FEATURE:
<223> OTHER INFORMATION: Description of Artificial Sequence:Artificially
      Synthesized DNA Sequence

<400> SEQUENCE: 248
tagtagtgtg aagttatttg ttat                                          24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 249
agtgaatgtt tgtaaagagt ttaa                                          24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 250
gataaatgag aattgagtaa ttgt                                          24

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 251
tgatgagaaa ttgtttaagt gttt                                          24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 252
aaataagtag tgtgagtaat agta                                          24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 253
tatgaaatat gtgatagtaa gaga                                          24

<210> SEQ ID NO 254
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 254
attgtaagag tgattataga tgat                                              24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 255
agagtaagaa tgaaagagat aata                                              24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 256
taagtaagta gatgttaaag agat                                              24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 257
aaatagaaag aattgtagag tagt                                              24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 258
atagatttaa gtgaagagag ttat                                              24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 259
gaatgtttgt aaatgtatag atag                                              24

<210> SEQ ID NO 260
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 260
aaatagaatg agtagtgaaa tatg                                          24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 261
ttgaattatg tagagaaagt aaag                                          24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 262
tagtaaattg agagtagttg aatt                                          24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 263
tgtaaagtgt ttatagtgtg taat                                          24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 264
atatgatttg agatgagaat gtaa                                          24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 265
aatattgata tgtgttgtga agta                                          24

<210> SEQ ID NO 266
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 266
agtgagatta tgagtattga ttta                                          24

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 267
ttgtatttag atagtgagat tatg                                          24

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 268
atagaaatga aagatagata gaag                                          24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 269
gattgtatat gtaaagtagt ttag                                          24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 270
tatgaatgtt attgtgtgtt gatt                                          24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 271
gatattagta gagtaagtat attg                                          24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 272
tgagatgaat ttgtgttatg atat                                          24

<210> SEQ ID NO 273
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 273
tatgaatgaa gtaaagagat gtaa                                          24

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 274
gagtgaattt gttgtaattt gttt                                          24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 275
agaaattgta gagttaattg tgta                                          24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 276
gtgttaatga aagttgtgaa taat                                          24

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 277
tgtgatttgt taagaagatt aatg                                          24

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 278
agtagtattg taaagtataa agag                                      24

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 279
tgattgttgt atagttattg tgta                                      24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 280
gattgtagtt taatgttaag aatg                                      24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 281
atgaaataag aaattgagta gaga                                      24

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 282
tatgatgata tttgttgtat gtgt                                      24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 283
tttagagttt gattagtatg tttg                                      24

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 284
```

```
ataagagat tgtgatgaga aata                                          24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 285
aatgaataga atagagaatg taga                                         24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 286
gtagtagtaa tttgaatgtt tgaa                                         24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 287
agtgagtaat tgattgattg ttaa                                         24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 288
gaataatgtt tagtgtgttt gaaa                                         24

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 289
atatgaaagt agagaaagtg ttat                                         24

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 290
```

-continued

```
tgagttattg tatttagttt gaag                                          24
```

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 291

```
tagttgagtt taaagttgaa agaa                                          24
```

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 292

```
taaagagtga tgtaaataga agtt                                          24
```

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 293

```
tgtagtgttt agagtaagtt atta                                          24
```

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 294

```
agagattaat gtgttgaaag atta                                          24
```

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 295

```
gtaataagtt gtgaaagaag atta                                          24
```

<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 296

```
gagatgttat agataatgaa agaa                                          24
```

```
<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 297
tttagttgat tgttgaatag agta                                            24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 298
attattgaaa gtagatgtta gatg                                            24

<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 299
tttatgtgtg attgagtgtt taat                                            24

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 300
tatttagtta gatagataga gagt                                            24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 301
atgtgtttat gtgaaagatt tgta                                            24

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 302
atagtaatta gaagagaaga atgt                                            24
```

```
<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 303
tatgagtgat tagaattgta tttg                                            24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 304
ttaatgtatt gtttaaagag tgtg                                            24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 305
atagagaatt aagaattgtt tgag                                            24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 306
gttataagta gaaatgtata gaag                                            24

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 307
agtaattagt ttgaaatgtg tagt                                            24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 308
gaaagattat gattgtaaag tgat                                            24
```

```
<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 309
gtaagattag aagttaatga agaa                                          24

<210> SEQ ID NO 310
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 310
gagaatgttg aataagaagt aatt                                          24

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 311
ttaagagtgt ttgaatagtg ttta                                          24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 312
ataaagaaag agtatgagat tatg                                          24

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 313
agttattgat tgaagatgag aaat                                          24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 314
gtttgtgttt gtataagttg ttaa                                          24

<210> SEQ ID NO 315
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 315
ttgtatgtga gtttagatta atga                                          24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 316
tagttaaagt atagttgttt gagt                                          24

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 317
aaatttgtgt tgagatttgt atag                                          24

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 318
tattagtgtt atgataaaga gaag                                          24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 319
tataagaagt aatttgagaa gagt                                          24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 320
taagttgaga tgtttgtttg ataa                                          24

<210> SEQ ID NO 321
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 321
gtgtagattt atgaattgag taat                                          24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 322
tatagagaag tgtttagttg tata                                          24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 323
ataaagaaga atagttgttg tgta                                          24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 324
agattgaaat agattagaaa gttg                                          24

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 325
gttgttataa gaaatagttt gttg                                          24

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 326
agaaatagag taagagtgtt taaa                                          24

<210> SEQ ID NO 327
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 327
agagatagta gtaaatagtt attg                                          24

<210> SEQ ID NO 328
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 328
aaatgattgt gtaagttatg tatg                                          24

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 329
aagaagtaag agagaaattt gaat                                          24

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 330
gtgtgtattt agttgataat tgat                                          24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 331
attgttgttg ttgagaaatg tatt                                          24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 332
agataagtta aagtaaagag aatg                                          24

<210> SEQ ID NO 333
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 333
tagttgaagt tagtttaagt gtta                                          24

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 334
agtaagaatg taatatgatg atag                                          24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 335
atgagattga aagatttatg aatg                                          24

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 336
tgattgaatt agagagaatg tata                                          24

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 337
agttagtaag agaatatagt gaat                                          24

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 338
attaagattg tatagttagt gatg                                          24

<210> SEQ ID NO 339
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 339
gagataaaga attgaaatag aaga                                            24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 340
agagtaaatg ttaagaaaga agtt                                            24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 341
aaagtttgtt atgtgtgaag aatt                                            24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 342
attgtgttta agaaatatga tgag                                            24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 343
tattgaaatg agatgtatgt agtt                                            24

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 344
atttgtgtga tgtttgaaat atga                                            24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence:Artificially -continued Synthesized DNA Sequence

<400> SEQUENCE: 345
taagataata gtgagagaaa ttga                                              24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 346
atttatgatt agtgtaagtg ttgt                                              24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 347
gattaagaat aaagtgtgaa gaat                                              24

<210> SEQ ID NO 348
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 348
gtaattgatg aagagttagt ttat                                              24

<210> SEQ ID NO 349
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 349
tgtgttatgt tataagaagt gata                                              24

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 350
agagaaattg aatttagaaa tgtg                                              24

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 351
ttattgaatg tgagaaagta tttg                                              24

<210> SEQ ID NO 352
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 352
tgttaatgag aagataatga tagt                                              24

<210> SEQ ID NO 353
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 353
gaaagtattt gttgattatt gttg                                              24

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 354
tagtttatgt agttaattgt tgag                                              24

<210> SEQ ID NO 355
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 355
gttgaaagat agtttgatat gtat                                              24

<210> SEQ ID NO 356
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 356
ttagaagata gattattgag aaag                                              24

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 357
aataatgttg tgaaatagat gtga                                              24

<210> SEQ ID NO 358
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 358
agtaagaaag tttagtttag ttag                                              24

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 359
tagtttaatg agatgtttga tatg                                              24

<210> SEQ ID NO 360
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 360
ttaaagatgt taaagaatga gtga                                              24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 361
aaagtgtgta tatgttagaa agta                                              24

<210> SEQ ID NO 362
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 362
attaagttat gtgtttatgt gttg                                              24

<210> SEQ ID NO 363
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 363
```
tttgaagaag tgtttgtatt atgt                                            24

<210> SEQ ID NO 364
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 364
tgttaagaag tttagttaaa gttg                                            24

<210> SEQ ID NO 365
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 365
tttaagtata agattgtgtg agat                                            24

<210> SEQ ID NO 366
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 366
agatatttga tagatagaag aaag                                            24

<210> SEQ ID NO 367
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 367
atttagagtt gtaagaagat attg                                            24

<210> SEQ ID NO 368
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 368
gagaaattgt aattgttaga gtat                                            24

<210> SEQ ID NO 369
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 369

```
gaagtatatg ttaagatgta atag                                         24

<210> SEQ ID NO 370
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 370
aatattgaag atgtagtgag ttat                                         24

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 371
gagtttagaa atgataaaga attg                                         24

<210> SEQ ID NO 372
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 372
taagaaatga gttatatgtt gaga                                         24

<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 373
ttgatataag aagttgtgat aagt                                         24

<210> SEQ ID NO 374
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 374
aagtgtttaa tgtaagagaa tgaa                                         24

<210> SEQ ID NO 375
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 375
gttgtgagaa ttagaaatag tata                                         24
```

```
<210> SEQ ID NO 376
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 376
tttagtttga tgtgtttatg agat                                          24

<210> SEQ ID NO 377
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 377
gtaattgaaa gtatgagtag taat                                          24

<210> SEQ ID NO 378
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 378
tagttgaata agattgagag aaat                                          24

<210> SEQ ID NO 379
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 379
ttaagtgaag tgttgtttat tgaa                                          24

<210> SEQ ID NO 380
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 380
attgatttgt tgaaataagt gttg                                          24

<210> SEQ ID NO 381
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 381
tgaattgttg ataagttatg aaga                                          24
```

```
<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 382
gtttgttatt gagtaagttg aatt                                              24

<210> SEQ ID NO 383
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 383
tgatttagta tgtattagag ttga                                              24

<210> SEQ ID NO 384
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 384
taaatagaga tgagaataag aaag                                              24

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 385
agaatgttat atgtagagaa attg                                              24

<210> SEQ ID NO 386
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 386
atttatgtag ttgagagtga taaa                                              24

<210> SEQ ID NO 387
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 387
gtaaagatag tttgagtaat ttga                                              24
```

```
<210> SEQ ID NO 388
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 388
gaaatagtat aatgttaagt gaga                                          24

<210> SEQ ID NO 389
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 389
attgtatatt gtgttgaaga aagt                                          24

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 390
gagttaagtg taaatgaaat gtaa                                          24

<210> SEQ ID NO 391
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 391
atagattgtg tgaaagaaag aatt                                          24

<210> SEQ ID NO 392
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 392
ttaatagaag tttgtagtat gatg                                          24

<210> SEQ ID NO 393
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 393
ttgtatgtga gaataaagtt tagt                                          24

<210> SEQ ID NO 394
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 394
gtgattagat atgatgatat gaat                                               24

<210> SEQ ID NO 395
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 395
tgaagaagaa tttagatttg taag                                               24

<210> SEQ ID NO 396
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 396
tgtatgatta ttgattagtg tgtt                                               24

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 397
tgtgaaagag aatgatagat attt                                               24

<210> SEQ ID NO 398
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 398
aattgaaatg agtgtgttta agaa                                               24

<210> SEQ ID NO 399
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 399
attatagagt tagtttagaa tgag                                               24

<210> SEQ ID NO 400
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 400
aaagatagaa attgagtgta tgat                                           24

<210> SEQ ID NO 401
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 401
gtagtttgtt aatgttgtat aatg                                           24

<210> SEQ ID NO 402
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 402
agagatatta gaatgtaaga atag                                           24

<210> SEQ ID NO 403
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 403
agaagtttga aatatgatag aatg                                           24

<210> SEQ ID NO 404
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 404
tagaatgtaa agtttagtat agag                                           24

<210> SEQ ID NO 405
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 405
agtagatgta tgttaatgtg aata                                           24

<210> SEQ ID NO 406
<211> LENGTH: 24
<212> TYPE: DNA
```

<213> ORGANISM: Artificial Sequence
<220> FEATURE:
<223> OTHER INFORMATION: Description of Artificial Sequence:Artificially
      Synthesized DNA Sequence

<400> SEQUENCE: 406
tgaaagtgaa atatgaaatg ttgt                                          24

<210> SEQ ID NO 407
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 407
atagtatatt gagtttgtat gaag                                          24

<210> SEQ ID NO 408
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 408
gaagaaatgt ttgtagaata agta                                          24

<210> SEQ ID NO 409
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 409
aatgagtatt gaagaaatgt atag                                          24

<210> SEQ ID NO 410
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 410
gtgatagaat ttgtgtttaa tgaa                                          24

<210> SEQ ID NO 411
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 411
tgtagtatga agaataatga aatg                                          24

<210> SEQ ID NO 412
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 412
atagaagtta atgataattg tgtg                                              24

<210> SEQ ID NO 413
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 413
gtgattgtaa gtaagtaaag ataa                                              24

<210> SEQ ID NO 414
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 414
tatgtagttt gtgttatttg aaga                                              24

<210> SEQ ID NO 415
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 415
tgagtaagtt tgtatgttta agta                                              24

<210> SEQ ID NO 416
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 416
taaatgtatg agtgtgtaaa gaaa                                              24

<210> SEQ ID NO 417
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 417
gtaagagtat tgaaattagt aaga                                              24

<210> SEQ ID NO 418
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 418
gttgagtgta aagattattg ataa                                         24

<210> SEQ ID NO 419
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 419
agtatgagtt attagataaa gtga                                         24

<210> SEQ ID NO 420
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 420
atttgttata gagttgtgtt gtat                                         24

<210> SEQ ID NO 421
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 421
taattagtag tgtgttgaaa tttg                                         24

<210> SEQ ID NO 422
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 422
tgtattgaga ttgttattgt attg                                         24

<210> SEQ ID NO 423
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 423
gttattagaa gagataattg agtt                                         24

<210> SEQ ID NO 424
<211> LENGTH: 24
<212> TYPE: DNA
<213> ORGANISM: Artificial Sequence
<220> FEATURE:
<223> OTHER INFORMATION: Description of Artificial Sequence:Artificially -continued Synthesized DNA Sequence

<400> SEQUENCE: 424
ttgagttgtg attaagtagt atat                                      24

<210> SEQ ID NO 425
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 425
gatagtataa tgattgaagt aatg                                      24

<210> SEQ ID NO 426
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 426
gtgaaagata tttgagagat aaat                                      24

<210> SEQ ID NO 427
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 427
agttatgatt tgaagaaatt gttg                                      24

<210> SEQ ID NO 428
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 428
gtaagtattt gaatttgatg agtt                                      24

<210> SEQ ID NO 429
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 429
taatagtgtt ataagtgaaa gagt                                      24

<210> SEQ ID NO 430
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence -continued

```
<400> SEQUENCE: 430
aaatgaattg atgtgtatat gaag                                          24

<210> SEQ ID NO 431
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 431
agaaagtgag ttgttaagta ttta                                          24

<210> SEQ ID NO 432
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 432
tttatgtgtg aattgtgtat atag                                          24

<210> SEQ ID NO 433
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 433
gtaatatgat agaaatgtaa agag                                          24

<210> SEQ ID NO 434
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 434
gagaattgtt taaagatagt tgta                                          24

<210> SEQ ID NO 435
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 435
gaatttgtta agaatgagtt tgat                                          24

<210> SEQ ID NO 436
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

-continued

```
<400> SEQUENCE: 436
atagtgatga ttaaagagaa tttg                                            24

<210> SEQ ID NO 437
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 437
atagatgttt agttgagatt attg                                            24

<210> SEQ ID NO 438
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 438
aagagtgtaa atagaaagtg atat                                            24

<210> SEQ ID NO 439
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 439
tgtgtattga ttgttgagat aaat                                            24

<210> SEQ ID NO 440
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 440
tagtatagtg agaaagagtt aaat                                            24

<210> SEQ ID NO 441
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 441
aaagataaga aagagatgat gttt                                            24

<210> SEQ ID NO 442
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 442
```

```
gaagttattg aaatagagaa gtat                                          24

<210> SEQ ID NO 443
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 443
atgtatgtat agaaagagta aatg                                          24

<210> SEQ ID NO 444
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 444
gatgtttgta aagattgaaa ttga                                          24

<210> SEQ ID NO 445
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 445
aatttagaga gtatttgtgt tgta                                          24

<210> SEQ ID NO 446
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 446
aatttgtttg aaagaaagta agtg                                          24

<210> SEQ ID NO 447
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 447
aaagagtagt gttattgtta gata                                          24

<210> SEQ ID NO 448
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 448
```

```
gtatgttgta tatgttgttg atat                                            24
```

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 449

```
gtagaatttg ttgagtattt gtaa                                            24
```

<210> SEQ ID NO 450
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 450

```
atgaatttag ttagtgtaag aaag                                            24
```

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 451

```
atgataagaa atgttgatga agta                                            24
```

<210> SEQ ID NO 452
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 452

```
ttgatgatga agataatgta gata                                            24
```

<210> SEQ ID NO 453
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 453

```
agatgatatg atatagatta gatg                                            24
```

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 454

```
ttgaaagtta gaaagataga tgtt                                            24
```

```
<210> SEQ ID NO 455
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 455
gtttaatgtt agttagaaag taag                                           24

<210> SEQ ID NO 456
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 456
gagatttaag tttgaagtga aata                                           24

<210> SEQ ID NO 457
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 457
tttgttagta gttgttataa gaga                                           24

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 458
tatgagaata gtttgttagt gaat                                           24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 459
ttgaaagttt aagaagaga taag                                            24

<210> SEQ ID NO 460
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 460
aagtgagttg aaatgaaata tgtt                                           24
```

```
<210> SEQ ID NO 461
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 461
gttagaaatg aaatgagtag ttat                                              24

<210> SEQ ID NO 462
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 462
taagtattgt atttgtgtgt gtat                                              24

<210> SEQ ID NO 463
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 463
tgtattagta aagaagagag aata                                              24

<210> SEQ ID NO 464
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 464
gagaagagaa ataagttgaa ataa                                              24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 465
gtaaagtaga aatagaattg agtt                                              24

<210> SEQ ID NO 466
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 466
gtgtgttatt tgtttgtaaa gtat                                              24
```

```
<210> SEQ ID NO 467
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 467
tttgatgtat gaatatagta tgag                                          24

<210> SEQ ID NO 468
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 468
aagattgtgt gaatagttga aatt                                          24

<210> SEQ ID NO 469
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 469
tataaagttt gaagatgagt gata                                          24

<210> SEQ ID NO 470
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 470
agataaagag atttaagatg tatg                                          24

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 471
gaagaattaa gttgagaatt aaga                                          24

<210> SEQ ID NO 472
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 472
tagagaaatt tgataaagaa agag                                          24

<210> SEQ ID NO 473
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 473
aaagtttatg aagttattga gtag                                              24

<210> SEQ ID NO 474
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 474
aaatagtgta agtaaagaga tgat                                              24

<210> SEQ ID NO 475
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 475
tatgatgatt tagttataag agtg                                              24

<210> SEQ ID NO 476
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 476
tagataaatg ttatgatgag taag                                              24

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 477
agattgattg tgatgatttg tata                                              24

<210> SEQ ID NO 478
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 478
ttaagaagaa ttgtatatga gagt                                              24

<210> SEQ ID NO 479
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 479
gtagaatgtt tagagttgaa tata                                           24

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 480
gagaaatagt aagaagtaaa taga                                           24

<210> SEQ ID NO 481
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 481
attgaagttg ttatgtgaag attt                                           24

<210> SEQ ID NO 482
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 482
taaatgttgt gtagagtaat taga                                           24

<210> SEQ ID NO 483
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 483
aaataagagt ttgagaagtt gttt                                           24

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 484
agttgtaata agaagtgatt taag                                           24

<210> SEQ ID NO 485
<211> LENGTH: 24
<212> TYPE: DNA
```

<213> ORGANISM: Artificial Sequence
<220> FEATURE:
<223> OTHER INFORMATION: Description of Artificial Sequence:Artificially
      Synthesized DNA Sequence

<400> SEQUENCE: 485
gttagaatgt atatagagtt agat                                          24

<210> SEQ ID NO 486
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 486
ttgatattga aagagaaagt tatg                                          24

<210> SEQ ID NO 487
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 487
ttaaagagag aaatgtttga ttag                                          24

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 488
tgtgaatttg agtattagta agaa                                          24

<210> SEQ ID NO 489
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 489
taatttgaat gtgaaagttg ttag                                          24

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 490
atgtgtttga aagatgatga ttta                                          24

<210> SEQ ID NO 491
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 491
aagttatgtt gatattgagt gaaa                                            24

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 492
tagataaaga agatagagat ttag                                            24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 493
gatgaatgta gatatatgta atga                                            24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 494
gaagaatagt ttatgtaaat gatg                                            24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 495
gtagtatata gttaaagatg agtt                                            24

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 496
gttatttgtg tatgattatg attg                                            24

<210> SEQ ID NO 497
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 497
agagattaga aattgagaga atta                                            24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 498
gtatgataga gtttatagtg ataa                                            24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 499
gttagaaaga atgaaattga agta                                            24

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 500
aagaatgaga atatagagat gaat                                            24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 501
aaagagaata gtgtttaaga agat                                            24

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 502
gatgtgttat tgatagaaat taga                                            24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 503
tagagttata gagatattgt atga                                              24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 504
gagagttgaa taagttaaag atat                                              24

<210> SEQ ID NO 505
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 505
agatatgaaa tagattgtta gaga                                              24

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 506
gagtgaatag aaagatatgt taat                                              24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 507
aaagagatat tgaagagaat aaag                                              24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 508
gttatagaat aagttgtaaa gtgt                                              24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 509
tgatagtatg ataatgtgtt tatg                                          24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 510
tttgttgtta agtatgtgat ttag                                          24

<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 511
taaagtgttg tgttaaagat taag                                          24

<210> SEQ ID NO 512
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 512
tgtgtttgat tgattaatgt tatg                                          24

<210> SEQ ID NO 513
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 513
attaatgaat gagtgttgta atgt                                          24

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 514
tagatgtttg tgagtttgat atta                                          24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 515
gaatgaatag taatagatga tttg                                              24

<210> SEQ ID NO 516
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 516
aatagtgtgt tgttatatga ttag                                              24

<210> SEQ ID NO 517
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 517
tagattagaa gatgttgtgt atta                                              24

<210> SEQ ID NO 518
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 518
aatgtgtgtg ttaaatgaat tgt                                               24

<210> SEQ ID NO 519
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 519
gaattaagta tatgagtgta gaaa                                              24

<210> SEQ ID NO 520
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 520
ttattgtgtg taagtagtgt aaat                                              24

<210> SEQ ID NO 521
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 521
```
gtagtaaaga gaattgttta gtat                                          24

<210> SEQ ID NO 522
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 522
aagtttgtaa gaagtagttg aata                                          24

<210> SEQ ID NO 523
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 523
agttatagta tagtagtata gaga                                          24

<210> SEQ ID NO 524
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 524
gaaagaaatg tgtatagttt aatg                                          24

<210> SEQ ID NO 525
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 525
ttgtgagtaa tgaatgatgt atta                                          24

<210> SEQ ID NO 526
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 526
gtagagttgt aaatagagaa taaa                                          24

<210> SEQ ID NO 527
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 527
attaatgtag attgtaagag atag                                          24

<210> SEQ ID NO 528
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 528
ttagtgtgtt tgtagataga atta                                          24

<210> SEQ ID NO 529
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 529
agagagtttg tgtatatgta taaa                                          24

<210> SEQ ID NO 530
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 530
ttaagtttag tgagatttgt taag                                          24

<210> SEQ ID NO 531
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 531
atgaagttta ttgaatagta gtga                                          24

<210> SEQ ID NO 532
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 532
atatttgtgt tgtatgtttg tgaa                                          24

<210> SEQ ID NO 533
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 533
aaagtgttta tagaagattt gatg                                          24

<210> SEQ ID NO 534
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 534
aagagatatg atttgttagt tgta                                          24

<210> SEQ ID NO 535
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 535
aagaagaaat gagtgataat gtaa                                          24

<210> SEQ ID NO 536
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 536
tagtgtttga tatgttaaga agtt                                          24

<210> SEQ ID NO 537
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 537
gtagaaagtg atagattagt aata                                          24

<210> SEQ ID NO 538
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 538
gataaatgtt aagttagtat gatg                                          24

<210> SEQ ID NO 539
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 539
agattagaag aattgtttag aatg                                          24

```
<210> SEQ ID NO 540
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 540
atatttgaga agtgtgaaat gaat                                              24

<210> SEQ ID NO 541
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 541
tgagtaaata gtttatgagt agta                                              24

<210> SEQ ID NO 542
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 542
ttagagagta gataaagatt tgat                                              24

<210> SEQ ID NO 543
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 543
attgtttaag ttgttgataa gatg                                              24

<210> SEQ ID NO 544
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 544
gttgtaaagt taaagtgtga attt                                              24

<210> SEQ ID NO 545
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 545
atagattgtg tgtttgttat agta                                              24
```

<210> SEQ ID NO 546
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 546
gtaagttatt gagaatgata atag                                            24

<210> SEQ ID NO 547
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 547
tagattagtt gataagtgtg taat                                            24

<210> SEQ ID NO 548
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 548
aaatgtaaat gaagagtgtt tgtt                                            24

<210> SEQ ID NO 549
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 549
gatagaagaa atgtatatag tgat                                            24

<210> SEQ ID NO 550
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 550
tatagagtgt atgttatgat aaag                                            24

<210> SEQ ID NO 551
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 551
tatgaagtga taagatgaag aatt                                            24

<210> SEQ ID NO 552

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 552
tgttgagaat agtaagagaa ttta                                              24

<210> SEQ ID NO 553
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 553
tagataatgt gaagtaataa gtga                                              24

<210> SEQ ID NO 554
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 554
gtattatgat gatagtagta agta                                              24

<210> SEQ ID NO 555
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 555
agatatgatt tagtattgaa tgtg                                              24

<210> SEQ ID NO 556
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 556
aattaagttt gtagagtgat ttga                                              24

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 557
aagaaataga tgtagtaaga tgtt                                              24

<210> SEQ ID NO 558
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 558
ttgagaagtt gttgtaataa gaat                                              24

<210> SEQ ID NO 559
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 559
agtgtgaaat agtgaaagtt taaa                                              24

<210> SEQ ID NO 560
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 560
tttatgtagt agatttatgt gaag                                              24

<210> SEQ ID NO 561
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 561
attaatgaga aattagtgtg ttag                                              24

<210> SEQ ID NO 562
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 562
atgttaatag tgatagtaaa gtga                                              24

<210> SEQ ID NO 563
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 563
tatgttgata aatgattatg agtg                                              24

<210> SEQ ID NO 564
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 564
ttattagagt tgtgtgtgat atat                                              24

<210> SEQ ID NO 565
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 565
tgttgttatg attgagttag aata                                              24

<210> SEQ ID NO 566
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 566
aatttgagtt aagaagaagt gtaa                                              24

<210> SEQ ID NO 567
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 567
aaagataaag ttaagtgttt gtag                                              24

<210> SEQ ID NO 568
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 568
tgttgagatg atattgtata agtt                                              24

<210> SEQ ID NO 569
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 569
taaatagtga atgagttata gagt                                              24

<210> SEQ ID NO 570
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 570
atagatgtta tgatagttag ttag                                          24

<210> SEQ ID NO 571
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 571
gttaagtgaa gatatgtatt gtta                                          24

<210> SEQ ID NO 572
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 572
taagaaagta agtttgtag atgt                                           24

<210> SEQ ID NO 573
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 573
aagagaaagt ttgattgaat aaag                                          24

<210> SEQ ID NO 574
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 574
atattagatg tgagttatat gtgt                                          24

<210> SEQ ID NO 575
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 575
agtttgagtt tagtattgtg aata                                          24

<210> SEQ ID NO 576
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 576
atgttaaatg agagattgtg tata                                              24

<210> SEQ ID NO 577
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 577
taaatgttgt gattattgtg agat                                              24

<210> SEQ ID NO 578
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 578
taagaattga agtaagagtt attg                                              24

<210> SEQ ID NO 579
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 579
agagatagaa ttaagtttgt tgat                                              24

<210> SEQ ID NO 580
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 580
gaagaatgtt aagaaatatg taag                                              24

<210> SEQ ID NO 581
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 581
tatttgtgat taagaagttg agaa                                              24

<210> SEQ ID NO 582
<211> LENGTH: 24
<212> TYPE: DNA
<213> ORGANISM: Artificial Sequence
<220> FEATURE:
<223> OTHER INFORMATION: Description of Artificial Sequence:Artificially
```

-continued

Synthesized DNA Sequence

<400> SEQUENCE: 582
agttagaatt tgtgtagtag aatt                                    24

<210> SEQ ID NO 583
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 583
aagtttattg ttgatgttgt attg                                    24

<210> SEQ ID NO 584
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 584
gaatgagttt aagagtttat agta                                    24

<210> SEQ ID NO 585
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 585
agtgaagatt gtatgtagta taaa                                    24

<210> SEQ ID NO 586
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 586
agttgaaatg agtattaagt aatg                                    24

<210> SEQ ID NO 587
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 587
atgtgttatt tgagatgagt aatt                                    24

<210> SEQ ID NO 588
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence -continued

```
<400> SEQUENCE: 588
aaatagtgtt gttgaagttg ttat                                            24

<210> SEQ ID NO 589
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 589
gtagagaaag atatatgtag ttta                                            24

<210> SEQ ID NO 590
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 590
gagagtattt gatgaatgat tata                                            24

<210> SEQ ID NO 591
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 591
gagtataagt ttagtgtata ttga                                            24

<210> SEQ ID NO 592
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 592
ataatgtgat tattgattga gaga                                            24

<210> SEQ ID NO 593
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 593
ttagttgtta tgtgagagta ataa                                            24

<210> SEQ ID NO 594
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 594
aaatgagtat attgaattgt gatg                                              24

<210> SEQ ID NO 595
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 595
aattagaagt aagtagagtt taag                                              24

<210> SEQ ID NO 596
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 596
tgtaagttta agtaagaaa tgtg                                               24

<210> SEQ ID NO 597
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 597
gaaatgataa gttgatataa gaag                                              24

<210> SEQ ID NO 598
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 598
aatgagtagt ttgtatttga gttt                                              24

<210> SEQ ID NO 599
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 599
agtgaatgta agattatgta tttg                                              24

<210> SEQ ID NO 600
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 600
```

```
gtaattgaat tgaaagataa gtgt                                          24

<210> SEQ ID NO 601
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 601
tatgtttaag tagtgaaata gagt                                          24

<210> SEQ ID NO 602
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 602
gtattgaaat tgaattagaa gtag                                          24

<210> SEQ ID NO 603
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 603
aatatgtaat gtagttgaaa gtga                                          24

<210> SEQ ID NO 604
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 604
tgaatattga gaattatgag agtt                                          24

<210> SEQ ID NO 605
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 605
tagtgtaaat gatgaagaaa gtat                                          24

<210> SEQ ID NO 606
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 606
```

```
gtatgtgtaa agaaatttga tgta                                          24

<210> SEQ ID NO 607
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 607
aattgtttga aagtttgttg agaa                                          24

<210> SEQ ID NO 608
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 608
aattgtttga gtagtattag tagt                                          24

<210> SEQ ID NO 609
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 609
taattgagtt tgaataagag agtt                                          24

<210> SEQ ID NO 610
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 610
tgttgattgt aagtgtttat tgtt                                          24

<210> SEQ ID NO 611
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 611
gaaatttgtg agtatgtatt tgaa                                          24

<210> SEQ ID NO 612
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 612
taagaatgaa tgtgaagtga atat                                          24
```

<210> SEQ ID NO 613
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 613
taatgtgaag tttgtgaaag atat                                            24

<210> SEQ ID NO 614
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 614
ttgtatatga aagtaagaag aagt                                            24

<210> SEQ ID NO 615
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 615
tagagagaag aagaaataag aata                                            24

<210> SEQ ID NO 616
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 616
atttgaaatg ttaatgagag agat                                            24

<210> SEQ ID NO 617
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 617
ttgtgtgtat atagtattag aatg                                            24

<210> SEQ ID NO 618
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 618
attgttagta ttgatgtgaa gtta                                            24

```
<210> SEQ ID NO 619
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 619
tgtttgtatt tgaatgaaat gaag                                              24

<210> SEQ ID NO 620
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 620
tgttagattg tgttaaatgt agtt                                              24

<210> SEQ ID NO 621
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 621
tatagagtat tgtatagaga gaaa                                              24

<210> SEQ ID NO 622
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 622
aaatagtaag aatgtagttg ttga                                              24

<210> SEQ ID NO 623
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 623
tgagtgtgat ttatgattaa gtta                                              24

<210> SEQ ID NO 624
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 624
agaatttgtt gtagtgttat gatt                                              24
```

```
<210> SEQ ID NO 625
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 625
gattgaagaa agaaatagtt tgaa                                            24

<210> SEQ ID NO 626
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 626
gataatagag aatagtagag ttaa                                            24

<210> SEQ ID NO 627
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 627
gattgaaatt tgtagttata gtga                                            24

<210> SEQ ID NO 628
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 628
gatttaagaa gatgaataat gtag                                            24

<210> SEQ ID NO 629
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 629
tttgagagaa agtagaataa gata                                            24

<210> SEQ ID NO 630
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 630
gattaagagt aaatgagtat aaga                                            24

<210> SEQ ID NO 631
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 631
tttgatagaa ttgaaatttg agag                                              24

<210> SEQ ID NO 632
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 632
tgaagaagag tgttataaga ttta                                              24

<210> SEQ ID NO 633
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 633
gtgaaatgat ttagagtaat aagt                                              24

<210> SEQ ID NO 634
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 634
aaataagaat agagagagaa agtt                                              24

<210> SEQ ID NO 635
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 635
gttgtaaagt aatagagaaa ttag                                              24

<210> SEQ ID NO 636
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 636
agtgatttag attatgtgat gatt                                              24

<210> SEQ ID NO 637
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 637
agagtatagt ttagatttat gtag                                          24

<210> SEQ ID NO 638
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 638
atgattagat agtgaaattg ttag                                          24

<210> SEQ ID NO 639
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 639
atgaaatgta ttagtttaga gttg                                          24

<210> SEQ ID NO 640
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 640
atattgagtg agagttattg ttaa                                          24

<210> SEQ ID NO 641
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 641
agatgtgtat tgaattaaga agtt                                          24

<210> SEQ ID NO 642
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 642
taatgtgttg atagaataga gata                                          24

<210> SEQ ID NO 643
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 643
aaattagttg aaagtatgag aaag                                              24

<210> SEQ ID NO 644
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 644
tttagagttg aagaaatgtt aatg                                              24

<210> SEQ ID NO 645
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 645
gattgttgat tattgatgaa tttg                                              24

<210> SEQ ID NO 646
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 646
tgttgttgtt gaattgaaga atta                                              24

<210> SEQ ID NO 647
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 647
attaagtaag aattgagagt ttga                                              24

<210> SEQ ID NO 648
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 648
gtatgttgta atgtattaag aaag                                              24

<210> SEQ ID NO 649
<211> LENGTH: 24
<212> TYPE: DNA
<213> ORGANISM: Artificial Sequence
```

-continued

```
<220> FEATURE:
<223> OTHER INFORMATION: Description of Artificial Sequence:Artificially
      Synthesized DNA Sequence

<400> SEQUENCE: 649
tagttgtgat ttatgtaatg attg                                           24

<210> SEQ ID NO 650
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 650
tgataatgaa agtttataga gaga                                           24

<210> SEQ ID NO 651
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 651
gtaagattgt ttgtatgata agat                                           24

<210> SEQ ID NO 652
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 652
ttgaattaag agtaagatgt ttag                                           24

<210> SEQ ID NO 653
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 653
aagtgtttgt ttagagtaaa gata                                           24

<210> SEQ ID NO 654
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 654
agagagataa agtatagaag ttaa                                           24

<210> SEQ ID NO 655
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 655
attatgaata gttagaaaga gagt                                              24

<210> SEQ ID NO 656
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 656
ttgttgatat tagagaatgt gttt                                              24

<210> SEQ ID NO 657
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 657
tttattgaga gtttgttatt tgtg                                              24

<210> SEQ ID NO 658
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 658
agtgttaaga agttgattat tgat                                              24

<210> SEQ ID NO 659
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 659
gagaaatgat tgaatgttga taat                                              24

<210> SEQ ID NO 660
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 660
gataagtatt agtatgagtg taat                                              24

<210> SEQ ID NO 661
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 661
tttgatttaa gagtgttgaa tgta                                              24

<210> SEQ ID NO 662
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 662
aagttagtaa atagagtaga aaga                                              24

<210> SEQ ID NO 663
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 663
gtaaagtatg aatatgtgaa atgt                                              24

<210> SEQ ID NO 664
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 664
taataagtgt gttgtgaatg taat                                              24

<210> SEQ ID NO 665
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 665
aaagatttag agtagaaaga gaat                                              24

<210> SEQ ID NO 666
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 666
ttagtttgag ttgaaatagt aaag                                              24

<210> SEQ ID NO 667
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 667
taatagtatg agtaagattg aaag                                            24

<210> SEQ ID NO 668
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 668
gaagattaga ttgatgttag ttaa                                            24

<210> SEQ ID NO 669
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 669
taaagagaga agttagtaat agaa                                            24

<210> SEQ ID NO 670
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 670
taagtatgag aaatgatgtg ttat                                            24

<210> SEQ ID NO 671
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 671
gagtttgttt gttagttatt gata                                            24

<210> SEQ ID NO 672
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 672
aagtaaagaa atgttaagag tagt                                            24

<210> SEQ ID NO 673
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

<400> SEQUENCE: 673
atgagaattg ttgttgaaat gtaa                                    24

<210> SEQ ID NO 674
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 674
ttagattaga gtagtagaag aata                                    24

<210> SEQ ID NO 675
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 675
tagtgatgaa gaagttagaa atta                                    24

<210> SEQ ID NO 676
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 676
taatgtagta atgtgatgat aagt                                    24

<210> SEQ ID NO 677
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 677
ttgagaaaga ataagtagtg taaa                                    24

<210> SEQ ID NO 678
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 678
taatgagtga gattatagat tgtt                                    24

<210> SEQ ID NO 679
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 679
gtataagaaa tgtgtgtttg atta                                          24

<210> SEQ ID NO 680
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 680
gtgaatgtgt taatgaagat atat                                          24

<210> SEQ ID NO 681
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 681
gaaagttatt agtagttaaa gatg                                          24

<210> SEQ ID NO 682
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 682
tagaattgtg tttgataagt gata                                          24

<210> SEQ ID NO 683
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 683
tgatttagat tgagagttaa atga                                          24

<210> SEQ ID NO 684
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 684
attattgagt ttgaatgttg atag                                          24

<210> SEQ ID NO 685
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 685

-continued

```
atagtagtta tgtttgattt agtg                                          24

<210> SEQ ID NO 686
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 686
atagaagaag aataaagtta gaga                                          24

<210> SEQ ID NO 687
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 687
gatgttgaaa gtaatgaatt tgta                                          24

<210> SEQ ID NO 688
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 688
gagattgata gtagaaatga taaa                                          24

<210> SEQ ID NO 689
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 689
tgagagaata aagtatgaat ttga                                          24

<210> SEQ ID NO 690
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 690
tataaagatg atgtgaatta gtag                                          24

<210> SEQ ID NO 691
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 691
ttatgtaaga atgtttgaga gaaa                                          24
```

```
<210> SEQ ID NO 692
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 692
agtaaatgat gaatgatatg atga                                            24

<210> SEQ ID NO 693
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 693
gaaatttgtg ttaaagttga atga                                            24

<210> SEQ ID NO 694
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 694
gatgaatgat tgtgtttaag tata                                            24

<210> SEQ ID NO 695
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 695
gaaataagtg agagttaatg aaat                                            24

<210> SEQ ID NO 696
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 696
tgttgaaata gttattagtt tgtg                                            24

<210> SEQ ID NO 697
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 697
tttgagagta tattgatatg agaa                                            24
```

```
<210> SEQ ID NO 698
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 698
attgtgtgta aagtaagatt taag                                              24

<210> SEQ ID NO 699
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 699
tatagtttga agtgtgatgt attt                                              24

<210> SEQ ID NO 700
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 700
gtgaagttat agtgtataaa gaat                                              24

<210> SEQ ID NO 701
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 701
gtatgttgaa tagtaaatag attg                                              24

<210> SEQ ID NO 702
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 702
ttagaaagtg tgatttgtgt attt                                              24

<210> SEQ ID NO 703
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 703
tttagtaata tgtaagagat gtga                                              24
```

```
<210> SEQ ID NO 704
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 704
agtatgtata gatgatgttt gttt                                             24

<210> SEQ ID NO 705
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 705
atttaagtaa agtgtagaga taag                                             24

<210> SEQ ID NO 706
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 706
atttgtgttg aattgtaaag tgaa                                             24

<210> SEQ ID NO 707
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 707
atgttattag attgtgatga atga                                             24

<210> SEQ ID NO 708
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 708
tagtagtaga atatgaaatt agag                                             24

<210> SEQ ID NO 709
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 709
tttaatgaga agagttagag tata                                             24

<210> SEQ ID NO 710
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 710
aaagtttagt agagtgtatg taaa                                          24

<210> SEQ ID NO 711
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 711
atatatgata gtagagtaga ttag                                          24

<210> SEQ ID NO 712
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 712
tgagaagtta attgtataga ttga                                          24

<210> SEQ ID NO 713
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 713
tatagagatg ttatatgaag ttgt                                          24

<210> SEQ ID NO 714
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 714
aaatttgtta agttgttgtt gttg                                          24

<210> SEQ ID NO 715
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 715
ttgttgaaga tgaaagtaga atta                                          24

<210> SEQ ID NO 716
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 716
aagagataag tagtgtttat gttt                                              24

<210> SEQ ID NO 717
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 717
aataagaaga agtgaaagat tgat                                              24

<210> SEQ ID NO 718
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 718
taagttaaag ttgatgattg atag                                              24

<210> SEQ ID NO 719
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 719
atataagata agagtgtaag tgat                                              24

<210> SEQ ID NO 720
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 720
gttaaatgtt gttgtttaag tgat                                              24

<210> SEQ ID NO 721
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 721
gagttaagtt attagttaag aagt                                              24

<210> SEQ ID NO 722
<211> LENGTH: 24
<212> TYPE: DNA
```

<213> ORGANISM: Artificial Sequence
<220> FEATURE:
<223> OTHER INFORMATION: Description of Artificial Sequence:Artificially
    Synthesized DNA Sequence

<400> SEQUENCE: 722
tattagagtt tgagaataag tagt                                          24

<210> SEQ ID NO 723
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 723
taatgttgtt atgtgttaga tgtt                                          24

<210> SEQ ID NO 724
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 724
gaaagttgat agaatgtaat gttt                                          24

<210> SEQ ID NO 725
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 725
tgatagatga attgattgat tagt                                          24

<210> SEQ ID NO 726
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 726
atgatagagt aaagaataag ttgt                                          24

<210> SEQ ID NO 727
<211> LENGTH: 24
<212> TYPE: DNA
<213> ORGANISM: Artificial Sequence
<220> FEATURE:
<223> OTHER INFORMATION: Description of Artificial Sequence:Artificially
    Synthesized DNA Sequence

<400> SEQUENCE: 727
agtaagtgtt agatagtatt gaat                                          24

<210> SEQ ID NO 728
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 728
atgtagatta aagtagtgta tgtt                                           24

<210> SEQ ID NO 729
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 729
ttattgataa tgagagagtt aaag                                           24

<210> SEQ ID NO 730
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 730
atttgttatg ataaatgtgt agtg                                           24

<210> SEQ ID NO 731
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 731
ttgaagaaat aagagtaata agag                                           24

<210> SEQ ID NO 732
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 732
tgtgtaataa gtagtaagat taga                                           24

<210> SEQ ID NO 733
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 733
atgaaagtta gagtttatga taag                                           24

<210> SEQ ID NO 734
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 734
attagttaag agagtttgta gatt                                              24

<210> SEQ ID NO 735
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 735
tgtagtattg tatgattaaa gtgt                                              24

<210> SEQ ID NO 736
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 736
agttgataaa gaagaagagt atat                                              24

<210> SEQ ID NO 737
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 737
gtaatgagat aaagagagat aatt                                              24

<210> SEQ ID NO 738
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 738
tgtgttgaag ataaagttta tgat                                              24

<210> SEQ ID NO 739
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 739
aagaagagta gttagaattg atta                                              24

<210> SEQ ID NO 740
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 740
gaatgaagat gaagtttgtt aata                                    24

<210> SEQ ID NO 741
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 741
aaattgttga gataagatag tgat                                    24

<210> SEQ ID NO 742
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 742
tgattgttta atgatgtgtg atta                                    24

<210> SEQ ID NO 743
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 743
atgaagtatt gttgagtgat ttaa                                    24

<210> SEQ ID NO 744
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 744
gtgtaaatgt ttgagatgta tatt                                    24

<210> SEQ ID NO 745
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 745
aattgatgag tttaaagagt tgat                                    24

<210> SEQ ID NO 746
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 746
tttgtgtaat atgattgaga gttt                                              24

<210> SEQ ID NO 747
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 747
gtagtagatg attaagaaga taaa                                              24

<210> SEQ ID NO 748
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 748
tttaatgtga aatttgttgt gagt                                              24

<210> SEQ ID NO 749
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 749
gtaaagaatt agataaagag tgat                                              24

<210> SEQ ID NO 750
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 750
aatagttaag tttaagagtt gtgt                                              24

<210> SEQ ID NO 751
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 751
gtgtgatgtt tatagatttg ttat                                              24

<210> SEQ ID NO 752
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 752
gtatagtgtg attagatttg taaa                                        24

<210> SEQ ID NO 753
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 753
gttgtaagaa agatatgtaa gaaa                                        24

<210> SEQ ID NO 754
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 754
atattagatt gtaaagagag tgaa                                        24

<210> SEQ ID NO 755
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 755
gagtgatatt gaaattagat tgta                                        24

<210> SEQ ID NO 756
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 756
taagaagtta aagaagagag ttta                                        24

<210> SEQ ID NO 757
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 757
gatgttagat aaagtttaag tagt                                        24

<210> SEQ ID NO 758
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 758
```
gtgattgtat gagaaatgtt aaat                                         24

<210> SEQ ID NO 759
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 759
tgattattgt aagaaagatt gaga                                         24

<210> SEQ ID NO 760
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 760
aagaattgtg taagtttatg agta                                         24

<210> SEQ ID NO 761
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 761
ttgtatttag aagatttgta gatg                                         24

<210> SEQ ID NO 762
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 762
tatatgtttg tgtaagaaga aatg                                         24

<210> SEQ ID NO 763
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 763
gataatgtgt gaatttgtga ataa                                         24

<210> SEQ ID NO 764
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 764

```
ttagaaatgt gagatttaag agtt                                          24
```

<210> SEQ ID NO 765
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 765

```
agtgtagaat ttgtatttag ttgt                                          24
```

<210> SEQ ID NO 766
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 766

```
tagttaagat agagtaaatg atag                                          24
```

<210> SEQ ID NO 767
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 767

```
gaagtgatat tgtaaattga taag                                          24
```

<210> SEQ ID NO 768
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 768

```
gtaattgtgt tagatttaag aagt                                          24
```

<210> SEQ ID NO 769
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 769

```
tgatatttgt gaattgatag tatg                                          24
```

<210> SEQ ID NO 770
<211> LENGTH: 24
<212> TYPE: DNA
<213> ORGANISM: Artificial Sequence
<220> FEATURE:
<223> OTHER INFORMATION: Description of Artificial Sequence:Artificially
     Synthesized DNA Sequence

<400> SEQUENCE: 770

```
aagtaaagag atatagttaa gttg                                          24
```

```
<210> SEQ ID NO 771
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 771
attagttaag ttatttgtga gtga                                              24

<210> SEQ ID NO 772
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 772
agatgaagta gtttatgaat taga                                              24

<210> SEQ ID NO 773
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 773
tgagttagtt aagtgatagt taaa                                              24

<210> SEQ ID NO 774
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 774
ttattgtaga tttagagaag atga                                              24

<210> SEQ ID NO 775
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 775
tatttgtgtt tgttgattag atag                                              24

<210> SEQ ID NO 776
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 776
gtataatgtg tgtgaaagtt ataa                                              24
```

```
<210> SEQ ID NO 777
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 777
tatatgttga gtataaagag agaa                                              24

<210> SEQ ID NO 778
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 778
ttagttagtt taaagattgt gagt                                              24

<210> SEQ ID NO 779
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 779
tttagaataa gtgatgtgat gaaa                                              24

<210> SEQ ID NO 780
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 780
agagtaatgt gtaaatagtt agat                                              24

<210> SEQ ID NO 781
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 781
tgtgataaag agaaattagt tgtt                                              24

<210> SEQ ID NO 782
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 782
gaatttagtg aatgtttgag atta                                              24
```

```
<210> SEQ ID NO 783
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 783
tgtgatgtgt aagtatatga aatt                                              24

<210> SEQ ID NO 784
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 784
ttgtgaatga ttaatgaata gaag                                              24

<210> SEQ ID NO 785
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 785
aatgttgttt agattgagaa agtt                                              24

<210> SEQ ID NO 786
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 786
agattgtgtt agtattagta taag                                              24

<210> SEQ ID NO 787
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 787
ttgatgtatt agaaagttta tgtg                                              24

<210> SEQ ID NO 788
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 788
tatgattgtg tgttagagaa ttta                                              24

<210> SEQ ID NO 789
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 789
tagtgtagat atttgatagt tatg                                          24

<210> SEQ ID NO 790
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 790
agtttaatgt gtttagttgt tatg                                          24

<210> SEQ ID NO 791
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 791
tgtgtaaagt agaaagtaaa gatt                                          24

<210> SEQ ID NO 792
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 792
gttatgatat agtgagttgt tatt                                          24

<210> SEQ ID NO 793
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 793
tttgattgaa tgttaatagt gtgt                                          24

<210> SEQ ID NO 794
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 794
agagtattag tagttattgt aagt                                          24

<210> SEQ ID NO 795
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 795
taagtagaaa gaagaagata tttg                                              24

<210> SEQ ID NO 796
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 796
agaaagagaa ttatgtaatg aaag                                              24

<210> SEQ ID NO 797
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 797
ttagatttgt tagtgtgatt taag                                              24

<210> SEQ ID NO 798
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 798
gatgattaag atatagagat agtt                                              24

<210> SEQ ID NO 799
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 799
atatttgagt gattaagagt aatg                                              24

<210> SEQ ID NO 800
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 800
tgtattgtga gttaagtata agtt                                              24

<210> SEQ ID NO 801
<211> LENGTH: 24
<212> TYPE: DNA
```

-continued

```
<213> ORGANISM: Artificial Sequence
<220> FEATURE:
<223> OTHER INFORMATION: Description of Artificial Sequence:Artificially
      Synthesized DNA Sequence

<400> SEQUENCE: 801
aatttagtag aaagtgttgt gttt                                              24

<210> SEQ ID NO 802
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 802
gttagaagat taagttgaat aatg                                              24

<210> SEQ ID NO 803
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 803
taaagtatgt gagatgattt atgt                                              24

<210> SEQ ID NO 804
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 804
tgaaatgatt aaagatgaag atga                                              24

<210> SEQ ID NO 805
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 805
ttattagatg ttgagtgttt gttt                                              24

<210> SEQ ID NO 806
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 806
tagtgtttaa agagtagtat atga                                              24

<210> SEQ ID NO 807
<211> LENGTH: 24
<212> TYPE: DNA
<213> ORGANISM: Artificial Sequence
```

-continued

```
<220> FEATURE:
<223> OTHER INFORMATION: Description of Artificial Sequence:Artificially
      Synthesized DNA Sequence

<400> SEQUENCE: 807
agttataagt aaatgatgtt gatg                                            24

<210> SEQ ID NO 808
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 808
ttaagagaga ataagtgta ttgt                                             24

<210> SEQ ID NO 809
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 809
gatattgaaa tgtgtaaatg atga                                            24

<210> SEQ ID NO 810
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 810
atgatgaatt aagaaagaaa gaga                                            24

<210> SEQ ID NO 811
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 811
gaatagtttg atttgtgttt gtta                                            24

<210> SEQ ID NO 812
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 812
agttgtttag atttgatttg taag                                            24

<210> SEQ ID NO 813
<211> LENGTH: 24
<212> TYPE: DNA
<213> ORGANISM: Artificial Sequence
<220> FEATURE:
```

```
<223> OTHER INFORMATION: Description of Artificial Sequence:Artificially
      Synthesized DNA Sequence

<400> SEQUENCE: 813
gtatgagatt tgatataaga ttag                                          24

<210> SEQ ID NO 814
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 814
tttatagtga gtatagtgat gatt                                          24

<210> SEQ ID NO 815
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 815
tatatgtgaa gatataagtg tttg                                          24

<210> SEQ ID NO 816
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 816
attgatagat gatagtaatt gagt                                          24

<210> SEQ ID NO 817
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 817
tgatagatgt gaagaatttg attt                                          24

<210> SEQ ID NO 818
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 818
gaagatattg aaagaatttg atgt                                          24

<210> SEQ ID NO 819
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 819
gatgtttagt gtagatatag attt                                         24

<210> SEQ ID NO 820
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 820
gaatattgag ttataagtag tagt                                         24

<210> SEQ ID NO 821
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 821
agtgagtaag taatagaaag attt                                         24

<210> SEQ ID NO 822
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 822
gtagaataag taatttgtga gata                                         24

<210> SEQ ID NO 823
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 823
gagttatttg agatttagat gttt                                         24

<210> SEQ ID NO 824
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 824
gaaatgatga ttgaatttag agat                                         24

<210> SEQ ID NO 825
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 825
aaatagtgtg agaatagtta agta                                              24

<210> SEQ ID NO 826
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 826
atgtgttaag ttgtagaaga ataa                                              24

<210> SEQ ID NO 827
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 827
ataatgagtt aatagtgtaa gaag                                              24

<210> SEQ ID NO 828
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 828
ataagagatg tttaagttag aaag                                              24

<210> SEQ ID NO 829
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 829
tgttagtgtt agaaatatga aaga                                              24

<210> SEQ ID NO 830
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 830
tttagaagat tgttagataa gttg                                              24

<210> SEQ ID NO 831
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 831
gtgtaatgta taagatagtt aagt                                          24

<210> SEQ ID NO 832
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 832
tattagagag aaattgtaga gatt                                          24

<210> SEQ ID NO 833
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 833
tagtgagata aagtaaagtt tatg                                          24

<210> SEQ ID NO 834
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 834
ttgtgaaagt taagtaagtt agtt                                          24

<210> SEQ ID NO 835
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 835
aaagtgtaag ttgaagaata ttga                                          24

<210> SEQ ID NO 836
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 836
gaatagagtg ttatttgaaa taga                                          24

<210> SEQ ID NO 837
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 837
```
tataagagag agataagtaa taag                    24

<210> SEQ ID NO 838
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 838
tgagtgaaat tgatagagta aatt                    24

<210> SEQ ID NO 839
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 839
gatgaataag tttaagtgag aaat                    24

<210> SEQ ID NO 840
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 840
gtgtgatatg tttattgatt aagt                    24

<210> SEQ ID NO 841
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 841
taaagtgagt gtaaatgata atga                    24

<210> SEQ ID NO 842
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 842
gtagagtttg atttgaaaga atat                    24

<210> SEQ ID NO 843
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 843
gaatattgtt atgtttgtta tgag                                                  24

<210> SEQ ID NO 844
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 844
gtgtaataag atgtattgtt gttt                                                  24

<210> SEQ ID NO 845
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 845
taaattgatt gtgagttgaa gaat                                                  24

<210> SEQ ID NO 846
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 846
tgagatagtt atagttaagt ttag                                                  24

<210> SEQ ID NO 847
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 847
agtttgttaa gattatgtag aaag                                                  24

<210> SEQ ID NO 848
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 848
gaatgtgtag aataagagat taaa                                                  24

<210> SEQ ID NO 849
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 849
gtattatgaa agaagttgtt gttt                                                  24

<210> SEQ ID NO 850
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 850
gtgttataga agttaaatgt taag          24

<210> SEQ ID NO 851
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 851
ttaagagtag tgaatatgat agta          24

<210> SEQ ID NO 852
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 852
aatgttataa gatgagagtt tagt          24

<210> SEQ ID NO 853
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 853
atataagatt tgatgtagtg tagt          24

<210> SEQ ID NO 854
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 854
tatgtttgtt gttgttaagt ttga          24

<210> SEQ ID NO 855
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 855
gatagtttag tatagaagat aaag          24

```
<210> SEQ ID NO 856
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 856
gttgaatata gagatagtaa atag                                              24

<210> SEQ ID NO 857
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 857
agagaagatt tagtaagaat gata                                              24

<210> SEQ ID NO 858
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 858
tgaatgagaa agatattgag tatt                                              24

<210> SEQ ID NO 859
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 859
tgaagattat agtagttgta taga                                              24

<210> SEQ ID NO 860
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 860
gattagtagt attgaagatt atgt                                              24

<210> SEQ ID NO 861
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 861
tgaaatgtgt atttgtatgt ttag                                              24
```

```
<210> SEQ ID NO 862
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 862
attaaagttg atatgaaaga agtg                                            24

<210> SEQ ID NO 863
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 863
aatgtagaga ttgtagtgaa tatt                                            24

<210> SEQ ID NO 864
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 864
ttatttgttg agtgtaaatg tgat                                            24

<210> SEQ ID NO 865
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 865
atgtaattgt gaataatgta tgtg                                            24

<210> SEQ ID NO 866
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 866
gatttgtata gagattagta agta                                            24

<210> SEQ ID NO 867
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 867
aatattgttg tttagagaaa gaag                                            24

<210> SEQ ID NO 868
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 868
atgatgatgt atttgtaaag agta                                           24

<210> SEQ ID NO 869
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 869
aatgtatttg tgtgattgtg taaa                                           24

<210> SEQ ID NO 870
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 870
agtgttatga agaatagtaa gaat                                           24

<210> SEQ ID NO 871
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 871
gttatgtaga gatgaaagaa atta                                           24

<210> SEQ ID NO 872
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 872
gtttgtatta gataaatgag ttgt                                           24

<210> SEQ ID NO 873
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 873
tgatttatga gattaagaga aaga                                           24

<210> SEQ ID NO 874
<211> LENGTH: 24
```

-continued

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 874
tttgtgtgtt attgtaattg agat                                            24

<210> SEQ ID NO 875
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 875
gatgtgtgat atgattaaag aaat                                            24

<210> SEQ ID NO 876
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 876
agattataga tttgtagaga aagt                                            24

<210> SEQ ID NO 877
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 877
gaagagtatg taatagtatt gtat                                            24

<210> SEQ ID NO 878
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 878
tttgtaatgt tgttgagttt aaga                                            24

<210> SEQ ID NO 879
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 879
agtaaatagt agtatgaata agag                                            24

<210> SEQ ID NO 880
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 880
gaatgttgaa ttgaaatatg agtt                                      24

<210> SEQ ID NO 881
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 881
agtagttaat tgatagtaag tttg                                      24

<210> SEQ ID NO 882
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 882
agtgtaaaga aatgaatgaa taag                                      24

<210> SEQ ID NO 883
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 883
tgttagatat ttgtgaaatg tgaa                                      24

<210> SEQ ID NO 884
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 884
tgtatgttga gtttgaattg ttat                                      24

<210> SEQ ID NO 885
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 885
tgagtgaatt agttatgttg ttat                                      24

<210> SEQ ID NO 886
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 886
gaagaaagaa atgagaaaga ttat                                              24

<210> SEQ ID NO 887
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 887
ttaagtaagt tgtgttgata ttag                                              24

<210> SEQ ID NO 888
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 888
atgatgtgtt tgatttgaat tgaa                                              24

<210> SEQ ID NO 889
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 889
aagtaagtga aattgttgtt tgaa                                              24

<210> SEQ ID NO 890
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 890
atgaagtgta aagtttgaaa gaaa                                              24

<210> SEQ ID NO 891
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 891
agagagtaag ataattgtat agta                                              24

<210> SEQ ID NO 892
<211> LENGTH: 24
<212> TYPE: DNA
<213> ORGANISM: Artificial Sequence
<220> FEATURE:
```

-continued

```
<223> OTHER INFORMATION: Description of Artificial Sequence:Artificially
      Synthesized DNA Sequence

<400> SEQUENCE: 892
tttatgagat agatgaaata agtg                                              24

<210> SEQ ID NO 893
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 893
agaaattagt agtaatgatt tgtg                                              24

<210> SEQ ID NO 894
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 894
gatttgagat tgaatgagaa tata                                              24

<210> SEQ ID NO 895
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 895
gattagaaag atgaataaag atga                                              24

<210> SEQ ID NO 896
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 896
tagatagaaa gtatatgttg tagt                                              24

<210> SEQ ID NO 897
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 897
gaagatagta aagtaaagta agtt                                              24

<210> SEQ ID NO 898
<211> LENGTH: 24
<212> TYPE: DNA
<213> ORGANISM: Artificial Sequence
<220> FEATURE:
<223> OTHER INFORMATION: Description of Artificial Sequence:Artificially
```

Synthesized DNA Sequence

<400> SEQUENCE: 898
aaatgtgtgt ttagtagttg taaa                                              24

<210> SEQ ID NO 899
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 899
ttgttgaagt aagagatgaa taaa                                              24

<210> SEQ ID NO 900
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 900
tatttgagag aaagaaagag ttta                                              24

<210> SEQ ID NO 901
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 901
tatttagtga tgaatttgtg atgt                                              24

<210> SEQ ID NO 902
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 902
ttatagtgat gatgataagt tgat                                              24

<210> SEQ ID NO 903
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 903
taaagataat tgtagaaagt agtg                                              24

<210> SEQ ID NO 904
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 904
gtttagtatt gatattgtgt gtaa                                          24

<210> SEQ ID NO 905
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 905
gtgttgtgaa taagattgaa atat                                          24

<210> SEQ ID NO 906
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 906
aaagaaagta taaagtgaga taga                                          24

<210> SEQ ID NO 907
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 907
tatttgtaag aagtgtagat attg                                          24

<210> SEQ ID NO 908
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 908
tagaagatga aattgtgatt tgtt                                          24

<210> SEQ ID NO 909
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 909
ataatagtaa gtgaatgatg agat                                          24

<210> SEQ ID NO 910
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 910
aatgtgaata agataaagtg tgta                                          24

<210> SEQ ID NO 911
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 911
attgaagata aagatgttgt ttag                                          24

<210> SEQ ID NO 912
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 912
tgaaatagaa gtgagattat agta                                          24

<210> SEQ ID NO 913
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 913
agttattgtg aaagagttta tgat                                          24

<210> SEQ ID NO 914
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 914
aaatagtagt gatagagaag attt                                          24

<210> SEQ ID NO 915
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 915
agtgtatgaa gtgtaataag atta                                          24

<210> SEQ ID NO 916
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 916
```

```
tgattaagat tgtgtagtgt tata                                           24

<210> SEQ ID NO 917
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 917
agtttatgat atttgtagat gagt                                           24

<210> SEQ ID NO 918
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 918
tatgtgtatg aagattatag ttag                                           24

<210> SEQ ID NO 919
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 919
gaaattgttg tatagagtga tata                                           24

<210> SEQ ID NO 920
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 920
tagaaatagt ttaagtatag tgtg                                           24

<210> SEQ ID NO 921
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 921
tgatttagat gtttattgtg agaa                                           24

<210> SEQ ID NO 922
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 922
```

```
aagttgatat tgttgttag atga                                              24
```

<210> SEQ ID NO 923
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 923

```
tgatgtgata atgagaataa agaa                                             24
```

<210> SEQ ID NO 924
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 924

```
aaagtttagt ttgtattagt agag                                             24
```

<210> SEQ ID NO 925
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 925

```
agtttgatgt gatagtaaat agaa                                             24
```

<210> SEQ ID NO 926
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 926

```
aagtgttatt gaatgtgatg ttat                                             24
```

<210> SEQ ID NO 927
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 927

```
aaattgaagt gtgataatgt ttgt                                             24
```

<210> SEQ ID NO 928
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 928

```
gtttagtgat taaagataga ttag                                             24
```

```
<210> SEQ ID NO 929
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 929
ataagtgtat aagagaagtg ttaa                                          24

<210> SEQ ID NO 930
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 930
atgaatttgt ttgtgatgaa gtta                                          24

<210> SEQ ID NO 931
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 931
aaagaattga gaaatgaaag ttag                                          24

<210> SEQ ID NO 932
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 932
agtgtaagag tataaagtat ttga                                          24

<210> SEQ ID NO 933
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 933
gaattaagat tgttatatgt gagt                                          24

<210> SEQ ID NO 934
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 934
tatgaaagtg ttgtttaagt aaga                                          24
```

```
<210> SEQ ID NO 935
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 935
taaagtaaat gttatgtgag agaa                                              24

<210> SEQ ID NO 936
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 936
aaagatattg attgagatag agtt                                              24

<210> SEQ ID NO 937
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 937
aagtgatatg aatatgtgag aaat                                              24

<210> SEQ ID NO 938
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 938
aaatagagtt tgttaatgta agtg                                              24

<210> SEQ ID NO 939
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 939
gatttagatg agttaagaat ttag                                              24

<210> SEQ ID NO 940
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 940
ttgtaaatga gtgtgaatat tgta                                              24
```

<210> SEQ ID NO 941
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 941
agtagtgtat ttgagataat agaa                                          24

<210> SEQ ID NO 942
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 942
tgagttaaag agttgttgat attt                                          24

<210> SEQ ID NO 943
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 943
aaagagtgta ttagaaatag tttg                                          24

<210> SEQ ID NO 944
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 944
gtttagttat ttgatgagat aatg                                          24

<210> SEQ ID NO 945
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 945
aagtgtaaat gaataaagag ttgt                                          24

<210> SEQ ID NO 946
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 946
aataaagtga gtagaagtgt aatt                                          24

<210> SEQ ID NO 947

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 947
tattgagttt gtgtaaagaa gata                                              24

<210> SEQ ID NO 948
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 948
tttatagttg ttgtgttgaa agtt                                              24

<210> SEQ ID NO 949
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 949
atgaaatatg attgtgtttg ttgt                                              24

<210> SEQ ID NO 950
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 950
aaagagatgt aaagtgagtt atta                                              24

<210> SEQ ID NO 951
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 951
ttgaagaaag ttagatgatg aatt                                              24

<210> SEQ ID NO 952
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 952
atgttatttg tttagtttgt gtga                                              24

<210> SEQ ID NO 953
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 953
aaatatgaat ttgaagagaa gtga                                          24

<210> SEQ ID NO 954
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 954
gattagatat agaatattga agag                                          24

<210> SEQ ID NO 955
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 955
ttagaataag agaaatgtat gtgt                                          24

<210> SEQ ID NO 956
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 956
tttatgaaag agaagtgtat tatg                                          24

<210> SEQ ID NO 957
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 957
gtaagtatta agtgtgattt agta                                          24

<210> SEQ ID NO 958
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 958
ataaagagaa gtaaagagta aagt                                          24

<210> SEQ ID NO 959
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 959
attgttaatt gaagtgtatg aaag                                          24

<210> SEQ ID NO 960
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 960
tatatagttg agttgagtaa gatt                                          24

<210> SEQ ID NO 961
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 961
tagatgagat atatgaaaga tagt                                          24

<210> SEQ ID NO 962
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 962
ataagaagat gatttgtgta aatg                                          24

<210> SEQ ID NO 963
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 963
ttagtaataa gaaagatgaa gaga                                          24

<210> SEQ ID NO 964
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 964
gatttgtgag taaagtaaat agaa                                          24

<210> SEQ ID NO 965
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 965
aaatagatgt agaatttgtg tgtt                                              24

<210> SEQ ID NO 966
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 966
gaaattagtg tttgtgtgta ttat                                              24

<210> SEQ ID NO 967
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 967
atttgagtat gatagaagat tgtt                                              24

<210> SEQ ID NO 968
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 968
atagagttga agtatgtaaa gttt                                              24

<210> SEQ ID NO 969
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 969
taatttgtga atgttgttat tgtg                                              24

<210> SEQ ID NO 970
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 970
ttagtttatg agagtgagat ttaa                                              24

<210> SEQ ID NO 971
<211> LENGTH: 24
<212> TYPE: DNA
<213> ORGANISM: Artificial Sequence
<220> FEATURE:
```

<210> SEQ ID NO 971
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 971
gttgttagag tgtttatgaa attt                                          24

<210> SEQ ID NO 972
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 972
tttattgtga tgtgaaataa gaga                                          24

<210> SEQ ID NO 973
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 973
gtaagtaata tgatagtgat taag                                          24

<210> SEQ ID NO 974
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 974
tgagatgatg tatatgtagt aata                                          24

<210> SEQ ID NO 975
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 975
aattgagaaa gagataaatg atag                                          24

<210> SEQ ID NO 976
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 976
tttgaagtga tgttagaatg ttta                                          24

<210> SEQ ID NO 977
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 977
agttgttgtg taattgttag taaa                                              24

<210> SEQ ID NO 978
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 978
atagtgagaa gtgataagat attt                                              24

<210> SEQ ID NO 979
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 979
gtgtgataag taattgagtt aaat                                              24

<210> SEQ ID NO 980
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 980
tagttattgt ttgtgaattt gaga                                              24

<210> SEQ ID NO 981
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 981
atagttgaat agtaatttga agag                                              24

<210> SEQ ID NO 982
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 982
atgtttgtgt ttgaatagag aata                                              24

<210> SEQ ID NO 983
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence -continued

```
<400> SEQUENCE: 983
tgataaagat atgagagatt gtaa                                          24

<210> SEQ ID NO 984
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 984
taaagatgag atgttgttaa agtt                                          24

<210> SEQ ID NO 985
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 985
aagtgaaatt tgtaagaatt agtg                                          24

<210> SEQ ID NO 986
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 986
gaaatgagag ttattgatag ttta                                          24

<210> SEQ ID NO 987
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 987
tttgtaaatg agatatagtg ttag                                          24

<210> SEQ ID NO 988
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 988
gttaattgtg atatttgatt agtg                                          24

<210> SEQ ID NO 989
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 989
agagtgttga taaagatgtt tata                                          24

<210> SEQ ID NO 990
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 990
aattgtgaga aattgataag aaga                                          24

<210> SEQ ID NO 991
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 991
ttaaagagaa ttgagaagag aaat                                          24

<210> SEQ ID NO 992
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 992
ttgttagaag aattgaatgt atgt                                          24

<210> SEQ ID NO 993
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 993
agttaagata tgtgtgatgt ttaa                                          24

<210> SEQ ID NO 994
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 994
tgagttatgt tgtaatagaa attg                                          24

<210> SEQ ID NO 995
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 995
```
ttagataagt ttagagattg agaa                                    24

<210> SEQ ID NO 996
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 996
atgagtaata agagtatttg aagt                                    24

<210> SEQ ID NO 997
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 997
tgtttaagtg taatgatttg ttag                                    24

<210> SEQ ID NO 998
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 998
ttgaagaaga ttgttattgt tgaa                                    24

<210> SEQ ID NO 999
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 999
tatagaaaga ttaaagagtg aatg                                    24

<210> SEQ ID NO 1000
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1000
taaattgtta gaaatttgag tgtg                                    24

<210> SEQ ID NO 1001
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1001

```
attgttagtg tgttattgat tatg                                          24
```

<210> SEQ ID NO 1002
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1002

```
gagaattatg tgtgaatata gaaa                                          24
```

<210> SEQ ID NO 1003
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1003

```
ttgattgata aagtaaagag tgta                                          24
```

<210> SEQ ID NO 1004
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1004

```
gtgtgtaaat tgaatatgtt aatg                                          24
```

<210> SEQ ID NO 1005
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1005

```
aaagtaaaga aagaagtttg aaag                                          24
```

<210> SEQ ID NO 1006
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1006

```
tttagttgaa gaatagaaag aaag                                          24
```

<210> SEQ ID NO 1007
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1007

```
gtgtaataag agtgaatagt aatt                                          24
```

```
<210> SEQ ID NO 1008
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1008
tattgaaata agagagattt gtga                                          24

<210> SEQ ID NO 1009
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1009
atgagaaaga agaagttaag attt                                          24

<210> SEQ ID NO 1010
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1010
aagagtgagt atattgttaa agaa                                          24

<210> SEQ ID NO 1011
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1011
tttgtaaagt gatgatgtaa gata                                          24

<210> SEQ ID NO 1012
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1012
gatgttatgt gatgaaatat gtat                                          24

<210> SEQ ID NO 1013
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1013
gtagaataaa gtgttaaagt gtta                                          24
```

```
<210> SEQ ID NO 1014
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1014
aaagagtatg tgtgtatgat attt                                              24

<210> SEQ ID NO 1015
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1015
aaagataaga gttagtaaat tgtg                                              24

<210> SEQ ID NO 1016
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1016
aagaattaga gaataagtgt gata                                              24

<210> SEQ ID NO 1017
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1017
gataagaaag tgaaatgtaa attg                                              24

<210> SEQ ID NO 1018
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1018
gatgaaagat gtttaaagtt tgtt                                              24

<210> SEQ ID NO 1019
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1019
agtgtaagta ataagtttga gaaa                                              24
```

```
<210> SEQ ID NO 1020
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1020
gttgagaatt agaatttgat aaag                                           24

<210> SEQ ID NO 1021
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1021
ttaagaaatt tgtatgtgtt gttg                                           24

<210> SEQ ID NO 1022
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1022
agaagattta gatgaaatga gttt                                           24

<210> SEQ ID NO 1023
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1023
taagtttgag ataaagatga tatg                                           24

<210> SEQ ID NO 1024
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1024
tgagatagtt tgtaatatgt ttgt                                           24

<210> SEQ ID NO 1025
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1025
agtttgaaat tgtaagtttg atga                                           24

<210> SEQ ID NO 1026
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1026
tagaattgat taatgatgag tagt                                          24

<210> SEQ ID NO 1027
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1027
agagatttgt aataagtatt gaag                                          24

<210> SEQ ID NO 1028
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1028
ataatgatgt aatgtaagta gtgt                                          24

<210> SEQ ID NO 1029
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1029
tgaaatttga tgagagatat gtta                                          24

<210> SEQ ID NO 1030
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1030
tgtgtaaagt atagtttatg ttag                                          24

<210> SEQ ID NO 1031
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1031
tgaataagtg aaatagaatg aatg                                          24

<210> SEQ ID NO 1032
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1032
aaagaaagat tgtaataagt agag                                              24

<210> SEQ ID NO 1033
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1033
aatgaaatag tgttaaatga gtgt                                              24

<210> SEQ ID NO 1034
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1034
gtagataaag atgtgaatta tgat                                              24

<210> SEQ ID NO 1035
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1035
gatagtatat gtgtgtattt gttt                                              24

<210> SEQ ID NO 1036
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1036
atgtttgtag aaatgtttga agat                                              24

<210> SEQ ID NO 1037
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1037
aaatttgtag agagaaattt gttg                                              24

<210> SEQ ID NO 1038
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 1038
tagaataaga ttagtaagtg taga                                               24

<210> SEQ ID NO 1039
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1039
tgatttagag aaatatgagt agaa                                               24

<210> SEQ ID NO 1040
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1040
aatagagtat gttgtttatg agaa                                               24

<210> SEQ ID NO 1041
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1041
gatgatgaag agtttattgt aaat                                               24

<210> SEQ ID NO 1042
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1042
aagtaaagaa gaagaaatgt gtta                                               24

<210> SEQ ID NO 1043
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1043
ttgaagaatt aagtgtttag tgta                                               24

<210> SEQ ID NO 1044
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 1044
agaaagaatg ttgatttatg atgt                                          24

<210> SEQ ID NO 1045
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1045
gattaaagag atgttgattg aaat                                          24

<210> SEQ ID NO 1046
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1046
aatgataatt gttgagagag taat                                          24

<210> SEQ ID NO 1047
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1047
gtttgttgaa agtgtaaagt atat                                          24

<210> SEQ ID NO 1048
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1048
tgagttatat gagaaagtgt aatt                                          24

<210> SEQ ID NO 1049
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1049
ttgtgagaaa gaagtatata gaat                                          24

<210> SEQ ID NO 1050
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 1050
gtaagtttag agttatagag ttta                                              24

<210> SEQ ID NO 1051
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1051
gatagataga taagttaatt gaag                                              24

<210> SEQ ID NO 1052
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1052
agagatgatt gtttatgtat tatg                                              24

<210> SEQ ID NO 1053
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1053
aaagttaaga aattgtagtg atag                                              24

<210> SEQ ID NO 1054
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1054
tttgatattg tttgtgagtg tata                                              24

<210> SEQ ID NO 1055
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1055
atttgtagaa agttgttatg agtt                                              24

<210> SEQ ID NO 1056
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 1056
gatttgagta agtttataga tgaa                                              24

<210> SEQ ID NO 1057
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1057
aagataaagt gagttgattt agat                                              24

<210> SEQ ID NO 1058
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1058
gatattgtaa gatatgttgt aaag                                              24

<210> SEQ ID NO 1059
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1059
gtaagagtgt attgtaagtt aatt                                              24

<210> SEQ ID NO 1060
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1060
gtgtgattag taatgaagta ttta                                              24

<210> SEQ ID NO 1061
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1061
gtaagaaaga ttaagtgtta gtaa                                              24

<210> SEQ ID NO 1062
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 1062
agtagaaagt tgaaattgat tatg                                              24

<210> SEQ ID NO 1063
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1063
taagagaagt tgagtaatgt attt                                              24

<210> SEQ ID NO 1064
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1064
gttaagaaat agtagataag tgaa                                              24

<210> SEQ ID NO 1065
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1065
taagtaaatt gaaagtgtat agtg                                              24

<210> SEQ ID NO 1066
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1066
aagatgtatg tttattgttg tgta                                              24

<210> SEQ ID NO 1067
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1067
atttagaata tagtgaagag atag                                              24

<210> SEQ ID NO 1068
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 1068
gttatgaaag agtatgtgtt aaat                                          24

<210> SEQ ID NO 1069
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1069
tattatgtga agaagaatga ttag                                          24

<210> SEQ ID NO 1070
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1070
taataagttg aagagaattg ttgt                                          24

<210> SEQ ID NO 1071
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1071
tgatgtttga tgtaattgtt aaag                                          24

<210> SEQ ID NO 1072
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1072
gtgaaagatt tgagtttgta taat                                          24

<210> SEQ ID NO 1073
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1073
agagaatata gattgagatt tgtt                                          24

<210> SEQ ID NO 1074
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1074
```

```
tttgagatgt gatgataaag ttaa                                        24

<210> SEQ ID NO 1075
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1075
gttgtaaatt gtagtaaaga agta                                        24

<210> SEQ ID NO 1076
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1076
gtgttatgat gttgtttgta ttat                                        24

<210> SEQ ID NO 1077
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1077
attattgtgt agatgtatta agag                                        24

<210> SEQ ID NO 1078
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1078
gttagaaaga tttagaagtt agtt                                        24

<210> SEQ ID NO 1079
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1079
ttgtgtatta agagagtgaa atat                                        24

<210> SEQ ID NO 1080
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1080
```
gtttaagata gaaagagtga ttta                                          24

<210> SEQ ID NO 1081
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1081
aatgagaaat agatagttat tgtg                                          24

<210> SEQ ID NO 1082
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1082
tgaattgaat aagaatttgt tgtg                                          24

<210> SEQ ID NO 1083
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1083
aataagattg aattagtgag taag                                          24

<210> SEQ ID NO 1084
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1084
aatgtttgag agatttagta aaga                                          24

<210> SEQ ID NO 1085
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1085
agtttagaat agaaatgtgt ttga                                          24

<210> SEQ ID NO 1086
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1086
tataagtaag tgttaagatt tgag                                          24

```
<210> SEQ ID NO 1087
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1087
gtagtgaata agttagtgtt aata                                              24

<210> SEQ ID NO 1088
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1088
aagtgtgtta agtaaatgt agat                                               24

<210> SEQ ID NO 1089
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1089
agagatgttt atgttgtgaa ttaa                                              24

<210> SEQ ID NO 1090
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1090
agttgaatat tgatgataag aaga                                              24

<210> SEQ ID NO 1091
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1091
tgaatgtgag atgtttagaa taat                                              24

<210> SEQ ID NO 1092
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1092
aataatgatg taagtttgag tttg                                              24
```

<210> SEQ ID NO 1093
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1093
aaagagtgaa tagaaataag agaa                                              24

<210> SEQ ID NO 1094
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1094
aataaagtta ttgagagagt ttag                                              24

<210> SEQ ID NO 1095
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1095
agtagtgttg tagtttagta tata                                              24

<210> SEQ ID NO 1096
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1096
gtaagaatgt attagatatt tgtg                                              24

<210> SEQ ID NO 1097
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1097
gataaatgtt tgataaagta gttg                                              24

<210> SEQ ID NO 1098
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1098
atagtatgta tgtgtgaaga ttta                                              24

```
<210> SEQ ID NO 1099
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1099
atgaatgtag agtgattagt ttaa                                             24

<210> SEQ ID NO 1100
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1100
gtagtattta gtgatgtaag aata                                             24

<210> SEQ ID NO 1101
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1101
agaattgtat tgaagaagaa tatg                                             24

<210> SEQ ID NO 1102
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1102
tttatagaat tgagagaagt taag                                             24

<210> SEQ ID NO 1103
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1103
aaagtagtag agatttgaga atta                                             24

<210> SEQ ID NO 1104
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1104
tttaaagaaa gtattgtaag agtg                                             24

<210> SEQ ID NO 1105
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1105
aaattgagaa agtgaatgaa gttt                                              24

<210> SEQ ID NO 1106
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1106
aagaaataag tatgatagta gtag                                              24

<210> SEQ ID NO 1107
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1107
atttgaattg tattgtagtt tgtg                                              24

<210> SEQ ID NO 1108
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1108
aagagaataa tgtagagata taag                                              24

<210> SEQ ID NO 1109
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1109
tgtgtaatag ttgttaatga gtaa                                              24

<210> SEQ ID NO 1110
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1110
tatagttgta gtttagatga atgt                                              24

<210> SEQ ID NO 1111
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1111
attgtgttag aatgatgtta atag                                          24

<210> SEQ ID NO 1112
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1112
gtttgtatag tatttgattg atgt                                          24

<210> SEQ ID NO 1113
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1113
agagtaaagt atgagttatg aata                                          24

<210> SEQ ID NO 1114
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1114
gaaagtttaa gtgatgtata ttgt                                          24

<210> SEQ ID NO 1115
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1115
ttaaatgata aagagtagtg aagt                                          24

<210> SEQ ID NO 1116
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1116
ttaaatgtgt gagaagatga ataa                                          24

<210> SEQ ID NO 1117
<211> LENGTH: 24
<212> TYPE: DNA
```

<213> ORGANISM: Artificial Sequence
<220> FEATURE:
<223> OTHER INFORMATION: Description of Artificial Sequence:Artificially
      Synthesized DNA Sequence

<400> SEQUENCE: 1117
atttgtataa agtgaagaag agaa                                              24

<210> SEQ ID NO 1118
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1118
tgattagtat ttgtgaagag attt                                              24

<210> SEQ ID NO 1119
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1119
tttgaatgaa attgatgata gatg                                              24

<210> SEQ ID NO 1120
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1120
agagtaagat taagaataag aaag                                              24

<210> SEQ ID NO 1121
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1121
attgaattga gaagtgaagt aaat                                              24

<210> SEQ ID NO 1122
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1122
tttagagaag tattgtttga aaga                                              24

<210> SEQ ID NO 1123
<211> LENGTH: 24
<212> TYPE: DNA
<213> ORGANISM: Artificial Sequence

```
<220> FEATURE:
<223> OTHER INFORMATION: Description of Artificial Sequence:Artificially
      Synthesized DNA Sequence

<400> SEQUENCE: 1123
taaagtgaaa gatttgaaat gatg                                              24

<210> SEQ ID NO 1124
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1124
gaaagttaga gaaatgtaga aatt                                              24

<210> SEQ ID NO 1125
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1125
gtgaataatg aagaagttat gtta                                              24

<210> SEQ ID NO 1126
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1126
ttgtgaataa agtagatgtg ttat                                              24

<210> SEQ ID NO 1127
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1127
ttatatgata tgagtttgtg ttga                                              24

<210> SEQ ID NO 1128
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1128
ttgatttgtg tgagtattag ttat                                              24

<210> SEQ ID NO 1129
<211> LENGTH: 24
<212> TYPE: DNA
<213> ORGANISM: Artificial Sequence
<220> FEATURE:
```

-continued

<223> OTHER INFORMATION: Description of Artificial Sequence:Artificially
      Synthesized DNA Sequence

<400> SEQUENCE: 1129
aaagtgatta agttagtttg agat                                          24

<210> SEQ ID NO 1130
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1130
ttgtatttgt ataatgttga agag                                          24

<210> SEQ ID NO 1131
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1131
gtttgaaatt agtgtgagaa atat                                          24

<210> SEQ ID NO 1132
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1132
aatgttgaga ttgataatgt tgaa                                          24

<210> SEQ ID NO 1133
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1133
tagtagtagt attgttgtaa taag                                          24

<210> SEQ ID NO 1134
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1134
gttgtaattt gagtgttagt tatt                                          24

<210> SEQ ID NO 1135
<211> LENGTH: 24
<212> TYPE: DNA
<213> ORGANISM: Artificial Sequence
<220> FEATURE:
<223> OTHER INFORMATION: Description of Artificial Sequence:Artificially -continued

```
      Synthesized DNA Sequence

<400> SEQUENCE: 1135
tgaatatgat agttagtaat tgtg                                          24

<210> SEQ ID NO 1136
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1136
tgatagtatg tttgtgatta aaga                                          24

<210> SEQ ID NO 1137
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1137
gatgtataaa gagtatgtta taag                                          24

<210> SEQ ID NO 1138
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1138
agtgagattt agaagatgtt atta                                          24

<210> SEQ ID NO 1139
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1139
atgagaattt gttaaagaga aagt                                          24

<210> SEQ ID NO 1140
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1140
aaagaattag tatgatagat gaga                                          24

<210> SEQ ID NO 1141
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 1141
tagagttgta tagtttatag ttga                                          24

<210> SEQ ID NO 1142
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1142
gtagaatgat tgtttagaag attt                                          24

<210> SEQ ID NO 1143
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1143
gtttatgttt gagaagagtt attt                                          24

<210> SEQ ID NO 1144
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1144
tagaagtttg aaagttattg attg                                          24

<210> SEQ ID NO 1145
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1145
gatgaagagt atttgttata tgta                                          24

<210> SEQ ID NO 1146
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1146
gatgaatata gtaagtattg agta                                          24

<210> SEQ ID NO 1147
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

-continued

```
<400> SEQUENCE: 1147
tagtgatgaa atttgagata gata                                            24

<210> SEQ ID NO 1148
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1148
gaaagaaatt gaagagtttg atat                                            24

<210> SEQ ID NO 1149
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1149
atttgagtat ttgtgtattg aatg                                            24

<210> SEQ ID NO 1150
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1150
atgagttgaa atttgaagta ttgt                                            24

<210> SEQ ID NO 1151
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1151
ttaatagtga gagagtatat gtaa                                            24

<210> SEQ ID NO 1152
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1152
attaagagag tgagtaaatg taaa                                            24

<210> SEQ ID NO 1153
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1153
```
aagaatagat gagattagaa atag 24

<210> SEQ ID NO 1154
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1154
agtttaaaga gttagaattg aaag 24

<210> SEQ ID NO 1155
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1155
gtaagatttg ttgaataaag aaga 24

<210> SEQ ID NO 1156
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1156
agagaaagaa gttaaagtga tatt 24

<210> SEQ ID NO 1157
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1157
taatagagaa gagatgtatg aata 24

<210> SEQ ID NO 1158
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1158
ttattagtga taagtgaagt ttag 24

<210> SEQ ID NO 1159
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1159
ataatgtaaa gatgagttta tgag                                         24

<210> SEQ ID NO 1160
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1160
ttgatttgag agttgataag attt                                         24

<210> SEQ ID NO 1161
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1161
atgattattg tgtgtagaat taga                                         24

<210> SEQ ID NO 1162
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1162
tataaagata tagtagatga tgtg                                         24

<210> SEQ ID NO 1163
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1163
tttagttgag atgaagttat taga                                         24

<210> SEQ ID NO 1164
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1164
attgaattga tatagtgtaa agtg                                         24

<210> SEQ ID NO 1165
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1165
gaagaaagat tattgtattg agtt                                         24

```
<210> SEQ ID NO 1166
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1166
attgagtgta gtgatttaga aata                                            24

<210> SEQ ID NO 1167
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1167
aataaagtgt ttaagagtag agta                                            24

<210> SEQ ID NO 1168
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1168
gtagagataa ttgatgtgta attt                                            24

<210> SEQ ID NO 1169
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1169
tgatcgtagc tacgccgcg                                                  19

<210> SEQ ID NO 1170
<211> LENGTH: 16
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1170
cgtacgattg caacgt                                                     16

<210> SEQ ID NO 1171
<211> LENGTH: 48
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1171
atgttaaagt aagtgttgaa atgttccagg gaagcgtgtc accgtcgt                  48
```

```
<210> SEQ ID NO 1172
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1172
tcatggcgac tgtccagctt tgtg                                          24
```